US012697383B2

(12) United States Patent
Gu et al.

(10) Patent No.: US 12,697,383 B2
(45) Date of Patent: Aug. 4, 2026

(54) MODIFIED ENVELOPE PROTEIN OF HUMAN IMMUNODEFICIENCY VIRUS AND USE THEREOF

(71) Applicants: XIAMEN UNIVERSITY, Xiamen (CN); XIAMEN INNOVAX BIOTECH CO., LTD., Xiamen (CN)

(72) Inventors: Ying Gu, Xiamen (CN); Tingting Deng, Xiamen (CN); Hui Zhang, Xiamen (CN); Fang Huang, Xiamen (CN); Gege Chen, Xiamen (CN); Yanling Lin, Xiamen (CN); Shaowei Li, Xiamen (CN); Ningshao Xia, Xiamen (CN)

(73) Assignees: Xiamen University, Xiamen (CN); Xiamen Innovax Biotech Co., Ltd., Xiamen (CN)

( * ) Notice: Subject to any disclaimer, the term of this patent is extended or adjusted under 35 U.S.C. 154(b) by 598 days.

(21) Appl. No.: 18/252,836

(22) PCT Filed: Nov. 12, 2021

(86) PCT No.: PCT/CN2021/130414
§ 371 (c)(1),
(2) Date: May 12, 2023

(87) PCT Pub. No.: WO2022/100703
PCT Pub. Date: May 19, 2022

(65) Prior Publication Data
US 2024/0000919 A1 Jan. 4, 2024

(30) Foreign Application Priority Data
Nov. 12, 2021 (CN) .......................... 202011260750.4

(51) Int. Cl.
*A61P 31/18* (2006.01)
*A61K 39/21* (2006.01)
*C07K 14/005* (2006.01)
*C07K 14/155* (2006.01)
*C07K 16/10* (2006.01)
*C12N 7/00* (2006.01)
*A61K 39/00* (2006.01)

(52) U.S. Cl.
CPC .............. *A61K 39/21* (2013.01); *A61P 31/18* (2018.01); *C07K 14/005* (2013.01); *C07K 16/10* (2013.01); *C12N 7/00* (2013.01); *A61K 2039/5258* (2013.01); *A61K 2039/645*

(2013.01); *C07K 2319/40* (2013.01); *C12N 2740/16122* (2013.01); *C12N 2740/16134* (2013.01); *C12N 2740/16171* (2013.01)

(58) Field of Classification Search
None
See application file for complete search history.

(56) References Cited

U.S. PATENT DOCUMENTS

2014/0212458 A1 7/2014 Caulfield et al.
2017/0233441 A1 8/2017 Kwong et al.

FOREIGN PATENT DOCUMENTS

| CN | 103992396 A | 8/2014 |
| CN | 109153704 A | 1/2019 |
| CN | 109689091 A | 4/2019 |
| CN | 110248954 A | 9/2019 |
| EP | 2765138 A2 | 8/2014 |
| WO | 2017055522 A1 | 4/2017 |
| WO | 2017192434 A1 | 11/2017 |
| WO | 2018050747 A1 | 3/2018 |
| WO | 2018069878 A1 | 4/2018 |

OTHER PUBLICATIONS

Sanders et al. Native-like Env trimers as a platform for HIV-1 vaccine design. Immunol Rev. Jan. 2017;275(1):161-182.*
English Translation of the International Search Report in PCT/CN2021/130414, mailed Feb. 10, 2022.
Pancera et al., "Structure of HIV-1 gp120 with gp41-interactive region reveals layered envelope architecture and basis of conformational mobility," Proc Natl Acad Sci USA, 107(3):1166-71 (2010).
Shen et al., "Progress in HIV-1 Env Trimer Design," Chinese Journal of Biotechnology, 36(1):25-32 (2020). English Abstract Attached.
Yang et al., "Expression and Characterization of Trimeric HIV-1 gp140 Membrane Protein from Mammalian Cells," Chinese Journal of Virology, 33(4):541-549 (2017). English Abstract Attached.
Sanders et al., "Native-like Env trimers as a platform for HIV-1 vaccine design," *Immunological Reviews*, 275(1): 161-182 (2017).
De Taeye et al., "HIV-1 Envelope Trimer Design and Immunization Strategies to Induce Broadly Neutralizing Antibodies," *Trends in Immunology*, 37(3): 221-232 (2016).

* cited by examiner

*Primary Examiner* — Nianxiang Zou
(74) *Attorney, Agent, or Firm* — Medler Ferro Woodhouse & Mills PLLC

(57) ABSTRACT

Provided are a newly designed HIV-1 Env trimer protein, and an HIV-1 pseudovirus and virus expressing the Env trimer protein, and the use thereof for the prevention and/or treatment of HIV infection.

29 Claims, 34 Drawing Sheets
Specification includes a Sequence Listing.

NL4-3 (Tier1-B)

2626 (Tier2-B)

BaL.26-WT

BaL.26-TSTIP

SEQUENCE LISTING

<160> NUMBER OF SEQ ID NOS: 41

<210> SEQ ID NO 1
<211> LENGTH: 659
<212> TYPE: PRT
<213> ORGANISM: Artificial Sequence
<220> FEATURE:
<223> OTHER INFORMATION: BG505 TST

<400> SEQUENCE: 1

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

Gly Ala Arg Ala Glu Asn Leu Ala Val Gly Ile Gly Ala Val Phe Leu
            35                  40                  45

Gly Phe Leu Gly Ala Ala Gly Ser Thr Met Gly Ala Ala Ser Met Thr
        50                  55                  60

Leu Thr Val Gln Ala Arg Asn Leu Leu Ser Gly Ile Val Gln Gln Gln
65                  70                  75                  80

Ser Asn Leu Leu Arg Ala Ile Glu Ala Gln Gln His Leu Leu Lys Leu
                85                  90                  95

Thr Val Trp Gly Ile Lys Gln Leu Gln Ala Arg Val Leu Ala Val Glu
                100                 105                 110

Arg Tyr Leu Arg Asp Gln Gln Leu Leu Gly Ile Trp Gly Cys Ser Gly
            115                 120                 125

Lys Leu Ile Cys Thr Thr Asn Val Pro Asn Leu Trp Val Thr Val Tyr
        130                 135                 140

Tyr Gly Val Pro Val Trp Lys Asp Ala Glu Thr Thr Leu Phe Cys Ala
145                 150                 155                 160

Ser Asp Ala Lys Ala Tyr Glu Thr Glu Lys His Asn Val Trp Ala Thr
                165                 170                 175

His Ala Cys Val Pro Thr Asp Pro Asn Pro Gln Glu Ile His Leu Glu
                180                 185                 190

Asn Val Thr Glu Glu Phe Asn Met Trp Lys Asn Asn Met Val Glu Gln
            195                 200                 205

Met His Thr Asp Ile Ile Ser Leu Trp Asp Gln Ser Leu Lys Pro Cys
        210                 215                 220

Val Lys Leu Thr Pro Leu Cys Val Thr Leu Gln Cys Thr Asn Val Thr
225                 230                 235                 240

Asn Asn Ile Thr Asp Asp Met Arg Gly Glu Leu Lys Asn Cys Ser Phe
                245                 250                 255

Asn Met Thr Thr Glu Leu Arg Asp Lys Lys Gln Lys Val Tyr Ser Leu
                260                 265                 270

Phe Tyr Arg Leu Asp Val Val Gln Ile Asn Glu Asn Gln Gly Asn Arg
            275                 280                 285

Ser Asn Asn Ser Asn Lys Glu Tyr Arg Leu Ile Asn Cys Asn Thr Ser
        290                 295                 300

Ala Ile Thr Gln Ala Cys Pro Lys Val Ser Phe Glu Pro Ile Pro Ile
305                 310                 315                 320

His Tyr Cys Ala Pro Ala Gly Phe Ala Ile Leu Lys Cys Lys Asp Lys
                325                 330                 335

Lys Phe Asn Gly Thr Gly Pro Cys Pro Ser Val Ser Thr Val Gln Cys
            340                 345                 350

Thr His Gly Ile Lys Pro Val Val Ser Thr Gln Leu Leu Leu Asn Gly
```

-continued

```
        355                 360                 365

Ser Leu Ala Glu Glu Glu Val Met Ile Arg Ser Glu Asn Ile Thr Asn
    370                 375                 380

Asn Ala Lys Asn Ile Leu Val Gln Phe Asn Thr Pro Val Gln Ile Asn
385                 390                 395                 400

Cys Thr Arg Pro Asn Asn Asn Thr Arg Lys Ser Ile Arg Ile Gly Pro
                405                 410                 415

Gly Gln Ala Phe Tyr Ala Thr Gly Asp Ile Ile Gly Asp Ile Arg Gln
                420                 425                 430

Ala His Cys Asn Val Ser Lys Ala Thr Trp Asn Glu Thr Leu Gly Lys
            435                 440                 445

Val Val Lys Gln Leu Arg Lys His Phe Gly Asn Asn Thr Ile Ile Arg
    450                 455                 460

Phe Ala Asn Ser Ser Gly Gly Asp Leu Glu Val Thr Thr His Ser Phe
465                 470                 475                 480

Asn Cys Gly Gly Glu Phe Phe Tyr Cys Asn Thr Ser Gly Leu Phe Asn
                485                 490                 495

Ser Thr Trp Ile Ser Asn Thr Ser Val Gln Gly Ser Asn Ser Thr Gly
                500                 505                 510

Ser Asn Asp Ser Ile Thr Leu Pro Cys Arg Ile Lys Gln Ile Ile Asn
            515                 520                 525

Met Trp Gln Arg Ile Gly Gln Ala Met Tyr Ala Pro Pro Ile Gln Gly
    530                 535                 540

Val Ile Arg Cys Val Ser Asn Ile Thr Gly Leu Ile Leu Thr Arg Asp
545                 550                 555                 560

Gly Gly Ser Thr Asn Ser Thr Thr Glu Thr Phe Arg Pro Gly Gly Gly
                565                 570                 575

Asp Met Arg Asp Asn Trp Arg Ser Glu Leu Tyr Lys Tyr Lys Val Val
                580                 585                 590

Lys Ile Glu Pro Leu Gly Val Ala Pro Thr Arg Arg Asn Leu Ser Glu
            595                 600                 605

Ile Trp Asp Asn Met Thr Trp Leu Gln Trp Asp Lys Glu Ile Ser Asn
    610                 615                 620

Tyr Thr Gln Ile Ile Tyr Gly Leu Leu Glu Glu Ser Gln Asn Gln Gln
625                 630                 635                 640

Glu Lys Asn Glu Gln Asp Leu Leu Ala Leu Asp His His His His His
                645                 650                 655

His His His
```

```
<210> SEQ ID NO 2
<211> LENGTH: 660
<212> TYPE: PRT
<213> ORGANISM: Artificial Sequence
<220> FEATURE:
<223> OTHER INFORMATION: NL4-3 TST

<400> SEQUENCE: 2

Met Asp Ala Met Lys Arg Gly Leu Cys Cys Val Leu Leu Leu Cys Gly
1                   5                   10                  15

Ala Val Phe Val Ser Pro Ser Gln Glu Ile His Ala Arg Phe Arg Arg
                20                  25                  30

Gly Ala Arg Ala Glu Asn Leu Ala Val Gly Ile Gly Ala Leu Phe Leu
            35                  40                  45

Gly Phe Leu Gly Ala Ala Gly Ser Thr Met Gly Ala Ala Ser Met Thr
    50                  55                  60
```

```
Leu Thr Val Gln Ala Arg Gln Leu Leu Ser Asp Ile Val Gln Gln Gln
65                  70                  75                  80

Asn Asn Leu Leu Arg Ala Ile Glu Ala Gln Gln His Leu Leu Gln Leu
                85                  90                  95

Thr Val Trp Gly Ile Lys Gln Leu Gln Ala Arg Ile Leu Ala Val Glu
            100                 105                 110

Arg Tyr Leu Lys Asp Gln Gln Leu Leu Gly Ile Trp Gly Cys Ser Gly
        115                 120                 125

Lys Leu Ile Cys Thr Thr Ala Val Pro Asn Leu Trp Val Thr Val Tyr
    130                 135                 140

Tyr Gly Val Pro Val Trp Lys Glu Ala Thr Thr Thr Leu Phe Cys Ala
145                 150                 155                 160

Ser Asp Ala Lys Ala Tyr Asp Thr Glu Val His Asn Val Trp Ala Thr
                165                 170                 175

His Ala Cys Val Pro Thr Asp Pro Asn Pro Gln Glu Val Val Leu Val
            180                 185                 190

Asn Val Thr Glu Asn Phe Asn Met Trp Lys Asn Asp Met Val Glu Gln
        195                 200                 205

Met His Glu Asp Ile Ile Ser Leu Trp Asp Gln Ser Leu Lys Pro Cys
    210                 215                 220

Val Lys Leu Thr Pro Leu Cys Val Ser Leu Lys Cys Thr Asp Leu Lys
225                 230                 235                 240

Asn Asp Thr Asn Thr Asn Ser Ser Ser Gly Arg Met Ile Met Glu Lys
                245                 250                 255

Gly Glu Ile Lys Asn Cys Ser Phe Asn Ile Ser Thr Ser Ile Arg Asp
            260                 265                 270

Lys Val Gln Lys Glu Tyr Ala Phe Phe Tyr Lys Leu Asp Ile Val Pro
        275                 280                 285

Ile Asp Asn Thr Ser Tyr Arg Leu Ile Ser Cys Asn Thr Ser Val Ile
    290                 295                 300

Thr Gln Ala Cys Pro Lys Val Ser Phe Glu Pro Ile Pro Ile His Tyr
305                 310                 315                 320

Cys Ala Pro Ala Gly Phe Ala Ile Leu Lys Cys Asn Asn Lys Thr Phe
                325                 330                 335

Asn Gly Thr Gly Pro Cys Thr Asn Val Ser Thr Val Gln Cys Thr His
            340                 345                 350

Gly Ile Arg Pro Val Val Ser Thr Gln Leu Leu Leu Asn Gly Ser Leu
        355                 360                 365

Ala Glu Glu Asp Val Val Ile Arg Ser Ala Asn Phe Thr Asp Asn Ala
    370                 375                 380

Lys Thr Ile Ile Val Gln Leu Asn Thr Ser Val Glu Ile Asn Cys Thr
385                 390                 395                 400

Arg Pro Asn Asn Asn Thr Arg Lys Ser Ile Arg Ile Gln Arg Gly Pro
                405                 410                 415

Gly Arg Ala Phe Val Thr Ile Gly Lys Ile Gly Asn Met Arg Gln Ala
            420                 425                 430

His Cys Asn Ile Ser Arg Ala Lys Trp Asn Ala Thr Leu Lys Gln Ile
            435                 440                 445

Ala Ser Lys Leu Arg Glu Gln Phe Gly Asn Asn Lys Thr Ile Ile Phe
        450                 455                 460

Lys Gln Ser Ser Gly Gly Asp Pro Glu Ile Val Thr His Ser Phe Asn
465                 470                 475                 480
```

-continued

```
Cys Gly Gly Glu Phe Phe Tyr Cys Asn Ser Thr Gln Leu Phe Asn Ser
                485                 490                 495

Thr Trp Phe Asn Ser Thr Trp Ser Thr Glu Gly Ser Asn Asn Thr Glu
                500                 505                 510

Gly Ser Asp Thr Ile Thr Leu Pro Cys Arg Ile Lys Gln Phe Ile Asn
                515                 520                 525

Met Trp Gln Glu Val Gly Lys Ala Met Tyr Ala Pro Pro Ile Ser Gly
        530                 535                 540

Gln Ile Arg Cys Ser Ser Asn Ile Thr Gly Leu Leu Leu Thr Arg Asp
545                 550                 555                 560

Gly Gly Asn Asn Asn Asn Gly Ser Glu Ile Phe Arg Pro Gly Gly Gly
                565                 570                 575

Asp Met Arg Asp Asn Trp Arg Ser Glu Leu Tyr Lys Tyr Lys Val Val
                580                 585                 590

Lys Ile Glu Pro Leu Gly Val Ala Pro Thr Lys Lys Ser Leu Glu Gln
                595                 600                 605

Ile Trp Asn Asn Met Thr Trp Met Glu Trp Asp Arg Glu Ile Asn Asn
        610                 615                 620

Tyr Thr Ser Leu Ile His Ser Leu Ile Glu Glu Ser Gln Asn Gln Gln
625                 630                 635                 640

Glu Lys Asn Glu Gln Glu Leu Leu Glu Leu Asp Lys His His His His
                645                 650                 655

His His His His
        660
```

```
<210> SEQ ID NO 3
<211> LENGTH: 659
<212> TYPE: PRT
<213> ORGANISM: Artificial Sequence
<220> FEATURE:
<223> OTHER INFORMATION: BG505 TSTIP

<400> SEQUENCE: 3
```

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

Gly Ala Arg Ala Glu Asn Leu Ala Val Gly Ile Gly Ala Val Phe Leu
        35                  40                  45

Gly Phe Leu Gly Ala Ala Gly Ser Thr Met Gly Ala Ala Ser Met Thr
        50                  55                  60

Leu Thr Val Gln Ala Arg Asn Leu Leu Ser Gly Ile Val Gln Gln Gln
65                  70                  75                  80

Ser Asn Leu Leu Arg Ala Pro Glu Ala Gln Gln His Leu Leu Lys Leu
                85                  90                  95

Thr Val Trp Gly Ile Lys Gln Leu Gln Ala Arg Val Leu Ala Val Glu
                100                 105                 110

Arg Tyr Leu Arg Asp Gln Gln Leu Leu Gly Ile Trp Gly Cys Ser Gly
            115                 120                 125

Lys Leu Ile Cys Thr Thr Asn Val Pro Asn Leu Trp Val Thr Val Tyr
        130                 135                 140

Tyr Gly Val Pro Val Trp Lys Asp Ala Glu Thr Thr Leu Phe Cys Ala
145                 150                 155                 160

Ser Asp Ala Lys Ala Tyr Glu Thr Glu Lys His Asn Val Trp Ala Thr
                165                 170                 175
```

-continued

```
His Ala Cys Val Pro Thr Asp Pro Asn Pro Gln Glu Ile His Leu Glu
             180             185             190

Asn Val Thr Glu Glu Phe Asn Met Trp Lys Asn Asn Met Val Glu Gln
         195             200             205

Met His Thr Asp Ile Ile Ser Leu Trp Asp Gln Ser Leu Lys Pro Cys
     210             215             220

Val Lys Leu Thr Pro Leu Cys Val Thr Leu Gln Cys Thr Asn Val Thr
225             230             235             240

Asn Asn Ile Thr Asp Asp Met Arg Gly Glu Leu Lys Asn Cys Ser Phe
             245             250             255

Asn Met Thr Thr Glu Leu Arg Asp Lys Lys Gln Lys Val Tyr Ser Leu
             260             265             270

Phe Tyr Arg Leu Asp Val Val Gln Ile Asn Glu Asn Gln Gly Asn Arg
         275             280             285

Ser Asn Asn Ser Asn Lys Glu Tyr Arg Leu Ile Asn Cys Asn Thr Ser
     290             295             300

Ala Ile Thr Gln Ala Cys Pro Lys Val Ser Phe Glu Pro Ile Pro Ile
305             310             315             320

His Tyr Cys Ala Pro Ala Gly Phe Ala Ile Leu Lys Cys Lys Asp Lys
             325             330             335

Lys Phe Asn Gly Thr Gly Pro Cys Pro Ser Val Ser Thr Val Gln Cys
             340             345             350

Thr His Gly Ile Lys Pro Val Val Ser Thr Gln Leu Leu Leu Asn Gly
         355             360             365

Ser Leu Ala Glu Glu Glu Val Met Ile Arg Ser Glu Asn Ile Thr Asn
     370             375             380

Asn Ala Lys Asn Ile Leu Val Gln Phe Asn Thr Pro Val Gln Ile Asn
385             390             395             400

Cys Thr Arg Pro Asn Asn Asn Thr Arg Lys Ser Ile Arg Ile Gly Pro
             405             410             415

Gly Gln Ala Phe Tyr Ala Thr Gly Asp Ile Ile Gly Asp Ile Arg Gln
             420             425             430

Ala His Cys Asn Val Ser Lys Ala Thr Trp Asn Glu Thr Leu Gly Lys
             435             440             445

Val Val Lys Gln Leu Arg Lys His Phe Gly Asn Asn Thr Ile Ile Arg
     450             455             460

Phe Ala Asn Ser Ser Gly Gly Asp Leu Glu Val Thr Thr His Ser Phe
465             470             475             480

Asn Cys Gly Gly Glu Phe Phe Tyr Cys Asn Thr Ser Gly Leu Phe Asn
             485             490             495

Ser Thr Trp Ile Ser Asn Thr Ser Val Gln Gly Ser Asn Ser Thr Gly
             500             505             510

Ser Asn Asp Ser Ile Thr Leu Pro Cys Arg Ile Lys Gln Ile Ile Asn
             515             520             525

Met Trp Gln Arg Ile Gly Gln Ala Met Tyr Ala Pro Pro Ile Gln Gly
     530             535             540

Val Ile Arg Cys Val Ser Asn Ile Thr Gly Leu Ile Leu Thr Arg Asp
545             550             555             560

Gly Gly Ser Thr Asn Ser Thr Thr Glu Thr Phe Arg Pro Gly Gly Gly
             565             570             575

Asp Met Arg Asp Asn Trp Arg Ser Glu Leu Tyr Lys Tyr Lys Val Val
             580             585             590

Lys Ile Glu Pro Leu Gly Val Ala Pro Thr Arg Arg Asn Leu Ser Glu
```

-continued

```
              595                 600                 605

Ile Trp Asp Asn Met Thr Trp Leu Gln Trp Asp Lys Glu Ile Ser Asn
    610                 615                 620

Tyr Thr Gln Ile Ile Tyr Gly Leu Leu Glu Glu Ser Gln Asn Gln Gln
625                 630                 635                 640

Glu Lys Asn Glu Gln Asp Leu Leu Ala Leu Asp His His His His His
                645                 650                 655

His His His

<210> SEQ ID NO 4
<211> LENGTH: 660
<212> TYPE: PRT
<213> ORGANISM: Artificial Sequence
<220> FEATURE:
<223> OTHER INFORMATION: NL4-3 TSTIP

<400> SEQUENCE: 4

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

Gly Ala Arg Ala Glu Asn Leu Ala Val Gly Ile Gly Ala Leu Phe Leu
            35                  40                  45

Gly Phe Leu Gly Ala Ala Gly Ser Thr Met Gly Ala Ala Ser Met Thr
        50                  55                  60

Leu Thr Val Gln Ala Arg Gln Leu Leu Ser Asp Ile Val Gln Gln Gln
65                  70                  75                  80

Asn Asn Leu Leu Arg Ala Pro Glu Ala Gln Gln His Leu Leu Gln Leu
                85                  90                  95

Thr Val Trp Gly Ile Lys Gln Leu Gln Ala Arg Ile Leu Ala Val Glu
            100                 105                 110

Arg Tyr Leu Lys Asp Gln Gln Leu Leu Gly Ile Trp Gly Cys Ser Gly
            115                 120                 125

Lys Leu Ile Cys Thr Thr Ala Val Pro Asn Leu Trp Val Thr Val Tyr
        130                 135                 140

Tyr Gly Val Pro Val Trp Lys Glu Ala Thr Thr Thr Leu Phe Cys Ala
145                 150                 155                 160

Ser Asp Ala Lys Ala Tyr Asp Thr Glu Val His Asn Val Trp Ala Thr
                165                 170                 175

His Ala Cys Val Pro Thr Asp Pro Asn Pro Gln Glu Val Val Leu Val
            180                 185                 190

Asn Val Thr Glu Asn Phe Asn Met Trp Lys Asn Asp Met Val Glu Gln
            195                 200                 205

Met His Glu Asp Ile Ile Ser Leu Trp Asp Gln Ser Leu Lys Pro Cys
        210                 215                 220

Val Lys Leu Thr Pro Leu Cys Val Ser Leu Lys Cys Thr Asp Leu Lys
225                 230                 235                 240

Asn Asp Thr Asn Thr Asn Ser Ser Ser Gly Arg Met Ile Met Glu Lys
                245                 250                 255

Gly Glu Ile Lys Asn Cys Ser Phe Asn Ile Ser Thr Ser Ile Arg Asp
            260                 265                 270

Lys Val Gln Lys Glu Tyr Ala Phe Phe Tyr Lys Leu Asp Ile Val Pro
            275                 280                 285

Ile Asp Asn Thr Ser Tyr Arg Leu Ile Ser Cys Asn Thr Ser Val Ile
        290                 295                 300
```

-continued

```
Thr Gln Ala Cys Pro Lys Val Ser Phe Glu Pro Ile Pro Ile His Tyr
305                 310                 315                 320

Cys Ala Pro Ala Gly Phe Ala Ile Leu Lys Cys Asn Asn Lys Thr Phe
                325                 330                 335

Asn Gly Thr Gly Pro Cys Thr Asn Val Ser Thr Val Gln Cys Thr His
            340                 345                 350

Gly Ile Arg Pro Val Val Ser Thr Gln Leu Leu Leu Asn Gly Ser Leu
            355                 360                 365

Ala Glu Glu Asp Val Val Ile Arg Ser Ala Asn Phe Thr Asp Asn Ala
        370                 375                 380

Lys Thr Ile Ile Val Gln Leu Asn Thr Ser Val Glu Ile Asn Cys Thr
385                 390                 395                 400

Arg Pro Asn Asn Asn Thr Arg Lys Ser Ile Arg Ile Gln Arg Gly Pro
                405                 410                 415

Gly Arg Ala Phe Val Thr Ile Gly Lys Ile Gly Asn Met Arg Gln Ala
            420                 425                 430

His Cys Asn Ile Ser Arg Ala Lys Trp Asn Ala Thr Leu Lys Gln Ile
            435                 440                 445

Ala Ser Lys Leu Arg Glu Gln Phe Gly Asn Asn Lys Thr Ile Ile Phe
        450                 455                 460

Lys Gln Ser Ser Gly Gly Asp Pro Glu Ile Val Thr His Ser Phe Asn
465                 470                 475                 480

Cys Gly Gly Glu Phe Phe Tyr Cys Asn Ser Thr Gln Leu Phe Asn Ser
                485                 490                 495

Thr Trp Phe Asn Ser Thr Trp Ser Thr Glu Gly Ser Asn Asn Thr Glu
            500                 505                 510

Gly Ser Asp Thr Ile Thr Leu Pro Cys Arg Ile Lys Gln Phe Ile Asn
            515                 520                 525

Met Trp Gln Glu Val Gly Lys Ala Met Tyr Ala Pro Pro Ile Ser Gly
        530                 535                 540

Gln Ile Arg Cys Ser Ser Asn Ile Thr Gly Leu Leu Leu Thr Arg Asp
545                 550                 555                 560

Gly Gly Asn Asn Asn Asn Gly Ser Glu Ile Phe Arg Pro Gly Gly Gly
                565                 570                 575

Asp Met Arg Asp Asn Trp Arg Ser Glu Leu Tyr Lys Tyr Lys Val Val
            580                 585                 590

Lys Ile Glu Pro Leu Gly Val Ala Pro Thr Lys Lys Ser Leu Glu Gln
            595                 600                 605

Ile Trp Asn Asn Met Thr Trp Met Glu Trp Asp Arg Glu Ile Asn Asn
        610                 615                 620

Tyr Thr Ser Leu Ile His Ser Leu Ile Glu Glu Ser Gln Asn Gln Gln
625                 630                 635                 640

Glu Lys Asn Glu Gln Glu Leu Leu Glu Leu Asp Lys His His His His
                645                 650                 655

His His His His
            660
```

```
<210> SEQ ID NO 5
<211> LENGTH: 673
<212> TYPE: PRT
<213> ORGANISM: Artificial Sequence
<220> FEATURE:
<223> OTHER INFORMATION: BG505 TSTIP full

<400> SEQUENCE: 5
```

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

Gly Ala Arg Ala Glu Asn Leu Ala Val Gly Ile Gly Ala Val Phe Leu
            35                  40                  45

Gly Phe Leu Gly Ala Ala Gly Ser Thr Met Gly Ala Ala Ser Met Thr
    50                  55                  60

Leu Thr Val Gln Ala Arg Asn Leu Leu Ser Gly Ile Val Gln Gln Gln
65                  70                  75                  80

Ser Asn Leu Leu Arg Ala Pro Glu Ala Gln Gln His Leu Leu Lys Leu
                85                  90                  95

Thr Val Trp Gly Ile Lys Gln Leu Gln Ala Arg Val Leu Ala Val Glu
            100                 105                 110

Arg Tyr Leu Arg Asp Gln Gln Leu Leu Gly Ile Trp Gly Cys Ser Gly
        115                 120                 125

Lys Leu Ile Cys Thr Thr Asn Val Pro Trp Asn Ser Ser Trp Ser Asn
    130                 135                 140

Asn Leu Trp Val Thr Val Tyr Tyr Gly Val Pro Val Trp Lys Asp Ala
145                 150                 155                 160

Glu Thr Thr Leu Phe Cys Ala Ser Asp Ala Lys Ala Tyr Glu Thr Glu
                165                 170                 175

Lys His Asn Val Trp Ala Thr His Ala Cys Val Pro Thr Asp Pro Asn
            180                 185                 190

Pro Gln Glu Ile His Leu Glu Asn Val Thr Glu Glu Phe Asn Met Trp
        195                 200                 205

Lys Asn Asn Met Val Glu Gln Met His Thr Asp Ile Ile Ser Leu Trp
    210                 215                 220

Asp Gln Ser Leu Lys Pro Cys Val Lys Leu Thr Pro Leu Cys Val Thr
225                 230                 235                 240

Leu Gln Cys Thr Asn Val Thr Asn Asn Ile Thr Asp Asp Met Arg Gly
                245                 250                 255

Glu Leu Lys Asn Cys Ser Phe Asn Met Thr Thr Glu Leu Arg Asp Lys
            260                 265                 270

Lys Gln Lys Val Tyr Ser Leu Phe Tyr Arg Leu Asp Val Val Gln Ile
        275                 280                 285

Asn Glu Asn Gln Gly Asn Arg Ser Asn Asn Ser Asn Lys Glu Tyr Arg
    290                 295                 300

Leu Ile Asn Cys Asn Thr Ser Ala Ile Thr Gln Ala Cys Pro Lys Val
305                 310                 315                 320

Ser Phe Glu Pro Ile Pro Ile His Tyr Cys Ala Pro Ala Gly Phe Ala
                325                 330                 335

Ile Leu Lys Cys Lys Asp Lys Lys Phe Asn Gly Thr Gly Pro Cys Pro
            340                 345                 350

Ser Val Ser Thr Val Gln Cys Thr His Gly Ile Lys Pro Val Val Ser
        355                 360                 365

Thr Gln Leu Leu Leu Asn Gly Ser Leu Ala Glu Glu Glu Val Met Ile
    370                 375                 380

Arg Ser Glu Asn Ile Thr Asn Asn Ala Lys Asn Ile Leu Val Gln Phe
385                 390                 395                 400

Asn Thr Pro Val Gln Ile Asn Cys Thr Arg Pro Asn Asn Asn Thr Arg
                405                 410                 415
```

-continued

```
Lys Ser Ile Arg Ile Gly Pro Gly Gln Ala Phe Tyr Ala Thr Gly Asp
            420             425             430

Ile Ile Gly Asp Ile Arg Gln Ala His Cys Asn Val Ser Lys Ala Thr
        435             440             445

Trp Asn Glu Thr Leu Gly Lys Val Val Lys Gln Leu Arg Lys His Phe
    450             455             460

Gly Asn Asn Thr Ile Ile Arg Phe Ala Asn Ser Ser Gly Gly Asp Leu
465             470             475             480

Glu Val Thr Thr His Ser Phe Asn Cys Gly Gly Glu Phe Phe Tyr Cys
            485             490             495

Asn Thr Ser Gly Leu Phe Asn Ser Thr Trp Ile Ser Asn Thr Ser Val
        500             505             510

Gln Gly Ser Asn Ser Thr Gly Ser Asn Asp Ser Ile Thr Leu Pro Cys
        515             520             525

Arg Ile Lys Gln Ile Ile Asn Met Trp Gln Arg Ile Gly Gln Ala Met
    530             535             540

Tyr Ala Pro Pro Ile Gln Gly Val Ile Arg Cys Val Ser Asn Ile Thr
545             550             555             560

Gly Leu Ile Leu Thr Arg Asp Gly Gly Ser Thr Asn Ser Thr Thr Glu
            565             570             575

Thr Phe Arg Pro Gly Gly Gly Asp Met Arg Asp Asn Trp Arg Ser Glu
            580             585             590

Leu Tyr Lys Tyr Lys Val Val Lys Ile Glu Pro Leu Gly Val Ala Pro
            595             600             605

Thr Arg Ala Lys Arg Arg Val Val Gly Arg Asn Leu Ser Glu Ile Trp
    610             615             620

Asp Asn Met Thr Trp Leu Gln Trp Asp Lys Glu Ile Ser Asn Tyr Thr
625             630             635             640

Gln Ile Ile Tyr Gly Leu Leu Glu Glu Ser Gln Asn Gln Gln Glu Lys
            645             650             655

Asn Glu Gln Asp Leu Leu Ala Leu Asp His His His His His His
        660             665             670

His
```

```
<210> SEQ ID NO 6
<211> LENGTH: 686
<212> TYPE: PRT
<213> ORGANISM: Artificial Sequence
<220> FEATURE:
<223> OTHER INFORMATION: NL4-3 TSTIP full

<400> SEQUENCE: 6

Met Asp Ala Met Lys Arg Gly Leu Cys Cys Val Leu Leu Leu Cys Gly
1               5               10              15

Ala Val Phe Val Ser Pro Ser Gln Glu Ile His Ala Arg Phe Arg Arg
            20              25              30

Gly Ala Arg Ala Glu Asn Leu Arg Glu Lys Arg Ala Val Gly Ile Gly
        35              40              45

Ala Leu Phe Leu Gly Phe Leu Gly Ala Ala Gly Ser Thr Met Gly Ala
    50              55              60

Ala Ser Met Thr Leu Thr Val Gln Ala Arg Gln Leu Leu Ser Asp Ile
65              70              75              80

Val Gln Gln Gln Asn Asn Leu Leu Arg Ala Pro Glu Ala Gln Gln His
            85              90              95

Leu Leu Gln Leu Thr Val Trp Gly Ile Lys Gln Leu Gln Ala Arg Ile
```

-continued

```
                100                 105                 110

Leu Ala Val Glu Arg Tyr Leu Lys Asp Gln Gln Leu Leu Gly Ile Trp
            115                 120                 125

Gly Cys Ser Gly Lys Leu Ile Cys Thr Thr Ala Val Pro Trp Asn Ala
        130                 135                 140

Ser Trp Ser Asn Asn Leu Trp Val Thr Val Tyr Tyr Gly Val Pro Val
145                 150                 155                 160

Trp Lys Glu Ala Thr Thr Thr Leu Phe Cys Ala Ser Asp Ala Lys Ala
                165                 170                 175

Tyr Asp Thr Glu Val His Asn Val Trp Ala Thr His Ala Cys Val Pro
            180                 185                 190

Thr Asp Pro Asn Pro Gln Glu Val Val Leu Val Asn Val Thr Glu Asn
            195                 200                 205

Phe Asn Met Trp Lys Asn Asp Met Val Glu Gln Met His Glu Asp Ile
        210                 215                 220

Ile Ser Leu Trp Asp Gln Ser Leu Lys Pro Cys Val Lys Leu Thr Pro
225                 230                 235                 240

Leu Cys Val Ser Leu Lys Cys Thr Asp Leu Lys Asn Asp Thr Asn Thr
            245                 250                 255

Asn Ser Ser Ser Gly Arg Met Ile Met Glu Lys Gly Glu Ile Lys Asn
            260                 265                 270

Cys Ser Phe Asn Ile Ser Thr Ser Ile Arg Asp Lys Val Gln Lys Glu
        275                 280                 285

Tyr Ala Phe Phe Tyr Lys Leu Asp Ile Val Pro Ile Asp Asn Thr Ser
        290                 295                 300

Tyr Arg Leu Ile Ser Cys Asn Thr Ser Val Ile Thr Gln Ala Cys Pro
305                 310                 315                 320

Lys Val Ser Phe Glu Pro Ile Pro Ile His Tyr Cys Ala Pro Ala Gly
            325                 330                 335

Phe Ala Ile Leu Lys Cys Asn Asn Lys Thr Phe Asn Gly Thr Gly Pro
            340                 345                 350

Cys Thr Asn Val Ser Thr Val Gln Cys Thr His Gly Ile Arg Pro Val
        355                 360                 365

Val Ser Thr Gln Leu Leu Leu Asn Gly Ser Leu Ala Glu Glu Asp Val
370                 375                 380

Val Ile Arg Ser Ala Asn Phe Thr Asp Asn Ala Lys Thr Ile Ile Val
385                 390                 395                 400

Gln Leu Asn Thr Ser Val Glu Ile Asn Cys Thr Arg Pro Asn Asn Asn
            405                 410                 415

Thr Arg Lys Ser Ile Arg Ile Gln Arg Gly Pro Gly Arg Ala Phe Val
            420                 425                 430

Thr Ile Gly Lys Ile Gly Asn Met Arg Gln Ala His Cys Asn Ile Ser
            435                 440                 445

Arg Ala Lys Trp Asn Ala Thr Leu Lys Gln Ile Ala Ser Lys Leu Arg
        450                 455                 460

Glu Gln Phe Gly Asn Asn Lys Thr Ile Ile Phe Lys Gln Ser Ser Gly
465                 470                 475                 480

Gly Asp Pro Glu Ile Val Thr His Ser Phe Asn Cys Gly Gly Glu Phe
            485                 490                 495

Phe Tyr Cys Asn Ser Thr Gln Leu Phe Asn Ser Thr Trp Phe Asn Ser
            500                 505                 510

Thr Trp Ser Thr Glu Gly Ser Asn Asn Thr Glu Gly Ser Asp Thr Ile
            515                 520                 525
```

```
Thr Leu Pro Cys Arg Ile Lys Gln Phe Ile Asn Met Trp Gln Glu Val
    530             535             540

Gly Lys Ala Met Tyr Ala Pro Pro Ile Ser Gly Gln Ile Arg Cys Ser
545             550             555             560

Ser Asn Ile Thr Gly Leu Leu Leu Thr Arg Asp Gly Gly Asn Asn Asn
                565             570             575

Asn Gly Ser Glu Ile Phe Arg Pro Gly Gly Gly Asp Met Arg Asp Asn
            580             585             590

Trp Arg Ser Glu Leu Tyr Lys Tyr Lys Val Val Lys Ile Glu Pro Leu
            595             600             605

Gly Val Ala Pro Thr Lys Ala Lys Arg Arg Val Val Gln Lys Ser Leu
    610             615             620

Glu Gln Ile Trp Asn Asn Met Thr Trp Met Glu Trp Asp Arg Glu Ile
625             630             635             640

Asn Asn Tyr Thr Ser Leu Ile His Ser Leu Ile Glu Glu Ser Gln Asn
                645             650             655

Gln Gln Glu Lys Asn Glu Gln Glu Leu Leu Glu Leu Asp Lys Gly Ser
            660             665             670

Gly Ser Gly Gly Ser Gly His His His His His His His
    675             680             685
```

```
<210> SEQ ID NO 7
<211> LENGTH: 669
<212> TYPE: PRT
<213> ORGANISM: Artificial Sequence
<220> FEATURE:
<223> OTHER INFORMATION: BG505 TSTIP G1

<400> SEQUENCE: 7

Met Asp Ala Met Lys Arg Gly Leu Cys Cys Val Leu Leu Leu Cys Gly
1               5               10              15

Ala Val Phe Val Ser Pro Ser Gln Glu Ile His Ala Arg Phe Arg Arg
            20              25              30

Gly Ala Arg Ala Glu Asn Leu Ala Val Gly Ile Gly Ala Val Phe Leu
        35              40              45

Gly Phe Leu Gly Ala Ala Gly Ser Thr Met Gly Ala Ala Ser Met Thr
    50              55              60

Leu Thr Val Gln Ala Arg Asn Leu Leu Ser Gly Ile Val Gln Gln Gln
65              70              75              80

Ser Asn Leu Leu Arg Ala Pro Glu Ala Gln Gln His Leu Leu Lys Leu
                85              90              95

Thr Val Trp Gly Ile Lys Gln Leu Gln Ala Arg Val Leu Ala Val Glu
            100             105             110

Arg Tyr Leu Arg Asp Gln Gln Leu Leu Gly Ile Trp Gly Cys Ser Gly
        115             120             125

Lys Leu Ile Cys Thr Thr Asn Val Pro Gly Gly Gly Ser Asn Leu
    130             135             140

Trp Val Thr Val Tyr Tyr Gly Val Pro Val Trp Lys Asp Ala Glu Thr
145             150             155             160

Thr Leu Phe Cys Ala Ser Asp Ala Lys Ala Tyr Glu Thr Glu Lys His
            165             170             175

Asn Val Trp Ala Thr His Ala Cys Val Pro Thr Asp Pro Asn Pro Gln
            180             185             190

Glu Ile His Leu Glu Asn Val Thr Glu Glu Phe Asn Met Trp Lys Asn
        195             200             205
```

```
Asn Met Val Glu Gln Met His Thr Asp Ile Ile Ser Leu Trp Asp Gln
    210             215             220

Ser Leu Lys Pro Cys Val Lys Leu Thr Pro Leu Cys Val Thr Leu Gln
225             230             235             240

Cys Thr Asn Val Thr Asn Asn Ile Thr Asp Asp Met Arg Gly Glu Leu
            245             250             255

Lys Asn Cys Ser Phe Asn Met Thr Thr Glu Leu Arg Asp Lys Lys Gln
            260             265             270

Lys Val Tyr Ser Leu Phe Tyr Arg Leu Asp Val Val Gln Ile Asn Glu
            275             280             285

Asn Gln Gly Asn Arg Ser Asn Asn Ser Asn Lys Glu Tyr Arg Leu Ile
    290             295             300

Asn Cys Asn Thr Ser Ala Ile Thr Gln Ala Cys Pro Lys Val Ser Phe
305             310             315             320

Glu Pro Ile Pro Ile His Tyr Cys Ala Pro Ala Gly Phe Ala Ile Leu
            325             330             335

Lys Cys Lys Asp Lys Lys Phe Asn Gly Thr Gly Pro Cys Pro Ser Val
            340             345             350

Ser Thr Val Gln Cys Thr His Gly Ile Lys Pro Val Val Ser Thr Gln
            355             360             365

Leu Leu Leu Asn Gly Ser Leu Ala Glu Glu Glu Val Met Ile Arg Ser
    370             375             380

Glu Asn Ile Thr Asn Asn Ala Lys Asn Ile Leu Val Gln Phe Asn Thr
385             390             395             400

Pro Val Gln Ile Asn Cys Thr Arg Pro Asn Asn Asn Thr Arg Lys Ser
            405             410             415

Ile Arg Ile Gly Pro Gly Gln Ala Phe Tyr Ala Thr Gly Asp Ile Ile
            420             425             430

Gly Asp Ile Arg Gln Ala His Cys Asn Val Ser Lys Ala Thr Trp Asn
            435             440             445

Glu Thr Leu Gly Lys Val Val Lys Gln Leu Arg Lys His Phe Gly Asn
    450             455             460

Asn Thr Ile Ile Arg Phe Ala Asn Ser Ser Gly Gly Asp Leu Glu Val
465             470             475             480

Thr Thr His Ser Phe Asn Cys Gly Gly Glu Phe Phe Tyr Cys Asn Thr
            485             490             495

Ser Gly Leu Phe Asn Ser Thr Trp Ile Ser Asn Thr Ser Val Gln Gly
            500             505             510

Ser Asn Ser Thr Gly Ser Asn Asp Ser Ile Thr Leu Pro Cys Arg Ile
            515             520             525

Lys Gln Ile Ile Asn Met Trp Gln Arg Ile Gly Gln Ala Met Tyr Ala
    530             535             540

Pro Pro Ile Gln Gly Val Ile Arg Cys Val Ser Asn Ile Thr Gly Leu
545             550             555             560

Ile Leu Thr Arg Asp Gly Gly Ser Thr Asn Ser Thr Thr Glu Thr Phe
            565             570             575

Arg Pro Gly Gly Gly Asp Met Arg Asp Asn Trp Arg Ser Glu Leu Tyr
            580             585             590

Lys Tyr Lys Val Val Lys Ile Glu Pro Leu Gly Val Ala Pro Thr Arg
            595             600             605

Gly Gly Gly Gly Ser Arg Asn Leu Ser Glu Ile Trp Asp Asn Met Thr
    610             615             620
```

```
Trp Leu Gln Trp Asp Lys Glu Ile Ser Asn Tyr Thr Gln Ile Ile Tyr
625                 630                 635                 640

Gly Leu Leu Glu Glu Ser Gln Asn Gln Gln Glu Lys Asn Glu Gln Asp
                645                 650                 655

Leu Leu Ala Leu Asp His His His His His His His
                660                 665

<210> SEQ ID NO 8
<211> LENGTH: 682
<212> TYPE: PRT
<213> ORGANISM: Artificial Sequence
<220> FEATURE:
<223> OTHER INFORMATION: NL4-3 TSTIP G1

<400> SEQUENCE: 8

Met Asp Ala Met Lys Arg Gly Leu Cys Cys Val Leu Leu Leu Cys Gly
1                   5                   10                  15

Ala Val Phe Val Ser Pro Ser Gln Glu Ile His Ala Arg Phe Arg Arg
                20                  25                  30

Gly Ala Arg Ala Glu Asn Leu Arg Glu Lys Arg Ala Val Gly Ile Gly
            35                  40                  45

Ala Leu Phe Leu Gly Phe Leu Gly Ala Ala Gly Ser Thr Met Gly Ala
        50                  55                  60

Ala Ser Met Thr Leu Thr Val Gln Ala Arg Gln Leu Leu Ser Asp Ile
65                  70                  75                  80

Val Gln Gln Gln Asn Asn Leu Leu Arg Ala Pro Glu Ala Gln Gln His
                85                  90                  95

Leu Leu Gln Leu Thr Val Trp Gly Ile Lys Gln Leu Gln Ala Arg Ile
                100                 105                 110

Leu Ala Val Glu Arg Tyr Leu Lys Asp Gln Gln Leu Leu Gly Ile Trp
            115                 120                 125

Gly Cys Ser Gly Lys Leu Ile Cys Thr Thr Ala Val Pro Gly Gly Gly
        130                 135                 140

Gly Ser Asn Leu Trp Val Thr Val Tyr Tyr Gly Val Pro Val Trp Lys
145                 150                 155                 160

Glu Ala Thr Thr Thr Leu Phe Cys Ala Ser Asp Ala Lys Ala Tyr Asp
                165                 170                 175

Thr Glu Val His Asn Val Trp Ala Thr His Ala Cys Val Pro Thr Asp
                180                 185                 190

Pro Asn Pro Gln Glu Val Val Leu Val Asn Val Thr Glu Asn Phe Asn
            195                 200                 205

Met Trp Lys Asn Asp Met Val Glu Gln Met His Glu Asp Ile Ile Ser
        210                 215                 220

Leu Trp Asp Gln Ser Leu Lys Pro Cys Val Lys Leu Thr Pro Leu Cys
225                 230                 235                 240

Val Ser Leu Lys Cys Thr Asp Leu Lys Asn Asp Thr Asn Thr Asn Ser
                245                 250                 255

Ser Ser Gly Arg Met Ile Met Glu Lys Gly Glu Ile Lys Asn Cys Ser
                260                 265                 270

Phe Asn Ile Ser Thr Ser Ile Arg Asp Lys Val Gln Lys Glu Tyr Ala
            275                 280                 285

Phe Phe Tyr Lys Leu Asp Ile Val Pro Ile Asp Asn Thr Ser Tyr Arg
        290                 295                 300

Leu Ile Ser Cys Asn Thr Ser Val Ile Thr Gln Ala Cys Pro Lys Val
305                 310                 315                 320
```

-continued

```
Ser Phe Glu Pro Ile Pro Ile His Tyr Cys Ala Pro Ala Gly Phe Ala
            325             330             335

Ile Leu Lys Cys Asn Asn Lys Thr Phe Asn Gly Thr Gly Pro Cys Thr
            340             345             350

Asn Val Ser Thr Val Gln Cys Thr His Gly Ile Arg Pro Val Val Ser
            355             360             365

Thr Gln Leu Leu Leu Asn Gly Ser Leu Ala Glu Glu Asp Val Val Ile
        370             375             380

Arg Ser Ala Asn Phe Thr Asp Asn Ala Lys Thr Ile Ile Val Gln Leu
385             390             395             400

Asn Thr Ser Val Glu Ile Asn Cys Thr Arg Pro Asn Asn Asn Thr Arg
            405             410             415

Lys Ser Ile Arg Ile Gln Arg Gly Pro Gly Arg Ala Phe Val Thr Ile
            420             425             430

Gly Lys Ile Gly Asn Met Arg Gln Ala His Cys Asn Ile Ser Arg Ala
            435             440             445

Lys Trp Asn Ala Thr Leu Lys Gln Ile Ala Ser Lys Leu Arg Glu Gln
        450             455             460

Phe Gly Asn Asn Lys Thr Ile Ile Phe Lys Gln Ser Ser Gly Gly Asp
465             470             475             480

Pro Glu Ile Val Thr His Ser Phe Asn Cys Gly Gly Glu Phe Phe Tyr
            485             490             495

Cys Asn Ser Thr Gln Leu Phe Asn Ser Thr Trp Phe Asn Ser Thr Trp
            500             505             510

Ser Thr Glu Gly Ser Asn Asn Thr Glu Gly Ser Asp Thr Ile Thr Leu
            515             520             525

Pro Cys Arg Ile Lys Gln Phe Ile Asn Met Trp Gln Glu Val Gly Lys
        530             535             540

Ala Met Tyr Ala Pro Pro Ile Ser Gly Gln Ile Arg Cys Ser Ser Asn
545             550             555             560

Ile Thr Gly Leu Leu Leu Thr Arg Asp Gly Gly Asn Asn Asn Asn Gly
            565             570             575

Ser Glu Ile Phe Arg Pro Gly Gly Gly Asp Met Arg Asp Asn Trp Arg
            580             585             590

Ser Glu Leu Tyr Lys Tyr Lys Val Val Lys Ile Glu Pro Leu Gly Val
            595             600             605

Ala Pro Thr Lys Gly Gly Gly Ser Lys Ser Leu Glu Gln Ile Trp
        610             615             620

Asn Asn Met Thr Trp Met Glu Trp Asp Arg Glu Ile Asn Asn Tyr Thr
625             630             635             640

Ser Leu Ile His Ser Leu Ile Glu Glu Ser Gln Asn Gln Gln Glu Lys
            645             650             655

Asn Glu Gln Glu Leu Leu Glu Leu Asp Lys Gly Ser Gly Ser Gly Gly
            660             665             670

Ser Gly His His His His His His
        675             680
```

<210> SEQ ID NO 9
<211> LENGTH: 679
<212> TYPE: PRT
<213> ORGANISM: Artificial Sequence
<220> FEATURE:
<223> OTHER INFORMATION: BG505 TSTIP G2

<400> SEQUENCE: 9

-continued

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

Gly Ala Arg Ala Glu Asn Leu Ala Val Gly Ile Gly Ala Val Phe Leu
            35                  40                  45

Gly Phe Leu Gly Ala Ala Gly Ser Thr Met Gly Ala Ala Ser Met Thr
        50                  55                  60

Leu Thr Val Gln Ala Arg Asn Leu Leu Ser Gly Ile Val Gln Gln Gln
65                  70                  75                  80

Ser Asn Leu Leu Arg Ala Pro Glu Ala Gln Gln His Leu Leu Lys Leu
                85                  90                  95

Thr Val Trp Gly Ile Lys Gln Leu Gln Ala Arg Val Leu Ala Val Glu
            100                 105                 110

Arg Tyr Leu Arg Asp Gln Gln Leu Leu Gly Ile Trp Gly Cys Ser Gly
        115                 120                 125

Lys Leu Ile Cys Thr Thr Asn Val Pro Gly Gly Gly Ser Gly Gly
        130                 135                 140

Gly Gly Ser Asn Leu Trp Val Thr Val Tyr Tyr Gly Val Pro Val Trp
145                 150                 155                 160

Lys Asp Ala Glu Thr Thr Leu Phe Cys Ala Ser Asp Ala Lys Ala Tyr
                165                 170                 175

Glu Thr Glu Lys His Asn Val Trp Ala Thr His Ala Cys Val Pro Thr
            180                 185                 190

Asp Pro Asn Pro Gln Glu Ile His Leu Glu Asn Val Thr Glu Glu Phe
        195                 200                 205

Asn Met Trp Lys Asn Asn Met Val Glu Gln Met His Thr Asp Ile Ile
    210                 215                 220

Ser Leu Trp Asp Gln Ser Leu Lys Pro Cys Val Lys Leu Thr Pro Leu
225                 230                 235                 240

Cys Val Thr Leu Gln Cys Thr Asn Val Thr Asn Asn Ile Thr Asp Asp
                245                 250                 255

Met Arg Gly Glu Leu Lys Asn Cys Ser Phe Asn Met Thr Thr Glu Leu
            260                 265                 270

Arg Asp Lys Lys Gln Lys Val Tyr Ser Leu Phe Tyr Arg Leu Asp Val
        275                 280                 285

Val Gln Ile Asn Glu Asn Gln Gly Asn Arg Ser Asn Asn Ser Asn Lys
    290                 295                 300

Glu Tyr Arg Leu Ile Asn Cys Asn Thr Ser Ala Ile Thr Gln Ala Cys
305                 310                 315                 320

Pro Lys Val Ser Phe Glu Pro Ile Pro Ile His Tyr Cys Ala Pro Ala
                325                 330                 335

Gly Phe Ala Ile Leu Lys Cys Lys Asp Lys Lys Phe Asn Gly Thr Gly
            340                 345                 350

Pro Cys Pro Ser Val Ser Thr Val Gln Cys Thr His Gly Ile Lys Pro
        355                 360                 365

Val Val Ser Thr Gln Leu Leu Leu Asn Gly Ser Leu Ala Glu Glu Glu
    370                 375                 380

Val Met Ile Arg Ser Glu Asn Ile Thr Asn Asn Ala Lys Asn Ile Leu
385                 390                 395                 400

Val Gln Phe Asn Thr Pro Val Gln Ile Asn Cys Thr Arg Pro Asn Asn
                405                 410                 415

Asn Thr Arg Lys Ser Ile Arg Ile Gly Pro Gly Gln Ala Phe Tyr Ala
```

-continued

```
                  420              425              430
Thr Gly Asp Ile Ile Gly Asp Ile Arg Gln Ala His Cys Asn Val Ser
        435              440              445

Lys Ala Thr Trp Asn Glu Thr Leu Gly Lys Val Val Lys Gln Leu Arg
    450              455              460

Lys His Phe Gly Asn Asn Thr Ile Ile Arg Phe Ala Asn Ser Ser Gly
465              470              475              480

Gly Asp Leu Glu Val Thr Thr His Ser Phe Asn Cys Gly Gly Glu Phe
                485              490              495

Phe Tyr Cys Asn Thr Ser Gly Leu Phe Asn Ser Thr Trp Ile Ser Asn
            500              505              510

Thr Ser Val Gln Gly Ser Asn Ser Thr Gly Ser Asn Asp Ser Ile Thr
        515              520              525

Leu Pro Cys Arg Ile Lys Gln Ile Ile Asn Met Trp Gln Arg Ile Gly
    530              535              540

Gln Ala Met Tyr Ala Pro Pro Ile Gln Gly Val Ile Arg Cys Val Ser
545              550              555              560

Asn Ile Thr Gly Leu Ile Leu Thr Arg Asp Gly Gly Ser Thr Asn Ser
            565              570              575

Thr Thr Glu Thr Phe Arg Pro Gly Gly Gly Asp Met Arg Asp Asn Trp
        580              585              590

Arg Ser Glu Leu Tyr Lys Tyr Lys Val Val Lys Ile Glu Pro Leu Gly
        595              600              605

Val Ala Pro Thr Arg Gly Gly Gly Ser Gly Gly Gly Gly Ser Arg
    610              615              620

Asn Leu Ser Glu Ile Trp Asp Asn Met Thr Trp Leu Gln Trp Asp Lys
625              630              635              640

Glu Ile Ser Asn Tyr Thr Gln Ile Ile Tyr Gly Leu Leu Glu Glu Ser
            645              650              655

Gln Asn Gln Gln Glu Lys Asn Glu Gln Asp Leu Leu Ala Leu Asp His
        660              665              670

His His His His His His
        675
```

<210> SEQ ID NO 10
<211> LENGTH: 692
<212> TYPE: PRT
<213> ORGANISM: Artificial Sequence
<220> FEATURE:
<223> OTHER INFORMATION: NL4-3 TSTIP G2

<400> SEQUENCE: 10

```
Met Asp Ala Met Lys Arg Gly Leu Cys Cys Val Leu Leu Leu Cys Gly
1               5               10               15

Ala Val Phe Val Ser Pro Ser Gln Glu Ile His Ala Arg Phe Arg Arg
            20              25              30

Gly Ala Arg Ala Glu Asn Leu Arg Glu Lys Arg Ala Val Gly Ile Gly
        35              40              45

Ala Leu Phe Leu Gly Phe Leu Gly Ala Ala Gly Ser Thr Met Gly Ala
    50              55              60

Ala Ser Met Thr Leu Thr Val Gln Ala Arg Gln Leu Leu Ser Asp Ile
65              70              75              80

Val Gln Gln Gln Asn Asn Leu Leu Arg Ala Pro Glu Ala Gln Gln His
                85              90              95

Leu Leu Gln Leu Thr Val Trp Gly Ile Lys Gln Leu Gln Ala Arg Ile
```

-continued

```
                100                 105                 110

Leu Ala Val Glu Arg Tyr Leu Lys Asp Gln Gln Leu Leu Gly Ile Trp
        115                 120                 125

Gly Cys Ser Gly Lys Leu Ile Cys Thr Thr Ala Val Pro Gly Gly Gly
        130                 135                 140

Gly Ser Gly Gly Gly Gly Ser Asn Leu Trp Val Thr Val Tyr Tyr Gly
145                 150                 155                 160

Val Pro Val Trp Lys Glu Ala Thr Thr Thr Leu Phe Cys Ala Ser Asp
                165                 170                 175

Ala Lys Ala Tyr Asp Thr Glu Val His Asn Val Trp Ala Thr His Ala
        180                 185                 190

Cys Val Pro Thr Asp Pro Asn Pro Gln Glu Val Val Leu Val Asn Val
        195                 200                 205

Thr Glu Asn Phe Asn Met Trp Lys Asn Asp Met Val Glu Gln Met His
        210                 215                 220

Glu Asp Ile Ile Ser Leu Trp Asp Gln Ser Leu Lys Pro Cys Val Lys
225                 230                 235                 240

Leu Thr Pro Leu Cys Val Ser Leu Lys Cys Thr Asp Leu Lys Asn Asp
                245                 250                 255

Thr Asn Thr Asn Ser Ser Ser Gly Arg Met Ile Met Glu Lys Gly Glu
                260                 265                 270

Ile Lys Asn Cys Ser Phe Asn Ile Ser Thr Ser Ile Arg Asp Lys Val
        275                 280                 285

Gln Lys Glu Tyr Ala Phe Phe Tyr Lys Leu Asp Ile Val Pro Ile Asp
        290                 295                 300

Asn Thr Ser Tyr Arg Leu Ile Ser Cys Asn Thr Ser Val Ile Thr Gln
305                 310                 315                 320

Ala Cys Pro Lys Val Ser Phe Glu Pro Ile Pro Ile His Tyr Cys Ala
                325                 330                 335

Pro Ala Gly Phe Ala Ile Leu Lys Cys Asn Asn Lys Thr Phe Asn Gly
                340                 345                 350

Thr Gly Pro Cys Thr Asn Val Ser Thr Val Gln Cys Thr His Gly Ile
        355                 360                 365

Arg Pro Val Val Ser Thr Gln Leu Leu Leu Asn Gly Ser Leu Ala Glu
        370                 375                 380

Glu Asp Val Val Ile Arg Ser Ala Asn Phe Thr Asp Asn Ala Lys Thr
385                 390                 395                 400

Ile Ile Val Gln Leu Asn Thr Ser Val Glu Ile Asn Cys Thr Arg Pro
                405                 410                 415

Asn Asn Asn Thr Arg Lys Ser Ile Arg Ile Gln Arg Gly Pro Gly Arg
                420                 425                 430

Ala Phe Val Thr Ile Gly Lys Ile Gly Asn Met Arg Gln Ala His Cys
        435                 440                 445

Asn Ile Ser Arg Ala Lys Trp Asn Ala Thr Leu Lys Gln Ile Ala Ser
        450                 455                 460

Lys Leu Arg Glu Gln Phe Gly Asn Asn Lys Thr Ile Ile Phe Lys Gln
465                 470                 475                 480

Ser Ser Gly Gly Asp Pro Glu Ile Val Thr His Ser Phe Asn Cys Gly
                485                 490                 495

Gly Glu Phe Phe Tyr Cys Asn Ser Thr Gln Leu Phe Asn Ser Thr Trp
                500                 505                 510

Phe Asn Ser Thr Trp Ser Thr Glu Gly Ser Asn Asn Thr Glu Gly Ser
        515                 520                 525
```

```
Asp Thr Ile Thr Leu Pro Cys Arg Ile Lys Gln Phe Ile Asn Met Trp
    530             535             540

Gln Glu Val Gly Lys Ala Met Tyr Ala Pro Pro Ile Ser Gly Gln Ile
545             550             555             560

Arg Cys Ser Ser Asn Ile Thr Gly Leu Leu Leu Thr Arg Asp Gly Gly
                565             570             575

Asn Asn Asn Asn Gly Ser Glu Ile Phe Arg Pro Gly Gly Gly Asp Met
                580             585             590

Arg Asp Asn Trp Arg Ser Glu Leu Tyr Lys Tyr Lys Val Val Lys Ile
                595             600             605

Glu Pro Leu Gly Val Ala Pro Thr Lys Gly Gly Gly Ser Gly Gly
    610             615             620

Gly Gly Ser Lys Ser Leu Glu Gln Ile Trp Asn Asn Met Thr Trp Met
625             630             635             640

Glu Trp Asp Arg Glu Ile Asn Asn Tyr Thr Ser Leu Ile His Ser Leu
                645             650             655

Ile Glu Glu Ser Gln Asn Gln Gln Glu Lys Asn Glu Gln Glu Leu Leu
                660             665             670

Glu Leu Asp Lys Gly Ser Gly Ser Gly Gly Ser Gly His His His His
                675             680             685

His His His His
    690
```

<210> SEQ ID NO 11
<211> LENGTH: 616
<212> TYPE: PRT
<213> ORGANISM: Artificial Sequence
<220> FEATURE:
<223> OTHER INFORMATION: 25710-TSTIP

<400> SEQUENCE: 11

```
Ala Val Gly Ile Gly Ala Val Phe Leu Gly Phe Leu Gly Ala Ala Gly
1               5               10              15

Ser Thr Met Gly Ala Ala Ser Ile Thr Leu Thr Val Gln Ala Arg Gln
                20              25              30

Leu Leu Ser Gly Ile Val Gln Gln Gln Ser Asn Leu Leu Arg Ala Pro
            35              40              45

Glu Ala Gln Gln His Leu Leu Gln Leu Thr Val Trp Gly Ile Lys Gln
    50              55              60

Leu Gln Thr Arg Val Leu Ala Ile Glu Arg Tyr Leu Lys Asp Gln Gln
65              70              75              80

Leu Leu Gly Ile Trp Gly Cys Ser Gly Lys Leu Ile Cys Thr Thr Ala
                85              90              95

Val Pro Asn Leu Trp Val Thr Val Tyr Tyr Gly Val Pro Val Trp Lys
                100             105             110

Glu Ala Thr Thr Thr Leu Phe Cys Ala Ser Asp Ala Lys Ala Tyr Asp
            115             120             125

Lys Glu Val His Asn Val Trp Ala Thr His Ala Cys Val Pro Thr Asp
    130             135             140

Pro Asn Pro Gln Glu Met Val Leu Gly Asn Val Thr Glu Asn Phe Asn
145             150             155             160

Met Trp Lys Asn Glu Met Val Asn Gln Met His Glu Asp Val Ile Ser
                165             170             175

Leu Trp Asp Gln Ser Leu Lys Pro Cys Val Lys Leu Thr Pro Leu Cys
                180             185             190
```

-continued

```
Val Thr Leu Glu Cys Ser Asn Val Thr Tyr Asn Glu Ser Met Lys Glu
        195                 200                 205

Val Lys Asn Cys Ser Phe Asn Leu Thr Thr Glu Leu Arg Asp Lys Lys
    210                 215                 220

Gln Lys Val His Ala Leu Phe Tyr Arg Leu Asp Ile Val Pro Leu Asn
225                 230                 235                 240

Asp Thr Glu Lys Lys Asn Ser Ser Arg Pro Tyr Arg Leu Ile Asn Cys
                245                 250                 255

Asn Thr Ser Ala Ile Thr Gln Ala Cys Pro Lys Val Thr Phe Asp Pro
                260                 265                 270

Ile Pro Ile His Tyr Cys Thr Pro Ala Gly Tyr Ala Ile Leu Lys Cys
                275                 280                 285

Asn Asp Lys Lys Phe Asn Gly Thr Gly Pro Cys His Lys Val Ser Thr
    290                 295                 300

Val Gln Cys Thr His Gly Ile Lys Pro Val Val Ser Thr Gln Leu Leu
305                 310                 315                 320

Leu Asn Gly Ser Leu Ala Glu Gly Glu Ile Ile Ile Arg Ser Glu Asn
                325                 330                 335

Leu Thr Asn Asn Ala Lys Thr Ile Ile Val His Leu Asn Gln Ser Val
                340                 345                 350

Glu Ile Val Cys Ala Arg Pro Ser Asn Asn Thr Arg Thr Ser Ile Arg
                355                 360                 365

Ile Gly Pro Gly Gln Thr Phe Tyr Ala Thr Gly Ala Ile Thr Gly Asp
    370                 375                 380

Ile Arg Gln Ala His Cys Asn Ile Ser Lys Asp Lys Trp Asn Glu Thr
385                 390                 395                 400

Leu Gln Arg Val Gly Glu Lys Leu Ala Glu His Phe Pro Asn Lys Thr
                405                 410                 415

Ile Lys Phe Asn Ser Ser Ser Gly Gly Asp Leu Glu Ile Thr Thr His
                420                 425                 430

Ser Phe Asn Cys Arg Gly Glu Phe Phe Tyr Cys Asn Thr Ser Gly Leu
                435                 440                 445

Phe Asn Gly Thr Phe Asn Gly Thr Tyr Val Ser Pro Asn Ser Thr Asp
    450                 455                 460

Ser Asn Ser Ser Ser Ile Ile Thr Ile Pro Cys Arg Ile Lys Gln Ile
465                 470                 475                 480

Ile Asn Met Trp Gln Glu Val Gly Arg Ala Met Tyr Ala Pro Pro Ile
                485                 490                 495

Ala Gly Asn Ile Thr Cys Lys Ser Asn Ile Thr Gly Leu Leu Leu Val
                500                 505                 510

Arg Asp Gly Gly Thr Gly Ser Glu Ser Asn Lys Thr Glu Ile Phe Arg
                515                 520                 525

Pro Gly Gly Gly Asp Met Arg Asp Asn Trp Arg Ser Glu Leu Tyr Lys
    530                 535                 540

Tyr Lys Val Val Glu Ile Lys Pro Leu Gly Val Ala Pro Thr Lys Arg
545                 550                 555                 560

Ser Gln Asp Asp Ile Trp Asp Asn Met Thr Trp Met Gln Trp Asp Lys
                565                 570                 575

Glu Ile Ser Asn Tyr Thr Asn Thr Ile Tyr Lys Leu Leu Glu Asp Ser
                580                 585                 590

Gln Ile Gln Gln Glu Lys Asn Glu Lys Asp Leu Leu Ala Leu Asp Ser
    595                 600                 605
```

-continued

```
His His His His His His His His
    610                 615

<210> SEQ ID NO 12
<211> LENGTH: 654
<212> TYPE: PRT
<213> ORGANISM: Artificial Sequence
<220> FEATURE:
<223> OTHER INFORMATION: X1632-TSTIP

<400> SEQUENCE: 12

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

Gly Ala Arg Ala Ile Gly Leu Gly Thr Val Leu Leu Gly Phe Leu Gly
            35                  40                  45

Thr Ala Gly Ser Thr Met Gly Ala Ala Ser Ile Thr Leu Thr Val Gln
        50                  55                  60

Val Arg Gln Leu Leu Ser Gly Ile Val Gln Gln Gln Ser Asn Leu Leu
65                  70                  75                  80

Arg Ala Pro Glu Ala Gln Gln His Leu Leu Gln Leu Thr Val Trp Gly
                85                  90                  95

Ile Lys Gln Leu Gln Ala Arg Val Leu Ala Val Glu Arg Tyr Leu Lys
                100                 105                 110

Asp Gln Gln Ile Leu Gly Ile Trp Gly Cys Ser Gly Lys Leu Ile Cys
            115                 120                 125

Thr Thr Asn Val Pro Asn Leu Trp Val Thr Val Tyr Tyr Gly Val Pro
        130                 135                 140

Val Trp Glu Asp Ala Asp Thr Thr Leu Phe Cys Ala Ser Asp Ala Lys
145                 150                 155                 160

Ala Tyr Ser Thr Glu Ser His Asn Val Trp Ala Thr His Ala Cys Val
                165                 170                 175

Pro Thr Asp Pro Asn Pro Gln Glu Ile Tyr Leu Glu Asn Val Thr Glu
                180                 185                 190

Asp Phe Asn Met Trp Glu Asn Asn Met Val Glu Gln Met Gln Glu Asp
            195                 200                 205

Ile Ile Ser Leu Trp Asp Glu Ser Leu Lys Pro Cys Val Lys Leu Thr
        210                 215                 220

Pro Leu Cys Val Thr Leu Thr Cys Thr Asn Val Thr Asn Val Thr Asp
225                 230                 235                 240

Ser Val Gly Thr Asn Ser Arg Leu Lys Gly Tyr Lys Glu Glu Leu Lys
                245                 250                 255

Asn Cys Ser Phe Asn Thr Thr Thr Glu Ile Arg Asp Lys Lys Lys Gln
                260                 265                 270

Glu Tyr Ala Leu Phe Tyr Lys Leu Asp Ile Val Pro Ile Asn Asp Asn
            275                 280                 285

Ser Asn Asn Ser Asn Gly Tyr Arg Leu Ile Asn Cys Asn Val Ser Thr
        290                 295                 300

Ile Lys Gln Ala Cys Pro Lys Val Ser Phe Asp Pro Ile Pro Ile His
305                 310                 315                 320

Tyr Cys Ala Pro Ala Gly Phe Ala Ile Leu Lys Cys Arg Asp Lys Glu
                325                 330                 335

Phe Asn Gly Thr Gly Thr Cys Arg Asn Val Ser Thr Val Gln Cys Thr
            340                 345                 350
```

-continued

```
His Gly Ile Lys Pro Val Val Ser Thr Gln Leu Leu Leu Asn Gly Ser
        355                 360                 365

Leu Ala Glu Gly Asp Ile Val Ile Arg Ser Glu Asn Ile Thr Asp Asn
        370                 375                 380

Ala Lys Thr Ile Ile Val His Leu Asn Lys Thr Val Ser Ile Thr Cys
385                 390                 395                 400

Thr Arg Pro Asn Asn Asn Thr Arg Lys Ser Ile Arg Ile Gly Pro Gly
                405                 410                 415

Gln Ala Leu Tyr Ala Thr Gly Ala Ile Ile Gly Asp Thr Arg Gln Ala
        420                 425                 430

His Cys Asn Ile Asn Gly Ser Glu Trp Tyr Glu Met Ile Gln Asn Val
        435                 440                 445

Lys Asn Lys Leu Asn Glu Thr Phe Lys Lys Asn Ile Thr Phe Asn Pro
        450                 455                 460

Ser Ser Gly Gly Asp Leu Glu Ile Thr Thr His Ser Phe Asn Cys Arg
465                 470                 475                 480

Gly Glu Phe Phe Tyr Cys Asn Thr Ser Glu Leu Phe Asn Ser Ser His
                485                 490                 495

Leu Phe Asn Gly Ser Thr Leu Ser Thr Asn Gly Thr Ile Thr Leu Pro
                500                 505                 510

Cys Arg Ile Lys Gln Ile Val Arg Met Trp Gln Arg Val Gly Gln Ala
        515                 520                 525

Met Tyr Ala Pro Pro Ile Ala Gly Asn Ile Thr Cys Arg Ser Asn Ile
        530                 535                 540

Thr Gly Leu Leu Leu Thr Arg Asp Gly Gly Thr Asn Lys Asp Thr Asn
545                 550                 555                 560

Glu Ala Glu Thr Phe Arg Pro Gly Gly Gly Asp Met Arg Asp Asn Trp
                565                 570                 575

Arg Ser Glu Leu Tyr Lys Tyr Lys Val Val Lys Ile Lys Pro Leu Gly
                580                 585                 590

Val Ala Pro Thr Arg Lys Ser Tyr Ser Asp Ile Trp Asp Asn Leu Thr
        595                 600                 605

Trp Ile Gln Trp Glu Arg Glu Ile Ser Asn Tyr Thr Gln Gln Ile Tyr
        610                 615                 620

Thr Leu Leu Glu Glu Ser Gln Asn Gln Gln Glu Lys Asn Glu Gln Glu
625                 630                 635                 640

Leu Leu Ala Leu Asp Lys His His His His His His His
                645                 650
```

```
<210> SEQ ID NO 13
<211> LENGTH: 656
<212> TYPE: PRT
<213> ORGANISM: Artificial Sequence
<220> FEATURE:
<223> OTHER INFORMATION: CH119-TSTIP (BC)

<400> SEQUENCE: 13

Met Asp Ala Met Lys Arg Gly Leu Cys Cys Val Leu Leu Leu Cys Gly
1                 5                   10                  15

Ala Val Phe Val Ser Pro Ser Gln Glu Ile His Ala Arg Phe Arg Arg
                20                  25                  30

Gly Ala Arg Ala Val Gly Ile Gly Ala Val Phe Leu Gly Phe Leu Gly
        35                  40                  45

Val Ala Gly Ser Thr Met Gly Ala Ala Ser Met Thr Leu Thr Val Gln
        50                  55                  60
```

```
Ala Arg Gln Leu Leu Ser Gly Ile Val Gln Gln Ser Asn Leu Leu
65              70              75              80

Arg Ala Pro Glu Ala Gln Gln His Leu Leu Gln Leu Thr Val Trp Gly
                85              90              95

Ile Lys Gln Leu Gln Thr Arg Val Leu Ala Ile Glu Arg Tyr Leu Lys
            100             105             110

Asp Gln Gln Leu Leu Gly Ile Trp Gly Cys Ser Gly Lys Leu Ile Cys
            115             120             125

Thr Thr Ala Val Pro Asn Leu Trp Val Thr Val Tyr Tyr Gly Val Pro
    130             135             140

Val Trp Lys Glu Ala Thr Thr Thr Leu Phe Cys Ala Ser Asp Ala Lys
145             150             155             160

Ala Tyr Asp Thr Glu Val His Asn Val Trp Ala Thr His Ala Cys Val
                165             170             175

Pro Thr Asp Pro Ser Pro Gln Glu Leu Val Leu Glu Asn Val Thr Glu
            180             185             190

Asn Phe Asn Met Trp Lys Asn Glu Met Val Asn Gln Met His Glu Asp
            195             200             205

Val Ile Ser Leu Trp Asp Gln Ser Leu Lys Pro Cys Val Lys Leu Thr
    210             215             220

Pro Leu Cys Val Thr Leu Glu Cys Ser Lys Val Ser Asn Asn Glu Thr
225             230             235             240

Asp Lys Tyr Asn Gly Thr Glu Glu Met Lys Asn Cys Ser Phe Asn Ala
                245             250             255

Thr Thr Val Val Arg Asp Arg Gln Gln Lys Val Tyr Ala Leu Phe Tyr
            260             265             270

Arg Leu Asp Ile Val Pro Leu Thr Glu Lys Asn Ser Ser Glu Asn Ser
            275             280             285

Ser Lys Tyr Tyr Arg Leu Ile Asn Cys Asn Thr Ser Ala Ile Thr Gln
    290             295             300

Ala Cys Pro Lys Val Ser Phe Glu Pro Ile Pro Ile His Tyr Cys Thr
305             310             315             320

Pro Ala Gly Tyr Ala Ile Leu Lys Cys Asn Asp Lys Thr Phe Asn Gly
                325             330             335

Thr Gly Pro Cys His Asn Val Ser Thr Val Gln Cys Thr His Gly Ile
            340             345             350

Lys Pro Val Val Ser Thr Gln Leu Leu Leu Asn Gly Ser Leu Ala Glu
            355             360             365

Gly Glu Ile Ile Ile Arg Ser Glu Asn Leu Thr Asn Asn Val Lys Thr
    370             375             380

Ile Leu Val His Leu Asn Gln Ser Val Glu Ile Val Cys Thr Arg Pro
385             390             395             400

Asn Asn Asn Thr Arg Lys Ser Ile Arg Ile Gly Pro Gly Gln Thr Phe
                405             410             415

Tyr Ala Thr Gly Asp Ile Ile Gly Asp Ile Arg Gln Ala His Cys Asn
            420             425             430

Ile Ser Lys Trp His Glu Thr Leu Lys Arg Val Ser Glu Lys Leu Ala
            435             440             445

Glu His Phe Pro Asn Lys Thr Ile Asn Phe Thr Ser Ser Ser Gly Gly
    450             455             460

Asp Leu Glu Ile Thr Thr His Ser Phe Thr Cys Arg Gly Glu Phe Phe
465             470             475             480

Tyr Cys Asn Thr Ser Gly Leu Phe Asn Ser Thr Tyr Met Pro Asn Gly
```

-continued

```
                    485                   490                   495
Thr Tyr Leu His Gly Asp Thr Asn Ser Asn Ser Ser Ile Thr Ile Pro
                500                   505                   510

Cys Arg Ile Lys Gln Ile Ile Asn Met Trp Gln Glu Val Gly Arg Ala
            515                   520                   525

Met Tyr Ala Pro Pro Ile Glu Gly Asn Ile Thr Cys Lys Ser Asn Ile
        530                   535                   540

Thr Gly Leu Leu Leu Val Arg Asp Gly Gly Thr Glu Ser Asn Asn Thr
545                   550                   555                   560

Glu Thr Asn Asn Thr Glu Ile Phe Arg Pro Gly Gly Gly Asp Met Arg
                565                   570                   575

Asp Asn Trp Arg Ser Glu Leu Tyr Lys Tyr Lys Val Val Glu Ile Lys
            580                   585                   590

Pro Leu Gly Val Ala Pro Thr Ala Lys Ser Gln Lys Glu Ile Trp Asp
            595                   600                   605

Asn Met Thr Trp Met Gln Trp Asp Lys Glu Ile Ser Asn Tyr Thr Asn
        610                   615                   620

Thr Ile Tyr Lys Leu Leu Glu Asp Ser Gln Asn Gln Gln Glu Ser Asn
625                   630                   635                   640

Glu Lys Asp Leu Leu Ala Leu Asp His His His His His His His
                645                   650                   655
```

```
<210> SEQ ID NO 14
<211> LENGTH: 646
<212> TYPE: PRT
<213> ORGANISM: Artificial Sequence
<220> FEATURE:
<223> OTHER INFORMATION: CNE8-TSTIP(AE)

<400> SEQUENCE: 14

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ala Val Gly Ile Gly Ala Met Ile Phe Gly Phe Leu Gly
        35                  40                  45

Ala Ala Gly Ser Thr Met Gly Ala Ala Ser Ile Thr Leu Thr Val Gln
    50                  55                  60

Ala Arg Gln Leu Leu Ser Gly Ile Val Gln Gln Gln Ser Asn Leu Leu
65                  70                  75                  80

Arg Ala Pro Glu Ala Gln Gln His Leu Leu Gln Leu Thr Val Trp Gly
                85                  90                  95

Ile Lys Gln Leu Gln Ala Arg Val Leu Ala Val Glu Arg Tyr Leu Lys
            100                 105                 110

Asp Gln Lys Phe Leu Gly Leu Trp Gly Cys Ser Gly Lys Ile Ile Cys
        115                 120                 125

Thr Thr Ala Val Pro Asn Leu Trp Val Thr Val Tyr Tyr Gly Val Pro
    130                 135                 140

Val Trp Arg Asp Ala Asp Thr Thr Leu Phe Cys Ala Ser Asp Ala Lys
145                 150                 155                 160

Ala Tyr Asp Thr Glu Val His Asn Val Trp Ala Thr His Ala Cys Val
                165                 170                 175

Pro Thr Asp Pro Asn Pro Gln Glu Ile His Leu Glu Asn Val Thr Glu
        180                 185                 190

Asn Phe Asn Met Trp Lys Asn Lys Met Ala Glu Gln Met Gln Glu Asp
```

-continued

```
                195                 200                 205

Val Ile Ser Leu Trp Asp Glu Ser Leu Lys Pro Cys Val Gln Leu Thr
    210                 215                 220

Pro Leu Cys Val Thr Leu Asn Cys Thr Asn Ala Asn Leu Asn Ala Thr
225                 230                 235                 240

Val Asn Ala Ser Thr Thr Ile Gly Asn Ile Thr Asp Glu Val Arg Asn
                245                 250                 255

Cys Ser Phe Asn Thr Thr Thr Glu Leu Arg Asp Lys Lys Gln Asn Val
                260                 265                 270

Tyr Ala Leu Phe Tyr Lys Leu Asp Ile Val Pro Ile Asn Asn Asn Ser
    275                 280                 285

Glu Tyr Arg Leu Ile Asn Cys Asn Thr Ser Val Ile Lys Gln Ala Cys
    290                 295                 300

Pro Lys Val Ser Phe Asp Pro Ile Pro Ile His Tyr Cys Ala Pro Ala
305                 310                 315                 320

Gly Tyr Ala Ile Leu Arg Cys Asn Asp Lys Asn Phe Asn Gly Thr Gly
                325                 330                 335

Pro Cys Lys Asn Val Ser Ser Val Gln Cys Thr His Gly Ile Lys Pro
                340                 345                 350

Val Val Ser Thr Gln Leu Leu Leu Asn Gly Ser Leu Ala Glu Asp Glu
                355                 360                 365

Ile Ile Ile Arg Ser Glu Asn Leu Thr Asp Asn Val Lys Thr Ile Ile
    370                 375                 380

Val His Leu Asn Lys Ser Val Glu Ile Asn Cys Thr Arg Pro Ser Asn
385                 390                 395                 400

Asn Thr Arg Thr Ser Val Arg Ile Gly Pro Gly Gln Val Phe Tyr Arg
                405                 410                 415

Thr Gly Asp Ile Ile Gly Asp Ile Arg Lys Ala Tyr Cys Glu Ile Asn
                420                 425                 430

Arg Thr Lys Trp His Glu Thr Leu Lys Gln Val Ala Thr Lys Leu Arg
                435                 440                 445

Glu His Phe Asn Lys Thr Ile Ile Phe Gln Pro Pro Ser Gly Gly Asp
    450                 455                 460

Ile Glu Ile Thr Met His His Phe Asn Cys Arg Gly Glu Phe Phe Tyr
465                 470                 475                 480

Cys Asn Thr Thr Lys Leu Phe Asn Ser Thr Trp Gly Glu Asn Thr Thr
                485                 490                 495

Met Glu Gly His Asn Asp Thr Ile Val Leu Pro Cys Arg Ile Lys Gln
                500                 505                 510

Ile Val Asn Met Trp Gln Gly Val Gly Gln Ala Met Tyr Ala Pro Pro
    515                 520                 525

Ile Arg Gly Ser Ile Asn Cys Val Ser Asn Ile Thr Gly Ile Leu Leu
    530                 535                 540

Thr Arg Asp Gly Gly Thr Asn Met Ser Asn Glu Thr Phe Arg Pro Gly
545                 550                 555                 560

Gly Gly Asn Ile Lys Asp Asn Trp Arg Ser Glu Leu Tyr Lys Tyr Lys
                565                 570                 575

Val Val Glu Ile Glu Pro Leu Gly Ile Ala Pro Thr Lys Arg Ser Tyr
                580                 585                 590

Glu Glu Ile Trp Asp Asn Met Thr Trp Ile Glu Trp Glu Arg Glu Ile
    595                 600                 605

Ser Asn Tyr Thr Ser Gln Ile Tyr Glu Ile Leu Thr Glu Ser Gln Asn
    610                 615                 620
```

```
Gln Gln Asp Arg Asn Glu Lys Asp Leu Leu Glu Leu Asp Lys His His
625                 630                 635                 640

His His His His His His
                645

<210> SEQ ID NO 15
<211> LENGTH: 647
<212> TYPE: PRT
<213> ORGANISM: Artificial Sequence
<220> FEATURE:
<223> OTHER INFORMATION: p246F3-TSTIP

<400> SEQUENCE: 15

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

Gly Ala Arg Ala Val Gly Ile Gly Ala Val Phe Ile Gly Phe Leu Gly
            35                  40                  45

Ala Ala Gly Ser Thr Met Gly Ala Ala Ser Ile Thr Leu Thr Val Gln
        50                  55                  60

Ala Arg Gln Leu Leu Ser Gly Ile Val Gln Gln Gln Ser Asn Leu Leu
65                  70                  75                  80

Arg Ala Pro Glu Ala Gln Gln His Leu Leu Lys Leu Thr Val Trp Gly
                85                  90                  95

Ile Lys Gln Leu Gln Ala Arg Val Leu Ala Val Glu Arg Tyr Leu Lys
                100                 105                 110

Asp Gln Gln Leu Leu Gly Ile Trp Gly Cys Ser Gly Lys Leu Ile Cys
            115                 120                 125

Thr Thr Asn Val Asp Leu Trp Val Thr Val Tyr Tyr Gly Val Pro Val
        130                 135                 140

Trp Lys Asp Ala Lys Thr Thr Leu Phe Cys Ala Ser Asp Ala Lys Ala
145                 150                 155                 160

Tyr Glu Lys Glu Val His Asn Val Trp Ala Thr His Ala Cys Val Pro
                165                 170                 175

Thr Asp Pro Asn Pro Gln Glu Ile Val Met Ala Asn Val Thr Glu Glu
            180                 185                 190

Phe Asn Met Trp Lys Asn Asn Met Val Glu Gln Met His Thr Asp Ile
            195                 200                 205

Ile Ser Leu Trp Asp Gln Ser Leu Lys Pro Cys Val Lys Leu Thr Pro
    210                 215                 220

Leu Cys Val Thr Leu Asp Cys Lys Asp Tyr Asn Tyr Ser Ile Thr Asn
225                 230                 235                 240

Asn Ser Thr Gly Met Glu Gly Glu Ile Lys Asn Cys Ser Tyr Asn Ile
                245                 250                 255

Thr Thr Glu Leu Arg Asp Lys Arg Gln Lys Val Tyr Ser Leu Phe Tyr
            260                 265                 270

Arg Leu Asp Val Val Gln Ile Asn Asp Ser Asn Asp Arg Asn Asn Ser
        275                 280                 285

Gln Tyr Arg Leu Ile Asn Cys Asn Thr Thr Thr Met Thr Gln Ala Cys
    290                 295                 300

Pro Lys Val Thr Phe Asp Pro Ile Pro Ile His Tyr Cys Ala Pro Ala
305                 310                 315                 320

Gly Phe Ala Ile Leu Lys Cys Asn Asn Lys Thr Phe Asn Gly Lys Gly
                325                 330                 335
```

```
Pro Cys Asn Asn Val Ser Ser Val Gln Cys Thr His Gly Ile Lys Pro
            340                 345                 350

Val Val Ser Thr Gln Leu Leu Leu Asn Gly Ser Leu Ala Glu Lys Glu
            355                 360                 365

Ile Val Ile Arg Ser Glu Asn Leu Thr Asp Asn Val Lys Thr Ile Ile
        370                 375                 380

Val His Leu Asn Glu Ser Val Glu Ile Asn Cys Thr Arg Pro Asn Asn
385                 390                 395                 400

Asn Thr Arg Lys Ser Val Arg Ile Gly Pro Gly Gln Thr Phe Tyr Ala
                405                 410                 415

Thr Gly Asp Ile Ile Gly Asn Ile Arg Gln Ala His Cys Asn Val Asn
            420                 425                 430

Lys Thr Glu Trp Asn Thr Ala Leu Thr Arg Val Ser Lys Lys Leu Lys
            435                 440                 445

Glu Tyr Phe Pro Asn Lys Thr Ile Ala Phe Gln Pro Ser Ser Gly Gly
        450                 455                 460

Asp Leu Glu Ile Thr Thr Phe Ser Phe Asn Cys Arg Gly Glu Phe Phe
465                 470                 475                 480

Tyr Cys Asn Thr Ser Asp Leu Phe Asn Gly Thr Phe Asn Glu Thr Ser
                485                 490                 495

Gly Gln Phe Asn Ser Thr Phe Asn Ser Thr Leu Gln Cys Arg Ile Lys
            500                 505                 510

Gln Ile Ile Asn Met Trp Gln Glu Val Gly Gln Ala Met Tyr Ala Pro
            515                 520                 525

Pro Ile Ala Gly Ser Ile Thr Cys Ile Ser Asn Ile Thr Gly Leu Ile
        530                 535                 540

Leu Thr Arg Asp Gly Gly Asn Thr Asn Ser Thr Lys Glu Thr Phe Arg
545                 550                 555                 560

Pro Gly Gly Gly Asn Met Arg Asp Asn Trp Arg Ser Glu Leu Tyr Lys
                565                 570                 575

Tyr Lys Val Val Lys Ile Glu Pro Leu Gly Val Ala Pro Thr Lys Lys
            580                 585                 590

Ser Gln Asp Glu Ile Trp Asp Asn Met Thr Trp Leu Gln Trp Asp Lys
            595                 600                 605

Glu Ile Ser Asn Tyr Thr Gln Ile Ile Tyr Asn Leu Ile Glu Glu Ser
        610                 615                 620

Gln Thr Gln Gln Glu Leu Asn Glu Arg Asp Leu Leu Ala Leu Asp His
625                 630                 635                 640

His His His His His His His
                645
```

```
<210> SEQ ID NO 16
<211> LENGTH: 836
<212> TYPE: PRT
<213> ORGANISM: Artificial Sequence
<220> FEATURE:
<223> OTHER INFORMATION: Bal.26-TSTIP-gp160 (AA:646-836 are
      transmembrane region and intracellular region)

<400> SEQUENCE: 16
```

```
Met Arg Val Thr Glu Ile Arg Lys Ser Tyr Gln His Trp Trp Arg Trp
1                   5                   10                  15

Gly Ile Met Leu Leu Gly Met Leu Met Ile Cys Asn Ala Glu Glu Lys
                20                  25                  30

Ala Val Gly Ile Gly Ala Val Leu Leu Gly Phe Leu Gly Ala Ala Gly
```

```
            35                    40                    45
Ser Thr Met Gly Ala Ala Ser Met Thr Leu Thr Val Gln Ala Arg Leu
            50                    55                    60

Leu Leu Ser Gly Ile Val Gln Gln Gln Asn Asn Leu Leu Arg Ala Ile
65                    70                    75                    80

Glu Ala Gln Gln His Leu Leu Gln Leu Thr Val Trp Gly Ile Lys Gln
                      85                    90                    95

Leu Gln Ala Arg Val Leu Ala Val Glu Arg Tyr Leu Arg Asp Gln Gln
                  100                   105                   110

Leu Leu Gly Pro Trp Gly Cys Ser Gly Lys Leu Ile Cys Thr Thr Ala
                  115                   120                   125

Val Pro Asn Leu Trp Val Thr Val Tyr Tyr Gly Val Pro Val Trp Lys
            130                   135                   140

Glu Ala Thr Thr Thr Leu Phe Cys Ala Ser Asp Ala Lys Ala Tyr Asp
145                   150                   155                   160

Thr Glu Val His Asn Val Trp Ala Thr His Ala Cys Val Pro Thr Asp
                  165                   170                   175

Pro Asn Pro Gln Glu Val Lys Met Glu Asn Val Thr Glu Asn Phe Asn
                  180                   185                   190

Met Trp Lys Asn Asn Val Val Glu Gln Met His Glu Asp Ile Ile Ser
                  195                   200                   205

Leu Trp Asp Gln Ser Leu Lys Pro Cys Val Lys Leu Thr Pro Leu Cys
            210                   215                   220

Val Thr Leu Asn Cys Thr Asp Leu Lys Asn Ala Thr Asn Gly Asn Asn
225                   230                   235                   240

Thr Asn Thr Thr Ser Ser Ser Gly Gly Met Met Gly Gly Gly Glu Met
                  245                   250                   255

Lys Asn Cys Ser Phe Asn Ile Thr Thr Asn Ile Arg Gly Lys Val Gln
                  260                   265                   270

Lys Glu Tyr Ala Leu Phe Tyr Glu Leu Asp Ile Val Pro Ile Asp Asn
                  275                   280                   285

Lys Ile Asp Ser Tyr Arg Leu Ile Ser Cys Asn Thr Ser Val Ile Thr
            290                   295                   300

Gln Ala Cys Pro Lys Val Ser Phe Glu Pro Ile Pro Ile His Tyr Cys
305                   310                   315                   320

Ala Pro Ala Gly Phe Ala Ile Leu Lys Cys Lys Asp Lys Lys Phe Asn
                  325                   330                   335

Gly Lys Gly Pro Cys Ser Asn Val Ser Thr Val Gln Cys Thr His Gly
                  340                   345                   350

Ile Arg Pro Val Val Ser Thr Gln Leu Leu Leu Asn Gly Ser Leu Ala
                  355                   360                   365

Glu Glu Glu Val Val Ile Arg Ser Glu Asn Phe Thr Asn Asn Ala Lys
            370                   375                   380

Ile Ile Val Val Gln Leu Asn Glu Ser Val Glu Ile Asn Cys Thr Arg
385                   390                   395                   400

Pro Asn Asn Asn Thr Arg Lys Ser Ile His Ile Gly Pro Gly Arg Ala
                  405                   410                   415

Phe Tyr Thr Thr Gly Glu Ile Ile Gly Asp Ile Arg Gln Ala His Cys
                  420                   425                   430

Asn Leu Ser Arg Ala Lys Trp Asn Asp Thr Leu Asn Lys Ile Val Ile
            435                   440                   445

Lys Leu Arg Glu Gln Phe Gly Asn Lys Thr Ile Val Phe Lys His Ser
            450                   455                   460
```

-continued

```
Ser Gly Gly Asp Pro Glu Ile Val Thr His Ser Phe Asn Cys Gly Gly
465                 470             475             480

Glu Phe Phe Tyr Cys Asn Ser Thr Gln Leu Phe Asn Ser Thr Trp Asn
                485             490             495

Val Thr Glu Glu Ser Asn Asn Thr Val Glu Asn Asn Thr Ile Thr Leu
            500             505             510

Pro Cys Arg Ile Lys Gln Ile Ile Asn Met Trp Gln Glu Val Gly Arg
            515             520             525

Ala Met Tyr Ala Pro Pro Ile Arg Gly Gln Ile Arg Cys Ser Ser Asn
            530             535             540

Ile Thr Gly Leu Leu Leu Thr Arg Asp Gly Gly Pro Glu Asp Asp Lys
545             550             555             560

Thr Glu Val Phe Arg Pro Gly Gly Gly Asp Met Arg Asp Asn Trp Arg
                565             570             575

Ser Glu Leu Tyr Lys Tyr Lys Val Val Lys Ile Glu Pro Leu Gly Val
                580             585             590

Ala Pro Thr Lys Lys Ser Leu Asn Lys Ile Trp Asp Asn Met Thr Trp
            595             600             605

Met Glu Trp Asp Arg Glu Ile Asn Asn Tyr Thr Ser Ile Ile Tyr Ser
            610             615             620

Leu Ile Glu Glu Ser Gln Asn Gln Gln Glu Lys Asn Glu Gln Glu Leu
625             630             635             640

Leu Glu Leu Asp Lys Trp Ala Ser Leu Trp Asn Trp Phe Asp Ile Thr
                645             650             655

Lys Trp Leu Trp Tyr Ile Lys Ile Phe Ile Met Ile Val Gly Gly Leu
                660             665             670

Ile Gly Leu Arg Ile Val Phe Ser Val Leu Ser Ile Val Asn Arg Val
            675             680             685

Arg Gln Gly Tyr Ser Pro Leu Ser Phe Gln Thr His Leu Pro Ala Ser
            690             695             700

Arg Gly Pro Asp Arg Pro Gly Gly Ile Glu Glu Glu Gly Gly Glu Arg
705             710             715             720

Asp Arg Asp Arg Ser Gly Pro Leu Val Asn Gly Phe Leu Thr Leu Ile
                725             730             735

Trp Val Asp Leu Arg Ser Leu Phe Leu Phe Ser Tyr His Arg Leu Arg
                740             745             750

Asp Leu Leu Leu Ile Val Thr Arg Ile Val Glu Leu Leu Gly Arg Arg
            755             760             765

Gly Trp Glu Val Leu Lys Tyr Trp Trp Asn Leu Leu Gln Tyr Trp Ser
770             775             780

Gln Glu Leu Lys Asn Ser Ala Val Ser Leu Leu Asn Thr Ile Ala Ile
785             790             795             800

Ala Val Ala Glu Gly Thr Asp Arg Val Ile Glu Val Val Gln Arg Ala
                805             810             815

Val Arg Ala Ile Leu His Ile Pro Arg Arg Ile Arg Gln Gly Leu Glu
            820             825             830

Arg Ala Leu Leu
        835
```

```
<210> SEQ ID NO 17
<211> LENGTH: 837
<212> TYPE: PRT
<213> ORGANISM: Artificial Sequence
<220> FEATURE:
```

-continued

<223> OTHER INFORMATION: NL4-3 TSTIP-gp160 (aa646-837 are transmembrane
     region and intracellular region)

<400> SEQUENCE: 17

Met Arg Val Lys Glu Lys Tyr Gln His Leu Trp Arg Trp Gly Trp Lys
1               5                   10                  15

Trp Gly Thr Met Leu Leu Gly Ile Leu Met Ile Cys Ser Ala Thr Glu
            20                  25                  30

Lys Ala Val Gly Ile Gly Ala Leu Phe Leu Gly Phe Leu Gly Ala Ala
        35                  40                  45

Gly Ser Thr Met Gly Ala Ala Ser Met Thr Leu Thr Val Gln Ala Arg
    50                  55                  60

Gln Leu Leu Ser Asp Ile Val Gln Gln Asn Asn Leu Leu Arg Ala
65                  70                  75                  80

Pro Glu Ala Gln Gln His Leu Leu Gln Leu Thr Val Trp Gly Ile Lys
                85                  90                  95

Gln Leu Gln Ala Arg Ile Leu Ala Val Glu Arg Tyr Leu Lys Asp Gln
            100                 105                 110

Gln Leu Leu Gly Ile Trp Gly Cys Ser Gly Lys Leu Ile Cys Thr Thr
            115                 120                 125

Ala Val Pro Asn Leu Trp Val Thr Val Tyr Tyr Gly Val Pro Val Trp
            130                 135                 140

Lys Glu Ala Thr Thr Thr Leu Phe Cys Ala Ser Asp Ala Lys Ala Tyr
145                 150                 155                 160

Asp Thr Glu Val His Asn Val Trp Ala Thr His Ala Cys Val Pro Thr
                165                 170                 175

Asp Pro Asn Pro Gln Glu Val Val Leu Val Asn Val Thr Glu Asn Phe
                180                 185                 190

Asn Met Trp Lys Asn Asp Met Val Glu Gln Met His Glu Asp Ile Ile
                195                 200                 205

Ser Leu Trp Asp Gln Ser Leu Lys Pro Cys Val Lys Leu Thr Pro Leu
    210                 215                 220

Cys Val Ser Leu Lys Cys Thr Asp Leu Lys Asn Asp Thr Asn Thr Asn
225                 230                 235                 240

Ser Ser Ser Gly Arg Met Ile Met Glu Lys Gly Glu Ile Lys Asn Cys
                245                 250                 255

Ser Phe Asn Ile Ser Thr Ser Ile Arg Asp Lys Val Gln Lys Glu Tyr
                260                 265                 270

Ala Phe Phe Tyr Lys Leu Asp Ile Val Pro Ile Asp Asn Thr Ser Tyr
            275                 280                 285

Arg Leu Ile Ser Cys Asn Thr Ser Val Ile Thr Gln Ala Cys Pro Lys
    290                 295                 300

Val Ser Phe Glu Pro Ile Pro Ile His Tyr Cys Ala Pro Ala Gly Phe
305                 310                 315                 320

Ala Ile Leu Lys Cys Asn Asn Lys Thr Phe Asn Gly Thr Gly Pro Cys
            325                 330                 335

Thr Asn Val Ser Thr Val Gln Cys Thr His Gly Ile Arg Pro Val Val
            340                 345                 350

Ser Thr Gln Leu Leu Leu Asn Gly Ser Leu Ala Glu Glu Asp Val Val
            355                 360                 365

Ile Arg Ser Ala Asn Phe Thr Asp Asn Ala Lys Thr Ile Ile Val Gln
    370                 375                 380

Leu Asn Thr Ser Val Glu Ile Asn Cys Thr Arg Pro Asn Asn Asn Thr
385                 390                 395                 400

```
Arg Lys Ser Ile Arg Ile Gln Arg Gly Pro Gly Arg Ala Phe Val Thr
            405                 410                 415

Ile Gly Lys Ile Gly Asn Met Arg Gln Ala His Cys Asn Ile Ser Arg
            420                 425                 430

Ala Lys Trp Asn Ala Thr Leu Lys Gln Ile Ala Ser Lys Leu Arg Glu
            435                 440                 445

Gln Phe Gly Asn Asn Lys Thr Ile Ile Phe Lys Gln Ser Ser Gly Gly
    450                 455                 460

Asp Pro Glu Ile Val Thr His Ser Phe Asn Cys Gly Gly Glu Phe Phe
465                 470                 475                 480

Tyr Cys Asn Ser Thr Gln Leu Phe Asn Ser Thr Trp Phe Asn Ser Thr
            485                 490                 495

Trp Ser Thr Glu Gly Ser Asn Asn Thr Glu Gly Ser Asp Thr Ile Thr
            500                 505                 510

Leu Pro Cys Arg Ile Lys Gln Phe Ile Asn Met Trp Gln Glu Val Gly
            515                 520                 525

Lys Ala Met Tyr Ala Pro Pro Ile Ser Gly Gln Ile Arg Cys Ser Ser
    530                 535                 540

Asn Ile Thr Gly Leu Leu Leu Thr Arg Asp Gly Gly Asn Asn Asn Asn
545                 550                 555                 560

Gly Ser Glu Ile Phe Arg Pro Gly Gly Gly Asp Met Arg Asp Asn Trp
            565                 570                 575

Arg Ser Glu Leu Tyr Lys Tyr Lys Val Val Lys Ile Glu Pro Leu Gly
            580                 585                 590

Val Ala Pro Thr Lys Lys Ser Leu Glu Gln Ile Trp Asn Asn Met Thr
    595                 600                 605

Trp Met Glu Trp Asp Arg Glu Ile Asn Asn Tyr Thr Ser Leu Ile His
    610                 615                 620

Ser Leu Ile Glu Glu Ser Gln Asn Gln Gln Glu Lys Asn Glu Gln Glu
625                 630                 635                 640

Leu Leu Glu Leu Asp Lys Trp Ala Ser Leu Trp Asn Trp Phe Asn Ile
            645                 650                 655

Thr Asn Trp Leu Trp Tyr Ile Lys Leu Phe Ile Met Ile Val Gly Gly
            660                 665                 670

Leu Val Gly Leu Arg Ile Val Phe Ala Val Leu Ser Ile Val Asn Arg
            675                 680                 685

Val Arg Gln Gly Tyr Ser Pro Leu Ser Phe Gln Thr His Leu Pro Ile
    690                 695                 700

Pro Arg Gly Pro Asp Arg Pro Glu Gly Ile Glu Glu Glu Gly Gly Glu
705                 710                 715                 720

Arg Asp Arg Asp Arg Ser Ile Arg Leu Val Asn Gly Ser Leu Ala Leu
            725                 730                 735

Ile Trp Asp Asp Leu Arg Ser Leu Cys Leu Phe Ser Tyr His Arg Leu
            740                 745                 750

Arg Asp Leu Leu Leu Ile Val Thr Arg Ile Val Glu Leu Leu Gly Arg
            755                 760                 765

Arg Gly Trp Glu Ala Leu Lys Tyr Trp Trp Asn Leu Leu Gln Tyr Trp
            770                 775                 780

Ser Gln Glu Leu Lys Asn Ser Ala Val Asn Leu Leu Asn Ala Thr Ala
785                 790                 795                 800

Ile Ala Val Ala Glu Gly Thr Asp Arg Val Ile Glu Val Leu Gln Ala
            805                 810                 815
```

Ala Tyr Arg Ala Ile Arg His Ile Pro Arg Arg Ile Arg Gln Gly Leu
                820                     825                 830

Glu Arg Ile Leu Leu
        835

<210> SEQ ID NO 18
<211> LENGTH: 859
<212> TYPE: PRT
<213> ORGANISM: Artificial Sequence
<220> FEATURE:
<223> OTHER INFORMATION: BG505 gp160 (aa662-859 are transmembrane region
      and intracellular region)

<400> SEQUENCE: 18

Met Arg Val Met Gly Ile Gln Arg Asn Cys Gln His Leu Phe Arg Trp
1               5                   10                  15

Gly Thr Met Ile Leu Gly Met Ile Ile Ile Cys Ser Ala Ala Glu Asn
            20                  25                  30

Leu Trp Val Thr Val Tyr Tyr Gly Val Pro Val Trp Lys Asp Ala Glu
        35                  40                  45

Thr Thr Leu Phe Cys Ala Ser Asp Ala Lys Ala Tyr Glu Thr Glu Lys
    50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Glu Phe Asn Met Trp Lys
                85                  90                  95

Asn Asn Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
        115                 120                 125

Gln Cys Thr Asn Val Thr Asn Asn Ile Thr Asp Asp Met Arg Gly Glu
    130                 135                 140

Leu Lys Asn Cys Ser Phe Asn Met Thr Thr Glu Leu Arg Asp Lys Lys
145                 150                 155                 160

Gln Lys Val Tyr Ser Leu Phe Tyr Arg Leu Asp Val Val Gln Ile Asn
                165                 170                 175

Glu Asn Gln Gly Asn Arg Ser Asn Asn Ser Asn Lys Glu Tyr Arg Leu
            180                 185                 190

Ile Asn Cys Asn Thr Ser Ala Ile Thr Gln Ala Cys Pro Lys Val Ser
        195                 200                 205

Phe Glu Pro Ile Pro Ile His Tyr Cys Ala Pro Ala Gly Phe Ala Ile
    210                 215                 220

Leu Lys Cys Lys Asp Lys Lys Phe Asn Gly Thr Gly Pro Cys Pro Ser
225                 230                 235                 240

Val Ser Thr Val Gln Cys Thr His Gly Ile Lys Pro Val Val Ser Thr
                245                 250                 255

Gln Leu Leu Leu Asn Gly Ser Leu Ala Glu Glu Glu Val Met Ile Arg
            260                 265                 270

Ser Glu Asn Ile Thr Asn Asn Ala Lys Asn Ile Leu Val Gln Phe Asn
        275                 280                 285

Thr Pro Val Gln Ile Asn Cys Thr Arg Pro Asn Asn Asn Thr Arg Lys
    290                 295                 300

Ser Ile Arg Ile Gly Pro Gly Gln Ala Phe Tyr Ala Thr Gly Asp Ile
305                 310                 315                 320

Ile Gly Asp Ile Arg Gln Ala His Cys Thr Val Ser Lys Ala Thr Trp
                325                 330                 335

-continued

```
Asn Glu Thr Leu Gly Lys Val Val Lys Gln Leu Arg Lys His Phe Gly
        340             345             350

Asn Asn Thr Ile Ile Arg Phe Ala Asn Ser Ser Gly Gly Asp Leu Glu
        355             360             365

Val Thr Thr His Ser Phe Asn Cys Gly Gly Glu Phe Phe Tyr Cys Asn
        370             375             380

Thr Ser Gly Leu Phe Asn Ser Thr Trp Ile Ser Asn Thr Ser Val Gln
385             390             395             400

Gly Ser Asn Ser Thr Gly Ser Asn Asp Ser Ile Thr Leu Pro Cys Arg
            405             410             415

Ile Lys Gln Ile Ile Asn Met Trp Gln Arg Ile Gly Gln Ala Met Tyr
        420             425             430

Ala Pro Pro Ile Gln Gly Val Ile Arg Cys Val Ser Asn Ile Thr Gly
        435             440             445

Leu Ile Leu Thr Arg Asp Gly Gly Ser Thr Asn Ser Thr Thr Glu Thr
        450             455             460

Phe Arg Pro Gly Gly Gly Asp Met Arg Asp Asn Trp Arg Ser Glu Leu
465             470             475             480

Tyr Lys Tyr Lys Val Val Lys Ile Glu Pro Leu Gly Val Ala Pro Thr
            485             490             495

Arg Ala Lys Arg Arg Val Val Gly Arg Glu Lys Arg Ala Val Gly Ile
            500             505             510

Gly Ala Val Phe Leu Gly Phe Leu Gly Ala Ala Gly Ser Thr Met Gly
            515             520             525

Ala Ala Ser Met Thr Leu Thr Val Gln Ala Arg Asn Leu Leu Ser Gly
        530             535             540

Ile Val Gln Gln Gln Ser Asn Leu Leu Arg Ala Ile Glu Ala Gln Gln
545             550             555             560

His Leu Leu Lys Leu Thr Val Trp Gly Ile Lys Gln Leu Gln Ala Arg
            565             570             575

Val Leu Ala Val Glu Arg Tyr Leu Arg Asp Gln Gln Leu Leu Gly Ile
            580             585             590

Trp Gly Cys Ser Gly Lys Leu Ile Cys Thr Thr Asn Val Pro Trp Asn
            595             600             605

Ser Ser Trp Ser Asn Arg Asn Leu Ser Glu Ile Trp Asp Asn Met Thr
        610             615             620

Trp Leu Gln Trp Asp Lys Glu Ile Ser Asn Tyr Thr Gln Ile Ile Tyr
625             630             635             640

Gly Leu Leu Glu Glu Ser Gln Asn Gln Gln Glu Lys Asn Glu Gln Asp
            645             650             655

Leu Leu Ala Leu Asp Lys Trp Ala Ser Leu Trp Asn Trp Phe Asp Ile
            660             665             670

Ser Asn Trp Leu Trp Tyr Ile Lys Ile Phe Ile Met Ile Val Gly Gly
        675             680             685

Leu Ile Gly Leu Arg Ile Val Phe Ala Val Leu Ser Val Ile His Arg
        690             695             700

Val Arg Gln Gly Tyr Ser Pro Leu Ser Phe Gln Thr His Thr Pro Asn
705             710             715             720

Pro Arg Gly Leu Asp Arg Pro Glu Arg Ile Glu Glu Glu Asp Gly Glu
            725             730             735

Gln Asp Arg Gly Arg Ser Thr Arg Leu Val Ser Gly Phe Leu Ala Leu
            740             745             750
```

```
Ala Trp Asp Asp Leu Arg Ser Leu Cys Leu Phe Cys Tyr His Arg Leu
        755             760             765

Arg Asp Phe Ile Leu Ile Ala Ala Arg Ile Val Glu Leu Leu Gly His
        770             775             780

Ser Ser Leu Lys Gly Leu Arg Leu Gly Trp Glu Gly Leu Lys Tyr Leu
785             790             795             800

Trp Asn Leu Leu Ala Tyr Trp Gly Arg Glu Leu Lys Ile Ser Ala Ile
            805             810             815

Asn Leu Phe Asp Thr Ile Ala Ile Ala Val Ala Glu Trp Thr Asp Arg
            820             825             830

Val Ile Glu Ile Gly Gln Arg Leu Cys Arg Ala Phe Leu His Ile Pro
        835             840             845

Arg Arg Ile Arg Gln Gly Leu Glu Arg Ala Leu
    850             855
```

```
<210> SEQ ID NO 19
<211> LENGTH: 854
<212> TYPE: PRT
<213> ORGANISM: Artificial Sequence
<220> FEATURE:
<223> OTHER INFORMATION: NL4-3 gp160 (aa663-854 are transmembrane region
      and intracellular region)

<400> SEQUENCE: 19
```

```
Met Arg Val Lys Glu Lys Tyr Gln His Leu Trp Arg Trp Gly Trp Lys
1               5               10              15

Trp Gly Thr Met Leu Leu Gly Ile Leu Met Ile Cys Ser Ala Thr Glu
            20              25              30

Lys Leu Trp Val Thr Val Tyr Tyr Gly Val Pro Val Trp Lys Glu Ala
        35              40              45

Thr Thr Thr Leu Phe Cys Ala Ser Asp Ala Lys Ala Tyr Asp Thr Glu
    50              55              60

Val His Asn Val Trp Ala Thr His Ala Cys Val Pro Thr Asp Pro Asn
65              70              75              80

Pro Gln Glu Val Val Leu Val Asn Val Thr Glu Asn Phe Asn Met Trp
            85              90              95

Lys Asn Asp Met Val Glu Gln Met His Glu Asp Ile Ile Ser Leu Trp
        100             105             110

Asp Gln Ser Leu Lys Pro Cys Val Lys Leu Thr Pro Leu Cys Val Ser
        115             120             125

Leu Lys Cys Thr Asp Leu Lys Asn Asp Thr Asn Thr Asn Ser Ser Ser
    130             135             140

Gly Arg Met Ile Met Glu Lys Gly Glu Ile Lys Asn Cys Ser Phe Asn
145             150             155             160

Ile Ser Thr Ser Ile Arg Asp Lys Val Gln Lys Glu Tyr Ala Phe Phe
            165             170             175

Tyr Lys Leu Asp Ile Val Pro Ile Asp Asn Thr Ser Tyr Arg Leu Ile
        180             185             190

Ser Cys Asn Thr Ser Val Ile Thr Gln Ala Cys Pro Lys Val Ser Phe
        195             200             205

Glu Pro Ile Pro Ile His Tyr Cys Ala Pro Ala Gly Phe Ala Ile Leu
    210             215             220

Lys Cys Asn Asn Lys Thr Phe Asn Gly Thr Gly Pro Cys Thr Asn Val
225             230             235             240

Ser Thr Val Gln Cys Thr His Gly Ile Arg Pro Val Val Ser Thr Gln
            245             250             255
```

-continued

```
Leu Leu Leu Asn Gly Ser Leu Ala Glu Glu Asp Val Val Ile Arg Ser
            260                 265                 270

Ala Asn Phe Thr Asp Asn Ala Lys Thr Ile Ile Val Gln Leu Asn Thr
            275                 280                 285

Ser Val Glu Ile Asn Cys Thr Arg Pro Asn Asn Asn Thr Arg Lys Ser
            290                 295                 300

Ile Arg Ile Gln Arg Gly Pro Gly Arg Ala Phe Val Thr Ile Gly Lys
305                 310                 315                 320

Ile Gly Asn Met Arg Gln Ala His Cys Asn Ile Ser Arg Ala Lys Trp
                325                 330                 335

Asn Ala Thr Leu Lys Gln Ile Ala Ser Lys Leu Arg Glu Gln Phe Gly
            340                 345                 350

Asn Asn Lys Thr Ile Ile Phe Lys Gln Ser Ser Gly Gly Asp Pro Glu
            355                 360                 365

Ile Val Thr His Ser Phe Asn Cys Gly Gly Glu Phe Phe Tyr Cys Asn
            370                 375                 380

Ser Thr Gln Leu Phe Asn Ser Thr Trp Phe Asn Ser Thr Trp Ser Thr
385                 390                 395                 400

Glu Gly Ser Asn Asn Thr Glu Gly Ser Asp Thr Ile Thr Leu Pro Cys
                405                 410                 415

Arg Ile Lys Gln Phe Ile Asn Met Trp Gln Glu Val Gly Lys Ala Met
                420                 425                 430

Tyr Ala Pro Pro Ile Ser Gly Gln Ile Arg Cys Ser Ser Asn Ile Thr
            435                 440                 445

Gly Leu Leu Leu Thr Arg Asp Gly Gly Asn Asn Asn Gly Ser Glu
            450                 455                 460

Ile Phe Arg Pro Gly Gly Gly Asp Met Arg Asp Asn Trp Arg Ser Glu
465                 470                 475                 480

Leu Tyr Lys Tyr Lys Val Val Lys Ile Glu Pro Leu Gly Val Ala Pro
                485                 490                 495

Thr Lys Ala Lys Arg Arg Val Val Gln Arg Glu Lys Arg Ala Val Gly
            500                 505                 510

Ile Gly Ala Leu Phe Leu Gly Phe Leu Gly Ala Ala Gly Ser Thr Met
            515                 520                 525

Gly Ala Ala Ser Met Thr Leu Thr Val Gln Ala Arg Gln Leu Leu Ser
            530                 535                 540

Asp Ile Val Gln Gln Gln Asn Asn Leu Leu Arg Ala Ile Glu Ala Gln
545                 550                 555                 560

Gln His Leu Leu Gln Leu Thr Val Trp Gly Ile Lys Gln Leu Gln Ala
                565                 570                 575

Arg Ile Leu Ala Val Glu Arg Tyr Leu Lys Asp Gln Gln Leu Leu Gly
            580                 585                 590

Ile Trp Gly Cys Ser Gly Lys Leu Ile Cys Thr Thr Ala Val Pro Trp
            595                 600                 605

Asn Ala Ser Trp Ser Asn Lys Ser Leu Glu Gln Ile Trp Asn Asn Met
            610                 615                 620

Thr Trp Met Glu Trp Asp Arg Glu Ile Asn Asn Tyr Thr Ser Leu Ile
625                 630                 635                 640

His Ser Leu Ile Glu Glu Ser Gln Asn Gln Glu Lys Asn Glu Gln
                645                 650                 655

Glu Leu Leu Glu Leu Asp Lys Trp Ala Ser Leu Trp Asn Trp Phe Asn
            660                 665                 670
```

```
Ile Thr Asn Trp Leu Trp Tyr Ile Lys Leu Phe Ile Met Ile Val Gly
        675             680             685

Gly Leu Val Gly Leu Arg Ile Val Phe Ala Val Leu Ser Ile Val Asn
        690             695             700

Arg Val Arg Gln Gly Tyr Ser Pro Leu Ser Phe Gln Thr His Leu Pro
705             710             715             720

Ile Pro Arg Gly Pro Asp Arg Pro Glu Gly Ile Glu Glu Gly Gly
            725             730             735

Glu Arg Asp Arg Asp Arg Ser Ile Arg Leu Val Asn Gly Ser Leu Ala
            740             745             750

Leu Ile Trp Asp Asp Leu Arg Ser Leu Cys Leu Phe Ser Tyr His Arg
            755             760             765

Leu Arg Asp Leu Leu Leu Ile Val Thr Arg Ile Val Glu Leu Leu Gly
        770             775             780

Arg Arg Gly Trp Glu Ala Leu Lys Tyr Trp Trp Asn Leu Leu Gln Tyr
785             790             795             800

Trp Ser Gln Glu Leu Lys Asn Ser Ala Val Asn Leu Leu Asn Ala Thr
            805             810             815

Ala Ile Ala Val Ala Glu Gly Thr Asp Arg Val Ile Glu Val Leu Gln
            820             825             830

Ala Ala Tyr Arg Ala Ile Arg His Ile Pro Arg Arg Ile Arg Gln Gly
        835             840             845

Leu Glu Arg Ile Leu Leu
    850
```

```
<210> SEQ ID NO 20
<211> LENGTH: 855
<212> TYPE: PRT
<213> ORGANISM: Artificial Sequence
<220> FEATURE:
<223> OTHER INFORMATION: 25710 gp160 (aa657-855 are transmembrane region
      and intracellular region)

<400> SEQUENCE: 20
```

```
Met Arg Val Arg Gly Thr Leu Arg Asn Tyr Gln Gln Trp Trp Ile Trp
1               5               10              15

Gly Val Leu Gly Phe Trp Met Leu Met Ile Cys Asn Val Gly Gly Asn
            20              25              30

Leu Trp Val Thr Val Tyr Tyr Gly Val Pro Val Trp Lys Glu Ala Thr
        35              40              45

Thr Thr Leu Phe Cys Ala Ser Asp Ala Lys Ala Tyr Asp Lys Glu Val
    50              55              60

His Asn Val Trp Ala Thr His Ala Cys Val Pro Thr Asp Pro Asn Pro
65              70              75              80

Gln Glu Met Val Leu Gly Asn Val Thr Glu Asn Phe Asn Met Trp Lys
            85              90              95

Asn Glu Met Val Asn Gln Met His Glu Asp Val Ile Ser Leu Trp Asp
            100             105             110

Gln Ser Leu Lys Pro Cys Val Lys Leu Thr Pro Leu Cys Val Thr Leu
        115             120             125

Glu Cys Ser Asn Val Thr Tyr Asn Glu Ser Met Lys Glu Val Lys Asn
        130             135             140

Cys Ser Phe Asn Leu Thr Thr Glu Leu Arg Asp Lys Lys Gln Lys Val
145             150             155             160

His Ala Leu Phe Tyr Arg Leu Asp Ile Val Pro Leu Asn Asp Thr Glu
            165             170             175
```

-continued

```
Lys Lys Asn Ser Ser Arg Pro Tyr Arg Leu Ile Asn Cys Asn Thr Ser
        180                 185                 190

Ala Ile Thr Gln Ala Cys Pro Lys Val Thr Phe Asp Pro Ile Pro Ile
        195                 200                 205

His Tyr Cys Thr Pro Ala Gly Tyr Ala Ile Leu Lys Cys Asn Asp Lys
        210                 215                 220

Lys Phe Asn Gly Thr Gly Pro Cys His Lys Val Ser Thr Val Gln Cys
225                 230                 235                 240

Thr His Gly Ile Lys Pro Val Val Ser Thr Gln Leu Leu Leu Asn Gly
                245                 250                 255

Ser Leu Ala Glu Gly Glu Ile Ile Ile Arg Ser Glu Asn Leu Thr Asn
        260                 265                 270

Asn Ala Lys Thr Ile Ile Val His Leu Asn Gln Ser Val Glu Ile Val
        275                 280                 285

Cys Ala Arg Pro Ser Asn Asn Thr Arg Thr Ser Ile Arg Ile Gly Pro
        290                 295                 300

Gly Gln Thr Phe Tyr Ala Thr Gly Ala Ile Thr Gly Asp Ile Arg Gln
305                 310                 315                 320

Ala His Cys Asn Ile Ser Lys Asp Lys Trp Asn Glu Thr Leu Gln Arg
                325                 330                 335

Val Gly Glu Lys Leu Ala Glu His Phe Pro Asn Lys Thr Ile Lys Phe
                340                 345                 350

Asn Ser Ser Ser Gly Gly Asp Leu Glu Ile Thr Thr His Ser Phe Asn
                355                 360                 365

Cys Arg Gly Glu Phe Phe Tyr Cys Asn Thr Ser Gly Leu Phe Asn Gly
        370                 375                 380

Thr Phe Asn Gly Thr Tyr Val Ser Pro Asn Ser Thr Asp Ser Asn Ser
385                 390                 395                 400

Ser Ser Ile Ile Thr Ile Pro Cys Arg Ile Lys Gln Ile Ile Asn Met
                405                 410                 415

Trp Gln Glu Val Gly Arg Ala Met Tyr Ala Pro Pro Ile Ala Gly Asn
                420                 425                 430

Ile Thr Cys Lys Ser Asn Ile Thr Gly Leu Leu Leu Val Arg Asp Gly
                435                 440                 445

Gly Thr Gly Ser Glu Ser Asn Lys Thr Glu Ile Phe Arg Pro Gly Gly
        450                 455                 460

Gly Asp Met Arg Asp Asn Trp Arg Ser Glu Leu Tyr Lys Tyr Lys Val
465                 470                 475                 480

Val Glu Ile Lys Pro Leu Gly Val Ala Pro Thr Lys Ala Lys Arg Arg
                485                 490                 495

Val Val Glu Arg Glu Lys Arg Ala Val Gly Ile Gly Ala Val Phe Leu
                500                 505                 510

Gly Phe Leu Gly Ala Ala Gly Ser Thr Met Gly Ala Ala Ser Ile Thr
        515                 520                 525

Leu Thr Val Gln Ala Arg Gln Leu Leu Ser Gly Ile Val Gln Gln Gln
        530                 535                 540

Ser Asn Leu Leu Arg Ala Ile Glu Ala Gln Gln His Leu Leu Gln Leu
545                 550                 555                 560

Thr Val Trp Gly Ile Lys Gln Leu Gln Thr Arg Val Leu Ala Ile Glu
                565                 570                 575

Arg Tyr Leu Lys Asp Gln Gln Leu Leu Gly Ile Trp Gly Cys Ser Gly
        580                 585                 590
```

-continued

```
Lys Leu Ile Cys Thr Thr Ala Val Pro Trp Asn Tyr Ser Trp Ser Asn
        595                 600                 605

Arg Ser Gln Asp Asp Ile Trp Asp Asn Met Thr Trp Met Gln Trp Asp
    610                 615                 620

Lys Glu Ile Ser Asn Tyr Thr Asn Thr Ile Tyr Lys Leu Leu Glu Asp
625                 630                 635                 640

Ser Gln Ile Gln Gln Glu Lys Asn Glu Lys Asp Leu Leu Ala Leu Asp
                645                 650                 655

Ser Trp Glu Asn Leu Trp Asn Trp Phe Asn Ile Thr Asn Trp Leu Trp
            660                 665                 670

Tyr Ile Lys Ile Phe Ile Ile Ile Val Gly Gly Leu Ile Gly Leu Arg
            675                 680                 685

Ile Ile Phe Ala Val Leu Pro Ile Val Asn Arg Val Arg Gln Gly Tyr
        690                 695                 700

Ser Pro Leu Ser Phe Gln Thr His Thr Pro Thr Pro Gly Gly Pro Asp
705                 710                 715                 720

Arg Leu Gly Arg Ile Glu Glu Glu Gly Gly Glu Gln Asp Asn Val Arg
                725                 730                 735

Ser Ile Arg Leu Val Asn Gly Phe Leu Ala Leu Ala Trp Asp Asp Leu
            740                 745                 750

Arg Asn Leu Cys Leu Phe Ser Tyr His Arg Leu Arg Asp Phe Ile Leu
            755                 760                 765

Val Ala Ala Arg Val Val Glu Leu Leu Gly Arg Asn Ser Leu Arg Gly
        770                 775                 780

Leu Gln Lys Gly Trp Glu Ala Leu Lys Tyr Leu Gly Ser Leu Val Gln
785                 790                 795                 800

Tyr Trp Gly Leu Glu Leu Lys Arg Ser Ala Ile Ser Leu Leu Asp Thr
                805                 810                 815

Ile Ala Ile Ala Val Ala Glu Gly Thr Asp Arg Ile Ile Gln Leu Gly
            820                 825                 830

Gln Gly Ile Cys Arg Ala Ile Cys Asn Ile Pro Arg Arg Ile Arg Gln
            835                 840                 845

Gly Leu Glu Ala Ala Leu Gln
    850                 855
```

```
<210> SEQ ID NO 21
<211> LENGTH: 858
<212> TYPE: PRT
<213> ORGANISM: Artificial Sequence
<220> FEATURE:
<223> OTHER INFORMATION: X1632 gp160 (aa660-858 are transmembrane region
      and intracellular region)

<400> SEQUENCE: 21
```

```
Met Lys Val Lys Gly Thr Gln Arg Asp Trp His Ser Leu Trp Asn Trp
1               5                   10                  15

Gly Ile Leu Ile Leu Gly Leu Val Ile Ile Cys Ser Ala Ser Asn Asn
            20                  25                  30

Leu Trp Val Thr Val Tyr Tyr Gly Val Pro Val Trp Glu Asp Ala Asp
        35                  40                  45

Thr Thr Leu Phe Cys Ala Ser Asp Ala Lys Ala Tyr Ser Thr Glu Ser
    50                  55                  60

His Asn Val Trp Ala Thr His Ala Cys Val Pro Thr Asp Pro Asn Pro
65                  70                  75                  80

Gln Glu Ile Tyr Leu Glu Asn Val Thr Glu Asp Phe Asn Met Trp Glu
                85                  90                  95
```

-continued

```
Asn Asn Met Val Glu Gln Met Gln Glu Asp Ile Ile Ser Leu Trp Asp
            100             105             110

Glu Ser Leu Lys Pro Cys Val Lys Leu Thr Pro Leu Cys Val Thr Leu
            115             120             125

Thr Cys Thr Asn Val Thr Asn Val Thr Asp Ser Val Gly Thr Asn Ser
            130             135             140

Arg Leu Lys Gly Tyr Lys Glu Glu Leu Lys Asn Cys Ser Phe Asn Thr
145             150             155             160

Thr Thr Glu Ile Arg Asp Lys Lys Gln Glu Tyr Ala Leu Phe Tyr
                165             170             175

Lys Leu Asp Ile Val Pro Ile Asn Asp Asn Ser Asn Asn Ser Asn Gly
            180             185             190

Tyr Arg Leu Ile Asn Cys Asn Val Ser Thr Ile Lys Gln Ala Cys Pro
            195             200             205

Lys Val Ser Phe Asp Pro Ile Pro Ile His Tyr Cys Ala Pro Ala Gly
            210             215             220

Phe Ala Ile Leu Lys Cys Arg Asp Lys Glu Phe Asn Gly Thr Gly Thr
225             230             235             240

Cys Arg Asn Val Ser Thr Val Gln Cys Thr His Gly Ile Lys Pro Val
            245             250             255

Val Ser Thr Gln Leu Leu Leu Asn Gly Ser Leu Ala Glu Gly Asp Ile
            260             265             270

Val Ile Arg Ser Glu Asn Ile Thr Asp Asn Ala Lys Thr Ile Ile Val
            275             280             285

His Leu Asn Lys Thr Val Ser Ile Thr Cys Thr Arg Pro Asn Asn Asn
            290             295             300

Thr Arg Lys Ser Ile Arg Ile Gly Pro Gly Gln Ala Leu Tyr Ala Thr
305             310             315             320

Gly Ala Ile Ile Gly Asp Thr Arg Gln Ala His Cys Asn Ile Asn Gly
            325             330             335

Ser Glu Trp Tyr Glu Met Ile Gln Asn Val Lys Asn Lys Leu Asn Glu
            340             345             350

Thr Phe Lys Lys Asn Ile Thr Phe Asn Pro Ser Ser Gly Gly Asp Leu
            355             360             365

Glu Ile Thr Thr His Ser Phe Asn Cys Arg Gly Glu Phe Phe Tyr Cys
            370             375             380

Asn Thr Ser Glu Leu Phe Asn Ser Ser His Leu Phe Asn Gly Ser Thr
385             390             395             400

Leu Ser Thr Asn Gly Thr Ile Thr Leu Pro Cys Arg Ile Lys Gln Ile
            405             410             415

Val Arg Met Trp Gln Arg Val Gly Gln Ala Met Tyr Ala Pro Pro Ile
            420             425             430

Ala Gly Asn Ile Thr Cys Arg Ser Asn Ile Thr Gly Leu Leu Leu Thr
            435             440             445

Arg Asp Gly Gly Thr Asn Lys Asp Thr Asn Glu Ala Glu Thr Phe Arg
            450             455             460

Pro Gly Gly Gly Asp Met Arg Asp Asn Trp Arg Ser Glu Leu Tyr Lys
465             470             475             480

Tyr Lys Val Val Lys Ile Lys Pro Leu Gly Val Ala Pro Thr Arg Ala
                485             490             495

Arg Arg Arg Val Val Glu Arg Glu Lys Arg Ala Ile Gly Leu Gly Thr
            500             505             510
```

-continued

```
Val Leu Leu Gly Phe Leu Gly Thr Ala Gly Ser Thr Met Gly Ala Ala
        515                 520                 525

Ser Ile Thr Leu Thr Val Gln Val Arg Gln Leu Leu Ser Gly Ile Val
        530                 535                 540

Gln Gln Gln Ser Asn Leu Leu Arg Ala Ile Glu Ala Gln Gln His Leu
545                 550                 555                 560

Leu Gln Leu Thr Val Trp Gly Ile Lys Gln Leu Gln Ala Arg Val Leu
                565                 570                 575

Ala Val Glu Arg Tyr Leu Lys Asp Gln Gln Ile Leu Gly Ile Trp Gly
            580                 585                 590

Cys Ser Gly Lys Leu Ile Cys Thr Thr Asn Val Pro Trp Asn Ser Ser
        595                 600                 605

Trp Ser Asn Lys Ser Tyr Ser Asp Ile Trp Asp Asn Leu Thr Trp Ile
        610                 615                 620

Gln Trp Glu Arg Glu Ile Ser Asn Tyr Thr Gln Gln Ile Tyr Thr Leu
625                 630                 635                 640

Leu Glu Glu Ser Gln Asn Gln Gln Glu Lys Asn Glu Gln Glu Leu Leu
                645                 650                 655

Ala Leu Asp Lys Trp Ala Ser Leu Trp Asn Trp Phe Asp Ile Thr Asn
            660                 665                 670

Trp Leu Trp Tyr Ile Lys Ile Phe Ile Met Ile Val Gly Gly Leu Ile
        675                 680                 685

Gly Leu Arg Ile Val Phe Ala Val Leu Ser Ile Ile Asn Arg Val Arg
        690                 695                 700

Lys Gly Tyr Ser Pro Leu Ser Phe Gln Thr Leu Thr Arg His Gln Arg
705                 710                 715                 720

Glu Pro Asp Arg Pro Gly Gly Ile Glu Glu Glu Asp Gly Glu Gln Asp
            725                 730                 735

Arg Asp Lys Ser Val Arg Phe Val Ser Gly Phe Leu Ser Pro Val Trp
            740                 745                 750

Asp Asp Leu Arg Ser Leu Cys Leu Phe Ser Tyr Arg Arg Leu Arg Asp
            755                 760                 765

Phe Ile Leu Val Ala Ala Arg Thr Val Glu Leu Leu Gly Arg Ser Ser
        770                 775                 780

Leu Lys Gly Leu Arg Leu Gly Trp Glu Gly Leu Lys Tyr Leu Trp Asn
785                 790                 795                 800

Leu Leu Leu Tyr Trp Gly Arg Glu Leu Lys Ser Ser Ala Ile Asn Leu
                805                 810                 815

Leu Asp Thr Thr Ala Ile Ala Val Ala Asn Trp Thr Asp Arg Val Ile
            820                 825                 830

Glu Val Gly Gln Arg Ile Val Arg Ala Phe Leu His Ile Pro Val Arg
            835                 840                 845

Ile Arg Gln Gly Leu Glu Arg Ala Leu Leu
        850                 855
```

```
<210> SEQ ID NO 22
<211> LENGTH: 862
<212> TYPE: PRT
<213> ORGANISM: Artificial Sequence
<220> FEATURE:
<223> OTHER INFORMATION: CH119 gp160 (aa663-862 are transmembrane region
      and intracellular region)

<400> SEQUENCE: 22
```

```
Met Arg Val Thr Gly Ile Arg Lys Asn Tyr Arg His Leu Trp Arg Trp
1               5                   10                  15
```

-continued

```
Gly Thr Met Leu Leu Gly Met Leu Met Ile Cys Ser Ala Val Gly Asn
        20              25              30

Leu Trp Val Thr Val Tyr Tyr Gly Val Pro Val Trp Lys Glu Ala Thr
        35              40              45

Thr Thr Leu Phe Cys Ala Ser Asp Ala Lys Ala Tyr Asp Thr Glu Val
    50              55              60

His Asn Val Trp Ala Thr His Ala Cys Val Pro Thr Asp Pro Ser Pro
65              70              75              80

Gln Glu Leu Val Leu Glu Asn Val Thr Glu Asn Phe Asn Met Trp Lys
            85              90              95

Asn Glu Met Val Asn Gln Met His Glu Asp Val Ile Ser Leu Trp Asp
            100             105             110

Gln Ser Leu Lys Pro Cys Val Lys Leu Thr Pro Leu Cys Val Thr Leu
        115             120             125

Glu Cys Ser Lys Val Ser Asn Asn Glu Thr Asp Lys Tyr Asn Gly Thr
    130             135             140

Glu Glu Met Lys Asn Cys Ser Phe Asn Ala Thr Thr Val Val Arg Asp
145             150             155             160

Arg Gln Gln Lys Val Tyr Ala Leu Phe Tyr Arg Leu Asp Ile Val Pro
            165             170             175

Leu Thr Glu Lys Asn Ser Ser Glu Asn Ser Ser Lys Tyr Tyr Arg Leu
            180             185             190

Ile Asn Cys Asn Thr Ser Ala Ile Thr Gln Ala Cys Pro Lys Val Ser
            195             200             205

Phe Glu Pro Ile Pro Ile His Tyr Cys Thr Pro Ala Gly Tyr Ala Ile
    210             215             220

Leu Lys Cys Asn Asp Lys Thr Phe Asn Gly Thr Gly Pro Cys His Asn
225             230             235             240

Val Ser Thr Val Gln Cys Thr His Gly Ile Lys Pro Val Val Ser Thr
            245             250             255

Gln Leu Leu Leu Asn Gly Ser Leu Ala Glu Gly Glu Ile Ile Ile Arg
            260             265             270

Ser Glu Asn Leu Thr Asn Asn Val Lys Thr Ile Leu Val His Leu Asn
            275             280             285

Gln Ser Val Glu Ile Val Cys Thr Arg Pro Asn Asn Asn Thr Arg Lys
    290             295             300

Ser Ile Arg Ile Gly Pro Gly Gln Thr Phe Tyr Ala Thr Gly Asp Ile
305             310             315             320

Ile Gly Asp Ile Arg Gln Ala His Cys Asn Ile Ser Lys Trp His Glu
            325             330             335

Thr Leu Lys Arg Val Ser Glu Lys Leu Ala Glu His Phe Pro Asn Lys
            340             345             350

Thr Ile Asn Phe Thr Ser Ser Ser Gly Gly Asp Leu Glu Ile Thr Thr
            355             360             365

His Ser Phe Thr Cys Arg Gly Glu Phe Phe Tyr Cys Asn Thr Ser Gly
    370             375             380

Leu Phe Asn Ser Thr Tyr Met Pro Asn Gly Thr Tyr Leu His Gly Asp
385             390             395             400

Thr Asn Ser Asn Ser Ser Ile Thr Ile Pro Cys Arg Ile Lys Gln Ile
            405             410             415

Ile Asn Met Trp Gln Glu Val Gly Arg Ala Met Tyr Ala Pro Pro Ile
            420             425             430
```

-continued

```
Glu Gly Asn Ile Thr Cys Lys Ser Asn Ile Thr Gly Leu Leu Leu Val
            435                 440                 445

Arg Asp Gly Gly Thr Glu Ser Asn Asn Thr Glu Thr Asn Asn Thr Glu
    450                 455                 460

Ile Phe Arg Pro Gly Gly Gly Asp Met Arg Asp Asn Trp Arg Ser Glu
465                 470                 475                 480

Leu Tyr Lys Tyr Lys Val Val Glu Ile Lys Pro Leu Gly Val Ala Pro
                485                 490                 495

Thr Ala Ala Lys Arg Arg Val Val Glu Arg Glu Lys Arg Ala Val Gly
            500                 505                 510

Ile Gly Ala Val Phe Leu Gly Phe Leu Gly Val Ala Gly Ser Thr Met
            515                 520                 525

Gly Ala Ala Ser Met Thr Leu Thr Val Gln Ala Arg Gln Leu Leu Ser
    530                 535                 540

Gly Ile Val Gln Gln Gln Ser Asn Leu Leu Arg Ala Ile Glu Ala Gln
545                 550                 555                 560

Gln His Leu Leu Gln Leu Thr Val Trp Gly Ile Lys Gln Leu Gln Thr
            565                 570                 575

Arg Val Leu Ala Ile Glu Arg Tyr Leu Lys Asp Gln Gln Leu Leu Gly
            580                 585                 590

Ile Trp Gly Cys Ser Gly Lys Leu Ile Cys Thr Thr Ala Val Pro Trp
            595                 600                 605

Asn Ser Ser Trp Ser Asn Lys Ser Gln Lys Glu Ile Trp Asp Asn Met
            610                 615                 620

Thr Trp Met Gln Trp Asp Lys Glu Ile Ser Asn Tyr Thr Asn Thr Ile
625                 630                 635                 640

Tyr Lys Leu Leu Glu Asp Ser Gln Asn Gln Gln Glu Ser Asn Glu Lys
            645                 650                 655

Asp Leu Leu Ala Leu Asp Ser Trp Asn Asn Leu Trp Asn Trp Phe Asn
            660                 665                 670

Ile Thr Gln Trp Leu Trp Tyr Ile Lys Ile Phe Ile Ile Ile Val Gly
            675                 680                 685

Gly Leu Ile Gly Leu Arg Ile Ile Phe Ala Val Leu Ser Ile Val Asn
    690                 695                 700

Arg Val Arg Gln Gly Tyr Ser Pro Leu Ser Phe Gln Thr Leu Thr Pro
705                 710                 715                 720

Thr Ser Gly Gly Arg Pro Asp Arg Leu Glu Arg Ile Glu Glu Glu Gly
            725                 730                 735

Gly Glu Gln Asp Arg Asp Arg Ser Ile Arg Leu Val Asn Gly Phe Leu
            740                 745                 750

Ala Leu Ala Trp Asp Asp Leu Arg Asn Leu Cys Leu Phe Ser Tyr His
            755                 760                 765

Arg Leu Arg Asp Phe Ile Leu Val Ala Ala Arg Val Val Glu Leu Leu
    770                 775                 780

Gly Arg Thr Ser Leu Arg Gly Leu Gln Arg Gly Trp Glu Ala Leu Lys
785                 790                 795                 800

Tyr Leu Gly Ser Leu Val Gln Tyr Trp Gly Gln Glu Leu Lys Lys Ser
            805                 810                 815

Ala Ile Ser Leu Val Asp Thr Ile Ala Ile Val Val Ala Glu Gly Thr
            820                 825                 830

Asp Arg Ile Ile Asp Ile Val Gln Ala Phe Cys Arg Ala Ile Tyr Asn
            835                 840                 845

Ile Pro Arg Arg Ile Arg Gln Gly Phe Glu Ala Ala Leu Gln
```

-continued 850                     855                     860

<210> SEQ ID NO 23
<211> LENGTH: 850
<212> TYPE: PRT
<213> ORGANISM: Artificial Sequence
<220> FEATURE:
<223> OTHER INFORMATION: CNE8 gp160 (aa652-850 are transmembrane region
      and intracellular region)

<400> SEQUENCE: 23

Met Arg Val Lys Glu Thr Gln Met Asn Trp Pro Asn Leu Trp Lys Trp
1               5                   10                  15

Gly Thr Leu Ile Leu Gly Leu Val Ile Ile Cys Ser Ala Ser Asp Asn
            20                  25                  30

Leu Trp Val Thr Val Tyr Tyr Gly Val Pro Val Trp Arg Asp Ala Asp
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Asn Phe Asn Met Trp Lys
                85                  90                  95

Asn Lys Met Ala Glu Gln Met Gln Glu Asp Val Ile Ser Leu Trp Asp
            100                 105                 110

Glu Ser Leu Lys Pro Cys Val Gln Leu Thr Pro Leu Cys Val Thr Leu
        115                 120                 125

Asn Cys Thr Asn Ala Asn Leu Asn Ala Thr Val Asn Ala Ser Thr Thr
    130                 135                 140

Ile Gly Asn Ile Thr Asp Glu Val Arg Asn Cys Ser Phe Asn Thr Thr
145                 150                 155                 160

Thr Glu Leu Arg Asp Lys Lys Gln Asn Val Tyr Ala Leu Phe Tyr Lys
                165                 170                 175

Leu Asp Ile Val Pro Ile Asn Asn Asn Ser Glu Tyr Arg Leu Ile Asn
            180                 185                 190

Cys Asn Thr Ser Val Ile Lys Gln Ala Cys Pro Lys Val Ser Phe Asp
        195                 200                 205

Pro Ile Pro Ile His Tyr Cys Ala Pro Ala Gly Tyr Ala Ile Leu Arg
    210                 215                 220

Cys Asn Asp Lys Asn Phe Asn Gly Thr Gly Pro Cys Lys Asn Val Ser
225                 230                 235                 240

Ser Val Gln Cys Thr His Gly Ile Lys Pro Val Val Ser Thr Gln Leu
                245                 250                 255

Leu Leu Asn Gly Ser Leu Ala Glu Asp Glu Ile Ile Ile Arg Ser Glu
            260                 265                 270

Asn Leu Thr Asp Asn Val Lys Thr Ile Ile Val His Leu Asn Lys Ser
        275                 280                 285

Val Glu Ile Asn Cys Thr Arg Pro Ser Asn Asn Thr Arg Thr Ser Val
    290                 295                 300

Arg Ile Gly Pro Gly Gln Val Phe Tyr Arg Thr Gly Asp Ile Ile Gly
305                 310                 315                 320

Asp Ile Arg Lys Ala Tyr Cys Glu Ile Asn Arg Thr Lys Trp His Glu
                325                 330                 335

Thr Leu Lys Gln Val Ala Thr Lys Leu Arg Glu His Phe Asn Lys Thr
            340                 345                 350

-continued

```
Ile Ile Phe Gln Pro Pro Ser Gly Gly Asp Ile Glu Ile Thr Met His
        355             360             365

His Phe Asn Cys Arg Gly Glu Phe Phe Tyr Cys Asn Thr Thr Lys Leu
    370             375             380

Phe Asn Ser Thr Trp Gly Glu Asn Thr Thr Met Glu Gly His Asn Asp
385             390             395             400

Thr Ile Val Leu Pro Cys Arg Ile Lys Gln Ile Val Asn Met Trp Gln
                405             410             415

Gly Val Gly Gln Ala Met Tyr Ala Pro Pro Ile Arg Gly Ser Ile Asn
            420             425             430

Cys Val Ser Asn Ile Thr Gly Ile Leu Leu Thr Arg Asp Gly Gly Thr
            435             440             445

Asn Met Ser Asn Glu Thr Phe Arg Pro Gly Gly Gly Asn Ile Lys Asp
    450             455             460

Asn Trp Arg Ser Glu Leu Tyr Lys Tyr Lys Val Val Glu Ile Glu Pro
465             470             475             480

Leu Gly Ile Ala Pro Thr Lys Ala Lys Arg Arg Val Val Glu Arg Glu
                485             490             495

Lys Arg Ala Val Gly Ile Gly Ala Met Ile Phe Gly Phe Leu Gly Ala
            500             505             510

Ala Gly Ser Thr Met Gly Ala Ala Ser Ile Thr Leu Thr Val Gln Ala
            515             520             525

Arg Gln Leu Leu Ser Gly Ile Val Gln Gln Gln Ser Asn Leu Leu Arg
    530             535             540

Ala Pro Glu Ala Gln Gln His Leu Leu Gln Leu Thr Val Trp Gly Ile
545             550             555             560

Lys Gln Leu Gln Ala Arg Val Leu Ala Val Glu Arg Tyr Leu Lys Asp
            565             570             575

Gln Lys Phe Leu Gly Leu Trp Gly Cys Ser Gly Lys Ile Ile Cys Thr
            580             585             590

Thr Ala Val Pro Trp Asn Ser Thr Trp Ser Asn Arg Ser Tyr Glu Glu
            595             600             605

Ile Trp Asp Asn Met Thr Trp Ile Glu Trp Glu Arg Glu Ile Ser Asn
    610             615             620

Tyr Thr Ser Gln Ile Tyr Glu Ile Leu Thr Glu Ser Gln Asn Gln Gln
625             630             635             640

Asp Arg Asn Glu Lys Asp Leu Leu Glu Leu Asp Lys Trp Ala Ser Leu
            645             650             655

Trp Asn Trp Phe Asp Ile Thr Arg Trp Leu Trp Tyr Ile Lys Ile Phe
            660             665             670

Ile Met Ile Val Gly Gly Leu Ile Gly Leu Arg Ile Ile Phe Ala Val
            675             680             685

Leu Ser Ile Val Asn Arg Val Arg Gln Gly Tyr Ser Pro Leu Ser Phe
    690             695             700

Gln Thr Pro Thr His His Gln Arg Glu Pro Asp Arg Pro Glu Arg Ile
705             710             715             720

Glu Glu Gly Gly Gly Glu Gln Asp Arg Asp Arg Ser Val Arg Leu Val
            725             730             735

Ser Gly Phe Leu Ala Leu Ala Trp Asp Asp Leu Arg Ser Leu Cys Leu
            740             745             750

Phe Ser Tyr His Arg Leu Arg Asp Leu Ile Leu Ile Ala Val Arg Thr
    755             760             765

Val Glu Leu Leu Gly His Gly Gly Leu Lys Gly Leu Arg Arg Gly Trp
```

-continued

```
            770              775              780

Glu Gly Leu Lys Tyr Leu Gly Asn Leu Leu Leu Tyr Trp Gly Gln Glu
785              790              795              800

Leu Lys Ile Ser Ala Ile Ser Leu Leu Asp Ala Thr Ala Ile Ala Val
                 805              810              815

Ala Gly Trp Thr Asp Arg Ile Ile Glu Val Ala Gln Arg Ala Trp Arg
             820              825              830

Ala Ile Leu His Ile Pro Arg Arg Ile Arg Gln Gly Leu Glu Arg Ser
         835              840              845

Leu Leu
   850

<210> SEQ ID NO 24
<211> LENGTH: 852
<212> TYPE: PRT
<213> ORGANISM: Artificial Sequence
<220> FEATURE:
<223> OTHER INFORMATION: p246F3 gp160 (aa654-852 are transmembrane
      region and intracellular region)

<400> SEQUENCE: 24

Met Arg Ala Arg Gly Met Leu Arg Thr Trp Gln His Trp Trp Ile Trp
1               5               10              15

Gly Ile Leu Gly Phe Trp Met Leu Met Ile Cys Asn Met Gln Asp Leu
            20              25              30

Trp Val Thr Val Tyr Tyr Gly Val Pro Val Trp Lys Asp Ala Lys Thr
            35              40              45

Thr Leu Phe Cys Ala Ser Asp Ala Lys Ala Tyr Glu Lys Glu Val His
    50              55              60

Asn Val Trp Ala Thr His Ala Cys Val Pro Thr Asp Pro Asn Pro Gln
65              70              75              80

Glu Ile Val Met Ala Asn Val Thr Glu Glu Phe Asn Met Trp Lys Asn
                85              90              95

Asn Met Val Glu Gln Met His Thr Asp Ile Ile Ser Leu Trp Asp Gln
            100             105             110

Ser Leu Lys Pro Cys Val Lys Leu Thr Pro Leu Cys Val Thr Leu Asp
        115             120             125

Cys Lys Asp Tyr Asn Tyr Ser Ile Thr Asn Asn Ser Thr Gly Met Glu
    130             135             140

Gly Glu Ile Lys Asn Cys Ser Tyr Asn Ile Thr Thr Glu Leu Arg Asp
145             150             155             160

Lys Arg Gln Lys Val Tyr Ser Leu Phe Tyr Arg Leu Asp Val Val Gln
                165             170             175

Ile Asn Asp Ser Asn Asp Arg Asn Asn Ser Gln Tyr Arg Leu Ile Asn
            180             185             190

Cys Asn Thr Thr Thr Met Thr Gln Ala Cys Pro Lys Val Thr Phe Asp
            195             200             205

Pro Ile Pro Ile His Tyr Cys Ala Pro Ala Gly Phe Ala Ile Leu Lys
    210             215             220

Cys Asn Asn Lys Thr Phe Asn Gly Lys Gly Pro Cys Asn Asn Val Ser
225             230             235             240

Ser Val Gln Cys Thr His Gly Ile Lys Pro Val Val Ser Thr Gln Leu
            245             250             255

Leu Leu Asn Gly Ser Leu Ala Glu Lys Glu Ile Val Ile Arg Ser Glu
            260             265             270
```

```
Asn Leu Thr Asp Asn Val Lys Thr Ile Ile Val His Leu Asn Glu Ser
    275                 280                 285

Val Glu Ile Asn Cys Thr Arg Pro Asn Asn Asn Thr Arg Lys Ser Val
    290                 295                 300

Arg Ile Gly Pro Gly Gln Thr Phe Tyr Ala Thr Gly Asp Ile Ile Gly
305                 310                 315                 320

Asn Ile Arg Gln Ala His Cys Thr Val Asn Lys Thr Glu Trp Asn Thr
                325                 330                 335

Ala Leu Thr Arg Val Ser Lys Lys Leu Lys Glu Tyr Phe Pro Asn Lys
                340                 345                 350

Thr Ile Ala Phe Gln Pro Ser Ser Gly Gly Asp Leu Glu Ile Thr Thr
                355                 360                 365

Phe Ser Phe Asn Cys Arg Gly Glu Phe Phe Tyr Cys Asn Thr Ser Asp
    370                 375                 380

Leu Phe Asn Gly Thr Phe Asn Glu Thr Ser Gly Gln Phe Asn Ser Thr
385                 390                 395                 400

Phe Asn Ser Thr Leu Gln Cys Arg Ile Lys Gln Ile Ile Asn Met Trp
                405                 410                 415

Gln Glu Val Gly Gln Ala Met Tyr Ala Pro Pro Ile Ala Gly Ser Ile
                420                 425                 430

Thr Cys Ile Ser Asn Ile Thr Gly Leu Ile Leu Thr Arg Asp Gly Gly
                435                 440                 445

Asn Thr Asn Ser Thr Lys Glu Thr Phe Arg Pro Gly Gly Gly Asn Met
    450                 455                 460

Arg Asp Asn Trp Arg Ser Glu Leu Tyr Lys Tyr Lys Val Val Lys Ile
465                 470                 475                 480

Glu Pro Leu Gly Val Ala Pro Thr Lys Ala Arg Arg Arg Val Val Glu
                485                 490                 495

Arg Glu Lys Arg Ala Val Gly Ile Gly Ala Val Phe Ile Gly Phe Leu
                500                 505                 510

Gly Ala Ala Gly Ser Thr Met Gly Ala Ala Ser Ile Thr Leu Thr Val
                515                 520                 525

Gln Ala Arg Gln Leu Leu Ser Gly Ile Val Gln Gln Gln Ser Asn Leu
    530                 535                 540

Leu Arg Ala Ile Glu Ala Gln Gln His Leu Leu Lys Leu Thr Val Trp
545                 550                 555                 560

Gly Ile Lys Gln Leu Gln Ala Arg Val Leu Ala Val Glu Arg Tyr Leu
                565                 570                 575

Lys Asp Gln Gln Leu Leu Gly Ile Trp Gly Cys Ser Gly Lys Leu Ile
                580                 585                 590

Cys Thr Thr Asn Val Pro Trp Asn Ser Ser Trp Ser Asn Lys Ser Gln
    595                 600                 605

Asp Glu Ile Trp Asp Asn Met Thr Trp Leu Gln Trp Asp Lys Glu Ile
    610                 615                 620

Ser Asn Tyr Thr Gln Ile Ile Tyr Asn Leu Ile Glu Glu Ser Gln Thr
625                 630                 635                 640

Gln Gln Glu Leu Asn Glu Arg Asp Leu Leu Ala Leu Asp Lys Trp Ala
                645                 650                 655

Asn Leu Trp Asn Trp Phe Asp Ile Thr Lys Trp Leu Trp Tyr Ile Lys
                660                 665                 670

Ile Phe Ile Met Ile Val Gly Gly Leu Ile Gly Leu Arg Ile Ile Phe
                675                 680                 685

Ala Val Leu Ser Ile Val Asn Arg Val Arg Gln Gly Tyr Ser Pro Leu
```

-continued

```
            690                 695                 700

Ser Phe Gln Thr Leu Thr Pro Asn Pro Arg Gly Pro Asp Arg Pro Gly
705                 710                 715                 720

Gly Ile Glu Glu Glu Gly Gly Glu Gln Gly Arg Asn Ser Tyr Thr Arg
                725                 730                 735

Leu Val Ser Gly Phe Leu Pro Leu Ala Trp Asp Asp Leu Arg Ser Leu
                740                 745                 750

Cys Leu Phe Ser Tyr His Leu Leu Arg Asp Phe Ile Leu Ile Ala Ala
                755                 760                 765

Arg Ala Ala Glu Leu Leu Gly Arg Ser Ser Leu Arg Gly Leu Gln Arg
        770                 775                 780

Gly Trp Glu Thr Leu Lys Tyr Leu Gly Ser Leu Val Gln Tyr Trp Gly
785                 790                 795                 800

Leu Glu Leu Lys Lys Ser Ala Ile Ser Leu Leu Asp Thr Ile Ala Ile
                805                 810                 815

Gln Val Ala Glu Gly Thr Asp Arg Ile Ile Glu Leu Ile Gln Gly Ile
                820                 825                 830

Tyr Arg Ala Ile Arg Asn Ile Pro Arg Arg Ile Arg Gln Gly Ala Glu
        835                 840                 845

Thr Ala Leu Val
    850

<210> SEQ ID NO 25
<211> LENGTH: 853
<212> TYPE: PRT
<213> ORGANISM: Artificial Sequence
<220> FEATURE:
<223> OTHER INFORMATION: Bal.26 gp160 (aa662-853 are transmembrane
      region and intracellular region)

<400> SEQUENCE: 25

Met Arg Val Thr Glu Ile Arg Lys Ser Tyr Gln His Trp Trp Arg Trp
1               5                   10                  15

Gly Ile Met Leu Leu Gly Met Leu Met Ile Cys Asn Ala Glu Glu Lys
                20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Lys Met Glu Asn Val Thr Glu Asn Phe Asn Met Trp Lys
                85                  90                  95

Asn Asn Val Val Glu Gln Met His Glu Asp Ile Ile Ser Leu Trp Asp
                100                 105                 110

Gln Ser Leu Lys Pro Cys Val Lys Leu Thr Pro Leu Cys Val Thr Leu
            115                 120                 125

Asn Cys Thr Asp Leu Lys Asn Ala Thr Asn Gly Asn Asn Thr Asn Thr
        130                 135                 140

Thr Ser Ser Ser Gly Gly Met Met Gly Gly Glu Met Lys Asn Cys
145                 150                 155                 160

Ser Phe Asn Ile Thr Thr Asn Ile Arg Gly Lys Val Gln Lys Glu Tyr
                165                 170                 175

Ala Leu Phe Tyr Glu Leu Asp Ile Val Pro Ile Asp Asn Lys Ile Asp
                180                 185                 190
```

-continued

```
Ser Tyr Arg Leu Ile Ser Cys Asn Thr Ser Val Ile Thr Gln Ala Cys
        195             200             205

Pro Lys Val Ser Phe Glu Pro Ile Pro Ile His Tyr Cys Ala Pro Ala
        210             215             220

Gly Phe Ala Ile Leu Lys Cys Lys Asp Lys Lys Phe Asn Gly Lys Gly
225             230             235             240

Pro Cys Ser Asn Val Ser Thr Val Gln Cys Thr His Gly Ile Arg Pro
            245             250             255

Val Val Ser Thr Gln Leu Leu Leu Asn Gly Ser Leu Ala Glu Glu Glu
            260             265             270

Val Val Ile Arg Ser Glu Asn Phe Thr Asn Asn Ala Lys Ile Ile Val
            275             280             285

Val Gln Leu Asn Glu Ser Val Glu Ile Asn Cys Thr Arg Pro Asn Asn
        290             295             300

Asn Thr Arg Lys Ser Ile His Ile Gly Pro Gly Arg Ala Phe Tyr Thr
305             310             315             320

Thr Gly Glu Ile Ile Gly Asp Ile Arg Gln Ala His Cys Asn Leu Ser
            325             330             335

Arg Ala Lys Trp Asn Asp Thr Leu Asn Lys Ile Val Ile Lys Leu Arg
            340             345             350

Glu Gln Phe Gly Asn Lys Thr Ile Val Phe Lys His Ser Ser Gly Gly
            355             360             365

Asp Pro Glu Ile Val Thr His Ser Phe Asn Cys Gly Gly Glu Phe Phe
        370             375             380

Tyr Cys Asn Ser Thr Gln Leu Phe Asn Ser Thr Trp Asn Val Thr Glu
385             390             395             400

Glu Ser Asn Asn Thr Val Glu Asn Asn Thr Ile Thr Leu Pro Cys Arg
            405             410             415

Ile Lys Gln Ile Ile Asn Met Trp Gln Glu Val Gly Arg Ala Met Tyr
            420             425             430

Ala Pro Pro Ile Arg Gly Gln Ile Arg Cys Ser Ser Asn Ile Thr Gly
            435             440             445

Leu Leu Leu Thr Arg Asp Gly Gly Pro Glu Asp Asp Lys Thr Glu Val
        450             455             460

Phe Arg Pro Gly Gly Gly Asp Met Arg Asp Asn Trp Arg Ser Glu Leu
465             470             475             480

Tyr Lys Tyr Lys Val Val Lys Ile Glu Pro Leu Gly Val Ala Pro Thr
            485             490             495

Lys Ala Lys Arg Arg Val Val Gln Arg Glu Lys Arg Ala Val Gly Ile
            500             505             510

Gly Ala Val Leu Leu Gly Phe Leu Gly Ala Ala Gly Ser Thr Met Gly
            515             520             525

Ala Ala Ser Met Thr Leu Thr Val Gln Ala Arg Leu Leu Leu Ser Gly
        530             535             540

Ile Val Gln Gln Gln Asn Asn Leu Leu Arg Ala Ile Glu Ala Gln Gln
545             550             555             560

His Leu Leu Gln Leu Thr Val Trp Gly Ile Lys Gln Leu Gln Ala Arg
            565             570             575

Val Leu Ala Val Glu Arg Tyr Leu Arg Asp Gln Gln Leu Leu Gly Ile
            580             585             590

Trp Gly Cys Ser Gly Lys Leu Ile Cys Thr Thr Ala Val Pro Trp Asn
            595             600             605

Ala Ser Trp Ser Asn Lys Ser Leu Asn Lys Ile Trp Asp Asn Met Thr
```

-continued

```
          610                 615                 620

Trp Met Glu Trp Asp Arg Glu Ile Asn Asn Tyr Thr Ser Ile Ile Tyr
625                 630                 635                 640

Ser Leu Ile Glu Glu Ser Gln Asn Gln Gln Glu Lys Asn Glu Gln Glu
                645                 650                 655

Leu Leu Glu Leu Asp Lys Trp Ala Ser Leu Trp Asn Trp Phe Asp Ile
                660                 665                 670

Thr Lys Trp Leu Trp Tyr Ile Lys Ile Phe Ile Met Ile Val Gly Gly
                675                 680                 685

Leu Ile Gly Leu Arg Ile Val Phe Ser Val Leu Ser Ile Val Asn Arg
                690                 695                 700

Val Arg Gln Gly Tyr Ser Pro Leu Ser Phe Gln Thr His Leu Pro Ala
705                 710                 715                 720

Ser Arg Gly Pro Asp Arg Pro Gly Gly Ile Glu Glu Glu Gly Gly Glu
                725                 730                 735

Arg Asp Arg Asp Arg Ser Gly Pro Leu Val Asn Gly Phe Leu Thr Leu
                740                 745                 750

Ile Trp Val Asp Leu Arg Ser Leu Phe Leu Phe Ser Tyr His Arg Leu
                755                 760                 765

Arg Asp Leu Leu Leu Ile Val Thr Arg Ile Val Glu Leu Leu Gly Arg
                770                 775                 780

Arg Gly Trp Glu Val Leu Lys Tyr Trp Trp Asn Leu Leu Gln Tyr Trp
785                 790                 795                 800

Ser Gln Glu Leu Lys Asn Ser Ala Val Ser Leu Leu Asn Thr Ile Ala
                805                 810                 815

Ile Ala Val Ala Glu Gly Thr Asp Arg Val Ile Glu Val Val Gln Arg
                820                 825                 830

Ala Val Arg Ala Ile Leu His Ile Pro Arg Arg Ile Arg Gln Gly Leu
                835                 840                 845

Glu Arg Ala Leu Leu
    850

<210> SEQ ID NO 26
<211> LENGTH: 7
<212> TYPE: PRT
<213> ORGANISM: Artificial Sequence
<220> FEATURE:
<223> OTHER INFORMATION: BG505- deleted sequence from gp41

<400> SEQUENCE: 26

Trp Asn Ser Ser Trp Ser Asn
1               5

<210> SEQ ID NO 27
<211> LENGTH: 11
<212> TYPE: PRT
<213> ORGANISM: Artificial Sequence
<220> FEATURE:
<223> OTHER INFORMATION: BG505- deleted sequence from gp120

<400> SEQUENCE: 27

Ala Lys Arg Arg Val Val Gly Arg Glu Lys Arg
1               5                   10

<210> SEQ ID NO 28
<211> LENGTH: 5
<212> TYPE: PRT
<213> ORGANISM: Artificial Sequence
<220> FEATURE:
```

<223> OTHER INFORMATION: Linker-1

<400> SEQUENCE: 28

Gly Gly Gly Gly Ser
1               5

<210> SEQ ID NO 29
<211> LENGTH: 10
<212> TYPE: PRT
<213> ORGANISM: Artificial Sequence
<220> FEATURE:
<223> OTHER INFORMATION: Linker-2

<400> SEQUENCE: 29

Gly Gly Gly Gly Ser Gly Gly Gly Gly Ser
1               5                   10

<210> SEQ ID NO 30
<211> LENGTH: 681
<212> TYPE: PRT
<213> ORGANISM: Artificial Sequence
<220> FEATURE:
<223> OTHER INFORMATION: BG-B1(1/1)

<400> SEQUENCE: 30

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ala Val Gly Ile Gly Ala Val Phe Leu Gly Phe Leu Gly
            35                  40                  45

Ala Ala Gly Ser Thr Met Gly Ala Ala Ser Met Thr Leu Thr Val Gln
    50                  55                  60

Ala Arg Asn Leu Leu Ser Gly Ile Val Gln Gln Gln Ser Asn Leu Leu
65                  70                  75                  80

Arg Ala Pro Glu Ala Gln Gln His Leu Leu Lys Leu Thr Val Trp Gly
            85                  90                  95

Ile Lys Gln Leu Gln Ala Arg Val Leu Ala Val Glu Arg Tyr Leu Arg
            100                 105                 110

Asp Gln Gln Leu Leu Gly Ile Trp Gly Cys Ser Gly Lys Leu Ile Cys
            115                 120                 125

Thr Thr Asn Val Pro Gly Gly Gly Ser Ala Glu Asn Leu Trp Val
    130                 135                 140

Thr Val Tyr Tyr Gly Val Pro Val Trp Lys Asp Ala Glu Thr Thr Leu
145                 150                 155                 160

Phe Cys Ala Ser Asp Ala Lys Ala Tyr Glu Thr Glu Lys His Asn Val
            165                 170                 175

Trp Ala Thr His Ala Cys Val Pro Thr Asp Pro Asn Pro Gln Glu Ile
            180                 185                 190

His Leu Glu Asn Val Thr Glu Glu Phe Asn Met Trp Lys Asn Asn Met
            195                 200                 205

Val Glu Gln Met His Thr Asp Ile Ile Ser Leu Trp Asp Gln Ser Leu
    210                 215                 220

Lys Pro Cys Val Lys Leu Thr Pro Leu Cys Val Thr Leu Gln Cys Thr
225                 230                 235                 240

Asn Val Thr Asn Asn Ile Thr Asp Asp Met Arg Gly Glu Leu Lys Asn
            245                 250                 255

Cys Ser Phe Asn Met Thr Thr Glu Leu Arg Asp Lys Lys Gln Lys Val

-continued

```
                    260                 265                 270

Tyr Ser Leu Phe Tyr Arg Leu Asp Val Val Gln Ile Asn Glu Asn Gln
        275                 280                 285

Gly Asn Arg Ser Asn Asn Ser Asn Lys Glu Tyr Arg Leu Ile Asn Cys
        290                 295                 300

Asn Thr Ser Ala Ile Thr Gln Ala Cys Pro Lys Val Ser Phe Glu Pro
305                 310                 315                 320

Ile Pro Ile His Tyr Cys Ala Pro Ala Gly Phe Ala Ile Leu Lys Cys
                325                 330                 335

Lys Asp Lys Lys Phe Asn Gly Thr Gly Pro Cys Pro Ser Val Ser Thr
        340                 345                 350

Val Gln Cys Thr His Gly Ile Lys Pro Val Val Ser Thr Gln Leu Leu
        355                 360                 365

Leu Asn Gly Ser Leu Ala Glu Glu Glu Val Met Ile Arg Ser Glu Asn
        370                 375                 380

Ile Thr Asn Asn Ala Lys Asn Ile Leu Val Gln Phe Asn Thr Pro Val
385                 390                 395                 400

Gln Ile Asn Cys Thr Arg Pro Asn Asn Asn Thr Arg Lys Ser Ile Arg
                405                 410                 415

Ile Gly Pro Gly Gln Ala Phe Tyr Ala Thr Gly Asp Ile Ile Gly Asp
                420                 425                 430

Ile Arg Gln Ala His Cys Asn Val Ser Lys Ala Thr Trp Asn Glu Thr
        435                 440                 445

Leu Gly Lys Val Val Lys Gln Leu Arg Lys His Phe Gly Asn Asn Thr
        450                 455                 460

Ile Ile Arg Phe Ala Asn Ser Ser Gly Gly Asp Leu Glu Val Thr Thr
465                 470                 475                 480

His Ser Phe Asn Cys Gly Gly Glu Phe Phe Tyr Cys Asn Thr Ser Gly
                485                 490                 495

Leu Phe Asn Ser Thr Trp Ile Ser Asn Thr Ser Val Gln Gly Ser Asn
        500                 505                 510

Ser Thr Gly Ser Asn Asp Ser Ile Thr Leu Pro Cys Arg Ile Lys Gln
        515                 520                 525

Ile Ile Asn Met Trp Gln Arg Ile Gly Gln Ala Met Tyr Ala Pro Pro
        530                 535                 540

Ile Gln Gly Val Ile Arg Cys Val Ser Asn Ile Thr Gly Leu Ile Leu
545                 550                 555                 560

Thr Arg Asp Gly Gly Ser Thr Asn Ser Thr Thr Glu Thr Phe Arg Pro
                565                 570                 575

Gly Gly Gly Asp Met Arg Asp Asn Trp Arg Ser Glu Leu Tyr Lys Tyr
                580                 585                 590

Lys Val Val Lys Ile Glu Pro Leu Gly Val Ala Pro Thr Arg Ala Lys
        595                 600                 605

Arg Arg Val Val Gly Gly Gly Gly Ser Trp Asn Ser Ser Trp Ser
        610                 615                 620

Asn Arg Asn Leu Ser Glu Ile Trp Asp Asn Met Thr Trp Leu Gln Trp
625                 630                 635                 640

Asp Lys Glu Ile Ser Asn Tyr Thr Gln Ile Ile Tyr Gly Leu Leu Glu
                645                 650                 655

Glu Ser Gln Asn Gln Gln Glu Lys Asn Glu Gln Asp Leu Leu Ala Leu
        660                 665                 670

Asp His His His His His His His His
        675                 680
```

-continued

```
<210> SEQ ID NO 31
<211> LENGTH: 686
<212> TYPE: PRT
<213> ORGANISM: Artificial Sequence
<220> FEATURE:
<223> OTHER INFORMATION: BG-B1(1/2)

<400> SEQUENCE: 31

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

Gly Ala Arg Ala Val Gly Ile Gly Ala Val Phe Leu Gly Phe Leu Gly
            35                  40                  45

Ala Ala Gly Ser Thr Met Gly Ala Ala Ser Met Thr Leu Thr Val Gln
        50                  55                  60

Ala Arg Asn Leu Leu Ser Gly Ile Val Gln Gln Gln Ser Asn Leu Leu
65                  70                  75                  80

Arg Ala Pro Glu Ala Gln Gln His Leu Leu Lys Leu Thr Val Trp Gly
                85                  90                  95

Ile Lys Gln Leu Gln Ala Arg Val Leu Ala Val Glu Arg Tyr Leu Arg
                100                 105                 110

Asp Gln Gln Leu Leu Gly Ile Trp Gly Cys Ser Gly Lys Leu Ile Cys
            115                 120                 125

Thr Thr Asn Val Pro Gly Gly Gly Ser Ala Glu Asn Leu Trp Val
        130                 135                 140

Thr Val Tyr Tyr Gly Val Pro Val Trp Lys Asp Ala Glu Thr Thr Leu
145                 150                 155                 160

Phe Cys Ala Ser Asp Ala Lys Ala Tyr Glu Thr Glu Lys His Asn Val
                165                 170                 175

Trp Ala Thr His Ala Cys Val Pro Thr Asp Pro Asn Pro Gln Glu Ile
            180                 185                 190

His Leu Glu Asn Val Thr Glu Glu Phe Asn Met Trp Lys Asn Asn Met
            195                 200                 205

Val Glu Gln Met His Thr Asp Ile Ile Ser Leu Trp Asp Gln Ser Leu
        210                 215                 220

Lys Pro Cys Val Lys Leu Thr Pro Leu Cys Val Thr Leu Gln Cys Thr
225                 230                 235                 240

Asn Val Thr Asn Asn Ile Thr Asp Asp Met Arg Gly Glu Leu Lys Asn
                245                 250                 255

Cys Ser Phe Asn Met Thr Thr Glu Leu Arg Asp Lys Lys Gln Lys Val
            260                 265                 270

Tyr Ser Leu Phe Tyr Arg Leu Asp Val Val Gln Ile Asn Glu Asn Gln
            275                 280                 285

Gly Asn Arg Ser Asn Asn Ser Asn Lys Glu Tyr Arg Leu Ile Asn Cys
        290                 295                 300

Asn Thr Ser Ala Ile Thr Gln Ala Cys Pro Lys Val Ser Phe Glu Pro
305                 310                 315                 320

Ile Pro Ile His Tyr Cys Ala Pro Ala Gly Phe Ala Ile Leu Lys Cys
                325                 330                 335

Lys Asp Lys Lys Phe Asn Gly Thr Gly Pro Cys Pro Ser Val Ser Thr
            340                 345                 350

Val Gln Cys Thr His Gly Ile Lys Pro Val Val Ser Thr Gln Leu Leu
            355                 360                 365
```

```
Leu Asn Gly Ser Leu Ala Glu Glu Glu Val Met Ile Arg Ser Glu Asn
    370             375             380

Ile Thr Asn Asn Ala Lys Asn Ile Leu Val Gln Phe Asn Thr Pro Val
385             390             395             400

Gln Ile Asn Cys Thr Arg Pro Asn Asn Asn Thr Arg Lys Ser Ile Arg
            405             410             415

Ile Gly Pro Gly Gln Ala Phe Tyr Ala Thr Gly Asp Ile Ile Gly Asp
            420             425             430

Ile Arg Gln Ala His Cys Asn Val Ser Lys Ala Thr Trp Asn Glu Thr
        435             440             445

Leu Gly Lys Val Val Lys Gln Leu Arg Lys His Phe Gly Asn Asn Thr
    450             455             460

Ile Ile Arg Phe Ala Asn Ser Ser Gly Gly Asp Leu Glu Val Thr Thr
465             470             475             480

His Ser Phe Asn Cys Gly Gly Glu Phe Phe Tyr Cys Asn Thr Ser Gly
            485             490             495

Leu Phe Asn Ser Thr Trp Ile Ser Asn Thr Ser Val Gln Gly Ser Asn
            500             505             510

Ser Thr Gly Ser Asn Asp Ser Ile Thr Leu Pro Cys Arg Ile Lys Gln
            515             520             525

Ile Ile Asn Met Trp Gln Arg Ile Gly Gln Ala Met Tyr Ala Pro Pro
    530             535             540

Ile Gln Gly Val Ile Arg Cys Val Ser Asn Ile Thr Gly Leu Ile Leu
545             550             555             560

Thr Arg Asp Gly Gly Ser Thr Asn Ser Thr Thr Glu Thr Phe Arg Pro
            565             570             575

Gly Gly Gly Asp Met Arg Asp Asn Trp Arg Ser Glu Leu Tyr Lys Tyr
            580             585             590

Lys Val Val Lys Ile Glu Pro Leu Gly Val Ala Pro Thr Arg Ala Lys
            595             600             605

Arg Arg Val Val Gly Gly Gly Gly Gly Ser Gly Gly Gly Gly Ser Trp
    610             615             620

Asn Ser Ser Trp Ser Asn Arg Asn Leu Ser Glu Ile Trp Asp Asn Met
625             630             635             640

Thr Trp Leu Gln Trp Asp Lys Glu Ile Ser Asn Tyr Thr Gln Ile Ile
            645             650             655

Tyr Gly Leu Leu Glu Glu Ser Gln Asn Gln Gln Glu Lys Asn Glu Gln
            660             665             670

Asp Leu Leu Ala Leu Asp His His His His His His His
    675             680             685
```

<210> SEQ ID NO 32
<211> LENGTH: 691
<212> TYPE: PRT
<213> ORGANISM: Artificial Sequence
<220> FEATURE:
<223> OTHER INFORMATION: BG-B1(2/2)

<400> SEQUENCE: 32

```
Met Asp Ala Met Lys Arg Gly Leu Cys Cys Val Leu Leu Leu Cys Gly
1               5               10              15

Ala Val Phe Val Ser Pro Ser Gln Glu Ile His Ala Arg Phe Arg Arg
            20              25              30

Gly Ala Arg Ala Val Gly Ile Gly Ala Val Phe Leu Gly Phe Leu Gly
        35              40              45
```

```
Ala Ala Gly Ser Thr Met Gly Ala Ala Ser Met Thr Leu Thr Val Gln
    50              55              60

Ala Arg Asn Leu Leu Ser Gly Ile Val Gln Gln Ser Asn Leu Leu
65              70              75              80

Arg Ala Pro Glu Ala Gln Gln His Leu Leu Lys Leu Thr Val Trp Gly
            85              90              95

Ile Lys Gln Leu Gln Ala Arg Val Leu Ala Val Glu Arg Tyr Leu Arg
            100             105             110

Asp Gln Gln Leu Leu Gly Ile Trp Gly Cys Ser Gly Lys Leu Ile Cys
            115             120             125

Thr Thr Asn Val Pro Gly Gly Gly Ser Gly Gly Gly Ser Ala
    130             135             140

Glu Asn Leu Trp Val Thr Val Tyr Tyr Gly Val Pro Val Trp Lys Asp
145             150             155             160

Ala Glu Thr Thr Leu Phe Cys Ala Ser Asp Ala Lys Ala Tyr Glu Thr
            165             170             175

Glu Lys His Asn Val Trp Ala Thr His Ala Cys Val Pro Thr Asp Pro
            180             185             190

Asn Pro Gln Glu Ile His Leu Glu Asn Val Thr Glu Glu Phe Asn Met
            195             200             205

Trp Lys Asn Asn Met Val Glu Gln Met His Thr Asp Ile Ile Ser Leu
    210             215             220

Trp Asp Gln Ser Leu Lys Pro Cys Val Lys Leu Thr Pro Leu Cys Val
225             230             235             240

Thr Leu Gln Cys Thr Asn Val Thr Asn Asn Ile Thr Asp Asp Met Arg
            245             250             255

Gly Glu Leu Lys Asn Cys Ser Phe Asn Met Thr Thr Glu Leu Arg Asp
            260             265             270

Lys Lys Gln Lys Val Tyr Ser Leu Phe Tyr Arg Leu Asp Val Val Gln
            275             280             285

Ile Asn Glu Asn Gln Gly Asn Arg Ser Asn Asn Ser Asn Lys Glu Tyr
    290             295             300

Arg Leu Ile Asn Cys Asn Thr Ser Ala Ile Thr Gln Ala Cys Pro Lys
305             310             315             320

Val Ser Phe Glu Pro Ile Pro Ile His Tyr Cys Ala Pro Ala Gly Phe
            325             330             335

Ala Ile Leu Lys Cys Lys Asp Lys Lys Phe Asn Gly Thr Gly Pro Cys
            340             345             350

Pro Ser Val Ser Thr Val Gln Cys Thr His Gly Ile Lys Pro Val Val
            355             360             365

Ser Thr Gln Leu Leu Leu Asn Gly Ser Leu Ala Glu Glu Glu Val Met
    370             375             380

Ile Arg Ser Glu Asn Ile Thr Asn Asn Ala Lys Asn Ile Leu Val Gln
385             390             395             400

Phe Asn Thr Pro Val Gln Ile Asn Cys Thr Arg Pro Asn Asn Asn Thr
            405             410             415

Arg Lys Ser Ile Arg Ile Gly Pro Gly Gln Ala Phe Tyr Ala Thr Gly
            420             425             430

Asp Ile Ile Gly Asp Ile Arg Gln Ala His Cys Asn Val Ser Lys Ala
            435             440             445

Thr Trp Asn Glu Thr Leu Gly Lys Val Val Lys Gln Leu Arg Lys His
    450             455             460
```

-continued

```
Phe Gly Asn Asn Thr Ile Ile Arg Phe Ala Asn Ser Ser Gly Gly Asp
465                 470                 475                 480

Leu Glu Val Thr Thr His Ser Phe Asn Cys Gly Gly Glu Phe Phe Tyr
                485                 490                 495

Cys Asn Thr Ser Gly Leu Phe Asn Ser Thr Trp Ile Ser Asn Thr Ser
            500                 505                 510

Val Gln Gly Ser Asn Ser Thr Gly Ser Asn Asp Ser Ile Thr Leu Pro
            515                 520                 525

Cys Arg Ile Lys Gln Ile Ile Asn Met Trp Gln Arg Ile Gly Gln Ala
            530                 535                 540

Met Tyr Ala Pro Pro Ile Gln Gly Val Ile Arg Cys Val Ser Asn Ile
545                 550                 555                 560

Thr Gly Leu Ile Leu Thr Arg Asp Gly Gly Ser Thr Asn Ser Thr Thr
                565                 570                 575

Glu Thr Phe Arg Pro Gly Gly Gly Asp Met Arg Asp Asn Trp Arg Ser
                580                 585                 590

Glu Leu Tyr Lys Tyr Lys Val Val Lys Ile Glu Pro Leu Gly Val Ala
                595                 600                 605

Pro Thr Arg Ala Lys Arg Arg Val Val Gly Gly Gly Gly Ser Gly
            610                 615                 620

Gly Gly Gly Ser Trp Asn Ser Ser Trp Ser Asn Arg Asn Leu Ser Glu
625                 630                 635                 640

Ile Trp Asp Asn Met Thr Trp Leu Gln Trp Asp Lys Glu Ile Ser Asn
                645                 650                 655

Tyr Thr Gln Ile Ile Tyr Gly Leu Leu Glu Glu Ser Gln Asn Gln Gln
                660                 665                 670

Glu Lys Asn Glu Gln Asp Leu Leu Ala Leu Asp His His His His His
            675                 680                 685

His His His
        690
```

```
<210> SEQ ID NO 33
<211> LENGTH: 686
<212> TYPE: PRT
<213> ORGANISM: Artificial Sequence
<220> FEATURE:
<223> OTHER INFORMATION: BG-B1(2/1)

<400> SEQUENCE: 33

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

Gly Ala Arg Ala Val Gly Ile Gly Ala Val Phe Leu Gly Phe Leu Gly
            35                  40                  45

Ala Ala Gly Ser Thr Met Gly Ala Ala Ser Met Thr Leu Thr Val Gln
        50                  55                  60

Ala Arg Asn Leu Leu Ser Gly Ile Val Gln Gln Gln Ser Asn Leu Leu
65                  70                  75                  80

Arg Ala Pro Glu Ala Gln Gln His Leu Leu Lys Leu Thr Val Trp Gly
                85                  90                  95

Ile Lys Gln Leu Gln Ala Arg Val Leu Ala Val Glu Arg Tyr Leu Arg
            100                 105                 110

Asp Gln Gln Leu Leu Gly Ile Trp Gly Cys Ser Gly Lys Leu Ile Cys
            115                 120                 125
```

-continued

```
Thr Thr Asn Val Pro Gly Gly Gly Gly Ser Gly Gly Gly Gly Ser Ala
    130             135             140

Glu Asn Leu Trp Val Thr Val Tyr Tyr Gly Val Pro Val Trp Lys Asp
145             150             155             160

Ala Glu Thr Thr Leu Phe Cys Ala Ser Asp Ala Lys Ala Tyr Glu Thr
            165             170             175

Glu Lys His Asn Val Trp Ala Thr His Ala Cys Val Pro Thr Asp Pro
            180             185             190

Asn Pro Gln Glu Ile His Leu Glu Asn Val Thr Glu Glu Phe Asn Met
            195             200             205

Trp Lys Asn Asn Met Val Glu Gln Met His Thr Asp Ile Ile Ser Leu
    210             215             220

Trp Asp Gln Ser Leu Lys Pro Cys Val Lys Leu Thr Pro Leu Cys Val
225             230             235             240

Thr Leu Gln Cys Thr Asn Val Thr Asn Asn Ile Thr Asp Asp Met Arg
            245             250             255

Gly Glu Leu Lys Asn Cys Ser Phe Asn Met Thr Thr Glu Leu Arg Asp
            260             265             270

Lys Lys Gln Lys Val Tyr Ser Leu Phe Tyr Arg Leu Asp Val Val Gln
    275             280             285

Ile Asn Glu Asn Gln Gly Asn Arg Ser Asn Asn Ser Asn Lys Glu Tyr
    290             295             300

Arg Leu Ile Asn Cys Asn Thr Ser Ala Ile Thr Gln Ala Cys Pro Lys
305             310             315             320

Val Ser Phe Glu Pro Ile Pro Ile His Tyr Cys Ala Pro Ala Gly Phe
            325             330             335

Ala Ile Leu Lys Cys Lys Asp Lys Lys Phe Asn Gly Thr Gly Pro Cys
            340             345             350

Pro Ser Val Ser Thr Val Gln Cys Thr His Gly Ile Lys Pro Val Val
            355             360             365

Ser Thr Gln Leu Leu Leu Asn Gly Ser Leu Ala Glu Glu Glu Val Met
    370             375             380

Ile Arg Ser Glu Asn Ile Thr Asn Asn Ala Lys Asn Ile Leu Val Gln
385             390             395             400

Phe Asn Thr Pro Val Gln Ile Asn Cys Thr Arg Pro Asn Asn Asn Thr
            405             410             415

Arg Lys Ser Ile Arg Ile Gly Pro Gly Gln Ala Phe Tyr Ala Thr Gly
            420             425             430

Asp Ile Ile Gly Asp Ile Arg Gln Ala His Cys Asn Val Ser Lys Ala
            435             440             445

Thr Trp Asn Glu Thr Leu Gly Lys Val Val Lys Gln Leu Arg Lys His
    450             455             460

Phe Gly Asn Asn Thr Ile Ile Arg Phe Ala Asn Ser Ser Gly Gly Asp
465             470             475             480

Leu Glu Val Thr Thr His Ser Phe Asn Cys Gly Gly Glu Phe Phe Tyr
            485             490             495

Cys Asn Thr Ser Gly Leu Phe Asn Ser Thr Trp Ile Ser Asn Thr Ser
            500             505             510

Val Gln Gly Ser Asn Ser Thr Gly Ser Asn Asp Ser Ile Thr Leu Pro
            515             520             525

Cys Arg Ile Lys Gln Ile Ile Asn Met Trp Gln Arg Ile Gly Gln Ala
    530             535             540

Met Tyr Ala Pro Pro Ile Gln Gly Val Ile Arg Cys Val Ser Asn Ile
```

-continued

```
545                 550                 555                 560

Thr Gly Leu Ile Leu Thr Arg Asp Gly Gly Ser Thr Asn Ser Thr Thr
                565                 570                 575

Glu Thr Phe Arg Pro Gly Gly Gly Asp Met Arg Asp Asn Trp Arg Ser
                580                 585                 590

Glu Leu Tyr Lys Tyr Lys Val Val Lys Ile Glu Pro Leu Gly Val Ala
                595                 600                 605

Pro Thr Arg Ala Lys Arg Arg Val Val Gly Gly Gly Gly Ser Trp
            610                 615                 620

Asn Ser Ser Trp Ser Asn Arg Asn Leu Ser Glu Ile Trp Asp Asn Met
625                 630                 635                 640

Thr Trp Leu Gln Trp Asp Lys Glu Ile Ser Asn Tyr Thr Gln Ile Ile
                645                 650                 655

Tyr Gly Leu Leu Glu Glu Ser Gln Asn Gln Gln Glu Lys Asn Glu Gln
                660                 665                 670

Asp Leu Leu Ala Leu Asp His His His His His His His
                675                 680                 685
```

```
<210> SEQ ID NO 34
<211> LENGTH: 696
<212> TYPE: PRT
<213> ORGANISM: Artificial Sequence
<220> FEATURE:
<223> OTHER INFORMATION: BG-B1(2/3)

<400> SEQUENCE: 34
```

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

Gly Ala Arg Ala Val Gly Ile Gly Ala Val Phe Leu Gly Phe Leu Gly
            35                  40                  45

Ala Ala Gly Ser Thr Met Gly Ala Ala Ser Met Thr Leu Thr Val Gln
        50                  55                  60

Ala Arg Asn Leu Leu Ser Gly Ile Val Gln Gln Gln Ser Asn Leu Leu
65                  70                  75                  80

Arg Ala Pro Glu Ala Gln Gln His Leu Leu Lys Leu Thr Val Trp Gly
                85                  90                  95

Ile Lys Gln Leu Gln Ala Arg Val Leu Ala Val Glu Arg Tyr Leu Arg
                100                 105                 110

Asp Gln Gln Leu Leu Gly Ile Trp Gly Cys Ser Gly Lys Leu Ile Cys
            115                 120                 125

Thr Thr Asn Val Pro Gly Gly Gly Ser Gly Gly Gly Gly Ser Ala
        130                 135                 140

Glu Asn Leu Trp Val Thr Val Tyr Tyr Gly Val Pro Val Trp Lys Asp
145                 150                 155                 160

Ala Glu Thr Thr Leu Phe Cys Ala Ser Asp Ala Lys Ala Tyr Glu Thr
                165                 170                 175

Glu Lys His Asn Val Trp Ala Thr His Ala Cys Val Pro Thr Asp Pro
            180                 185                 190

Asn Pro Gln Glu Ile His Leu Glu Asn Val Thr Glu Glu Phe Asn Met
            195                 200                 205

Trp Lys Asn Asn Met Val Glu Gln Met His Thr Asp Ile Ile Ser Leu
    210                 215                 220

Trp Asp Gln Ser Leu Lys Pro Cys Val Lys Leu Thr Pro Leu Cys Val
```

```
225            230            235            240

Thr Leu Gln Cys Thr Asn Val Thr Asn Asn Ile Thr Asp Asp Met Arg
            245            250            255

Gly Glu Leu Lys Asn Cys Ser Phe Asn Met Thr Thr Glu Leu Arg Asp
            260            265            270

Lys Lys Gln Lys Val Tyr Ser Leu Phe Tyr Arg Leu Asp Val Val Gln
            275            280            285

Ile Asn Glu Asn Gln Gly Asn Arg Ser Asn Asn Ser Asn Lys Glu Tyr
            290            295            300

Arg Leu Ile Asn Cys Asn Thr Ser Ala Ile Thr Gln Ala Cys Pro Lys
305            310            315            320

Val Ser Phe Glu Pro Ile Pro Ile His Tyr Cys Ala Pro Ala Gly Phe
            325            330            335

Ala Ile Leu Lys Cys Lys Asp Lys Lys Phe Asn Gly Thr Gly Pro Cys
            340            345            350

Pro Ser Val Ser Thr Val Gln Cys Thr His Gly Ile Lys Pro Val Val
            355            360            365

Ser Thr Gln Leu Leu Leu Asn Gly Ser Leu Ala Glu Glu Glu Val Met
            370            375            380

Ile Arg Ser Glu Asn Ile Thr Asn Asn Ala Lys Asn Ile Leu Val Gln
385            390            395            400

Phe Asn Thr Pro Val Gln Ile Asn Cys Thr Arg Pro Asn Asn Asn Thr
            405            410            415

Arg Lys Ser Ile Arg Ile Gly Pro Gly Gln Ala Phe Tyr Ala Thr Gly
            420            425            430

Asp Ile Ile Gly Asp Ile Arg Gln Ala His Cys Asn Val Ser Lys Ala
            435            440            445

Thr Trp Asn Glu Thr Leu Gly Lys Val Val Lys Gln Leu Arg Lys His
            450            455            460

Phe Gly Asn Asn Thr Ile Ile Arg Phe Ala Asn Ser Ser Gly Gly Asp
465            470            475            480

Leu Glu Val Thr Thr His Ser Phe Asn Cys Gly Gly Glu Phe Phe Tyr
            485            490            495

Cys Asn Thr Ser Gly Leu Phe Asn Ser Thr Trp Ile Ser Asn Thr Ser
            500            505            510

Val Gln Gly Ser Asn Ser Thr Gly Ser Asn Asp Ser Ile Thr Leu Pro
            515            520            525

Cys Arg Ile Lys Gln Ile Ile Asn Met Trp Gln Arg Ile Gly Gln Ala
            530            535            540

Met Tyr Ala Pro Pro Ile Gln Gly Val Ile Arg Cys Val Ser Asn Ile
545            550            555            560

Thr Gly Leu Ile Leu Thr Arg Asp Gly Gly Ser Thr Asn Ser Thr Thr
            565            570            575

Glu Thr Phe Arg Pro Gly Gly Gly Asp Met Arg Asp Asn Trp Arg Ser
            580            585            590

Glu Leu Tyr Lys Tyr Lys Val Val Lys Ile Glu Pro Leu Gly Val Ala
            595            600            605

Pro Thr Arg Ala Lys Arg Arg Val Val Gly Gly Gly Gly Ser Gly
            610            615            620

Gly Gly Gly Ser Gly Gly Gly Ser Trp Asn Ser Ser Trp Ser Asn
625            630            635            640

Arg Asn Leu Ser Glu Ile Trp Asp Asn Met Thr Trp Leu Gln Trp Asp
            645            650            655
```

```
Lys Glu Ile Ser Asn Tyr Thr Gln Ile Ile Tyr Gly Leu Leu Glu Glu
            660             665             670

Ser Gln Asn Gln Gln Glu Lys Asn Glu Gln Asp Leu Leu Ala Leu Asp
        675             680             685

His His His His His His His His
    690             695

<210> SEQ ID NO 35
<211> LENGTH: 678
<212> TYPE: PRT
<213> ORGANISM: Artificial Sequence
<220> FEATURE:
<223> OTHER INFORMATION: BG-B2(1-1)

<400> SEQUENCE: 35

Met Asp Ala Met Lys Arg Gly Leu Cys Cys Val Leu Leu Leu Cys Gly
1               5               10              15

Ala Val Phe Val Ser Pro Ser Gln Glu Ile His Ala Arg Phe Arg Arg
            20              25              30

Gly Ala Arg Ala Val Gly Ile Gly Ala Val Phe Leu Gly Phe Leu Gly
        35              40              45

Ala Ala Gly Ser Thr Met Gly Ala Ala Ser Met Thr Leu Thr Val Gln
    50              55              60

Ala Arg Asn Leu Leu Ser Gly Ile Val Gln Gln Ser Asn Leu Leu
65              70              75              80

Arg Ala Pro Glu Ala Gln Gln His Leu Leu Lys Leu Thr Val Trp Gly
            85              90              95

Ile Lys Gln Leu Gln Ala Arg Val Leu Ala Val Glu Arg Tyr Leu Arg
            100             105             110

Asp Gln Gln Leu Leu Gly Ile Trp Gly Cys Ser Gly Lys Leu Ile Cys
            115             120             125

Thr Thr Asn Val Pro Gly Gly Gly Ser Leu Trp Val Thr Val Tyr
    130             135             140

Tyr Gly Val Pro Val Trp Lys Asp Ala Glu Thr Thr Leu Phe Cys Ala
145             150             155             160

Ser Asp Ala Lys Ala Tyr Glu Thr Glu Lys His Asn Val Trp Ala Thr
            165             170             175

His Ala Cys Val Pro Thr Asp Pro Asn Pro Gln Glu Ile His Leu Glu
            180             185             190

Asn Val Thr Glu Glu Phe Asn Met Trp Lys Asn Asn Met Val Glu Gln
            195             200             205

Met His Thr Asp Ile Ile Ser Leu Trp Asp Gln Ser Leu Lys Pro Cys
    210             215             220

Val Lys Leu Thr Pro Leu Cys Val Thr Leu Gln Cys Thr Asn Val Thr
225             230             235             240

Asn Asn Ile Thr Asp Asp Met Arg Gly Glu Leu Lys Asn Cys Ser Phe
            245             250             255

Asn Met Thr Thr Glu Leu Arg Asp Lys Lys Gln Lys Val Tyr Ser Leu
            260             265             270

Phe Tyr Arg Leu Asp Val Val Gln Ile Asn Glu Asn Gln Gly Asn Arg
            275             280             285

Ser Asn Asn Ser Asn Lys Glu Tyr Arg Leu Ile Asn Cys Asn Thr Ser
    290             295             300

Ala Ile Thr Gln Ala Cys Pro Lys Val Ser Phe Glu Pro Ile Pro Ile
305             310             315             320
```

```
His Tyr Cys Ala Pro Ala Gly Phe Ala Ile Leu Lys Cys Lys Asp Lys
                325                 330                 335

Lys Phe Asn Gly Thr Gly Pro Cys Pro Ser Val Ser Thr Val Gln Cys
                340                 345                 350

Thr His Gly Ile Lys Pro Val Val Ser Thr Gln Leu Leu Leu Asn Gly
                355                 360                 365

Ser Leu Ala Glu Glu Glu Val Met Ile Arg Ser Glu Asn Ile Thr Asn
        370                 375                 380

Asn Ala Lys Asn Ile Leu Val Gln Phe Asn Thr Pro Val Gln Ile Asn
385                 390                 395                 400

Cys Thr Arg Pro Asn Asn Asn Thr Arg Lys Ser Ile Arg Ile Gly Pro
                405                 410                 415

Gly Gln Ala Phe Tyr Ala Thr Gly Asp Ile Ile Gly Asp Ile Arg Gln
                420                 425                 430

Ala His Cys Asn Val Ser Lys Ala Thr Trp Asn Glu Thr Leu Gly Lys
                435                 440                 445

Val Val Lys Gln Leu Arg Lys His Phe Gly Asn Asn Thr Ile Ile Arg
        450                 455                 460

Phe Ala Asn Ser Ser Gly Gly Asp Leu Glu Val Thr Thr His Ser Phe
465                 470                 475                 480

Asn Cys Gly Gly Glu Phe Phe Tyr Cys Asn Thr Ser Gly Leu Phe Asn
                485                 490                 495

Ser Thr Trp Ile Ser Asn Thr Ser Val Gln Gly Ser Asn Ser Thr Gly
                500                 505                 510

Ser Asn Asp Ser Ile Thr Leu Pro Cys Arg Ile Lys Gln Ile Ile Asn
                515                 520                 525

Met Trp Gln Arg Ile Gly Gln Ala Met Tyr Ala Pro Pro Ile Gln Gly
        530                 535                 540

Val Ile Arg Cys Val Ser Asn Ile Thr Gly Leu Ile Leu Thr Arg Asp
545                 550                 555                 560

Gly Gly Ser Thr Asn Ser Thr Thr Glu Thr Phe Arg Pro Gly Gly Gly
                565                 570                 575

Asp Met Arg Asp Asn Trp Arg Ser Glu Leu Tyr Lys Tyr Lys Val Val
                580                 585                 590

Lys Ile Glu Pro Leu Gly Val Ala Pro Thr Arg Ala Lys Arg Arg Val
                595                 600                 605

Val Gly Gly Gly Gly Ser Trp Asn Ser Ser Trp Ser Asn Arg Asn
        610                 615                 620

Leu Ser Glu Ile Trp Asp Asn Met Thr Trp Leu Gln Trp Asp Lys Glu
625                 630                 635                 640

Ile Ser Asn Tyr Thr Gln Ile Ile Tyr Gly Leu Leu Glu Glu Ser Gln
                645                 650                 655

Asn Gln Gln Glu Lys Asn Glu Gln Asp Leu Leu Ala Leu Asp His His
                660                 665                 670

His His His His His His
        675
```

<210> SEQ ID NO 36
<211> LENGTH: 684
<212> TYPE: PRT
<213> ORGANISM: Artificial Sequence
<220> FEATURE:
<223> OTHER INFORMATION: BG-B2(1-2)

<400> SEQUENCE: 36

-continued

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
                20                  25                  30

Gly Ala Arg Ala Val Gly Ile Gly Ala Val Phe Leu Gly Phe Leu Gly
            35                  40                  45

Ala Ala Gly Ser Thr Met Gly Ala Ala Ser Met Thr Leu Thr Val Gln
    50                  55                  60

Ala Arg Asn Leu Leu Ser Gly Ile Val Gln Gln Gln Ser Asn Leu Leu
65                  70                  75                  80

Arg Ala Pro Glu Ala Gln Gln His Leu Leu Lys Leu Thr Val Trp Gly
                85                  90                  95

Ile Lys Gln Leu Gln Ala Arg Val Leu Ala Val Glu Arg Tyr Leu Arg
            100                 105                 110

Asp Gln Gln Leu Leu Gly Ile Trp Gly Cys Ser Gly Lys Leu Ile Cys
            115                 120                 125

Thr Thr Asn Val Pro Gly Gly Gly Ser Leu Trp Val Thr Val Tyr
    130                 135                 140

Tyr Gly Val Pro Val Trp Lys Asp Ala Glu Thr Thr Leu Phe Cys Ala
145                 150                 155                 160

Ser Asp Ala Lys Ala Tyr Glu Thr Glu Lys His Asn Val Trp Ala Thr
                165                 170                 175

His Ala Cys Val Pro Thr Asp Pro Asn Pro Gln Glu Ile His Leu Glu
                180                 185                 190

Asn Val Thr Glu Glu Phe Asn Met Trp Lys Asn Asn Met Val Glu Gln
                195                 200                 205

Met His Thr Asp Ile Ile Ser Leu Trp Asp Gln Ser Leu Lys Pro Cys
    210                 215                 220

Val Lys Leu Thr Pro Leu Cys Val Thr Leu Gln Cys Thr Asn Val Thr
225                 230                 235                 240

Asn Asn Ile Thr Asp Asp Met Arg Gly Glu Leu Lys Asn Cys Ser Phe
                245                 250                 255

Asn Met Thr Thr Glu Leu Arg Asp Lys Lys Gln Lys Val Tyr Ser Leu
            260                 265                 270

Phe Tyr Arg Leu Asp Val Val Gln Ile Asn Glu Asn Gln Gly Asn Arg
    275                 280                 285

Ser Asn Asn Ser Asn Lys Glu Tyr Arg Leu Ile Asn Cys Asn Thr Ser
    290                 295                 300

Ala Ile Thr Gln Ala Cys Pro Lys Val Ser Phe Glu Pro Ile Pro Ile
305                 310                 315                 320

His Tyr Cys Ala Pro Ala Gly Phe Ala Ile Leu Lys Cys Lys Asp Lys
                325                 330                 335

Lys Phe Asn Gly Thr Gly Pro Cys Pro Ser Val Ser Thr Val Gln Cys
            340                 345                 350

Thr His Gly Ile Lys Pro Val Val Ser Thr Gln Leu Leu Leu Asn Gly
            355                 360                 365

Ser Leu Ala Glu Glu Glu Val Met Ile Arg Ser Glu Asn Ile Thr Asn
    370                 375                 380

Asn Ala Lys Asn Ile Leu Val Gln Phe Asn Thr Pro Val Gln Ile Asn
385                 390                 395                 400

Cys Thr Arg Pro Asn Asn Asn Thr Arg Lys Ser Ile Arg Ile Gly Pro
                405                 410                 415
```

-continued

```
Gly Gln Ala Phe Tyr Ala Thr Gly Asp Ile Ile Gly Asp Ile Arg Gln
            420                 425                 430

Ala His Cys Asn Val Ser Lys Ala Thr Trp Asn Glu Thr Leu Gly Lys
            435                 440                 445

Val Val Lys Gln Leu Arg Lys His Phe Gly Asn Asn Thr Ile Ile Arg
    450                 455                 460

Phe Ala Asn Ser Ser Gly Gly Asp Leu Glu Val Thr Thr His Ser Phe
465                 470                 475                 480

Asn Cys Gly Gly Glu Phe Phe Tyr Cys Asn Thr Ser Gly Leu Phe Asn
                485                 490                 495

Ser Thr Trp Ile Ser Asn Thr Ser Val Gln Gly Ser Asn Ser Thr Gly
            500                 505                 510

Ser Asn Asp Ser Ile Thr Leu Pro Cys Arg Ile Lys Gln Ile Ile Asn
            515                 520                 525

Met Trp Gln Arg Ile Gly Gln Ala Met Tyr Ala Pro Pro Ile Gln Gly
    530                 535                 540

Val Ile Arg Cys Val Ser Asn Ile Thr Gly Leu Ile Leu Thr Arg Asp
545                 550                 555                 560

Gly Gly Ser Thr Asn Ser Thr Thr Glu Thr Phe Arg Pro Gly Gly Gly
                565                 570                 575

Asp Met Arg Asp Asn Trp Arg Ser Glu Leu Tyr Lys Tyr Lys Val Val
            580                 585                 590

Lys Ile Glu Pro Leu Gly Val Ala Pro Thr Arg Ala Lys Arg Arg Val
            595                 600                 605

Val Gly Gly Gly Gly Ser Gly Gly Gly Gly Ser Trp Asn Ser
    610                 615                 620

Ser Trp Ser Asn Arg Asn Leu Ser Glu Ile Trp Asp Asn Met Thr Trp
625                 630                 635                 640

Leu Gln Trp Asp Lys Glu Ile Ser Asn Tyr Thr Gln Ile Ile Tyr Gly
                645                 650                 655

Leu Leu Glu Glu Ser Gln Asn Gln Gln Glu Lys Asn Glu Gln Asp Leu
            660                 665                 670

Leu Ala Leu Asp His His His His His His His
            675                 680
```

```
<210> SEQ ID NO 37
<211> LENGTH: 688
<212> TYPE: PRT
<213> ORGANISM: Artificial Sequence
<220> FEATURE:
<223> OTHER INFORMATION: BG-B2(1-3)

<400> SEQUENCE: 37
```

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ala Val Gly Ile Gly Ala Val Phe Leu Gly Phe Leu Gly
            35                  40                  45

Ala Ala Gly Ser Thr Met Gly Ala Ala Ser Met Thr Leu Thr Val Gln
    50                  55                  60

Ala Arg Asn Leu Leu Ser Gly Ile Val Gln Gln Gln Ser Asn Leu Leu
65                  70                  75                  80

Arg Ala Pro Glu Ala Gln Gln His Leu Leu Lys Leu Thr Val Trp Gly
                85                  90                  95
```

-continued

```
Ile Lys Gln Leu Gln Ala Arg Val Leu Ala Val Glu Arg Tyr Leu Arg
            100                 105                 110

Asp Gln Gln Leu Leu Gly Ile Trp Gly Cys Ser Gly Lys Leu Ile Cys
            115                 120                 125

Thr Thr Asn Val Pro Gly Gly Gly Gly Ser Leu Trp Val Thr Val Tyr
        130                 135                 140

Tyr Gly Val Pro Val Trp Lys Asp Ala Glu Thr Thr Leu Phe Cys Ala
145                 150                 155                 160

Ser Asp Ala Lys Ala Tyr Glu Thr Glu Lys His Asn Val Trp Ala Thr
                165                 170                 175

His Ala Cys Val Pro Thr Asp Pro Asn Pro Gln Glu Ile His Leu Glu
            180                 185                 190

Asn Val Thr Glu Glu Phe Asn Met Trp Lys Asn Asn Met Val Glu Gln
            195                 200                 205

Met His Thr Asp Ile Ile Ser Leu Trp Asp Gln Ser Leu Lys Pro Cys
        210                 215                 220

Val Lys Leu Thr Pro Leu Cys Val Thr Leu Gln Cys Thr Asn Val Thr
225                 230                 235                 240

Asn Asn Ile Thr Asp Asp Met Arg Gly Glu Leu Lys Asn Cys Ser Phe
                245                 250                 255

Asn Met Thr Thr Glu Leu Arg Asp Lys Lys Gln Lys Val Tyr Ser Leu
            260                 265                 270

Phe Tyr Arg Leu Asp Val Val Gln Ile Asn Glu Asn Gln Gly Asn Arg
            275                 280                 285

Ser Asn Asn Ser Asn Lys Glu Tyr Arg Leu Ile Asn Cys Asn Thr Ser
        290                 295                 300

Ala Ile Thr Gln Ala Cys Pro Lys Val Ser Phe Glu Pro Ile Pro Ile
305                 310                 315                 320

His Tyr Cys Ala Pro Ala Gly Phe Ala Ile Leu Lys Cys Lys Asp Lys
                325                 330                 335

Lys Phe Asn Gly Thr Gly Pro Cys Pro Ser Val Ser Thr Val Gln Cys
            340                 345                 350

Thr His Gly Ile Lys Pro Val Val Ser Thr Gln Leu Leu Leu Asn Gly
            355                 360                 365

Ser Leu Ala Glu Glu Glu Val Met Ile Arg Ser Glu Asn Ile Thr Asn
        370                 375                 380

Asn Ala Lys Asn Ile Leu Val Gln Phe Asn Thr Pro Val Gln Ile Asn
385                 390                 395                 400

Cys Thr Arg Pro Asn Asn Asn Thr Arg Lys Ser Ile Arg Ile Gly Pro
                405                 410                 415

Gly Gln Ala Phe Tyr Ala Thr Gly Asp Ile Ile Gly Asp Ile Arg Gln
            420                 425                 430

Ala His Cys Asn Val Ser Lys Ala Thr Trp Asn Glu Thr Leu Gly Lys
            435                 440                 445

Val Val Lys Gln Leu Arg Lys His Phe Gly Asn Asn Thr Ile Ile Arg
        450                 455                 460

Phe Ala Asn Ser Ser Gly Gly Asp Leu Glu Val Thr Thr His Ser Phe
465                 470                 475                 480

Asn Cys Gly Gly Glu Phe Phe Tyr Cys Asn Thr Ser Gly Leu Phe Asn
                485                 490                 495

Ser Thr Trp Ile Ser Asn Thr Ser Val Gln Gly Ser Asn Ser Thr Gly
            500                 505                 510

Ser Asn Asp Ser Ile Thr Leu Pro Cys Arg Ile Lys Gln Ile Ile Asn
```

-continued

```
              515                    520                    525

Met Trp Gln Arg Ile Gly Gln Ala Met Tyr Ala Pro Pro Ile Gln Gly
    530                    535                    540

Val Ile Arg Cys Val Ser Asn Ile Thr Gly Leu Ile Leu Thr Arg Asp
545                    550                    555                    560

Gly Gly Ser Thr Asn Ser Thr Thr Glu Thr Phe Arg Pro Gly Gly Gly
                565                    570                    575

Asp Met Arg Asp Asn Trp Arg Ser Glu Leu Tyr Lys Tyr Lys Val Val
                580                    585                    590

Lys Ile Glu Pro Leu Gly Val Ala Pro Thr Arg Ala Lys Arg Arg Val
                595                    600                    605

Val Gly Gly Gly Gly Ser Gly Gly Gly Gly Ser Gly Gly Gly Gly
                610                    615                    620

Ser Trp Asn Ser Ser Trp Ser Asn Arg Asn Leu Ser Glu Ile Trp Asp
625                    630                    635                    640

Asn Met Thr Trp Leu Gln Trp Asp Lys Glu Ile Ser Asn Tyr Thr Gln
                645                    650                    655

Ile Ile Tyr Gly Leu Leu Glu Glu Ser Gln Asn Gln Gln Glu Lys Asn
                660                    665                    670

Glu Gln Asp Leu Leu Ala Leu Asp His His His His His His His His
                675                    680                    685

<210> SEQ ID NO 38
<211> LENGTH: 681
<212> TYPE: PRT
<213> ORGANISM: Artificial Sequence
<220> FEATURE:
<223> OTHER INFORMATION: BG-C1(1/1)

<400> SEQUENCE: 38

Met Asp Ala Met Lys Arg Gly Leu Cys Cys Val Leu Leu Leu Cys Gly
1                5                   10                   15

Ala Val Phe Val Ser Pro Ser Gln Glu Ile His Ala Arg Phe Arg Arg
                20                   25                   30

Gly Ala Arg Ala Val Gly Ile Gly Ala Val Phe Leu Gly Phe Leu Gly
                35                   40                   45

Ala Ala Gly Ser Thr Met Gly Ala Ala Ser Met Thr Leu Thr Val Gln
    50                   55                   60

Ala Arg Asn Leu Leu Ser Gly Ile Val Gln Gln Gln Ser Asn Leu Leu
65                   70                   75                   80

Arg Ala Pro Glu Ala Gln Gln His Leu Leu Lys Leu Thr Val Trp Gly
                85                   90                   95

Ile Lys Gln Leu Gln Ala Arg Val Leu Ala Val Glu Arg Tyr Leu Arg
                100                  105                  110

Asp Gln Gln Leu Leu Gly Ile Trp Gly Cys Ser Gly Lys Leu Ile Cys
                115                  120                  125

Thr Thr Asn Val Pro Trp Asn Ser Ser Trp Ser Asn Gly Gly Gly Gly
    130                  135                  140

Ser Ala Glu Asn Leu Trp Val Thr Val Tyr Tyr Gly Val Pro Val Trp
145                  150                  155                  160

Lys Asp Ala Glu Thr Thr Leu Phe Cys Ala Ser Asp Ala Lys Ala Tyr
                165                  170                  175

Glu Thr Glu Lys His Asn Val Trp Ala Thr His Ala Cys Val Pro Thr
                180                  185                  190

Asp Pro Asn Pro Gln Glu Ile His Leu Glu Asn Val Thr Glu Glu Phe
```

-continued

```
              195                 200                 205

Asn Met Trp Lys Asn Asn Met Val Glu Gln Met His Thr Asp Ile Ile
    210                 215                 220

Ser Leu Trp Asp Gln Ser Leu Lys Pro Cys Val Lys Leu Thr Pro Leu
225                 230                 235                 240

Cys Val Thr Leu Gln Cys Thr Asn Val Thr Asn Asn Ile Thr Asp Asp
                245                 250                 255

Met Arg Gly Glu Leu Lys Asn Cys Ser Phe Asn Met Thr Thr Glu Leu
                260                 265                 270

Arg Asp Lys Lys Gln Lys Val Tyr Ser Leu Phe Tyr Arg Leu Asp Val
                275                 280                 285

Val Gln Ile Asn Glu Asn Gln Gly Asn Arg Ser Asn Asn Ser Asn Lys
    290                 295                 300

Glu Tyr Arg Leu Ile Asn Cys Asn Thr Ser Ala Ile Thr Gln Ala Cys
305                 310                 315                 320

Pro Lys Val Ser Phe Glu Pro Ile Pro Ile His Tyr Cys Ala Pro Ala
                325                 330                 335

Gly Phe Ala Ile Leu Lys Cys Lys Asp Lys Lys Phe Asn Gly Thr Gly
                340                 345                 350

Pro Cys Pro Ser Val Ser Thr Val Gln Cys Thr His Gly Ile Lys Pro
                355                 360                 365

Val Val Ser Thr Gln Leu Leu Leu Asn Gly Ser Leu Ala Glu Glu Glu
    370                 375                 380

Val Met Ile Arg Ser Glu Asn Ile Thr Asn Asn Ala Lys Asn Ile Leu
385                 390                 395                 400

Val Gln Phe Asn Thr Pro Val Gln Ile Asn Cys Thr Arg Pro Asn Asn
                405                 410                 415

Asn Thr Arg Lys Ser Ile Arg Ile Gly Pro Gly Gln Ala Phe Tyr Ala
                420                 425                 430

Thr Gly Asp Ile Ile Gly Asp Ile Arg Gln Ala His Cys Asn Val Ser
                435                 440                 445

Lys Ala Thr Trp Asn Glu Thr Leu Gly Lys Val Val Lys Gln Leu Arg
    450                 455                 460

Lys His Phe Gly Asn Asn Thr Ile Ile Arg Phe Ala Asn Ser Ser Gly
465                 470                 475                 480

Gly Asp Leu Glu Val Thr Thr His Ser Phe Asn Cys Gly Gly Glu Phe
                485                 490                 495

Phe Tyr Cys Asn Thr Ser Gly Leu Phe Asn Ser Thr Trp Ile Ser Asn
                500                 505                 510

Thr Ser Val Gln Gly Ser Asn Ser Thr Gly Ser Asn Asp Ser Ile Thr
                515                 520                 525

Leu Pro Cys Arg Ile Lys Gln Ile Ile Asn Met Trp Gln Arg Ile Gly
    530                 535                 540

Gln Ala Met Tyr Ala Pro Pro Ile Gln Gly Val Ile Arg Cys Val Ser
545                 550                 555                 560

Asn Ile Thr Gly Leu Ile Leu Thr Arg Asp Gly Gly Ser Thr Asn Ser
                565                 570                 575

Thr Thr Glu Thr Phe Arg Pro Gly Gly Gly Asp Met Arg Asp Asn Trp
                580                 585                 590

Arg Ser Glu Leu Tyr Lys Tyr Lys Val Val Lys Ile Glu Pro Leu Gly
                595                 600                 605

Val Ala Pro Thr Arg Ala Lys Arg Arg Val Val Gly Gly Gly Gly Gly
    610                 615                 620
```

```
Ser Arg Asn Leu Ser Glu Ile Trp Asp Asn Met Thr Trp Leu Gln Trp
625                 630                 635                 640

Asp Lys Glu Ile Ser Asn Tyr Thr Gln Ile Ile Tyr Gly Leu Leu Glu
                    645                 650                 655

Glu Ser Gln Asn Gln Gln Glu Lys Asn Glu Gln Asp Leu Leu Ala Leu
                660                 665                 670

Asp His His His His His His His
        675                 680

<210> SEQ ID NO 39
<211> LENGTH: 686
<212> TYPE: PRT
<213> ORGANISM: Artificial Sequence
<220> FEATURE:
<223> OTHER INFORMATION: BG-C1(1/2)

<400> SEQUENCE: 39

Met Asp Ala Met Lys Arg Gly Leu Cys Cys Val Leu Leu Leu Cys Gly
1                 5                  10                  15

Ala Val Phe Val Ser Pro Ser Gln Glu Ile His Ala Arg Phe Arg Arg
                20                  25                  30

Gly Ala Arg Ala Val Gly Ile Gly Ala Val Phe Leu Gly Phe Leu Gly
                35                  40                  45

Ala Ala Gly Ser Thr Met Gly Ala Ala Ser Met Thr Leu Thr Val Gln
        50                  55                  60

Ala Arg Asn Leu Leu Ser Gly Ile Val Gln Gln Gln Ser Asn Leu Leu
65                  70                  75                  80

Arg Ala Pro Glu Ala Gln Gln His Leu Leu Lys Leu Thr Val Trp Gly
                85                  90                  95

Ile Lys Gln Leu Gln Ala Arg Val Leu Ala Val Glu Arg Tyr Leu Arg
                100                 105                 110

Asp Gln Gln Leu Leu Gly Ile Trp Gly Cys Ser Gly Lys Leu Ile Cys
        115                 120                 125

Thr Thr Asn Val Pro Trp Asn Ser Ser Trp Ser Asn Gly Gly Gly Gly
        130                 135                 140

Ser Ala Glu Asn Leu Trp Val Thr Val Tyr Tyr Gly Val Pro Val Trp
145                 150                 155                 160

Lys Asp Ala Glu Thr Thr Leu Phe Cys Ala Ser Asp Ala Lys Ala Tyr
                165                 170                 175

Glu Thr Glu Lys His Asn Val Trp Ala Thr His Ala Cys Val Pro Thr
                180                 185                 190

Asp Pro Asn Pro Gln Glu Ile His Leu Glu Asn Val Thr Glu Glu Phe
        195                 200                 205

Asn Met Trp Lys Asn Asn Met Val Glu Gln Met His Thr Asp Ile Ile
        210                 215                 220

Ser Leu Trp Asp Gln Ser Leu Lys Pro Cys Val Lys Leu Thr Pro Leu
225                 230                 235                 240

Cys Val Thr Leu Gln Cys Thr Asn Val Thr Asn Asn Ile Thr Asp Asp
                245                 250                 255

Met Arg Gly Glu Leu Lys Asn Cys Ser Phe Asn Met Thr Thr Glu Leu
                260                 265                 270

Arg Asp Lys Lys Gln Lys Val Tyr Ser Leu Phe Tyr Arg Leu Asp Val
        275                 280                 285

Val Gln Ile Asn Glu Asn Gln Gly Asn Arg Ser Asn Asn Ser Asn Lys
        290                 295                 300
```

-continued

```
Glu Tyr Arg Leu Ile Asn Cys Asn Thr Ser Ala Ile Thr Gln Ala Cys
305                 310                 315                 320

Pro Lys Val Ser Phe Glu Pro Ile Pro Ile His Tyr Cys Ala Pro Ala
                325                 330                 335

Gly Phe Ala Ile Leu Lys Cys Lys Asp Lys Lys Phe Asn Gly Thr Gly
                340                 345                 350

Pro Cys Pro Ser Val Ser Thr Val Gln Cys Thr His Gly Ile Lys Pro
                355                 360                 365

Val Val Ser Thr Gln Leu Leu Leu Asn Gly Ser Leu Ala Glu Glu Glu
                370                 375                 380

Val Met Ile Arg Ser Glu Asn Ile Thr Asn Asn Ala Lys Asn Ile Leu
385                 390                 395                 400

Val Gln Phe Asn Thr Pro Val Gln Ile Asn Cys Thr Arg Pro Asn Asn
                405                 410                 415

Asn Thr Arg Lys Ser Ile Arg Ile Gly Pro Gly Gln Ala Phe Tyr Ala
                420                 425                 430

Thr Gly Asp Ile Ile Gly Asp Ile Arg Gln Ala His Cys Asn Val Ser
                435                 440                 445

Lys Ala Thr Trp Asn Glu Thr Leu Gly Lys Val Val Lys Gln Leu Arg
                450                 455                 460

Lys His Phe Gly Asn Asn Thr Ile Ile Arg Phe Ala Asn Ser Ser Gly
465                 470                 475                 480

Gly Asp Leu Glu Val Thr Thr His Ser Phe Asn Cys Gly Gly Glu Phe
                485                 490                 495

Phe Tyr Cys Asn Thr Ser Gly Leu Phe Asn Ser Thr Trp Ile Ser Asn
                500                 505                 510

Thr Ser Val Gln Gly Ser Asn Ser Thr Gly Ser Asn Asp Ser Ile Thr
                515                 520                 525

Leu Pro Cys Arg Ile Lys Gln Ile Ile Asn Met Trp Gln Arg Ile Gly
                530                 535                 540

Gln Ala Met Tyr Ala Pro Pro Ile Gln Gly Val Ile Arg Cys Val Ser
545                 550                 555                 560

Asn Ile Thr Gly Leu Ile Leu Thr Arg Asp Gly Gly Ser Thr Asn Ser
                565                 570                 575

Thr Thr Glu Thr Phe Arg Pro Gly Gly Gly Asp Met Arg Asp Asn Trp
                580                 585                 590

Arg Ser Glu Leu Tyr Lys Tyr Lys Val Val Lys Ile Glu Pro Leu Gly
                595                 600                 605

Val Ala Pro Thr Arg Ala Lys Arg Arg Val Val Gly Gly Gly Gly Gly
                610                 615                 620

Ser Gly Gly Gly Gly Ser Arg Asn Leu Ser Glu Ile Trp Asp Asn Met
625                 630                 635                 640

Thr Trp Leu Gln Trp Asp Lys Glu Ile Ser Asn Tyr Thr Gln Ile Ile
                645                 650                 655

Tyr Gly Leu Leu Glu Glu Ser Gln Asn Gln Gln Glu Lys Asn Glu Gln
                660                 665                 670

Asp Leu Leu Ala Leu Asp His His His His His His
                675                 680                 685
```

```
<210> SEQ ID NO 40
<211> LENGTH: 691
<212> TYPE: PRT
<213> ORGANISM: Artificial Sequence
<220> FEATURE:
```

<223> OTHER INFORMATION: BG-C1(1/3)

<400> SEQUENCE: 40

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ala Val Gly Ile Gly Ala Val Phe Leu Gly Phe Leu Gly
            35                  40                  45

Ala Ala Gly Ser Thr Met Gly Ala Ala Ser Met Thr Leu Thr Val Gln
        50                  55                  60

Ala Arg Asn Leu Leu Ser Gly Ile Val Gln Gln Gln Ser Asn Leu Leu
65                  70                  75                  80

Arg Ala Pro Glu Ala Gln Gln His Leu Leu Lys Leu Thr Val Trp Gly
                85                  90                  95

Ile Lys Gln Leu Gln Ala Arg Val Leu Ala Val Glu Arg Tyr Leu Arg
            100                 105                 110

Asp Gln Gln Leu Leu Gly Ile Trp Gly Cys Ser Gly Lys Leu Ile Cys
            115                 120                 125

Thr Thr Asn Val Pro Trp Asn Ser Ser Trp Ser Asn Gly Gly Gly Gly
    130                 135                 140

Ser Ala Glu Asn Leu Trp Val Thr Val Tyr Tyr Gly Val Pro Val Trp
145                 150                 155                 160

Lys Asp Ala Glu Thr Thr Leu Phe Cys Ala Ser Asp Ala Lys Ala Tyr
                165                 170                 175

Glu Thr Glu Lys His Asn Val Trp Ala Thr His Ala Cys Val Pro Thr
            180                 185                 190

Asp Pro Asn Pro Gln Glu Ile His Leu Glu Asn Val Thr Glu Glu Phe
            195                 200                 205

Asn Met Trp Lys Asn Asn Met Val Glu Gln Met His Thr Asp Ile Ile
    210                 215                 220

Ser Leu Trp Asp Gln Ser Leu Lys Pro Cys Val Lys Leu Thr Pro Leu
225                 230                 235                 240

Cys Val Thr Leu Gln Cys Thr Asn Val Thr Asn Asn Ile Thr Asp Asp
                245                 250                 255

Met Arg Gly Glu Leu Lys Asn Cys Ser Phe Asn Met Thr Thr Glu Leu
            260                 265                 270

Arg Asp Lys Lys Gln Lys Val Tyr Ser Leu Phe Tyr Arg Leu Asp Val
            275                 280                 285

Val Gln Ile Asn Glu Asn Gln Gly Asn Arg Ser Asn Asn Ser Asn Lys
    290                 295                 300

Glu Tyr Arg Leu Ile Asn Cys Asn Thr Ser Ala Ile Thr Gln Ala Cys
305                 310                 315                 320

Pro Lys Val Ser Phe Glu Pro Ile Pro Ile His Tyr Cys Ala Pro Ala
                325                 330                 335

Gly Phe Ala Ile Leu Lys Cys Lys Asp Lys Lys Phe Asn Gly Thr Gly
            340                 345                 350

Pro Cys Pro Ser Val Ser Thr Val Gln Cys Thr His Gly Ile Lys Pro
            355                 360                 365

Val Val Ser Thr Gln Leu Leu Leu Asn Gly Ser Leu Ala Glu Glu Glu
    370                 375                 380

```
Val Met Ile Arg Ser Glu Asn Ile Thr Asn Asn Ala Lys Asn Ile Leu
385                 390                 395                 400

Val Gln Phe Asn Thr Pro Val Gln Ile Asn Cys Thr Arg Pro Asn Asn
                405                 410                 415

Asn Thr Arg Lys Ser Ile Arg Ile Gly Pro Gly Gln Ala Phe Tyr Ala
            420                 425                 430

Thr Gly Asp Ile Ile Gly Asp Ile Arg Gln Ala His Cys Asn Val Ser
            435                 440                 445

Lys Ala Thr Trp Asn Glu Thr Leu Gly Lys Val Val Lys Gln Leu Arg
        450                 455                 460

Lys His Phe Gly Asn Asn Thr Ile Ile Arg Phe Ala Asn Ser Ser Gly
465                 470                 475                 480

Gly Asp Leu Glu Val Thr Thr His Ser Phe Asn Cys Gly Gly Glu Phe
                485                 490                 495

Phe Tyr Cys Asn Thr Ser Gly Leu Phe Asn Ser Thr Trp Ile Ser Asn
            500                 505                 510

Thr Ser Val Gln Gly Ser Asn Ser Thr Gly Ser Asn Asp Ser Ile Thr
            515                 520                 525

Leu Pro Cys Arg Ile Lys Gln Ile Ile Asn Met Trp Gln Arg Ile Gly
        530                 535                 540

Gln Ala Met Tyr Ala Pro Pro Ile Gln Gly Val Ile Arg Cys Val Ser
545                 550                 555                 560

Asn Ile Thr Gly Leu Ile Leu Thr Arg Asp Gly Gly Ser Thr Asn Ser
                565                 570                 575

Thr Thr Glu Thr Phe Arg Pro Gly Gly Gly Asp Met Arg Asp Asn Trp
            580                 585                 590

Arg Ser Glu Leu Tyr Lys Tyr Lys Val Val Lys Ile Glu Pro Leu Gly
            595                 600                 605

Val Ala Pro Thr Arg Ala Lys Arg Arg Val Val Gly Gly Gly Gly Gly
        610                 615                 620

Ser Gly Gly Gly Gly Ser Gly Gly Gly Gly Ser Arg Asn Leu Ser Glu
625                 630                 635                 640

Ile Trp Asp Asn Met Thr Trp Leu Gln Trp Asp Lys Glu Ile Ser Asn
                645                 650                 655

Tyr Thr Gln Ile Ile Tyr Gly Leu Leu Glu Glu Ser Gln Asn Gln Gln
            660                 665                 670

Glu Lys Asn Glu Gln Asp Leu Leu Ala Leu Asp His His His His His
            675                 680                 685

His His His
    690
```

```
<210> SEQ ID NO 41
<211> LENGTH: 4
<212> TYPE: PRT
<213> ORGANISM: Artificial Sequence
<220> FEATURE:
<223> OTHER INFORMATION: gp160 protein-furin cleavage site

<400> SEQUENCE: 41

Arg Glu Lys Arg
1
```

MODIFIED ENVELOPE PROTEIN OF HUMAN IMMUNODEFICIENCY VIRUS AND USE THEREOF

REFERENCE TO AN ELECTRONIC SEQUENCE LISTING

The contents of the sequence listing (0199-XU12US1_SeqList.txt; Size: 222 KB; and Date of Creation: May 11, 2023) is herein incorporated by reference in its entirety.

TECHNICAL FIELD

The present invention relates to the field of virology. Specifically, the present invention relates to a novel designed HIV-1 Env trimer protein, HIV-1 pseudovirus and virus expressing the Env trimer protein, and use thereof for preventing and/or treating HIV infection.

BACKGROUND ART

Human immunodeficiency virus type 1 HIV-1 (Human immunodeficiency virus-1) is the main pathogen that induces AIDS, and belongs to the genus of *Lentivirus*, the family of Retrovirus. Its virus particle is composed of core/envelope proteins and genetic materials of diploid single-stranded positive-sense RNA. The single-stranded genome is about 9.8 kb, encoding three structural proteins: Env, Gag, Pol, and six auxiliary proteins: vpr, vif, vpu, nef, tat, rev. The auxiliary proteins coordinate with each other to form a regulatory network for HIV-1 viral replication. The Pol gene encodes a polymerase precursor protein, which forms protease (PR), reverse transcriptase (RT) and integrase (IN) after cleavage, which are key enzymes for virus maturation, replication and infection. The Gag protein encoded by the Gag gene is the main structural protein of the virus and is responsible for the assembly process of the virus, accounting for 50% of the entire virus mass; the Gag protein has MA, CA, NC and p6 in sequence from the N-terminal to the C-terminal. MA is a matrix protein, which aggregates to the plasma membrane of infected cells to recruit another structural protein Env so as to start the virus assembly process; CA is a capsid protein, and the capsid protein of mature HIV-1 virus is cone-shaped, which drives virus maturation through protein interaction; NC is a nucleocapsid protein, which can capture the genome during the packaging process of the virus and make it a complete virus particle; p6 has binding sites for other proteins including auxiliary proteins, which are closely related to the process such as replication and transcription of HIV-1. There are PR cleavage sites between different components of Gag protein, and mature particles are gradually formed through its action (Sundquist, W. I. and H. G. Krausslich, HIV-1 assembly, budding, and maturation. Cold Spring Harb Perspect Med, 2012.). Env is the only antigen on the surface of HIV-1. The number of Env trimers on the surface of each virus is very small, about 7-14, but they can effectively trigger the infection of host cells, which shows the importance thereof. Env is a heterotrimeric protein, its precursor is gp160 protein with a molecular weight of 160 KD, which is digested by furin enzyme into gp120 and gp41 during the process of virus maturation, and gp120 and gp41 form a heterotrimer through non-covalent interaction; gp120 exists extracellularly, and during virus infection, gp120 recognizes the receptor molecule CD4 on the host cell to trigger virus infection. There are key epitopes such as CD4bs, V1V2, V3, and CD4i on gp120, in which CD4bs epitope recognizes the receptor molecule; gp41 comprises an extracellular region, a membrane-proximal external region (MPER), a transmembrane region (TM) and an intracellular region (CT), on which there are epitopes such as fusion peptide (FP), membrane-proximal external region (MPER), interface between gp120 and gp41; after gp120 recognizes the CD4 molecule, it will induce a change in the conformation of gp120, exposing the co-receptor binding site and binding to the co-receptor on the cell, which will further lead to a conformational change, so that the FP epitope of gp41 is exposed from the viral membrane instantaneously, and inserted into host cells to mediate virus infection (Guttman, Garcia et al. CD4-induced activation in a soluble HIV-1 Env trimer, structure. 2014.).

Env is the main component of many HIV-1 vaccine clinical studies. Early AIDS vaccine researches mostly used gp120 monomer as the antigen, which retained some known Nab epitopes, but it proved difficult to induce Tier2 neutralizing antibodies, and Phase III clinical trials proved that it had no clinical protective effect. The researchers thought that it might because that there are many epitopes on the gp120 monomer that do not exist on the natural Env, and gradually shifted the focus to the native-like Env trimer. However, because the transmembrane region of gp41 is extremely hydrophobic and has low antigenicity as the intracellular region, the researchers increased the soluble expression of Env by removing its transmembrane region and intracellular region, and this type of HIV-1 antigen molecule was named as gp140 (Sanders, R. W. and J. P. Moore. Native-like Env trimers as a platform for HIV-1 vaccine design. Immunol Rev, 2017.). BG505 SOSIP, NFL2P, UFO, etc. are all designed on the basis of gp140. By introducing disulfide bonds in the extracellular region of gp120 and gp41, introducing a mutation I559P for stabilizing into gp41 or replacing the furin cleavage site between gp120 and gp41 with linker, the interaction between subunits and the stability of the trimer are enhanced. These designs can effectively expose the Nab epitope without exposing non-neutralizing epitopes, and thus are considered to well mimic the conformation of the natural trimer on virus. This type of antigen and its virus-like particle antigen prepared by nanotechnology have been used in animal experiments one after another, and it has been confirmed that it can only induce neutralizing antibodies against the same type of virus, with limited broad-spectrum. Therefore, HIV-1 immunogen design still needs to find another way.

The physical and chemical properties of the modified gp140 are optimized. Taking BG505-SOSIP as an example, its trimer content is significantly increased, its thermal stability is about 14° C. higher than that of monomer gp120, its binding ability to many kinds of bNabs is maintained, while its binding to some antibodies against non-neutralizing epitopes such as CD4i is weak (Sanders, Derking et al. A next-generation cleaved, soluble HIV-1 Env trimer, BG505 SOSIP.664 gp140, expresses multiple epitopes for broadly neutralizing but not non-neutralizing antibodies, 2013.). Immunization of mice with BG505-SOSIP trimer can induce stronger IgG, Tfh and GC responses, but it cannot induce the production of Tier2 neutralizing antibodies, and the epitope map analysis shows that the induced antibodies are mostly directed to the base region of the trimer (Hu, Crampton et al. 2015, Murine Antibody Responses to Cleaved Soluble HIV-1 Envelope Trimers Are Highly Restricted in Specificity, 2015.), while this region is less masked by glycosyl, but does not exist on the surface of natural virus. This result suggests that the design of Env trimer immunogen should minimize the exposure of non-neutralizing antibodies, and stabilize the conformation of the trimer, which will further advance the HIV-1 vaccine research, but it still has certain limitations to use the Env trimer as a vaccine candidate molecule, for example, it is difficult to induce Tier2 neutralization response, and it is difficult to induce cross-neutralization effect between different strains.

Inactivated or attenuated viruses are the main active ingredients of many vaccines, but so far there is no effective vaccine and radical cure for AIDS. Inactivated or attenuated viruses contain all the antigenic components on the viruses, and can induce the body to produce humoral immunity and cellular immunity simultaneously, induce a strong cytotoxic T lymphocyte response (CTL), and the SIV live attenuated vaccine has been proven to successfully protect rhesus macaques from SIV infection (Protection by Live, Attenuated Simian Immunodeficiency Virus against Heterologous Challenge. Journal of Virology, 1999.). However, due to the pathogenicity and incurability of HIV-1, attenuated or inactivated HIV-1 vaccines have the potential to infect the human body, which limits the application of HIV-1 inactivated or attenuated viruses in the development of AIDS vaccines. It is a very novel and safe vaccine design to obtain a modified HIV-1 virus particle that has completely lost its pathogenicity and cannot regain its infectivity through reverse mutation, and thereby preparing an HIV-1 virus vaccine without potential infection risk, which will bring breakthroughs in the field of AIDS vaccine research and development.

CONTENTS OF THE PRESENT INVENTION

Modified gp140/gp160 Protein and Trimer

In a first aspect, the present invention provides a recombinant protein, which comprises gp120 and gp41 ectodomain (gp41ECTO), wherein the gp120 is located between β27 and α8 of the gp41ECTO. In certain embodiments, the recombinant protein of the present invention is a modified gp140 protein.

Herein, the expression "gp120 is located between β27 and α8 of gp41ECTO" means that the position of gp120 in the recombinant protein of the present invention is between β27 and α8 of gp41ECTO, and is not intended to limit to any specific way of introducing it between β27 and α8. For example, gp120 can be inserted directly between adjacent amino acids between β27 and α8 of gp41ECTO, or gp120 can be used to replace one or more consecutive amino acids between β27 and α8 of gp41ECTO. Furthermore, gp120 can be native or modified, and gp41ECTO can be native or modified. It is easy to understand that gp41ECTO described in the technical solution of the present invention being natural means that the gp41ECTO does not contain other artificial modifications except for the modification of containing gp120 between β27 and α8. Herein, the term "modification" preferably refers to deletion, addition or substitution of one or more amino acid residues.

In some embodiments, the recombinant protein comprises: α6, α7, β27 of gp41ECTO; gp120; α8, α9 of gp41ECTO from the N-terminal to the C-terminal.

In certain embodiments, one or more (e.g., 1-12, 5-12, 5-10; for example 1, 2, 3, 4, 5, 6, 7, 8, 9, 10, 11, or 12) consecutive amino acids in the linkage region between β27 and α8 of the gp41ECTO are substituted with gp120. In certain embodiments, the linkage region corresponds to amino acid positions 607-618 of a gp160 sequence of isolate HXB2.

In certain embodiments, one or more (e.g., 1-7, for example 5-7; for example 1, 2, 3, 4, 5, 6, or 7) consecutive amino acids in a region of the gp41ECTO corresponding to amino acid positions 610-616 of the gp160 sequence of isolate HXB2 are substituted with gp120.

In certain exemplary embodiments, 7 consecutive amino acids in a region of the gp41ECTO corresponding to amino acid positions 610-616 of gp160 sequence of isolate HXB2 are substituted with gp120. In certain embodiments, the linkage region between β27 and α8 of the gp41ECTO comprises a deletion of a sequence set forth in SEQ ID NO: 26 (WNSSWSN) or an amino acid sequence at corresponding position thereof. The expression "amino acid sequence at corresponding position" refers to an amino acid sequence located at a position equivalent to WNSSWSN when the gp160 sequences of different strains are optimally aligned, i.e., when the sequences are aligned for the highest percentage identity. In certain embodiments, the gp120 is located between amino acid positions corresponding to positions 606 and 619 of the gp160 sequence of isolate HXB2.

In certain embodiments, the gp120 is inserted between adjacent amino acids in the linkage region between β27 and α8 of the gp41ECTO. In certain embodiments, the linkage region corresponds to amino acid positions 607-618 of the gp160 sequence of isolate HXB2. In certain embodiments, the gp120 is located between amino acid positions corresponding to positions 609 and 610 of the gp160 sequence of isolate HXB2. In certain embodiments, the gp120 is located between amino acid positions corresponding to positions 616 and 617 of the gp160 sequence of isolate HXB2.

Alteration of gp120

In some embodiments, the gp120 inserted in gp41ECTO may be a natural gp120. In certain embodiments, the natural gp120 protein corresponds to amino acid positions 31-511 of the gp160 sequence of isolate HXB2.

In other embodiments, the gp120 inserted in gp41ECTO may be a modified gp120, which may comprise a mutation (e.g., substitution, deletion, or insertion) of one or more amino acids compared to the natural gp120.

In certain embodiments, the gp120 is a modified gp120 that comprises a mutation at the furin cleavage site compared to a natural gp120 to prevent the cleavage. The method of modifying the cleavage site to remove furin dependence is well known to those skilled in the art, for example, amino acid substitution, insertion or deletion can be introduced into the furin cleavage site sequence, or the furin cleavage site sequence or part thereof can be replaced with another sequence (e.g., linker sequence).

In certain embodiments, the furin cleavage site corresponds to amino acid positions 508-511 of the gp160 sequence of isolate HXB2. In certain exemplary embodiments, the furin cleavage site is set forth in SEQ ID NO: 41 (REKR).

In certain embodiments, the furin cleavage site in the modified gp120 is deleted compared to the natural gp120.

In certain embodiments, the gp120 is a modified gp120 with 1-11 (e.g., 4-11; for example 1, 2, 3, 4, 5, 6, 7, 8, 9, 10, or 11) amino acids truncated at the C-terminal compared to the natural gp120.

In certain embodiments, the modified gp120 comprises a deletion of one or more (e.g., 1-11, 4-11; for example, 1, 2, 3, 4, 5, 6, 7, 8, 9, 10, or 11) consecutive amino acids in the region corresponding to amino acid positions 501-511 of the gp160 sequence of isolate HXB2.

In certain exemplary embodiments, the modified gp120 has a deletion of a region corresponding to amino acid positions 501-511 of the gp160 sequence of isolate HXB2.

In certain embodiments, the modified gp120 is truncated at C-terminal by a sequence set forth in SEQ ID NO: 27 (AKRRVVGREKR) or an amino acid sequence at corresponding position thereof. The expression "amino acid sequence at corresponding position" refers to an amino acid sequence at a position equivalent to AKRRVVGREKR when the gp160 sequences of different strains are optimally aligned, i.e., when the sequences are aligned for the highest percentage identity.

In certain exemplary embodiments, the modified gp120 has a deletion of a region corresponding to amino acid positions 508-511 of the gp160 sequence of isolate HXB2. In certain embodiments, the modified gp120 is truncated at C-terminal with a deletion of a sequence set forth in SEQ ID NO: 41 (REKR) or an amino acid sequence at corresponding position thereof. The expression "amino acid sequence at corresponding position" refers to an amino acid sequence at a position equivalent to REKR when the gp160 sequences of different strains are optimally aligned, i.e., when the sequences are aligned for the highest percentage identity.

In certain embodiments, the gp120 is a modified gp120 with 1-5 (e.g., 1-4; for example 1, 2, 3, 4, or 5) amino acids truncated at the N-terminal, compared to the natural gp120.

In certain embodiments, the modified gp120 has a deletion of a region corresponding to amino acid positions 31-34 of the gp160 sequence of isolate HXB2. In certain embodiments, the modified gp120 comprises a replacement of a region corresponding to amino acid positions 31-34 of the gp160 sequence of isolate HXB2 with an exogenous nucleic acid sequence. In certain embodiments, the exogenous nucleic acid sequence consists of 4 amino acid residues.

In certain embodiments, the modified gp120 has a deletion of an amino acid residue corresponding to amino acid position 499 of the gp160 sequence of isolate HXB2.

In certain embodiments, the modified gp120 is located between amino acid positions corresponding to positions 606 and 610 of the gp160 sequence of isolate HXB2, that is, the modified gp120 is substituted for a region in the gp41ECTO corresponding to amino acid positions 607-609 of the gp160 sequence of isolate HXB2.

In certain embodiments, a disulfide bond is contained between the gp120 and gp41ECTO. In certain embodiments, the recombinant protein has a disulfide bond between amino acid positions corresponding to positions 501 and 605 of the gp160 sequence of isolate HXB2. In certain embodiments, the recombinant protein has a replacement of residues corresponding to amino acid positions 501 and 605 of the gp160 sequence of isolate HXB2 with residue Cys.

In certain embodiments, the gp120 inserted into the gp41ECTO may further comprise a mutation of one or more amino acids to increase the exposure of epitope recognized by broad-spectrum neutralizing antibody and/or stabilize the trimer structure of HIV envelope protein.

In certain embodiments, the gp120 comprises one or more of the following mutations:

(1) the gp120 comprises a substitution of T332N to increase the exposure of epitope recognized by broad-spectrum neutralizing antibody;

(2) the gp120 comprises substitutions of E64K and H66R to stabilize the trimer conformation so that it is not easy to change into open conformation, so that it is not easy to expose CD4i non-neutralizing epitope;

(3) the gp120 comprises a substitution of A316W to enhance the hydrophobic interaction between gp120 subunits, hinder the movement of V3 region, and avoid the exposure of non-neutralizing epitope in the V3 region;

(4) a N-linked glycosylation site (PNGS) near the CD4bs epitope of the gp120 is substituted to prevent glycosylation; preferably, the PNGS is selected from the group consisting of N276, N301, N360, N463;

(5) the gp120 comprises an internal disulfide bond; preferably, the gp120 comprises an internal disulfide bond between I201C and A433C;

(6) a disulfide bond is further contained between the gp120 and gp41ECTO; for example, the recombinant protein has a disulfide bond between E49C and L555C;

the numbering of the above positions is based on the numbering in the gp160 of HIV-1 isolate HXB2.

Alteration of gp41ECTO

In the recombinant protein of the present invention, the gp41ECTO contains a gp120 between β27 and α8. Other parts of the gp41ECTO can be the corresponding sequences of a natural gp41, or can also contain an artificial modification.

In certain embodiments, the gp41ECTO may comprise a stabilization mutation. Mutations for stabilizing the trimer structure of the HIV envelope protein are known to those skilled in the art, see for example, WO 03/022869. In certain embodiments, the stabilization mutation is I559P, and the numbering of the position is according to the numbering in gp160 of the HIV-1 isolate HXB2.

In the recombinant protein of the present invention, the gp120 inserted into the gp41ECTO can be directly linked to the gp41ECTO, or through a peptide linker.

In certain embodiments, the N-terminal and/or C-terminal of the gp120 is linked to the gp41ECTO optionally via a peptide linker. In certain embodiments, the peptide linker comprises or consists of a sequence represented by $(G_mS)_n$, wherein m is an integer selected from 1-4, and n is an integer selected from 1-3. In certain exemplary embodiments, the peptide linker comprises or consists of a sequence represented by $(G_mS)_n$, wherein m is 4 and n is 1, 2 or 3, preferably 1 or 2.

In the recombinant protein of the present invention, the gp41ECTO and gp120 can be from the same or different HIV-1 strains. In certain embodiments, the gp41ECTO and gp120 are from the same HIV-1 strain.

In the recombinant protein of the present invention, the gp41ECTO and gp120 can be from any subtype of HIV-1, such as group M, N, O or P, or subtype A, B, C, D, F, G, H, J or K etc. In certain embodiments, the HIV-1 strain is selected from the group consisting of subtypes A, B, C, G, BC, AE, DC. In certain exemplary embodiments, the HIV-1 strain is selected from the group consisting of BG505, NL4-3, 246F3, 25710, CH119, CNE8, X1632, Bal.26.

In certain embodiments, the gp160 of BG505 has the sequence set forth in SEQ ID NO:18. In certain embodiments, the gp160 of NL4-3 has the sequence set forth in SEQ ID NO:19. In certain embodiments, the gp160 of 25710 has the sequence set forth in SEQ ID NO:20. In certain embodiments, the gp160 of X1632 has the sequence set forth in SEQ ID NO:21. In certain embodiments, the gp160 of CH119 has the sequence set forth in SEQ ID NO:22. In certain embodiments, the gp160 of CNE8 has the sequence set forth in SEQ ID NO:23. In certain embodiments, the gp160 of 246F3 has the sequence set forth in SEQ ID NO:24. In certain embodiments, the gp160 of Bal.26 has the sequence set forth in SEQ ID NO:25.

In certain exemplary embodiments, the recombinant protein of the present invention comprises an amino acid sequence selected from:

(1) an amino acid sequence consisting of amino acid residues at positions 40 to 651 of the sequence set forth in SEQ ID NO: 1;

(2) an amino acid sequence consisting of amino acid residues at positions 40 to 652 of the sequence set forth in SEQ ID NO:2;

(3) an amino acid sequence consisting of amino acid residues at positions 40 to 651 of the sequence set forth in SEQ ID NO:3;

(4) an amino acid sequence consisting of amino acid residues at positions 40 to 652 of the sequence set forth in SEQ ID NO:4;

(5) an amino acid sequence consisting of amino acid residues at positions 40 to 665 of the sequence set forth in SEQ ID NO:5;

(6) an amino acid sequence consisting of amino acid residues at positions 40 to 678 of the sequence set forth in SEQ ID NO:6;

(7) an amino acid sequence consisting of amino acid residues at positions 40 to 661 of the sequence set forth in SEQ ID NO:7;

(8) an amino acid sequence consisting of amino acid residues at positions 40 to 666 of the sequence set forth in SEQ ID NO:8;

(9) an amino acid sequence consisting of amino acid residues at positions 40 to 671 of the sequence set forth in SEQ ID NO:9;

(10) an amino acid sequence consisting of amino acid residues at positions 40 to 676 of the sequence set forth in SEQ ID NO:10;

(11) an amino acid sequence consisting of amino acid residues at positions 36 to 607 of the sequence set forth in SEQ ID NO:11;

(12) an amino acid sequence consisting of amino acid residues at positions 36 to 646 of the sequence set forth in SEQ ID NO:12;

(13) an amino acid sequence consisting of amino acid residues at positions 36 to 648 of the sequence set forth in SEQ ID NO:13;

(14) an amino acid sequence consisting of amino acid residues at positions 36 to 638 of the sequence set forth in SEQ ID NO:14;

(15) an amino acid sequence consisting of amino acid residues at positions 36 to 639 of the sequence set forth in SEQ ID NO:15;

(16) an amino acid sequence consisting of amino acid residues at positions 36 to 836 of the sequence set forth in SEQ ID NO:16;

(17) an amino acid sequence consisting of amino acid residues at positions 36 to 673 of the sequence set forth in SEQ ID NO:30;

(18) an amino acid sequence consisting of amino acid residues at positions 36 to 678 of the sequence set forth in SEQ ID NO:31;

(19) an amino acid sequence consisting of amino acid residues at positions 36 to 683 of the sequence set forth in SEQ ID NO:32;

(20) an amino acid sequence consisting of amino acid residues at positions 36 to 678 of the sequence set forth in SEQ ID NO:33;

(21) an amino acid sequence consisting of amino acid residues at positions 36 to 688 of the sequence set forth in SEQ ID NO:34;

(22) an amino acid sequence consisting of amino acid residues at positions 36 to 670 of the sequence set forth in SEQ ID NO:35;

(23) an amino acid sequence consisting of amino acid residues at positions 36 to 676 of the sequence set forth in SEQ ID NO:36;

(24) an amino acid sequence consisting of amino acid residues at positions 36 to 680 of the sequence set forth in SEQ ID NO:37;

(25) an amino acid sequence consisting of amino acid residues at positions 36 to 673 of the sequence set forth in SEQ ID NO:38;

(26) an amino acid sequence consisting of amino acid residues at positions 36 to 678 of the sequence set forth in SEQ ID NO:39;

(27) an amino acid sequence consisting of amino acid residues at positions 36 to 683 of the sequence set forth in SEQ ID NO:40; or (28) a variant of the sequence described in any one of (1) to (27), in which the variant has a substitution, deletion or addition of one or several amino acids (e.g., a substitution, deletion or addition of 1, 2, 3, 4, 5, 6, 7, 8, 9 or 10 amino acids) or has a sequence identity of at least 80%, at least 85%, at least 90%, at least 91%, at least 92%, at least 93%, at least 94%, at least 95%, at least 96%, at least 97%, at least 98%, or at least 99% compared to the sequence from which it is derived, and the variant retains the properties of the sequence from which it is derived.

In certain embodiments, the recombinant protein of the present invention optionally comprises one or more sequences selected from the following at its N-terminal or C-terminal: signal peptide, translation initiation sequence (e.g., Kozak consensus sequence), tag sequence.

In certain embodiments, the signal peptide is tPA.

In certain embodiments, the translation initiation sequence is a Kozak consensus sequence (Kozak M., Nucleic Acids Research, 1984, 12, 857-872), and the consensus sequence may comprise at least part of the sequence CCRGCCAUGG, where R may be A or G. The position-3 (i.e., position of the $3^{rd}$ nucleotide upstream of ATG codon) and the position+4 have the greatest effect on translation (Kozak M., Nucleic Acids Research, 1987, 15, 8125-8148). Thus, the consensus sequence may also be RXXAUGG, XXAUGG or RXXAUG.

In certain embodiments, the tag sequence is a purification tag, such as a polyhistidine tag, myc tag, or HA tag.

In certain embodiments, the recombinant protein optionally comprises a signal peptide and/or a translation initiation sequence (e.g., a Kozak consensus sequence) at its N-terminal.

In certain embodiments, the recombinant protein optionally comprises a tag sequence at its C-terminal.

In the second aspect, the present invention provides a fusion protein, which comprises the recombinant protein described in the first aspect and transmembrane region and intracellular region sequences of gp41 linked to its C-terminal. In certain embodiments, the fusion protein of the present invention is a modified gp160 protein.

In certain embodiments, the transmembrane region and intracellular region sequences of gp41 and the gp41ECTO in the recombinant protein are from the same HIV-1 strain.

In certain exemplary embodiments, the fusion protein of the present invention comprises an amino acid sequence selected from:

(1) an amino acid sequence consisting of amino acid residues at positions 33 to 836 of the sequence set forth in SEQ ID NO: 16;

(2) an amino acid sequence consisting of amino acid residues at positions 34 to 837 of the sequence set forth in SEQ ID NO:17;

(3) a variant of the sequence described in any one of (1) to (2), in which the variant has a substitution, deletion or addition of one or several amino acids (e.g., a substitution, deletion or addition of 1, 2, 3, 4, 5, 6, 7, 8, 9 or 10 amino acids) or has a sequence identity of at least 80%, at least 85%, at least 90%, at least 91%, at least 92%, at least 93%, at least 94%, at least 95%, at least 96%, at least 97%, at least 98%, or at least 99% compared to the sequence from which it is derived, and the variant retains the properties of the sequence from which it is derived.

In certain embodiments, the fusion protein of the present invention optionally comprises one or more sequences selected from the following at its N-terminal or C-terminal: signal peptide, translation initiation sequence (e.g., Kozak consensus sequence), tag sequence.

In certain embodiments, the signal peptide is the signal peptide contained in a natural gp160. In certain embodiments, the signal peptide, the transmembrane region and intracellular region sequences of gp41, and the gp41ECTO and gp120 in the recombinant protein are from the same HIV-1 strain.

In certain embodiments, the tag sequence is a purification tag, such as a polyhistidine tag, myc tag, or HA tag.

In certain embodiments, the recombinant protein optionally comprises a signal peptide and/or a translation initiation sequence (e.g., a Kozak consensus sequence) at its N-terminal.

In certain embodiments, the recombinant protein optionally comprises a tag sequence at its C-terminal.

In a third aspect, the present invention provides a multimer comprising a plurality of monomers, wherein each monomer is independently selected from the recombinant protein described in the first aspect, or independently selected from the fusion protein described in the second aspect.

In certain embodiments, the individual monomers are identical to each other.

In certain embodiments, the multimer is a trimer or a dimer.

Preparation of Envelope Protein and Trimer

The recombinant protein or fusion protein or multimer thereof of the present invention can be prepared by various methods known in the art, for example, genetic engineering methods (recombinant technology), or chemical synthesis methods (e.g., Fmoc solid phase method). The recombinant protein or fusion protein or multimer thereof of the present invention is not limited by its production method.

In a fourth aspect, the present invention provides an isolated nucleic acid molecule, which comprises a nucleotide sequence encoding the recombinant protein described in the first aspect, the fusion protein described in the second aspect or the multimer described in the third aspect.

In a fifth aspect, the present invention provides a vector, which comprises the isolated nucleic acid molecule as described above. In certain embodiments, the vector is, for example, a plasmid, cosmid, phage, and the like.

In a sixth aspect, the present invention provides a host cell, which comprises the isolated nucleic acid molecule or the vector as described above. Such host cells include, but are not limited to, prokaryotic cell such as *E. coli* cell, and eukaryotic cell such as yeast cell, insect cell, plant cell, and animal cell (e.g., mammalian cell, such as mouse cell, human cell, etc.). Preferably, the host cell is a mammalian cell, such as a human cell.

In the seventh aspect, the present invention provides a method for preparing the recombinant protein described in the first aspect, the fusion protein described in the second aspect, or the multimer described in the third aspect, which comprises culturing the host cell of the sixth aspect under suitable conditions, and recovering the recombinant protein, the fusion protein or the multimer from a cell culture. In some embodiments, the recombinant protein or the fusion protein exists in the form of multimer (e.g., trimer or dimer).

Display Platform

The protein described in the first or second aspect of the present invention or the multimer described in the third aspect can be displayed on particles such as liposomes, virus-like particles (VLPs), nanoparticles, virosomes or exosomes to enhance in vivo antigen presentation efficacy.

Therefore, in the eighth aspect, the present invention provides a particle, displaying on its surface the recombinant protein described in the first aspect, the fusion protein described in the second aspect or the multimer described in the third aspect on its surface.

In certain embodiments, the particle is a liposome or a nanoparticle.

In certain embodiments, the recombinant protein, the fusion protein or the multimer of the present invention is fused to and/or displayed on a liposome. The liposome is a spherical vesicle with at least one lipid bilayer. In certain embodiments, the multimer protein (e.g., trimer or dimer protein) of the present invention can for instance be non-covalently coupled to such liposomes by electrostatic interactions, e.g. by adding a His-tag to the C-terminus of the multimer and a bivalent chelating atom such as Ni2+ or Co2+ incorporated into the head group of derivatized lipids in the liposome. In certain embodiments, the multimer protein (e.g., trimer or dimer protein) of the present invention is covalently coupled to the surface of liposome, for example, via a maleimide functional group integrated in the liposome surface. In certain embodiments, the multimer protein (e.g., trimer or dimer protein) of the present invention can be coupled thereto, for example, via a C-terminal cysteine added in the multimer protein. Methods for preparing HIV Env trimers coupled to liposomes and their characterization, are known and described in detail, for example, in Bale S et al. J Virol. 2017; 91(16):e00443-17, and this document is incorporated herein by reference.

In certain embodiments, the recombinant protein, the fusion protein or the multimer of the present invention is fused to a self-assembling particle or displayed on a nanoparticle. Antigen nanoparticles are assemblies of polypeptides that present multiple copies of antigen (e.g., the HIV Env protein of the present invention), resulting in multiple binding sites (avidity) and providing an improved antigen stability and immunogenicity. The preparation of self-assembling protein nanoparticle and use thereof in vaccines are well known to those skilled in the art, see for example, Zhao L et al. (2014) Vaccine 32:327-337, Lopez-Sagaseta J et al. (2016) Computational and Struct Biotechnol J 14:58-68. As non-limiting examples, the self-assembling nanoparticle may be based on ferritin, bacterial ferritin or DPS. DPS nanoparticles displaying proteins on the surface are described in, for example, WO 2011/082087. The description of trimeric HIV-1 antigens on such particles has been described in, for example, He L et al. (2016) Nat Commun. 2016 Jun. 28; 7:1 2041. Other self-assembling protein nanoparticles and their preparation are disclosed in, for example, WO 2014/124301 and US 2016/0122392, which are hereby incorporated by reference.

Pseudoviral Particle

In the ninth aspect, the present invention provides a pseudoviral particle, comprising on its surface the recombinant protein described in the first aspect, the fusion protein described in the second aspect or the multimer described in the third aspect.

The pseudoviral particle of the present invention presents a typical form of pseudoviral particle, but has completely lost its infection ability. Compared with traditional protein vaccines, this type of pseudoviral particle not only has components such as envelope and capsid proteins of HIV-1 virus, etc., with high similarity to the natural virus in shape, but also has completely lost the infection ability, has good immunogenicity, and thus can be used as a virus-based vaccine.

In certain embodiments, the pseudoviral particle is produced by a lentiviral packaging system or a retroviral packaging system.

In certain embodiments, the pseudoviral particle is obtained by co-expressing (i) a vector comprising the nucleic acid molecule described in the fourth aspect, and (ii) a packaging vector (e.g., a backbone plasmid) in a host cell.

In certain embodiments, the packaging vector is capable of expressing gag, pol, tat, rev genes. In certain embodiments, the packaging vector is a vector comprising an HIV-1 genome with a deletion of env gene. In certain embodiments, the packaging vector is a plasmid. In certain embodiments, the backbone plasmid includes, for example, pSPAX, pNL4-3.Luc.R-E-, G3Δenv, pfNL43-dGPE-EGFP.

In certain embodiments, the vector described in (i) is an eukaryotic expression vector, including but not limited to, VRC8400, PTT5, pCDN3.1 and the like.

In another aspect, the present invention provides a method for preparing the pseudoviral particle of the present invention, which comprises: (1) co-transfecting a host cell with the expression vector comprising the nucleic acid molecule described in the fourth aspect and the packaging vector; (2) expressing the proteins encoded by the expression vector and the packaging vector in the host cell, in which the proteins are capable of self-assembling to form an HIV pseudovirus; and (3) collecting the HIV pseudovirus.

In certain preferred embodiments, the host cell is an eukaryotic cell, such as a mammalian cell, such as a primate cell, such as a human cell.

In another aspect, the present invention provides a packaging system for producing the above-mentioned pseudoviral particle, which comprises: (i) an expression vector comprising the nucleic acid molecule described in the fourth aspect, (ii) a packaging vector.

Modified HIV Virus

In the tenth aspect, the present invention provides a modified HIV virus, which expresses the fusion protein or multimer (e.g., trimer or dimer) thereof described in the second aspect as its envelope protein. In certain embodiments, the HIV virus is HIV-1 virus.

The modified HIV virus of the present invention will lose the ability to infect cells and animals, and as an immunogen of vaccine, it can simulate the immune response process of HIV-1 infection of the human body to the greatest extent, thus may produce protective immunity, and at the same time has good safety. The modified HIV virus of the present invention can also simulate a natural variation of HIV-1 virus when it is cultured in cells, and this kind of variation cannot be back-mutated to form an infectious virus particle, because the viral replication process cannot complete the rearrangement with the gene fragment encoding the Env protein of the present invention. Therefore, this type of live virus vaccine will have the immunogenicity of the natural virus to the body, but it is impossible to have infectivity and pathogenicity, so that it is also a feasible vaccine strategy.

In certain embodiments, the genome of the modified HIV virus comprises the following modification: the wild-type env gene is replaced with the nucleotide sequence encoding the fusion protein described in the second aspect.

In an eleventh aspect, the present invention provides an isolated nucleic acid molecule or vector, which comprises a nucleotide sequence encoding the genome of the modified HIV virus described above.

Composition

In the twelfth aspect, the present invention provides a composition, which comprises the recombinant protein described in the first aspect, the fusion protein described in the second aspect or the multimer described in the third aspect, the isolated nucleic acid molecule described in the fourth aspect, the vector described in the fifth aspect, the host cell described in the sixth aspect, the particle described in the eighth aspect, the pseudoviral particle described in the ninth aspect, the modified HIV virus described in the tenth aspect, or the isolated nucleic acid molecule or vector described in the eleventh aspect.

In certain embodiments, the composition further comprises a pharmaceutically acceptable carrier and/or excipient.

In certain embodiments, the composition is an immunogenic composition or vaccine. In such embodiments, the recombinant protein described in the first aspect, the fusion protein described in the second aspect or the multimer described in the third aspect, the isolated nucleic acid molecule described in the fourth aspect, the vector described in the fifth aspect, the host cell described in the sixth aspect, the particle described in the eighth aspect, the pseudoviral particle described in the ninth aspect, the modified HIV virus described in the tenth aspect, or the isolated nucleic acid molecule or vector described in the eleventh aspect is used as an immunogen.

In certain embodiments, the composition is a protein vaccine, which comprises the recombinant protein described in the first aspect, the fusion protein described in the second aspect, or the multimer described in the third aspect, or the particle described in the eighth aspect as an immunogen.

In some embodiments, the composition is a virus-based vaccine, which comprises the pseudoviral particle described in the ninth aspect, or the modified HIV virus described in the tenth aspect as an immunogen.

In certain embodiments, the composition is a nucleic acid vaccine, which comprises the isolated nucleic acid molecule described in the fourth aspect, the vector described in the fifth aspect, or the isolated nucleic acid molecule or vector described in the eleventh aspect as an immunogen. As used herein, the term "nucleic acid vaccine" refers to a vaccine based on DNA or RNA (e.g., plasmid, such as expression plasmid), optionally further comprising an adjuvant.

In certain embodiments, the nucleic acid vaccine comprises DNA or RNA. In certain embodiments, the DNA or RNA can be naked or can be packaged within a shell with delivery and/or protection functions. In some embodiments, the shell can be a shell of adenovirus, adeno-associated virus, lentivirus, retrovirus, etc., or other material that is synthesized by a chemical method and capable of performing similar function.

In certain embodiments, the pharmaceutically acceptable carrier and/or excipient comprises an adjuvant. Adjuvants for co-administration with or being included in the composition according to the present invention should preferably be those that are potentially safe, well tolerated and effective in humans. Such adjuvants are well known to those skilled in the art, and non-limiting examples thereof include:

QS-21, Detox-PC, MPL-SE, MoGM-CSF, TiterMax-G, CRL-1005, GERBU, TER amide, PSC97B, Adjumer, PG-026, GSK-I, GcMAF, B-alethine, MPC-026, Adjuvax, CpG ODN, Betafectin, aluminum salts such as aluminum phosphate (e.g., AdjuPhos) or aluminum hydroxide and MF59.

The immunogenic composition or vaccine of the present invention can also be used in combination with an additional agent known in the art for the treatment or prevention of an HIV infection. Thus, in certain embodiments, the composition of the present invention may also comprise an antiretroviral agent. In certain embodiments, the antiretroviral agent comprises: a nucleoside reverse transcriptase inhibitor, such as abacavir, AZT, didanosine, emtricitabine, lamivudine, stavudine, tenofovir, zalcitabine, zidovudine, etc.; a non-nucleoside reverse transcriptase inhibitor, such as delavirdine, efavirenz, nevirapine; a protease inhibitor, such as amprenavir, atazanavir, indinavir, lopinavir, nelfinavir, osamprenavir, ritonavir, saquinavir, tipranavir, etc., and a fusion protein inhibitor, such as enfuvirtide and so on.

In certain embodiments, the immunogenic composition or vaccine of the present invention and the antiretroviral agent are present as separate components or as a single formulation. In certain embodiments, the immunogenic composition or vaccine of the present invention and the antiretroviral agent are present as separate components or as a single formulation. In certain embodiments, the immunogenic composition or vaccine of the present invention and the antiretroviral agent may be administered simultaneously, separately or sequentially.

The composition (e.g., immunogenic composition) of the present invention may be formulated into any dosage form known in the medical art, for example, tablets, pills, suspensions, emulsions, solutions, gels, capsules, powders, granules, elixirs, lozenges, suppositories, injections (including injections, sterile powders for injection and concentrated solutions for injection), inhalants, sprays, etc. The preferred dosage form depends on the intended mode of administration and therapeutic use. The composition of the present invention should be sterile and stable under the conditions of manufacture and storage. A preferred dosage form is injection. Such injection can be a sterile injectable solution. In addition, the sterile injectable solution can be prepared as a sterile lyophilized powder (e.g., by vacuum drying or freeze-drying) for ease of storage and use. Such sterile lyophilized powder can be dispersed in a suitable vehicle before use, such as water for injection (WFI), bacteriostatic water for injection (BWFI), sodium chloride solution (e.g., 0.9% (w/v) NaCl), dextrose solution (e.g., 5% dextrose), surfactant-containing solution (e.g., 0.01% polysorbate 20), pH buffer solution (e.g., phosphate buffered saline), Ringer's solution and any combination thereof.

The composition (e.g., immunogenic composition) of the present invention may be administered by any suitable method known in the art, including, but not limited to, oral, buccal, sublingual, ocular, topical, parenteral, rectal, intrathecal, intra-cisterna, inguinal, intravesical, topical (e.g., powder, ointment, or drop), or nasal routes. However, for many therapeutic uses, the preferred route/mode of administration is parenteral administration (e.g., intravenous or bolus injection, subcutaneous injection, intraperitoneal injection, intramuscular injection). The skilled artisan will understand that the route and/or mode of administration will vary depending on the intended purpose.

The immunogenic composition of the present invention should be administered in an amount sufficient to induce an immune response against HIV-1. The appropriate amount of immunogen can be determined according to the particular disease or condition to be treated or prevented, its severity, the age of the subject, and other personal attributes of the particular subject (e.g., the general state of the subject's health and the robustness of the subject's immune system). Determination of effective doses is also guided by animal model studies followed by human clinical trials, and by administration regimens that significantly reduce the occurrence or severity of the target disease symptom or condition in subjects.

Applications

The composition (e.g., immunogenic composition) of the present invention can readily be used in a variety of therapeutic or prophylactic applications for treating an HIV-1 infection or inducing an immune response to HIV-1 in a subject. For example, the composition can be administered to a subject to induce an immune response to HIV-1, for example, to induce broad-spectrum neutralizing antibodies against HIV-1. To subjects at risk of developing HIV infection, the immunogenic composition of the present invention can be administered to provide prophylactic protection against viral infection.

Accordingly, in another aspect, the present invention provides a method for inducing an immune response against HIV in a subject or for preventing and/or treating an HIV infection in a subject, which comprises administering to the subject in need thereof an immunologically effective amount of the recombinant protein described in the first aspect, the fusion protein described in the second aspect or the multimer described in the third aspect, the isolated nucleic acid molecule described in the fourth aspect, the vector described in the fifth aspect, the host cell described in the sixth aspect, the particle described in the eighth aspect, the pseudoviral particle described in the ninth aspect, the modified HIV virus described in the tenth aspect, or the isolated nucleic acid molecule or vector described in the eleventh aspect.

In certain embodiments, the method may further comprise administering to the subject an additional agent in combination for the treatment or prevention of an HIV infection. In certain embodiments, the method comprises administering an antiretroviral agent, such as a nucleoside reverse transcriptase inhibitor, a non-nucleoside reverse transcriptase inhibitor, a protease inhibitor, or a fusion protein inhibitor, among others.

For prophylactic applications, the recombinant protein, the fusion protein, the multimer, the isolated nucleic acid molecule, the vector, the host cell, the particle, the pseudoviral particle, the modified HIV virus, or the composition (e.g., immunogenic composition) of the present invention is provided before any symptoms, such as before infection. The prophylactic administration of the immunogenic composition is used for the prevention or amelioration of any subsequent infection, to attenuate the expected severity, duration or extent of infection and/or associated disease symptoms following the exposure or suspected exposure to the virus or after actual infection. Thus, in some embodiments, the subject to be treated is a subject who has an HIV infection or is at risk of developing an HIV infection, for example, being or likely being exposed to HIV. Following the administration of a therapeutically effective amount of the disclosed therapeutic composition, HIV-1 infection, or symptoms associated with HIV-1 infection of the subject can be monitored.

For therapeutic applications, the recombinant protein, the fusion protein, the multimer, the isolated nucleic acid molecule, the vector, the host cell, the particle, the pseudoviral particle, the modified HIV virus, or the composition (e.g., immunogenic composition) of the present invention is provided at or after the onset of symptoms of a disease or infection, for example, after the onset of symptoms of HIV-1 infection or after a diagnosis of HIV-1 infection.

In another aspect, the present invention also relates a use of the recombinant protein described in the first aspect, the fusion protein described in the second aspect or the multimer described in the third aspect, the isolated nucleic acid molecule described in the fourth aspect, the vector described in the fifth aspect, the host cell described in the sixth aspect, the particle described in the eighth aspect, the pseudoviral particle described in the ninth aspect, the modified HIV virus described in the tenth aspect, or the isolated nucleic acid molecule or vector described in the eleventh aspect in the manufacture of a medicament for inducing an immune response against HIV in a subject and/or for preventing and/or treating an HIV infection in a subject. Preferably, the medicament is a vaccine. Preferably, the subject is a human.

In another aspect, the present invention also relates to a use of the recombinant protein described in the first aspect, the fusion protein described in the second aspect or the multimer described in the third aspect, or the particle described in the eighth aspect in the manufacture of a protein vaccine, the protein vaccine is used for inducing an immune response against HIV in a subject and/or for preventing and/or treating an HIV infection in a subject.

In another aspect, the present invention also relates to a use of the pseudoviral particle described in the ninth aspect, or the modified HIV virus described in the tenth aspect, in the manufacture of a virus-based vaccine, and the virus-based vaccine is used for inducing an immune response against HIV in a subject and/or for preventing and/or treating an HIV infection in a subject.

In another aspect, the present invention also relates to a use of the isolated nucleic acid molecule described in the fourth aspect, the vector described in the fifth aspect, or the isolated nucleic acid molecule or vector described in the eleventh aspect in the manufacture of a nucleic acid vaccine, the nucleic acid vaccine is used for inducing an immune response against HIV in a subject and/or for preventing and/or treating an HIV infection in a subject.

Definition of Terms

In the present invention, unless otherwise specified, the scientific and technical terms used herein have the meanings commonly understood by those skilled in the art. In addition, the laboratory procedures of virology, biochemistry, nucleic acid chemistry, and immunology used herein are routine procedures widely used in the corresponding fields. Meanwhile, in order to better understand the present invention, definitions and explanations of related terms are provided below.

As used herein, the term "Env" refers to an envelope protein (envelope) on the surface of HIV-1 virus. Env is synthesized on the surface of HIV-1 in the form of full-length gp160 (full-length molecular weight 160 KD), and the precursor protein formed by translation is cleaved by protease into gp120 (with a molecular weight of 120 KD) and gp41 after the viral maturation, in which gp120 is located on the surface of virus and is a molecule that recognizes CD4 receptor and induces infection, while gp41 comprises an extracellular region transmembrane region and an intracellular region and has a molecular weight of 41 KD, gp120 and gp41 form a heterodimer through non-covalent interaction between subunits, and the heterodimer forms a typical trimer structure through non-covalent interaction. This trimer protein is Env.

As used herein, the term "gp140" refers to a protein composed of gp120 and gp41 extracellular segment in which the gp41 intracellular segment and transmembrane region have been deleted, and the trimer formed by the monomeric protein can be called as gp140 trimer. The gp140 trimer includes trimer proteins whose conformation is further stabilized by introducing a disulfide bond, a point mutation, etc. into monomers. The "BG505 SOSIP" herein refers to that on the basis of the full-length Env of the BG505 strain, the intracellular segment and the transmembrane region sequences are deleted, and cys mutations are introduced at the amino acid position 501 and the amino acid position 605 to form a disulfide bond between gp120 and gp41 extracellular regions, and Ile at the amino acid position 559 is further mutated into pro to stabilize the pre-fusion conformation of gp140 trimer, this modification method is named as SOSIP, and this modified protein is BG505 SOSIP. The deletion of the intracellular and transmembrane regions of gp160 will facilitate the soluble expression of membrane proteins.

As used herein, the term "furin" refers to a major protein convertase in the secretory pathway that catalyzes the cleavage of the carboxy-terminal peptide bond of Arg-X-Y-Arg in proteins (X is any amino acid, Y is Arg or Lys) to produce mature proteins. Furin recognizes the REKR sequence between the immature HIV-1 Env gp120 and gp41 subunits and cleaves the full-length gp160 into gp120 and gp41, allowing them to undergo conformational rearrangement and maturation.

As used herein, the HXB2 numbering system is a reference numbering system for HIV proteins and nucleic acid sequences, using the HIV-1 HXB2 strain sequence as a reference for all other HIV strain sequences. Those of ordinary skill in the art are familiar with the HXB2 numbering system. The amino acid numbers described herein, such as 559, 501, 605, etc., are given according to the HXB2 numbering system, which can be determined by using the amino acid numbering of the strain HXB2 as a template and performing sequence homologous alignment, and those of ordinary skill in the art will understand that the amino acid numbers described herein do not refer to the actual amino acid number in the protein. Herein, the expression "a region corresponding to specific amino acid positions of gp160 sequence of isolate HXB2" refers to the positions in a strain to be compared that are equivalent to the specific amino acid positions in isolate HXB2 when the gp160 sequence of the strain to be compared is optimally aligned with the gp160 sequence of isolate HXB2, that is, when the sequences are aligned to obtain the highest percent identity.

As used herein, "subtype," "strain," etc. of HIV are well known to those skilled in the art. It is now known that HIV-1 has at least 13 subtypes, including A, B, C, D, E, F, G, H, I, J, K, O, and N subtypes, which are classified as three groups M, O, and N, in which A to K belong to the group M. There are many strains in each of different subtypes, and one strain corresponds to one Env sequence. For example, BG505 used in the present invention is a strain in the subtype A, and NL4-3 and Bal.26 are strains in the subtype B.

As used herein, the term "vector" refers to a nucleic acid delivery vehicle into which a polynucleotide can be inserted. When the vector is capable of achieving expression of the protein encoded by the inserted polynucleotide, the vector is called an expression vector. A vector can be introduced into a host cell by transformation, transduction or transfection, so that the genetic material elements it carries can be expressed in the host cell. Vectors are well known to those skilled in the art, including but not limited to: plasmids; phagemids; cosmids; artificial chromosomes, such as yeast artificial chromosome (YAC), bacterial artificial chromosome (BAC) or P1-derived artificial chromosome (PAC); phages such as λ phage or M13 phage and animal viruses, etc. Animal viruses that can be used as vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40). A vector may contain a variety of elements that control expression, including but not limited to, promoter sequence, transcription initiation sequence, enhancer sequence, selection element, and reporter gene. In addition, the vector may also contain an origin of replication.

In the present invention, the term "packaging vector" refers to a vector capable of expressing proteins necessary for the formation of HIV virus-like particle (VLP) other than the envelope protein, including gag, pol, tat and vpu proteins of HIV. Usually, the packaging vector can be constructed by modifying or deleting the coding gene and regulatory gene of envelope protein in the complete HIV genome. Furthermore, packaging vectors for assembly of HIV VLP/ pseudovirus and methods for constructing such packaging vectors are known in the art.

In the present invention, the term "backbone plasmid" refers to a plasmid used to encode structural proteins such as gag and pol in the production of pseudovirus. When using the lentivirus system to produce pseudovirus, packaging plasmid, envelope plasmid, transfer plasmid and regulatory plasmid are required to be co-transfected into a packaging cell to produce a pseudoviral particle for easy detection; the transfer plasmid generally contains a reporter gene that can indicate the infection and entry of pseudovirus into the cell; the reporter gene can be integrated into the packaging plasmid; the regulatory gene can regulate the transcription and translation of the pseudovirus structural gene, and can also be integrated into the packaging plasmid.

As used herein, the term "host cell" refers to a cell into which a vector can be introduced, which includes but is not limited to, prokaryotic cell such as *Escherichia coli* or *Bacillus subtilis*, fungal cell such as yeast cell or *Aspergillus*, insect cell such as S2 *Drosophila* cell or Sf9, or animal cell such as fibroblast, CHO cell, COS cell, NSO cell, HeLa cell, BHK cell, HEK 293 cell or human cell.

As used herein, the term "pseudovirus" refers to a virus-like particle formed by viral capsid protein or envelope protein, which generally does not encapsulate nucleic acid or encapsulate viral nucleic acid after gene deletion or modification. Generally speaking, because the pseudovirus does not contain nucleic acid or the viral nucleic acid genome contained therein is incomplete, the pseudovirus only has the ability of single-round infection, but does not have the ability to replicate to produce progeny viruses, and thus has high biological safety.

As used herein, the term "Tier2 strain" is well known to those skilled in the art. HIV-1 strains can be neutralized by some specific antibodies. According to the difficulty of being neutralized, HIV-1 strains are divided into three levels: Tier1, Tier2 and Tier3. Tier1 refers to a strain that is most easily neutralized, and Tier2 refers to a strain that is least easily neutralized.

As used herein, the term "identity" refers to the match degree between two polypeptides or between two nucleic acids. When two sequences for comparison have the same monomer sub-unit of base or amino acid at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The writing of the twenty conventional amino acids referred to herein follows conventional usage. See, for example, Immunology-A Synthesis (2 nd Edition, E. S. Golub and D. R. Gren, Eds., Sinauer Associates, Sunderland, Mass. (1991)), which is incorporated herein by reference. In the present invention, amino acids are generally represented by single-letter and three-letter abbreviations known in the art. For example, alanine can be represented by A or Ala.

As used herein, the term "pharmaceutically acceptable carrier and/or excipient" refers to a carrier and/or excipient that is pharmacologically and/or physiologically compatible with the subject and the active ingredient, which are well known in the art (see for example. Remington's Pharmaceutical Sciences. Edited by Gennaro AR, 19$^{th}$ ed. Pennsylvania: Mack Publishing Company, 1995), and include, but are not limited to: pH adjuster, surfactant, ionic strength enhancer, agent for maintaining osmotic pressure, agent for delaying absorption, diluent, adjuvant, preservative, stabilizer, etc. For example, the pH adjusting agent includes, but is not limited to, phosphate buffer. The surfactant includes but is not limited to cationic, anionic or nonionic surfactant such as Tween-80. the ionic strength enhancer includes, but is not limited to, sodium chloride. The agent for maintaining osmotic pressure includes, but is not limited to, sugar, NaCl, and the like. The agent for delaying absorption includes, but is not limited to, monostearate and gelatin. The diluent includes, but is not limited to, water, aqueous buffer (e.g., buffered saline), alcohol and polyol (e.g., glycerol), and the like. The adjuvant includes, but is not limited to, aluminum adjuvant (e.g., aluminum hydroxide), Freund's adjuvant (e.g., complete Freund's adjuvant), and the like. The preservative includes, but is not limited to, various antibacterial and antifungal agents, such as thimerosal, 2-phenoxyethanol, paraben, chlorobutanol, phenol, sorbic acid, and the like. The stabilizer has the meaning generally understood by those skilled in the art, which can stabilize a desired activity of the active ingredient in the drug (e.g., the inhibitory activity on PSD-95 ubiquitination), including but not limited to sodium glutamate, gelatin, SPGA, saccharide (e.g., sorbitol, mannitol, starch, sucrose, lactose, dextran, or glucose), amino acid (e.g., glutamic acid, glycine), protein (e.g., dried whey, albumin, or casein) or degradation product thereof (e.g., lactalbumin hydrolyzate), etc.

Beneficial Effects of the Present Invention

Env, as the main antigen protein of HIV-1 virus surface recognition receptor molecule, is a key molecule in the development of HIV-1 vaccine. Env on the surface of natural viruses is a non-covalently linked heterotrimer. When the virus binds to the CD4 molecule on the host cell, the conformation of Env gradually changes from a closed pre-fusion conformation to an opened conformation. Studies have shown that Env has more bNab epitopes exposed in the pre-fusion conformation. Based on the instability of the natural Env trimer, it is particularly important to perform HIV-1 Env immunogen design to stabilize its conformation.

The Env trimer protein of the present invention can be efficiently expressed in mammalian cells, with increased trimer content, improved uniformity, and significantly improved thermal stability. The Env trimeric protein of the present invention can effectively expose key epitopes such as CD4bs/V3, and is not conducive to the exposure of non-neutralizing epitopes, thus has the potential as a protein vaccine. In addition, the HIV pseudovirus and virus obtained based on the Env trimer protein are highly similar to the natural virus in shape, so they have the immunogenicity of the natural virus to the body, but they have lost the ability to infect and cause disease, and thus show the potential as virus-based vaccines, thereby having important clinical value.

Embodiments of the present invention will be described in detail below with reference to the drawings and examples, but those skilled in the art will understand that the following drawings and examples are only for illustrating the present invention, rather than limiting the scope of the present invention. Various objects and advantages of the present invention will become apparent to those skilled in the art from the accompanying drawings and the following detailed description of the preferred embodiment.

BRIEF DESCRIPTION OF THE DRAWINGS

FIG. 2A shows the BG505 strain, and FIG. 2B shows the NL4-3 strain. 1 represents TSTIP protein, 2 represents TST protein, 3 represents SOSIP protein. Both TSTIP and TST showed a single band under reducing conditions, with a molecular weight of about 140 KD, while SOSIP showed two bands under reducing conditions, which were gp120 and gp41 extracellular segment. This shows that the protein of the present invention contains a stable covalent linkage between subunits as expected.

FIG. 15A: BG-B1(1/1); FIG. 15B: BG-B1(1/2); FIG. 15C: BG-B1 (2/2); FIG. 15D: BG-B1 (2/1); FIG. 15E: BG-B1(2/3); FIG. 15F: BG-B2(1-1); FIG. 15G: BG-B2(1-2); FIG. 15H: BG-B2(1-3); FIG. 15I: BG-C1 (1/1); FIG. 15J: BG-C1 (1/2); FIG. 15K: BG-C1 (1/3).

SEQUENCE INFORMATION

Figure 1A:
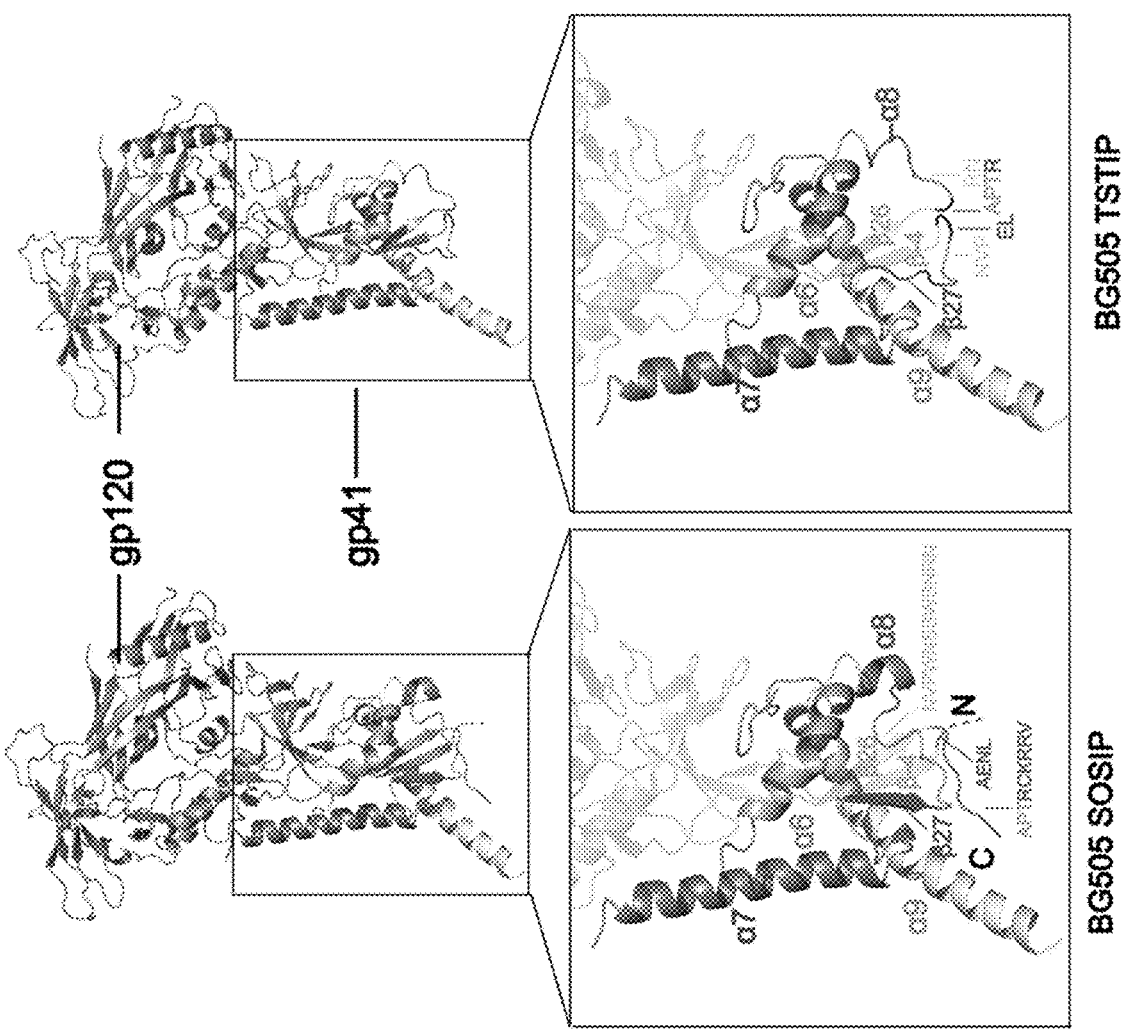
FIGS. 1A to 1B show the hypothetical spatial structure (1A) and secondary structure topology (1B) of monomeric protein of the gp140 trimer before modification (BG505 SOSIP, PDB No. 4TVP) and the trimer after modification (BG505 TSTIP).

Information on some sequences involved in the present invention is provided in Table 1 below.

TABLE 1

| Description of sequences | | |
|---|---|---|
| SEQ ID NO | Description | Sequence information |
| 1 | BG505 TST | MDAMKRGLCCVLLLCGAVFVSPSQEIHARFRRGARAENLAVGIGA VFLGFLGAAGSTMGAASMTLTVQARNLLSGIVQQQSNLLRAIEAQQ HLLKLTVWGIKQLQARVLAVERYLRDQQLLGIWGCSGKLICTTNVP NLWVTVYYGVPVWKDAETTLFCASDAKAYETEKHNVWATHACVP TDPNPQEIHLENVTEEFNMWKNNMVEQMHTDIISLWDQSLKPCVK LTPLCVTLQCTNVTNNITDDMRGELKNCSFNMTTELRDKKQKVYSL FYRLDVVQINENQGNRSNNSNKEYRLINCNTSAITQACPKVSFEPIPI HYCAPAGFAILKCKDKKFNGTGPCPSVSTVQCTHGIKPVVSTQLLLN GSLAEEEVMIRSENITNNAKNILVQFNTPVQINCTRPNNNTRKSIRIG PGQAFYATGDIIGDIRQAHCNVSKATWNETLGKVVKQLRKHFGNN TIIRFANSSGGDLEVTTHSFNCGGEFFYCNTSGLFNSTWISNTSVQGS NSTGSNDSITLPCRIKQIINMWQRIGQAMYAPPIQGVIRCVSNITGLIL TRDGGSTNSTTETFRPGGGDMRDNWRSELYKYKVVKIEPLGVAPTR RNLSEIWDNMTWLQWDKEISNYTQIIYGLLEESQNQQEKNEQDLLA LDHHHHHHHH* |
| 2 | NL4-3 TST | MDAMKRGLCCVLLLCGAVFVSPSQEIHARFRRGARAENLAVGIGA LFLGFLGAAGSTMGAASMTLTVQARQLLSDIVQQQNNLLRAIEAQQ HLLQLTVWGIKQLQARILAVERYLKDQQLLGIWGCSGKLICTTAVP NLWVTVYYGVPVWKEATTTLFCASDAKAYDTEVHNVWATHACVP TDPNPQEVVLVNVTENFNMWKNDMVEQMHEDIISLWDQSLKPCV KLTPLCVSLKCTDLKNDTNTNSSSGRMIMEKGEIKNCSFNISTSIRDK VQKEYAFFYKLDIVPIDNTSYRLISCNTSVITQACPKVSFEPIPIHYCA PAGFAILKCNNKTFNGTGPCTNVSTVQCTHGIRPVVSTQLLLNGSLA EEDVVIRSANFTDNAKTIIVQLNTSVEINCTRPNNNTRKSIRIQRGPG RAFVTIGKIGNMRQAHCNISRAKWNATLKQIASKLREQFGNNKTIIF |

TABLE 1-continued

| Description of sequences | | |
| --- | --- | --- |

| SEQ ID NO | Description | Sequence information |
| --- | --- | --- |
| | | KQSSGGDPEIVTHSFNCGGEFFYCNSTQLFNSTWFNSTWSTEGSNNT |
| | | EGSDTITLPCRIKQFINMWQEVGKAMYAPPISGQIRCSSNITGLLLTR |
| | | DGGNNNNGSEIFRPGGGDMRDNWRSELYKYKVVKIEPLGVAPTKK |
| | | SLEQIWNNMTWMEWDREINNYTSLIHSLIEESQNQQEKNEQELLEL |
| | | DKHHHHHHHH* |
| 3 | BG505 TSTIP | MDAMKRGLCCVLLLCGAVFVSPSQEIHARFRRGARAENLAVGIGA |
| | | VFLGFLGAAGSTMGAASMTLTVQARNLLSGIVQQQSNLLRAPEAQ |
| | | QHLLKLTVWGIKQLQARVLAVERYLRDQQLLGIWGCSGKLICTTN |
| | | VPNLWVTVYYGVPVWKDAETTLFCASDAKAYETEKHNVWATHAC |
| | | VPTDPNPQEIHLENVTEEFNMWKNNMVEQMHTDIISLWDQSLKPCV |
| | | KLTPLCVTLQCTNVTNNITDDMRGELKNCSFNMTTELRDKKQKVY |
| | | SLFYRLDVVQINENQGNRSNNSNKEYRLINCNTSAITQACPKVSFEPI |
| | | PIHYCAPAGFAILKCKDKKFNGTGPCPSVSTVQCTHGIKPVVSTQLL |
| | | LNGSLAEEEVMIRSENITNNAKNILVQFNTPVQINCTRPNNNTRKSIR |
| | | IGPGQAFYATGDIIGDIRQAHCNVSKATWNETLGKVVKQLRKHFGN |
| | | NTIIRFANSSGGDLEVTTHSFNCGGEFFYCNTSGLFNSTWISNTSVQG |
| | | SNSTGSNDSITLPCRIKQIINMWQRIGQAMYAPPIQGVIRCVSNITGLI |
| | | LTRDGGSTNSTTETFRPGGGDMRDNWRSELYKYKVVKIEPLGVAPT |
| | | RRNLSEIWDNMTWLQWDKEISNYTQIIYGLLEESQNQQEKNEQDLL |
| | | ALDHHHHHHHH* |
| 4 | NL4-3 TSTIP | MDAMKRGLCCVLLLCGAVFVSPSQEIHARFRRGARAENLAVGIGA |
| | | LFLGFLGAAGSTMGAASMTLTVQARQLLSDIVQQQNNLLRAPEAQ |
| | | QHLLQLTVWGIKQLQARILAVERYLKDQQLLGIWGCSGKLICTTAV |
| | | PNLWVTVYYGVPVWKEATTTLFCASDAKAYDTEVHNVWATHACV |
| | | PTDPNPQEVVLVNVTENFNMWKNDMVEQMHEDIISLWDQSLKPCV |
| | | KLTPLCVSLKCTDLKNDTNTNSSSGRMIMEKGEIKNCSFNISTSIRDK |
| | | VQKEYAFFYKLDIVPIDNTSYRLISCNTSVITQACPKVSFEPIPIHYCA |
| | | PAGFAILKCNNKTFNGTGPCTNVSTVQCTHGIRPVVSTQLLLNGSLA |
| | | EEDVVIRSANFTDNAKTIIVQLNTSVEINCTRPNNNTRKSIRIQRGPG |
| | | RAFVTIGKIGNMRQAHCNISRAKWNATLKQIASKLREQFGNNKTIIF |
| | | KQSSGGDPEIVTHSFNCGGEFFYCNSTQLFNSTWFNSTWSTEGSNNT |
| | | EGSDTITLPCRIKQFINMWQEVGKAMYAPPISGQIRCSSNITGLLLTR |
| | | DGGNNNNGSEIFRPGGGDMRDNWRSELYKYKVVKIEPLGVAPTKK |
| | | SLEQIWNNMTWMEWDREINNYTSLIHSLIEESQNQQEKNEQELLEL |
| | | DKHHHHHHHH* |
| 5 | BG505 TSTIP full | MDAMKRGLCCVLLLCGAVFVSPSQEIHARFRRGARAENLAVGIGA |
| | | VFLGFLGAAGSTMGAASMTLTVQARNLLSGIVQQQSNLLRAPEAQ |
| | | QHLLKLTVWGIKQLQARVLAVERYLRDQQLLGIWGCSGKLICTTN |
| | | VPWNSSWSNNLWVTVYYGVPVWKDAETTLFCASDAKAYETEKHN |
| | | VWATHACVPTDPNPQEIHLENVTEEFNMWKNNMVEQMHTDIISLW |
| | | DQSLKPCVKLTPLCVTLQCTNVTNNITDDMRGELKNCSFNMTTELR |
| | | DKKQKVYSLFYRLDVVQINENQGNRSNNSNKEYRLINCNTSAITQA |
| | | CPKVSFEPIPIHYCAPAGFAILKCKDKKFNGTGPCPSVSTVQCTHGIK |
| | | PVVSTQLLLNGSLAEEEVMIRSENITNNAKNILVQFNTPVQINCTRPN |
| | | NNTRKSIRIGPGQAFYATGDIIGDIRQAHCNVSKATWNETLGKVVK |
| | | QLRKHFGNNTIIRFANSSGGDLEVTTHSFNCGGEFFYCNTSGLFNST |
| | | WISNTSVQGSNSTGSNDSITLPCRIKQIINMWQRIGQAMYAPPIQGVI |
| | | RCVSNITGLILTRDGGSTNSTTETFRPGGGDMRDNWRSELYKYKVV |
| | | KIEPLGVAPTRAKRRVVGRNLSEIWDNMTWLQWDKEISNYTQIIYG |
| | | LLEESQNQQEKNEQDLLALDHHHHHHHH* |
| 6 | NL4-3 TSTIP full | MDAMKRGLCCVLLLCGAVFVSPSQEIHARFRRGARAENLREKRAV |
| | | GIGALFLGFLGAAGSTMGAASMTLTVQARQLLSDIVQQQNNLLRAP |
| | | EAQQHLLQLTVWGIKQLQARILAVERYLKDQQLLGIWGCSGKLICT |
| | | TAVPWNASWSNNLWVTVYYGVPVWKEATTTLFCASDAKAYDTEV |
| | | HNVWATHACVPTDPNPQEVVLVNVTENFNMWKNDMVEQMHEDII |
| | | SLWDQSLKPCVKLTPLCVSLKCTDLKNDTNTNSSSGRMIMEKGEIK |
| | | NCSFNISTSIRDKVQKEYAFFYKLDIVPIDNTSYRLISCNTSVITQACP |
| | | KVSFEPIPIHYCAPAGFAILKCNNKTFNGTGPCTNVSTVQCTHGIRPV |
| | | VSTQLLLNGSLAEEDVVIRSANFTDNAKTIIVQLNTSVEINCTRPNNN |
| | | TRKSIRIQRGPGRAFVTIGKIGNMRQAHCNISRAKWNATLKQIASKL |
| | | REQFGNNKTIIPKQSSGGDPEIVTHSFNCGGEFFYCNSTQLFNSTWFN |
| | | STWSTEGSNNTEGSDTITLPCRIKQFINMWQEVGKAMYAPPISGQIR |
| | | CSSNITGLLLTRDGGNNNNGSEIFRPGGGDMRDNWRSELYKYKVV |
| | | KIEPLGVAPTKAKRRVVQKSLEQIWNNMTWMEWDREINNYTSLIHS |
| | | LIEESQNQQEKNEQELLELDKGSGSGGSGHHHHHHHH* |
| 7 | BG505 TSTIP G1 | MDAMKRGLCCVLLLCGAVFVSPSQEIHARFRRGARAENLAVGIGA |
| | | VFLGFLGAAGSTMGAASMTLTVQARNLLSGIVQQQSNLLRAPEAQ |
| | | QHLLKLTVWGIKQLQARVLAVERYLRDQQLLGIWGCSGKLICTTN |
| | | VPGGGGSNLWVTVYYGVPVWKDAETTLFCASDAKAYETEKHNVW |

TABLE 1-continued

Description of sequences

| SEQ ID NO | Description | Sequence information |
|---|---|---|
| | | ATHACVPTDPNPQEIHLENVTEEFNMWKNNMVEQMHTDIISLWDQ<br>SLKPCVKLTPLCVTLQCTNVTNNITDDMRGELKNCSFNMTTELRDK<br>KQKVYSLFYRLDVVQINENQGNRSNNSNKEYRLINCNTSAITQACP<br>KVSFEPIPIHYCAPAGFAILKCKDKKFNGTGPCPSVSTVQCTHGIKPV<br>VSTQLLLNGSLAEEEVMIRSENITNNAKNILVQFNTPVQINCTRPNN<br>NTRKSIRIGPGQAFYATGDIIGDIRQAHCNVSKATWNETLGKVVKQL<br>RKHFGNNTIIRFANSSGGDLEVTTHSFNCGGEFFYCNTSGLFNSTWIS<br>NTSVQGSNSTGSNDSITLPCRIKQIINMWQRIGQAMYAPPIQGVIRCV<br>SNITGLILTRDGGSTNSTTETFRPGGGDMRDNWRSELYKYKVVKIEP<br>LGVAPTRGGGGSRNLSEIWDNMTWLQWDKEISNYTQIIYGLLEESQ<br>NQQEKNEQDLLALDHHHHHHHH* |
| 8 | NL4-3 TSTIP G1 | MDAMKRGLCCVLLLCGAVFVSPSQEIHARFRRGARAENLREKRAV<br>GIGALFLGFLGAAGSTMGAASMTLTVQARQLLSDIVQQQNNLLRAP<br>EAQQHLLQLTVWGIKQLQARILAVERYLKDQQLLGIWGCSGKLICT<br>TAVPGGGGSNLWVTVYYGVPVWKEATTTLFCASDAKAYDTEVHN<br>VWATHACVPTDPNPQEVVLVNVTENFNMWKNDMVEQMHEDIISL<br>WDQSLKPCVKLTPLCVSLKCTDLKNDTNTNSSSGRMIMEKGEIKNC<br>SFNISTSIRDKVQKEYAFFYKLDIVPIDNTSYRLISCNTSVITQACPKV<br>SFEPIPIHYCAPAGFAILKCNNKTFNGTGPCTNVSTVQCTHGIRPVVS<br>TQLLLNGSLAEEDVVIRSANFTDNAKTIIVQLNTSVEINCTRPNNNTR<br>KSIRIQRGPGRAFVTIGKIGNMRQAHCNISRAKWNATLKQIASKLRE<br>QFGNNKTIIFKQSSGGDPEIVTHSFNCGGEFFYCNSTQLFNSTWFNST<br>WSTEGSNNTEGSDTITLPCRIKQFINMWQEVGKAMYAPPISGQIRCS<br>SNITGLLLTRDGGNNNNGSEIFRPGGGDMRDNWRSELYKYKVVKIE<br>PLGVAPTKGGGGSKSLEQIWNNMTWMEWDREINNYTSLIHSLIEES<br>QNQQEKNEQELLELDKGSGSGGSGHHHHHHHH* |
| 9 | BG505 TSTIP G2 | MDAMKRGLCCVLLLCGAVFVSPSQEIHARFRRGARAENLAVGIGA<br>VFLGFLGAAGSTMGAASMTLTVQARNLLSGIVQQQSNLLRAPEAQ<br>QHLLKLTVWGIKQLQARVLAVERYLRDQQLLGIWGCSGKLICTTN<br>VPGGGGSGGGGSNLWVTVYYGVPVWKDAETTLFCASDAKAYETE<br>KHNVWATHACVPTDPNPQEIHLENVTEEFNMWKNNMVEQMHTDII<br>SLWDQSLKPCVKLTPLCVTLQCTNVTNNITDDMRGELKNCSFNMTT<br>ELRDKKQKVYSLFYRLDVVQINENQGNRSNNSNKEYRLINCNTSAI<br>TQACPKVSFEPIPIHYCAPAGFAILKCKDKKFNGTGPCPSVSTVQCTH<br>GIKPVVSTQLLLNGSLAEEEVMIRSENITNNAKNILVQFNTPVQINCT<br>RPNNNTRKSIRIGPGQAFYATGDIIGDIRQAHCNVSKATWNETLGKV<br>VKQLRKHFGNNTIIRFANSSGGDLEVTTHSFNCGGEFFYCNTSGLFN<br>STWISNTSVQGSNSTGSNDSITLPCRIKQIINMWQRIGQAMYAPPIQG<br>VIRCVSNITGLILTRDGGSTNSTTETFRPGGGDMRDNWRSELYKYK<br>VVKIEPLGVAPTRGGGGSGGGGSRNLSEIWDNMTWLQWDKEISNY<br>TQIIYGLLEESQNQQEKNEQDLLALDHHHHHHHH* |
| 10 | NL4-3 TSTIP G2 | MDAMKRGLCCVLLLCGAVFVSPSQEIHARFRRGARAENLREKRAV<br>GIGALFLGFLGAAGSTMGAASMTLTVQARQLLSDIVQQQNNLLRAP<br>EAQQHLLQLTVWGIKQLQARILAVERYLKDQQLLGIWGCSGKLICT<br>TAVPGGGGSGGGGSNLWVTVYYGVPVWKEATTTLFCASDAKAYD<br>TEVHNVWATHACVPTDPNPQEVVLVNVTENFNMWKNDMVEQMH<br>EDIISLWDQSLKPCVKLTPLCVSLKCTDLKNDTNTNSSSGRMIMEKG<br>EIKNCSFNISTSIRDKVQKEYAFFYKLDIVPIDNTSYRLISCNTSVITQ<br>ACPKVSFEPIPIHYCAPAGFAILKCNNKTFNGTGPCTNVSTVQCTHGI<br>RPVVSTQLLLNGSLAEEDVVIRSANFTDNAKTIIVQLNTSVEINCTRP<br>NNNTRKSIRIQRGPGRAFVTIGKIGNMRQAHCNISRAKWNATLKQIA<br>SKLREQFGNNKTIIFKQSSGGDPEIVTHSFNCGGEFFYCNSTQLFNST<br>WFNSTWSTEGSNNTEGSDTITLPCRIKQFINMWQEVGKAMYAPPIS<br>GQIRCSSNITGLLLTRDGGNNNNGSEIFRPGGGDMRDNWRSELYKY<br>KVVKIEPLGVAPTKGGGGSGGGGSKSLEQIWNNMTWMEWDREINN<br>YTSLIHSLIEESQNQQEKNEQELLELDKGSGSGGSGHHHHHHHH* |
| 11 | 25710-TSTIP | AVGIGAVFLGFLGAAGSTMGAASITLTVQARQLLSGIVQQQSNLLR<br>APEAQQHLLQLTVWGIKQLQTRVLAIERYLKDQQLLGIWGCSGKLI<br>CTTAVPNLWVTVYYGVPVWKEATTTLFCASDAKAYDKEVHNVWA<br>THACVPTDPNPQEMVLGNVTENFNMWKNEMVNQMHEDVISLWD<br>QSLKPCVKLTPLCVTLECSNVTYNESMKEVKNCSFNLTTELRDKKQ<br>KVHALFYRLDIVPLNDTEKKNSSRPYRLINCNTSAITQACPKVTFDPI<br>PIHYCTPAGYAILKCNDKKFNGTGPCHKVSTVQCTHGIKPVVSTQLL<br>LNGSLAEGEIIIRSENLTNNAKTIIVHLNQSVEIVCARPSNNTRTSIRIG<br>PGQTFYATGAIITGDIRQAHCNISKDKWNETLQRVGEKLAEHFPNKTI<br>KFNSSSGGDLEITTHSFNCRGEFFYCNTSGLFNGTFNGTYVSPNSTDS<br>NSSSIITIPCRIKQIINMWQEVGRAMYAPPIAGNITCKSNITGLLLVRD<br>GGTGSESNKTEIFRPGGGDMRDNWRSELYKYKVVEIKPLGVAPTKR<br>SQDDIWDNMTWMQWDKEISNYTNTIYKLLEDSQIQQEKNEKDLLA<br>LDSHHHHHHHH |

TABLE 1-continued

Description of sequences

| SEQ ID NO | Description | Sequence information |
|---|---|---|
| 12 | X1632-TSTIP | MDAMKRGLCCVLLLCGAVFVSPSQEIHARFRRGARAIGLGTVLLGF LGTAGSTMGAASITLTVQVRQLLSGIVQQQSNLLRAPEAQQHLLQLT VWGIKQLQARVLAVERYLKDQQILGIWGCSGKLICTTNVPNLWVTV YYGVPVWEDADTTLFCASDAKAYSTESHNVWATHACVPTDPNPQEI YLENVTEDFNMWENNMVEQMQEDIISLWDESLKPCVKLTPLCVTLT CTNVTNVTDSVGTNSRLKGYKEELKNCSFNTTTEIRDKKKQEYALF YKLDIVPINDNSNNSNGYRLINCNVSTIKQACPKVSFDPIPIHYCAPA GFAILKCRDKEFNGTGTCRNVSTVQCTHGIKPVVSTQLLLNGSLAEG DIVIRSENITDNAKTIIVHLNKTVSITCTRPNNNTRKSIRIGPGQALYAT GAIIGDTRQAHCNINGSEWYEMIQNVKNKLNETFKKNITFNPSSGGD LEITTHSFNCRGEFFYCNTSELFNSSHLFNGSTLSTNGTITLPCRIKQI VRMWQRVGQAMYAPPIAGNITCRSNITGLLLTRDGGTNKDTNEAET FRPGGGDMRDNWRSELYKYKVVKIKPLGVAPTRKSYSDIWDNLTWI QWEREISNYTQQIYTLLEESQNQQEKNEQELLALDKHHHHHHHH |
| 13 | CH119-TSTIP(BC) | MDAMKRGLCCVLLLCGAVFVSPSQEIHARFRRGARAVGIGAVFLGF LGVAGSTMGAASMTLTVQARQLLSGIVQQQSNLLRAPEAQQHLLQ LTVWGIKQLQTRVLAIERYLKDQQLLGIWGCSGKLICTTAVPNLWV TVYYGVPVWKEATTTLFCASDAKAYDTEVHNVWATHACVPTDPSP QELVLENVTENFNMWKNEMVNQMHEDVISLWDQSLKPCVKLTPL CVTLECSKVSNNETDKYNGTEEMKNCSFNATTVVRDRQQKVYALF YRLDIVPLTEKNSSENSSKYYRLINCNTSAITQACPKVSFEPIPIHYCT PAGYAILKCNDKTFNGTGPCHNVSTVQCTHGIKPVVSTQLLLNGSL AEGEIIIRSENLTNNVKTILVHLNQSVEIVCTRPNNNTRKSIRIGPGQT FYATGDIIGDIRQAHCNISKWHETLKRVSEKLAEHFPNKTINFTSSSG GDLEITTHSFTCRGEFFYCNTSGLFNSTYMPNGTYLHGDTNSNSSITI PCRIKQIINMWQEVGRAMYAPPIEGNITCKSNITGLLLVRDGGTESN NTETNNTEIFRPGGGDMRDNWRSELYKYKVVEIKPLGVAPTAKSQK EIWDNMTWMQWDKEISNYTNTIYKLLEDSQNQQESNEKDLLALDH HHHHHHH |
| 14 | CNE8-TSTIP(AE) | MDAMKRGLCCVLLLCGAVFVSPSQEIHARFRRGARAVGIGAMIFGF LGAAGSTMGAASITLTVQARQLLSGIVQQQSNLLRAPEAQQHLLQL TVWGIKQLQARVLAVERYLKDQKFLGIWGCSGKIICTTAVPNLWV TVYYGVPVWRDADTTLFCASDAKAYDTEVHNVWATHACVPTDPN PQEIHLENVTENFNMWKNKMAEQMQEDVISLWDESLKPCVQLTPL CVTLNCTNANLNATVNASTTIGNITDEVRNCSFNTTTELRDKKQNV YALFYKLDIVPINNNSEYRLINCNTSVIKQACPKVSFDPIPIHYCAPA GYAILRCNDKNFNGTGPCKNVSSVQCTHGIKPVVSTQLLLNGSLAE DEIIIRSENLTDNVKTIIVHLNKSVEINCTRPSNNTRTSVRIGPGQVFY RTGDIIGDIRKAYCEINRTKWHETLKQVATKLREHFNKTIIFQPPSGG DIEITMHHFNCRGEFFYCNTTKLFNSTWGENTTMEGHNDTIVLPCRI KQIVNMWQGVGQAMYAPPIRGSINCVSNITGILLTRDGGTNMSNET FRPGGGNIKDNWRSELYKYKVVEIEPLGIAPTKRSYEEIWDNMTWIE WEREISNYTSQIYEILTESQNQQDRNEKDLLELDKHHHHHHHH |
| 15 | p246F3-TSTIP | MDAMKRGLCCVLLLCGAVFVSPSQEIHARFRRGARAVGIGAVFIGF LGAAGSTMGAASITLTVQARQLLSGIVQQQSNLLRAPEAQQHLLKL TVWGIKQLQARVLAVERYLKDQQLLGIWGCSGKLICTTNVDLWVT VYYGVPVWKDAKTTLFCASDAKAYEKEVHNVWATHACVPTDPNP QEIVMANVTEEFNMWKNNMVEQMHTDIISLWDQSLKPCVKLTPLC VTLDCKDYNYSITNNSTGMEGEIKNCSYNITTELRDKRQKVYSLFY RLDVVQINDSNDRNNSQYRLINCNTTTMTQACPKVTFDPIPIHYCAP AGFAILKCNNKTFNGKGPCNNVSSVQCTHGIKPVVSTQLLINGSLA EKEIVIRSENLTDNVKTIIVHLNESVEINCTRPNNNTRKSVRIGPGQTF YATGDIIGNIRQAHCNVNKTEWNTALTRVSKKLKEYFPNKTIAFQPS SGGDLEITTFSFNCRGEFFYCNTSDLFNGTFNETSGQFNSTFNSTLQC RIKQIINMWQEVGQAMYAPPIAGSITCISNITGLILTRDGGNTNSTKE TFRPGGGNMRDNWRSELYKYKVVKIEPLGVAPTKKSQDEIWDNMT WLQWDKEISNYTQIIYNLIEESQTQQELNERDLLALDHHHHHHHH |
| 16 | Bal.26-TSTIP-gp160 (AA:646-836 are transmembrane region and intracellular region) | MRVTEIRKSYQHWWRWGIMLLGMLMICNAEEKAVGIGAVLLGFL GAAGSTMGAASMTLTVQARLLLSGIVQQQNNLLRAIEAQQHLLQL TVWGIKQLQARVLAVERYLRDQQLLGPWGCSGKLICTTAVPNLWV TVYYGVPVWKEATTTLFCASDAKAYDTEVHNVWATHACVPTDPN PQEVKMENVTENFNMWKNNVVEQMHEDIISLWDQSLKPCVKLTPL CVTLNCTDLKNATNGNNTNTTSSSGGMMGGGEMKNCSFNITTNIR GKVQKEYALFYELDIVPIDNKIDSYRLISCNTSVITQACPKVSFEPIPI HYCAPAGFAILKCKDKKFNGKGPCSNVSTVQCTHGIRPVVSTQLLL NGSLAEEEVVIRSENFTNNAKIIVVQLNESVEINCTRPNNNTRKSIHI GPGRAFYTTGEIIGDIRQAHCNLSRAKWNDTLNKIVIKLREQFGNKT IVFKHSSGGDPEIVTHSFNCGGEFFYCNSTQLFNSTWNVTEESNNTV ENNTITLPCRIKQIINMWQEVGRAMYAPPIRGQIRCSSNITGLLLTRD |

TABLE 1-continued

| | | Description of sequences |
|---|---|---|

| SEQ ID NO | Description | Sequence information |
|---|---|---|
| | | GGPEDDKTEVFRPGGGDMRDNWRSELYKYKVVKIEPLGVAPTKKS<br>LNKIWDNMTWMEWDREINNYTSIIYSLIEESQNQQEKNEQELLELD<br>KWASLWNWFDITKWLWYIKIFIMIVGGLIGLRIVESVLSIVNRVRQG<br>YSPLSFQTHLPASRGPDRPGGIEEEGGERDRDRSGPLVNGFLTLIWV<br>DLRSLFLFSYHRLRDLLLIVTRIVELLGRRGWEVLKYWWNLLQYWS<br>QELKNSAVSLLNTIAIAVAEGTDRVIEVVQRAVRAILHIPRRIRQGLE<br>RALL |
| 17 | NL4-3 TSTIP-gp160<br>(aa646-837 are<br>transmembrane<br>region<br>and intracellular<br>region) | MRVKEKYQHLWRWGWKWGTMLLGILMICSATEKAVGIGALFLGF<br>LGAAGSTMGAASMTLTVQARQLLSDIVQQQNNLLRAPEAQQHLLQ<br>LTVWGIKQLQARILAVERYLKDQQLLGIWGCSGKLICTTAVPNLWV<br>TVYYGVPVWKEATTTLFCASDAKAYDTEVHNVWATHACVPTDPN<br>PQEVVLVNVTENFNMWKNDMVEQMHEDIISLWDQSLKPCVKLTPL<br>CVSLKCTDLKNDTNTNSSSGRMIMEKGEIKNCSFNISTSIRDKVQKE<br>YAFFYKLDIVPIDNTSYRLISCNTSVITQACPKVSFEPIPIHYCAPAGF<br>AILKCNNKTFNGTGPCTNVSTVQCTHGIRPVVSTQLLLNGSLAEEDV<br>VIRSANFTDNAKTIIVQLNTSVEINCTRPNNNTRKSIRIQRGPGRAFV<br>TIGKIGNMRQAHCNISRAKWNATLKQIASKLREQFGNNKTIIFKQSS<br>GGDPEIVTHSFNCGGEFFYCNSTQLFNSTWFNSTWSTEGSNNTEGSD<br>TITLPCRIKQFINMWQEVGKAMYAPPISGQIRCSSNITGLLLTRDGGN<br>NNNGSEIFRPGGGDMRDNWRSELYKYKVVKIEPLGVAPTKKSLEQI<br>WNNMTWMEWDREINNYTSLIHSLIEESQNQQEKNEQELLELDKWA<br>SLWNWFNITNWLWYIKLFIMIVGGLVGLRIVFAVLSIVNRVRQGYSP<br>LSFQTHLPIPRGPDRPEGIEEEGGERDRDRSIRLVNGSLALIWDDLRS<br>LCLFSYHRLRDLLLIVTRIVELLGRRGWEALKYWWNLLQYWSQEL<br>KNSAVNLLNATAIAVAEGTDRVIEVLQAAYRAIRHIPRRIRQGLERIL<br>L |
| 18 | BG505 gp160<br>(aa662-859 are<br>transmembrane<br>region<br>and intracellular<br>region) | MRVMGIQRNCQHLFRWGTMILGMIIICSAAENLWVTVYYGVPVWK<br>DAETTLFCASDAKAYETEKHNVWATHACVPTDPNPQEIHLENVTEE<br>FNMWKNNMVEQMHTDIISLWDQSLKPCVKLTPLCVTLQCTNVTNN<br>ITDDMRGELKNCSFNMTTELRDKKQKVYSLFYRLDVVQINENQGN<br>RSNNSNKEYRLINCNTSAITQACPKVSFEPIPIHYCAPAGFAILKCKD<br>KKFNGTGPCPSVSTVQCTHGIKPVVSTQLLLNGSLAEEEVMIRSENIT<br>NNAKNILVQFNTPVQINCTRPNNNTRKSIRIGPGQAFYATGDIIGDIR<br>QAHCTVSKATWNETLGKVVKQLRKHFGNNTIIRFANSSGGDLEVTT<br>HSFNCGGEFFYCNTSGLFNSTWISNTSVQGSNSTGSNDSITLPCRIKQ<br>IINMWQRIGQAMYAPPIQGVIRCVSNITGLILTRDGGSTNSTTETFRP<br>GGGDMRDNWRSELYKYKVVKIEPLGVAPTRAKRRVGREKRAVGI<br>GAVFLGFLGAAGSTMGAASMTLTVQARNLLSGIVQQQSNLLRAIEA<br>QQHLLKLTVWGIKQLQARVLAVERYLRDQQLLGIWGCSGKLICTT<br>NVPWNSSWSNRNLSEIWDNMTWLQWDKEISNYTQIIYGLLEESQN<br>QQEKNEQDLLALDKWASLWNWFDISNWLWYIKIFIMIVGGLIGLRI<br>VFAVLSVIHRVRQGYSPLSFQTHTPNPRGLDRPERIEEEDGEQDRGR<br>STRLVSGFLALAWDDLRSLCLFCYHRLRDFILIAARIVELLGHSSLKG<br>LRLGWEGLKYLWNLLAYWGRELKISAINLFDTIAIAVAEWTDRVIEI<br>GQRLCRAFLHIPRRIRQGLERAL |
| 19 | NL4-3 gp160<br>(aa663-854 are<br>transmembrane<br>region<br>and intracellular<br>region) | MRVKEKYQHLWRWGWKWGTMLLGILMICSATEKLWVTVYYGVP<br>VWKEATTTLFCASDAKAYDTEVHNVWATHACVPTDPNPQEVVLV<br>NVTENFNMWKNDMVEQMHEDIISLWDQSLKPCVKLTPLCVSLKCT<br>DLKNDTNTNSSSGRMIMEKGEIKNCSFNISTSIRDKVQKEYAFFYKL<br>DIVPIDNTSYRLISCNTSVITQACPKVSFEPIPIHYCAPAGFAILKCNN<br>KTFNGTGPCTNVSTVQCTHGIRPVVSTQLLLNGSLAEEDVVIRSANF<br>TDNAKTIIVQLNTSVEINCTRPNNNTRKSIRIQRGPGRAFVTIGKIGN<br>MRQAHCNISRAKWNATLKQIASKLREQFGNNKTIIFKQSSGGDPEIV<br>THSFNCGGEFFYCNSTQLFNSTWFNSTWSTEGSNNTEGSDTITLPCRI<br>KQFINMWQEVGKAMYAPPISGQIRCSSNITGLLLTRDGGNNNNGSEI<br>FRPGGGDMRDNWRSELYKYKVVKIEPLGVAPTKAKRRVVQREKR<br>AVGIGALFLGFLGAAGSTMGAASMTLTVQARQLLSDIVQQQNNLL<br>RAIEAQQHLLQLTVWGIKQLQARILAVERYLKDQQLLGIWGCSGKL<br>ICTTAVPWNASWSNKSLEQIWNNMTWMEWDREINNYTSLIHSLIEE<br>SQNQQEKNEQELLELDKWASLWNWFNITNWLWYIKLFIMIVGGLV<br>GLRIVFAVLSIVNRVRQGYSPLSFQTHLPIPRGPDRPEGIEEEGGERD<br>RDRSIRLVNGSLALIWDDLRSLCLFSYHRLRDLLLIVTRIVELLGRRG<br>WEALKYWWNLLQYWSQELKNSAVNLLNATAIAVAEGTDRVIEVL<br>QAAYRAIRHIPRRIRQGLERILL* |

TABLE 1-continued

| | | Description of sequences |
|---|---|---|

| SEQ ID NO | Description | Sequence information |
|---|---|---|
| 20 | 25710 gp160 (aa657-855 are transmembrane region and intracellular region) | MRVRGTLRNYQQWWIWGVLGFWMLMICNVGGNLWVTVYYGVP<br>VWKEATTTLFCASDAKAYDKEVHNVWATHACVPTDPNPQEMVLG<br>NVTENFNMWKNEMVNQMHEDVISLWDQSLKPCVKLTPLCVTLECS<br>NVTYNESMKEVKNCSFNLTTELRDKKQKVHALFYRLDIVPLNDTEK<br>KNSSRPYRLINCNTSAITQACPKVTFDPIPIHYCTPAGYAILKCNDKK<br>FNGTGPCHKVSTVQCTHGIKPVVSTQLLLNGSLAEGEIIIRSENLTNN<br>AKTIIVHLNQSVEIVCARPSNNTRTSIRIGPGQTFYATGAITGDIRQAH<br>CNISKDKWNETLQRVGEKLAEHFPNKTIKFNSSSGGDLEITTHSFNC<br>RGEFFYCNTSGLFNGTFNGTYVSPNSTDSNSSSIITIPCRIKQIINMWQ<br>EVGRAMYAPPIAGNITCKSNITGLLLVRDGGTGSESNKTEIFRPGGG<br>DMRDNWRSELYKYKVVEIKPLGVAPTKAKRRVVEREKRAVGIGAV<br>FLGFLGAAGSTMGAASITLTVQARQLLSGIVQQQSNLLRAIEAQQHL<br>LQLTVWGIKQLQTRVLAIERYLKDQQLLGIWGCSGKLICTTAVPWN<br>YSWSNRSQDDIWDNMTWMQWDKEISNYTNTIYKLLEDSQIQQEKN<br>EKDLLALDSWENLWNWFNITNWLWYIKIFIIIVGGLIGLRIIFAVLPIV<br>NRVRQGYSPLSFQTHTPTPGGPDRLGRIEEEGGEQDNVRSIRLVNGF<br>LALAWDDLRNLCLFSYHRLRDFILVAARVVELLGRNSLRGLQKGW<br>EALKYLGSLVQYWGLELKRSAISLLDTIAIAVAEGTDRIIQLGQGICR<br>AICNIPRRIRQGLEAALQ |
| 21 | X1632 gp160 (aa660-858 are transmembrane region and intracellular region) | MKVKGTQRDWHSLWNWGILILGLVIICSASNNLWVTVYYGVPVWE<br>DADTTLFCASDAKAYSTESHNVWATHACVPTDPNPQEIYLENVTED<br>FNMWENNMVEQMQEDIISLWDESLKPCVKLTPLCVTLTCTNVTNV<br>TDSVGTNSRLKGYKEELKNCSFNTTTEIRDKKKQEYALFYKLDIVPI<br>NDNSNNSNGYRLINCNVSTIKQACPKVSFDPIPIHYCAPAGFAILKCR<br>DKEFNGTGTCRNVSTVQCTHGIKPVVSTQLLLNGSLAEGDIVIRSENI<br>TDNAKTIIVHLNKTVSITCTRPNNNTRKSIRIGPGQALYATGAIIGDT<br>RQAHCNINGSEWYEMIQNVKNKLNETFKKNITFNPSSGGDLEITTHS<br>FNCRGEFFYCNTSELFNSSHLFNGSTLSTNGTITLPCRIKQIVRMWQR<br>VGQAMYAPPIAGNITCRSNITGLLLTRDGGTNKDTNEAETFRPGGG<br>DMRDNWRSELYKYKVVKIKPLGVAPTRARRRVVEREKRAIGLGTV<br>LLGFLGTAGSTMGAASITLTVQVRQLLSGIVQQQSNLLRAIEAQQHL<br>LQLTVWGIKQLQARVLAVERYLKDQQILGIWGCSGKLICTTNVPWN<br>SSWSNKSYSDIWDNLTWIQWEREISNYTQQIYTLLEESQNQQEKNE<br>QELLALDKWASLWNWFDITNWLWYIKIFIMIVGGLIGLRIVFAVLSII<br>NRVRKGYSPLSFQTLTRHQREPDRPGGIEEEDGEQDRDKSVRFVSGF<br>LSPVWDDLRSLCLFSYRRLRDFILVAARTVELLGRSSLKGLRLGWE<br>GLKYLWNLLLYWGRELKSSAINLLDTTAIAVANWTDRVIEVGQRIV<br>RAFLHIPVRIRQGLERALL |
| 22 | CH119 gp160 (aa663-862 are transmembrane region and intracellular region) | MRVTGIRKNYRHLWRWGTMLLGMLMICSAVGNLWVTVYYGVPV<br>WKEATTTLFCASDAKAYDTEVHNVWATHACVPTDPSPQELVLENVT<br>ENFNMWKNEMVNQMHEDVISLWDQSLKPCVKLTPLCVTLECSKVS<br>NNETDKYNGTEEMKNCSFNATTVVRDRQQKVYALFYRLDIVPLTEK<br>NSSENSSKYYRLINCNTSAITQACPKVSFEPIPIHYCTPAGYAILKCND<br>KTFNGTGPCHNVSTVQCTHGIKPVVSTQLLLNGSLAEGEIIIRSENLT<br>NNVKTILVHLNQSVEIVCTRPNNNTRKSIRIGPGQTFYATGDIIGDIRQ<br>AHCNISKWHETLKRVSEKLAEHFPNKTINFTSSSGGDLEITTHSFTCR<br>GEFFYCNTSGLFNSTYMPNGTYLHGDTNSNSSITIPCRIKQIINMWQE<br>VGRAMYAPPIEGNITCKSNITGLLLVRDGGTESNNTETNNTEIFRPGG<br>GDMRDNWRSELYKYKVVEIKPLGVAPTAAKRRVVEREKRAVGIGA<br>VFLGFLGVAGSTMGAASMTLTVQARQLLSGIVQQQSNLLRAIEAQQ<br>HLLQLTVWGIKQLQTRVLAIERYLKDQQLLGIWGCSGKLICTTAVPW<br>NSSWSNKSQKEIWDNMTWMQWDKEISNYTNTIYKLLEDSQNQQES<br>NEKDLLALDSWNNLWNWFNITQWLWYIKIFIIIVGGLIGLRIIFAVLSI<br>VNRVRQGYSPLSFQTLTPTSGGRPDRLERIEEEGGEQDRDRSIRLVNG<br>FLALAWDDLRNLCLFSYHRLRDFILVAARVVELLGRTSLRGLQRGW<br>EALKYLGSLVQYWGQELKKSAISLVDTIAIVVAEGTDRIIDIVQAFCR<br>AIYNIPRRIRQGFEAALQ |
| 23 | CNE8 gp160 (aa652-850 are transmembrane region and intracellular region) | MRVKETQMNWPNLWKWGTLILGLVIICSASDNLWVTVYYGVPVW<br>RDADTTLFCASDAKAYDTEVHNVWATHACVPTDPNPQEIHLENVT<br>ENFNMWKNKMAEQMQEDVISLWDESLKPCVQLTPLCVTLNCTNA<br>NLNATVNASTTIGNITDEVRNCSFNTTTELRDKKQNVYALFYKLDIV<br>PINNNSEYRLINCNTSVIKQACPKVSFDPIPIHYCAPAGYAILRCNDK<br>NFNGTGPCKNVSSVQCTHGIKPVVSTQLLLNGSLAEDEIIIRSENLTD<br>NVKTIIVHLNKSVEINCTRPSNNTRTSVRIGPGQVFYRTGDIIGDIRKA<br>YCEINRTKWHETLKQVATKLREHFNKTIIFQPPSGGDIEITMHHFNC<br>RGEFFYCNTTKLFNSTWGENTTMEGHNDTIVLPCRIKQIVNMWQGV<br>GQAMYAPPIRGSINCVSNITGILLTRDGGTNMSNETFRPGGGNIKDN<br>WRSELYKYKVVEIEPLGIAPTKAKRRVVEREKRAVGIGAMIFGFLG<br>AAGSTMGAASITLTVQARQLLSGIVQQQSNLLRAPEAQQHLLQLTV<br>WGIKQLQARVLAVERYLKDQKFLGLWGCSGKIICTTAVPWNSTWS |

TABLE 1-continued

| | | Description of sequences |
|---|---|---|

| SEQ ID NO | Description | Sequence information |
|---|---|---|
| | | NRSYEEIWDNMTWIEWEREISNYTSQIYEILTESQNQQDRNEKDLLE LDKWASLWNWFDITRWLWYIKIFIMIVGGLIGLRIIFAVLSIVNRVR QGYSPLSFQTPTHHQREPDRPERIEEGGGEQDRDRSVRLVSGFLALA WDDLRSLCLFSYHRLRDLILIAVRTVELLGHGGLKGLRRGWEGLKY LGNLLLYWGQELKISAISLLDATAIAVAGWTDRIIEVAQRAWRAILH IPRRIRQGLERSLL |
| 24 | p246F3 gp160 (aa654-852 are transmembrane region and intracellular region) | MRARGMLRTWQHWWIWGILGFWMLMICNMQDLWVTVYYGVPV WKDAKTTLFCASDAKAYEKEVHNVWATHACVPTDPNPQEIVMAN VTEEFNMWKNNMVEQMHTDIISLWDQSLKPCVKLTPLCVTLDCKD YNYSITNNSTGMEGEIKNCSYNITTELRDKRQKVYSLFYRLDVVQIN DSNDRNNSQYRLINCNTTTMTQACPKVTFDPIPIHYCAPAGFAILKC NNKTFNGKGPCNNVSSVQCTHGIKPVVSTQLLLNGSLAEKEIVIRSE NLTDNVKTIIVHLNESVEINCTRPNNNTRKSVRIGPGQTFYATGDIIG NIRQAHCTVNKTEWNTALTRVSKKLKEYFPNKTIAFQPSSGGDLEIT TFSFNCRGEFFYCNTSDLFNGTFNETSGQFNSTFNSTLQCRIKQIINM WQEVGQAMYAPPIAGSITCISNITGLILTRDGGNTNSTKETFRPGGGN MRDNWRSELYKYKVVKIEPLGVAPTKARRRVVEREKRAVGIGAVFI GFLGAAGSTMGAASITLTVQARQLLSGIVQQQSNLLRAIEAQQHLL KLTVWGIKQLQARVLAVERYLKDQQLLGIWGCSGKLICTTNVPWNS SWSNKSQDEIWDNMTWLQWDKEISNYTQIIYNLIEESQTQQELNER DLLALDKWANLWNWFDITKWLWYIKIFIMIVGGLIGLRIIFAVLSIVN RVRQGYSPLSFQTLTPNPRGPDRPGGIEEEGGEQGRNSYTRLVSGFLP LAWDDLRSLCLFSYHLLRDFILIAARAAELLGRSSLRGLQRGWETLK YLGSLVQYWGLELKKSAISLLDTIAIQVAEGTDRIIELIQGIYRAIRNIP RRIRQGAETALV |
| 25 | Bal.26 gp160 (aa662-853 are transmembrane region and intracellular region) | MRVTEIRKSYQHWWRWGIMLLGMLMICNAEEKLWVTVYYGVPV WKEATTTLFCASDAKAYDTEVHNVWATHACVPTDPNPQEVKMEN VTENFNMWKNNVVEQMHEDIISLWDQSLKPCVKLTPLCVTLNCTD LKNATNGNNTNTTSSSGGMMGGGEMKNCSFNITTNIRGKVQKEYA LFYELDIVPIDNKIDSYRLISCNTSVITQACPKVSFEPIPIHYCAPAGFA ILKCKDKKFNGKGPCSNVSTVQCTHGIRPVVSTQLLLNGSLAEEEVV IRSENFTNNAKIIVVQLNESVEINCTRPNNNTRKSIHIGPGRAFYTTGE IIGDIRQAHCNLSRAKWNDTLNKIVIKLREQFGNKTIVFKHSSGGDPE IVTHSFNCGGEFFYCNSTQLFNSTWNVTEESNNTVENNTITLPCRIKQ IINMWQEVGRAMYAPPIRGQIRCSSNITGLLLTRDGGPEDDKTEVFR PGGGDMRDNWRSELYKYKVVKIEPLGVAPTKAKRRVVQREKRAV GIGAVLLGFLGAAGSTMGAASMTLTVQARLLLSGIVQQQNNLLRAI EAQQHLLQLTVWGIKQLQARVLAVERYLRDQQLLGIWGCSGKLIC TTAVPWNASWSNKSLNKIWDNMTWMEWDREINNYTSIIYSLIEESQ NQQEKNEQELLELDKWASLWNWFDITKWLWYIKIFIMIVGGLIGLR IVFSVLSIVNRVRQGYSPLSFQTHLPASRGPDRPGGIEEEGGERDRDR SGPLVNGFLTLIWVDLRSLFLFSYHRLRDLLLIVTRIVELLGRRGWE VLKYWWNLLQYWSQELKNSAVSLLNTIAIAVAEGTDRVIEVVQRA VRAILHIPRRIRQGLERALL* |
| 26 | BG505-deleted sequence from gp41 | WNSSWSN |
| 27 | BG505-deleted sequence from gp120 | AKRRVVGREKR |
| 28 | Linker-1 | GGGGS |
| 29 | Linker-2 | GGGGSGGGGS |
| 30 | BG-B1(1/1) | MDAMKRGLCCVLLLCGAVFVSPSQEIHARFRRGARAVGIGAVFLGF LGAAGSTMGAASMTLTVQARNLLSGIVQQQSNLLRAPEAQQHLLK LTVWGIKQLQARVLAVERYLRDQQLLGIWGCSGKLICTTNVPGGG GSAENLWVTVYYGVPVWKDAETTLFCASDAKAYETEKHNVWATH ACVPTDPNPQEIHLENVTEEFNMWKNNMVEQMHTDIISLWDQSLKP CVKLTPLCVTLQCTNVTNNITDDMRGELKNCSFNMTTELRDKKQK VYSLFYRLDVVQINENQGNRSNNSNKEYRLINCNTSAITQACPKVSF EPIPIHYCAPAGFAILKCKDKKFNGTGPCPSVSTVQCTHGIKPVVSTQ LLLNGSLAEEEVMIRSENITNNAKNILVQFNTPVQINCTRPNNNTRK SIRIGPGQAFYATGDIIGDIRQAHCNVSKATWNETLGKVVKQLRKHF GNNTIIRFANSSGGDLEVTTHSFNCGGEFFYCNTSGLFNSTWISNTSV QGSNSTGSNDSITLPCRIKQIINMWQRIGQAMYAPPIQGVIRCVSNIT GLILTRDGGSTNSTTETFRPGGGDMRDNWRSELYKYKVVKIEPLGV APTRAKRRVVGGGGGSWNSSWSNRNLSEIWDNMTWLQWDKEISN YTQIIYGLLEESQNQQEKNEQDLLALDHHHHHH |

TABLE 1-continued

Description of sequences

| SEQ ID NO | Description | Sequence information |
|---|---|---|
| 31 | BG-B1(1/2) | MDAMKRGLCCVLLLCGAVFVSPSQEIHARFRRGARAVGIGAVFLGF LGAAGSTMGAASMTLTVQARNLLSGIVQQQSNLLRAPEAQQHLLK LTVWGIKQLQARVLAVERYLRDQQLLGIWGCSGKLICTTNVPGGG GSAENLWVTVYYGVPVWKDAETTLFCASDAKAYETEKHNVWATH ACVPTDPNPQEIHLENVTEEFNMWKNNMVEQMHTDIISLWDQSLKP CVKLTPLCVTLQCTNVTNNITDDMRGELKNCSFNMTTELRDKKQK VYSLFYRLDVVQINENQGNRSNNSNKEYRLINCNTSAITQACPKVSF EPIPIHYCAPAGFAILKCKDKKFNGTGPCPSVSTVQCTHGIKPVVSTQ LLLNGSLAEEEVMIRSENITNNAKNILVQFNTPVQINCTRPNNNTRK SIRIGPGQAFYATGDIIGDIRQAHCNVSKATWNETLGKVVKQLRKHF GNNTIIRFANSSGGDLEVTTHSFNCGGEFFYCNTSGLFNSTWISNTSV QGSNSTGSNDSITLPCRIKQIINMWQRIGQAMYAPPIQGVIRCVSNIT GLILTRDGGSTNSTTETFRPGGGDMRDNWRSELYKYKVVKIEPLGV APTRAKRRVVGGGGSGGGGSWNSSWSNRNLSEIWDNMTWLQW DKEISNYTQIIYGLLEESQNQQEKNEQDLLALDHHHHHHHH |
| 32 | BG-B1(2/2) | MDAMKRGLCCVLLLCGAVFVSPSQEIHARFRRGARAVGIGAVFLGF LGAAGSTMGAASMTLTVQARNLLSGIVQQQSNLLRAPEAQQHLLK LTVWGIKQLQARVLAVERYLRDQQLLGIWGCSGKLICTTNVPGGG GSGGGGSAENLWVTVYYGVPVWKDAETTLFCASDAKAYETEKHN VWATHACVPTDPNPQEIHLENVTEEFNMWKNNMVEQMHTDIISLW DQSLKPCVKLTPLCVTLQCTNVTNNITDDMRGELKNCSFNMTTELR DKKQKVYSLFYRLDVVQINENQGNRSNNSNKEYRLINCNTSAITQA CPKVSFEPIPIHYCAPAGFAILKCKDKKFNGTGPCPSVSTVQCTHGIK PVVSTQLLLNGSLAEEEVMIRSENITNNAKNILVQFNTPVQINCTRPN NNTRKSIRIGPGQAFYATGDIIGDIRQAHCNVSKATWNETLGKVVK QLRKHFGNNTIIRFANSSGGDLEVTTHSFNCGGEFFYCNTSGLFNST WISNTSVQGSNSTGSNDSITLPCRIKQIINMWQRIGQAMYAPPIQGVI RCVSNITGLILTRDGGSTNSTTETFRPGGGDMRDNWRSELYKYKVV KIEPLGVAPTRAKRRVVGGGGGSGGGGSWNSSWSNRNLSEIWDNM TWLQWDKEISNYTQIIYGLLEESQNQQEKNEQDLLALDHHHHHHH H |
| 33 | BG-B1(2/1) | MDAMKRGLCCVLLLCGAVFVSPSQEIHARFRRGARAVGIGAVFLGF LGAAGSTMGAASMTLTVQARNLLSGIVQQQSNLLRAPEAQQHLLK LTVWGIKQLQARVLAVERYLRDQQLLGIWGCSGKLICTTNVPGGG GSGGGGSAENLWVTVYYGVPVWKDAETTLFCASDAKAYETEKHN VWATHACVPTDPNPQEIHLENVTEEFNMWKNNMVEQMHTDIISLW DQSLKPCVKLTPLCVTLQCTNVTNNITDDMRGELKNCSFNMTTELR DKKQKVYSLFYRLDVVQINENQGNRSNNSNKEYRLINCNTSAITQA CPKVSFEPIPIHYCAPAGFAILKCKDKKFNGTGPCPSVSTVQCTHGIK PVVSTQLLLNGSLAEEEVMIRSENITNNAKNILVQFNTPVQINCTRPN NNTRKSIRIGPGQAFYATGDIIGDIRQAHCNVSKATWNETLGKVVK QLRKHFGNNTIIRFANSSGGDLEVTTHSFNCGGEFFYCNTSGLFNST WISNTSVQGSNSTGSNDSITLPCRIKQIINMWQRIGQAMYAPPIQGVI RCVSNITGLILTRDGGSTNSTTETFRPGGGDMRDNWRSELYKYKVV KIEPLGVAPTRAKRRVVGGGGGSWNSSWSNRNLSEIWDNMTWLQ WDKEISNYTQIIYGLLEESQNQQEKNEQDLLALDHHHHHHH |
| 34 | BG-B1(2/3) | MDAMKRGLCCVLLLCGAVFVSPSQEIHARFRRGARAVGIGAVFLGF LGAAGSTMGAASMTLTVQARNLLSGIVQQQSNLLRAPEAQQHLLK LTVWGIKQLQARVLAVERYLRDQQLLGIWGCSGKLICTTNVPGGG GSGGGGSAENLWVTVYYGVPVWKDAETTLFCASDAKAYETEKHN VWATHACVPTDPNPQEIHLENVTEEFNMWKNNMVEQMHTDIISLW DQSLKPCVKLTPLCVTLQCTNVTNNITDDMRGELKNCSFNMTTELR DKKQKVYSLFYRLDVVQINENQGNRSNNSNKEYRLINCNTSAITQA CPKVSFEPIPIHYCAPAGFAILKCKDKKFNGTGPCPSVSTVQCTHGIK PVVSTQLLLNGSLAEEEVMIRSENITNNAKNILVQFNTPVQINCTRPN NNTRKSIRIGPGQAFYATGDIIGDIRQAHCNVSKATWNETLGKVVK QLRKHFGNNTIIRFANSSGGDLEVTTHSFNCGGEFFYCNTSGLFNST WISNTSVQGSNSTGSNDSITLPCRIKQIINMWQRIGQAMYAPPIQGVI RCVSNITGLILTRDGGSTNSTTETFRPGGGDMRDNWRSELYKYKVV KIEPLGVAPTRAKRRVVGGGGGSGGGGSGGGGSWNSSWSNRNLSE IWDNMTWLQWDKEISNYTQIIYGLLEESQNQQEKNEQDLLALDHH HHHHHH |
| 35 | BG-B2(1-1) | MDAMKRGLCCVLLLCGAVFVSPSQEIHARFRRGARAVGIGAVFLGF LGAAGSTMGAASMTLTVQARNLLSGIVQQQSNLLRAPEAQQHLLK LTVWGIKQLQARVLAVERYLRDQQLLGIWGCSGKLICTTNVPGGG GSLWVTVYYGVPVWKDAETTLFCASDAKAYETEKHNVWATHACV PTDPNPQEIHLENVTEEFNMWKNNMVEQMHTDIISLWDQSLKPCVK LTPLCVTLQCTNVTNNITDDMRGELKNCSFNMTTELRDKKQKVYSL FYRLDVVQINENQGNRSNNSNKEYRLINCNTSAITQACPKVSFEPIPI |

TABLE 1-continued

| | | Description of sequences |
|---|---|---|
| SEQ ID NO | Description | Sequence information |

|  |  | HYCAPAGFAILKCKDKKFNGTGPCPSVSTVQCTHGIKPVVSTQLLLN |
|---|---|---|
|  |  | GSLAEEEVMIRSENITNNAKNILVQFNTPVQINCTRPNNNTRKSIRIG |
|  |  | PGQAFYATGDIIGDIRQAHCNVSKATWNETLGKVVKQLRKHFGNN |
|  |  | TIIRFANSSGGDLEVTTHSFNCGGEFFYCNTSGLFNSTWISNTSVQGS |
|  |  | NSTGSNDSITLPCRIKQIINMWQRIGQAMYAPPIQGVIRCVSNITGLIL |
|  |  | TRDGGSTNSTTETFRPGGGDMRDNWRSELYKYKVVKIEPLGVAPTR |
|  |  | AKRRVVGGGGGSWNSSWSNRNLSEIWDNMTWLQWDKEISNYTQII |
|  |  | YGLLEESQNQQEKNEQDLLALDHHHHHHHH |
| 36 | BG-B2(1-2) | MDAMKRGLCCVLLLCGAVFVSPSQEIHARFRRGARAVGIGAVFLGF |
|  |  | LGAAGSTMGAASMTLTVQARNLLSGIVQQQSNLLRAPEAQQHLLK |
|  |  | LTVWGIKQLQARVLAVERYLRDQQLLGIWGCSGKLICTTNVPGGG |
|  |  | GSLWVTVYYGVPVWKDAETTLFCASDAKAYETEKHNVWATHACV |
|  |  | PTDPNPQEIHLENVTEEFNMWKNNMVEQMHTDIISLWDQSLKPCVK |
|  |  | LTPLCVTLQCTNVTNNITDDMRGELKNCSFNMTTELRDKKQKVYSL |
|  |  | FYRLDVVQINENQGNRSNNSNKEYRLINCNTSAITQACPKVSFEPIPI |
|  |  | HYCAPAGFAILKCKDKKFNGTGPCPSVSTVQCTHGIKPVVSTQLLLN |
|  |  | GSLAEEEVMIRSENITNNAKNILVQFNTPVQINCTRPNNNTRKSIRIG |
|  |  | PGQAFYATGDIIGDIRQAHCNVSKATWNETLGKVVKQLRKHFGNN |
|  |  | TIIRFANSSGGDLEVTTHSFNCGGEFFYCNTSGLFNSTWISNTSVQGS |
|  |  | NSTGSNDSITLPCRIKQIINMWQRIGQAMYAPPIQGVIRCVSNITGLIL |
|  |  | TRDGGSTNSTTETFRPGGGDMRDNWRSELYKYKVVKIEPLGVAPTR |
|  |  | AKRRVVGGGGGSGGGGGSWNSSWSNRNLSEIWDNMTWLQWDKEI |
|  |  | SNYTQIIYGLLEESQNQQEKNEQDLLALDHHHHHHHH |
| 37 | BG-B2(1-3) | MDAMKRGLCCVLLLCGAVFVSPSQEIHARFRRGARAVGIGAVFLGF |
|  |  | LGAAGSTMGAASMTLTVQARNLLSGIVQQQSNLLRAPEAQQHLLK |
|  |  | LTVWGIKQLQARVLAVERYLRDQQLLGIWGCSGKLICTTNVPGGG |
|  |  | GSLWVTVYYGVPVWKDAETTLFCASDAKAYETEKHNVWATHACV |
|  |  | PTDPNPQEIHLENVTEEFNMWKNNMVEQMHTDIISLWDQSLKPCVK |
|  |  | LTPLCVTLQCTNVTNNITDDMRGELKNCSFNMTTELRDKKQKVYSL |
|  |  | FYRLDVVQINENQGNRSNNSNKEYRLINCNTSAITQACPKVSFEPIPI |
|  |  | HYCAPAGFAILKCKDKKFNGTGPCPSVSTVQCTHGIKPVVSTQLLLN |
|  |  | GSLAEEEVMIRSENITNNAKNILVQFNTPVQINCTRPNNNTRKSIRIG |
|  |  | PGQAFYATGDIIGDIRQAHCNVSKATWNETLGKVVKQLRKHFGNN |
|  |  | TIIRFANSSGGDLEVTTHSFNCGGEFFYCNTSGLFNSTWISNTSVQGS |
|  |  | NSTGSNDSITLPCRIKQIINMWQRIGQAMYAPPIQGVIRCVSNITGLIL |
|  |  | TRDGGSTNSTTETFRPGGGDMRDNWRSELYKYKVVKIEPLGVAPTR |
|  |  | AKRRVVGGGGGSGGGGSGGGGSWNSSWSNRNLSEIWDNMTWLQ |
|  |  | WDKEISNYTQIIYGLLEESQNQQEKNEQDLLALDHHHHHHHH |
| 38 | BG-C1(1/1) | MDAMKRGLCCVLLLCGAVFVSPSQEIHARFRRGARAVGIGAVFLGF |
|  |  | LGAAGSTMGAASMTLTVQARNLLSGIVQQQSNLLRAPEAQQHLLK |
|  |  | LTVWGIKQLQARVLAVERYLRDQQLLGIWGCSGKLICTTNVPWNSS |
|  |  | WSNGGGGSAENLWVTVYYGVPVWKDAETTLFCASDAKAYETEKH |
|  |  | NVWATHACVPTDPNPQEIHLENVTEEFNMWKNNMVEQMHTDIISL |
|  |  | WDQSLKPCVKLTPLCVTLQCTNVTNNITDDMRGELKNCSFNMTTE |
|  |  | LRDKKQKVYSLFYRLDVVQINENQGNRSNNSNKEYRLINCNTSAIT |
|  |  | QACPKVSFEPIPIHYCAPAGFAILKCKDKKFNGTGPCPSVSTVQCTH |
|  |  | GIKPVVSTQLLLNGSLAEEEVMIRSENITNNAKNILVQFNTPVQINCT |
|  |  | RPNNNTRKSIRIGPGQAFYATGDIIGDIRQAHCNVSKATWNETLGKV |
|  |  | VKQLRKHFGNNTIIRFANSSGGDLEVTTHSFNCGGEFFYCNTSGLFN |
|  |  | STWISNTSVQGSNSTGSNDSITLPCRIKQIINMWQRIGQAMYAPPIQG |
|  |  | VIRCVSNITGLILTRDGGSTNSTTETFRPGGGDMRDNWRSELYKYK |
|  |  | VVKIEPLGVAPTRAKRRVVGGGGGSRNLSEIWDNMTWLQWDKEIS |
|  |  | NYTQIIYGLLEESQNQQEKNEQDLLALDHHHHHHHH |
| 39 | BG-C1(1/2) | MDAMKRGLCCVLLLCGAVFVSPSQEIHARFRRGARAVGIGAVFLGF |
|  |  | LGAAGSTMGAASMTLTVQARNLLSGIVQQQSNLLRAPEAQQHLLK |
|  |  | LTVWGIKQLQARVLAVERYLRDQQLLGIWGCSGKLICTTNVPWNSS |
|  |  | WSNGGGGSAENLWVTVYYGVPVWKDAETTLFCASDAKAYETEKH |
|  |  | NVWATHACVPTDPNPQEIHLENVTEEFNMWKNNMVEQMHTDIISL |
|  |  | WDQSLKPCVKLTPLCVTLQCTNVTNNITDDMRGELKNCSFNMTTE |
|  |  | LRDKKQKVYSLFYRLDVVQINENQGNRSNNSNKEYRLINCNTSAIT |
|  |  | QACPKVSFEPIPIHYCAPAGFAILKCKDKKFNGTGPCPSVSTVQCTH |
|  |  | GIKPVVSTQLLLNGSLAEEEVMIRSENITNNAKNILVQFNTPVQINCT |
|  |  | RPNNNTRKSIRIGPGQAFYATGDIIGDIRQAHCNVSKATWNETLGKV |
|  |  | VKQLRKHFGNNTIIRFANSSGGDLEVTTHSFNCGGEFFYCNTSGLFN |
|  |  | STWISNTSVQGSNSTGSNDSITLPCRIKQIINMWQRIGQAMYAPPIQG |
|  |  | VIRCVSNITGLILTRDGGSTNSTTETFRPGGGDMRDNWRSELYKYK |
|  |  | VVKIEPLGVAPTRAKRRVVGGGGGSGGGGGSRNLSEIWDNMTWLQ |
|  |  | WDKEISNYTQIIYGLLEESQNQQEKNEQDLLALDHHHHHHHH |

TABLE 1-continued

Description of sequences

| SEQ ID NO | Description | Sequence information |
|---|---|---|
| 40 | BG-C1(1/3) | MDAMKRGLCCVLLLCGAVFVSPSQEIHARFRRGARAVGIGAVFLGF<br>LGAAGSTMGAASMTLTVQARNLLSGIVQQQSNLLRAPEAQQHLLK<br>LTVWGIKQLQARVLAVERYLRDQQLLGIWGCSGKLICTTNVPWNSS<br>WSNGGGGSAENLWVTVYYGVPVWKDAETTLFCASDAKAYETEKH<br>NVWATHACVPTDPNPQEIHLENVTEEFNMWKNNMVEQMHTDIISL<br>WDQSLKPCVKLTPLCVTLQCTNVTNNITDDMRGELKNCSFNMTTE<br>LRDKKQKVYSLFYRLDVVQINENQGNRSNNSNKEYRLINCNTSAIT<br>QACPKVSFEPIPIHYCAPAGFAILKCKDKKFNGTGPCPSVSTVQCTH<br>GIKPVVSTQLLLNGSLAEEEVMIRSENITNNAKNILVQFNTPVQINCT<br>RPNNNTRKSIRIGPGQAFYATGDIIGDIRQAHCNVSKATWNETLGKV<br>VKQLRKHFGNNTIIRFANSSGGDLEVTTHSFNCGGEFFYCNTSGLEN<br>STWISNTSVQGSNSTGSNDSITLPCRIKQIINMWQRIGQAMYAPPIQG<br>VIRCVSNITGLILTRDGGSTNSTTETFRPGGGDMRDNWRSELYKYK<br>VVKIEPLGVAPTRAKRRVVGGGGGSGGGGSGGGGSRNLSEIWDNM<br>TWLQWDKEISNYTQIIYGLLEESQNQQEKNEQDLLALDHHHHHHH<br>H |
| 41 | gp160 protein-furin cleavage site | REKR |

EXAMPLES

The present invention will now be described with reference to the following examples, which are intended to illustrate the present invention, but not to limit it.

Unless otherwise specified, the molecular biology experiment methods and immunoassay methods used in the present invention were basically referred to the methods described by J. Sambrook et al., Molecular Cloning: A Laboratory Manual, 2nd Edition, Cold Spring Harbor Laboratory Press, 1989, and F. M. Ausubel et al., Short protocols in Molecular Biology, 3rd Edition, John Wiley & Sons, Inc., 1995; the restriction enzymes were used in accordance with the conditions recommended by the product manufacturer. Those skilled in the art understand that the examples describe the present invention by way of example and are not intended to limit the scope of the present invention.

Example 1: Expression of TSTIP Proteins of Two Strains of NL4-3/BG505

Modification Design of 4-3/BG505 TSTIP

The base and amino acid sequences of gp160 of the two strains BG505/pNL4-3 on NCBI were used as templates for modification. Taking the modification of BG505 as an example, according to the three-dimensional cryoelectron microscope structure of BG505-SOSIP (PDB: 4tvp), part of the loop sequence (aa610-616, WNSSWSN) at the C-terminal of β27 of BG505 gp41 was removed, and the sequence of 10 amino acids including furin cleavage site at the C-terminal of gp120 (aa501-511, AKRRVVGREKR) was also removed. Subsequently, the truncated C-terminal of β27 of gp41 was linked to the N-terminal of gp120, and the truncated C-terminal of gp120 was linked to the N-terminal of the α8 domain of gp41. The amino acids of the complete gp140 after modification were arranged in sequence as follows: α6/α7/β27 (501-606)+part of the loop region between β27 and α8 (607-609)+gp120 (33-500)+part of the C-terminal sequence of the loop region between β27 and α8 (617-618)+α8/α9 (619-664).

Figure 1B:
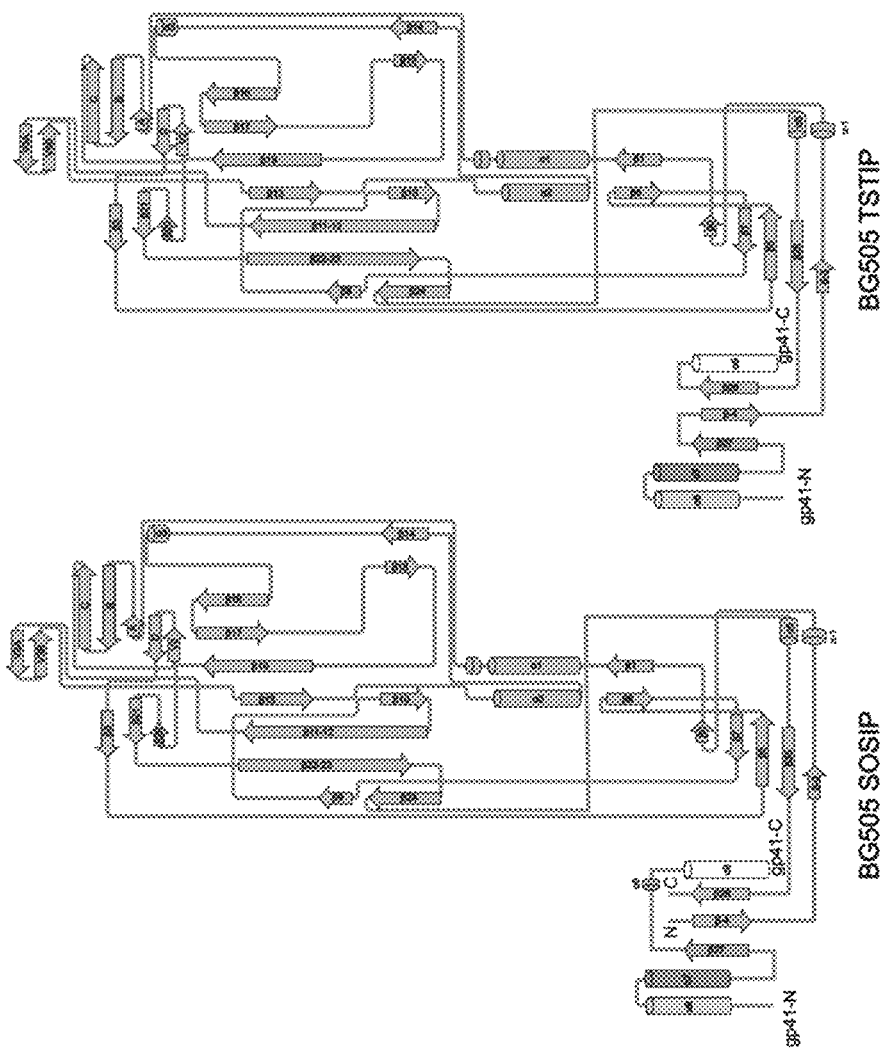
Figures 2A, 2B:
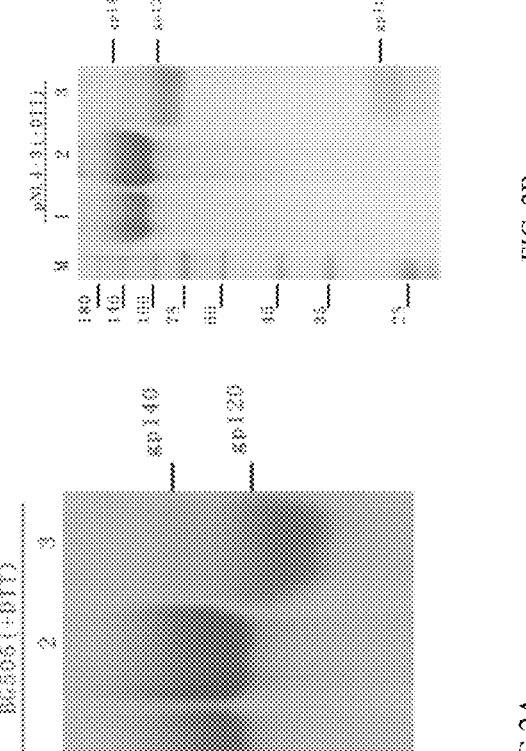
FIGS. 2A to 2B show the results of reducing SDS polyacrylamide gel electrophoresis of the modified gp140 trimer after one-step Ni Sepharose excel purification.

In addition, 8His tag was added to the C-terminal of the above sequence to facilitate purification, and tPA signal peptide and kozak sequence were added in front of the sequence to promote secretion and expression. The protein designed above was named as BG505-TST (SEQ ID NO: 1). On the basis of the above structure, I559P and T332N mutations were introduced, and the protein designed was named as BG505-TSTIP (SEQ ID NO: 3). NL4-3 strain was modified in the same way to obtain NL4-3-TST (SEQ ID NO: 2) and NL4-3-TSTIP (SEQ ID NO: 4), respectively. The structure of each of the above proteins is shown in FIG. 1.

The designed amino acid sequences of BG505/pNL4-3-TSTIP were converted into base sequences suitable for mammalian cell expression, and then sent to Sangon Biotech (Shanghai) Co., Ltd. for gene synthesis, and constructed between the ECORI and Xbal restriction sites of pcDNA3.1 vector. 1 μl of the synthesized pcDNA3.1-BG505SOSIP/4-3TSTIP plasmid was taken to transform 50pl of DH5a competent cells (purchased from Shenzhen Kangti Life Technology Co., Ltd.), which were plated on ampicillin-containing solid medium; after static culture at 37° C. for 10-12 hours, single colony was clearly visible, and was picked and placed into a test tube containing 3 ml of ampicillin-containing LB medium, and cultured under shaking at 220 rpm at 37° C. for 10 hours; 500 μl of the bacterial solution was taken and mixed with 500111 of 50% glycerol, then cryopreserved at −20° C.

Extraction of PcDNA3.1 NL4-3/B G505 TSTIP Plasmid:

10 μl of the pcDA3.1 NL4-3/BG505 TSTIP bacterial solution cryopreserved at −20° C. was taken, transferred into a test tube containing 3 ml of ampicillin-containing LB medium, cultured for 10-12 h, then inoculated in a conical flask containing 500 ml of ampicillin-containing LB medium and cultured at 37° C. for 12 hours; the bacterial solution was collected and centrifuged at 7000 g for 10 minutes, the supernatant was discarded. The pcDNA3.1-BG505/NL4-3TSTIP plasmid was extracted by using Tiangen Endotoxin-Free Maxi Plasmid Kit.

Culture and Passage of 293F Cells 293F cells cryopreserved in −80° C. refrigerator were taken, thawed at 37° C., then centrifuged at 1300 rpm for 4 min; the supernatant was discarded in an ultra-clean bench, the cells were lightly flicked and resuspended in 293freestyle medium warmed at 37° C. in advance, then transferred into a conical flask containing 50 ml of warm culture medium, for suspension culture at 37° C., 5% $CO_2$, 120 rpm; the cells were passaged when the cell density reached $2.0*10^6$, to gradually expand the culture system.

Transient Transfection

The 293F cells were transiently transfected with PEG2000. After the cell density reached $2.0*10^6$, the cells were harvested in a sterile 50 ml tube, centrifuged at 1300 rpm for 4 min; the cells were flicked, then resuspended in medium incubated at 37° C., transferred to a conical flask containing 450 ml of medium incubated at 37° C., and placed on a shaker at 37° C. for later use.

The extracted pcDNA3.1-BG505/NL4-3TSTIP plasmid and PEG2000 in a ratio of 1:2 was added into 50 ml of culture medium, mixed well and allowed to stand for 18 min, then transferred into the above 450 ml of culture medium, for suspension-culture at 37° C., 5% $CO_2$, 120 rpm for 6 days to express BG505/NL4-3TSTIP protein. It should be aware the PEG operation should be carried out in the dark during transfection.

Example 2: Purification of NL4-3/BG505 TSTIP Protein

After 6 days of transient transfection, the cell culture medium was collected, centrifuged at 7000 g for 10 minutes with JA-14 rotor; the cell supernatant was collected, centrifuged at 20000 g for 10 minutes; the supernatant was taken and filtered twice with a 0.22 μm pore size membrane filter, and this sample was used for the next step of Ni-excel column purification.

Purification by Ni affinity chromatography using the AKTA system;

Instrument system: AKTA Pure type preparative liquid chromatograph;

Purification medium: Ni Sepharose excel affinity medium; buffer: buffers A and B, buffer A was 1×PBS buffer, buffer B was 1×PBS+250 mmol/L imidazole buffer;

System sample-loading flow rate: 8 mL/min; detection wavelength: UV @280 nm

System elution flow rate: 4 ml/min; detection wavelength: UV @280 nm

Elution conditions: 20 mM imidazole was used to elute impurity proteins, and the product eluted by 250 mM imidazole was collected. The eluate was dialyzed against 1×PBS overnight with two dialysate changes. About 30 ml of low-concentration target protein was harvested, and concentrated in Vivaspin 20 ml, 100 KD ultrafiltration concentrator tube to 5 ml for later use.

Example 3: Identification of Biochemical Properties of NL4-3/BG505 TSTIP Protein

SDS-PAGE:

The concentrated sample in Example 2 and BG505/4-3SOSIP protein were diluted to 1 μg/μl, two tubes of 50 μl samples were then taken, added with 10 μl of reducing 6 Loading Buffer and 10 μl non-reducing 6Loading Buffer, respectively, to prepare reduced samples and non-reduced samples, the reduced samples were placed in a boiling water bath at 100° C. for 10 minutes. 10 μl of the reduced and non-reduced samples were electrophoresed in 8% SDS-PAGE at a voltage of 80V for 120 min, and the electrophoresis bands were displayed after staining with Coomassie brilliant blue. The electrophoresis results are shown in FIGS.

2A to 2B. SDS-PAGE analysis showed that after one-step Ni-EXCEL purification, high-purity BG505/NL4-3TSTIP protein could be obtained, and the TSTIP protein showed a complete 140 KD band in the presence of DTT, while the BG505/NL4-3SOSIP protein presented a 120 KD band under reducing conditions, indicating that the gp120 and gp41 extracellular regions were stably and covalently linked in the protein designed by the inventors as expected.

Molecular Sieve Purification:

Instrument system: AKTA Pure type preparative liquid chromatograph;

Chromatographic column: superdex 200 16/600

Column volume: 120 ml

Buffer: PBS (20 mM phosphate buffer, pH7.5, 150 mM NaCl)

Detector wavelength: 280 nm

Flow rate: 1 ml/min

The sample was the purified concentrated protein of Example 2.

The purification procedure comprised: superdex200 16/600 was equilibrated with 1 column volume of PBS, the target protein purified in Example 2 was loaded using a 5 ml loading loop, and the molecular sieve purification of the purified sample was performed at inject mode, and the components of the sample would be eluted in sequence according to their molecular weights, from high to low, and the elution peaks at different elution volumes were collected, which are the target proteins in different multimer forms.

Figure 3:
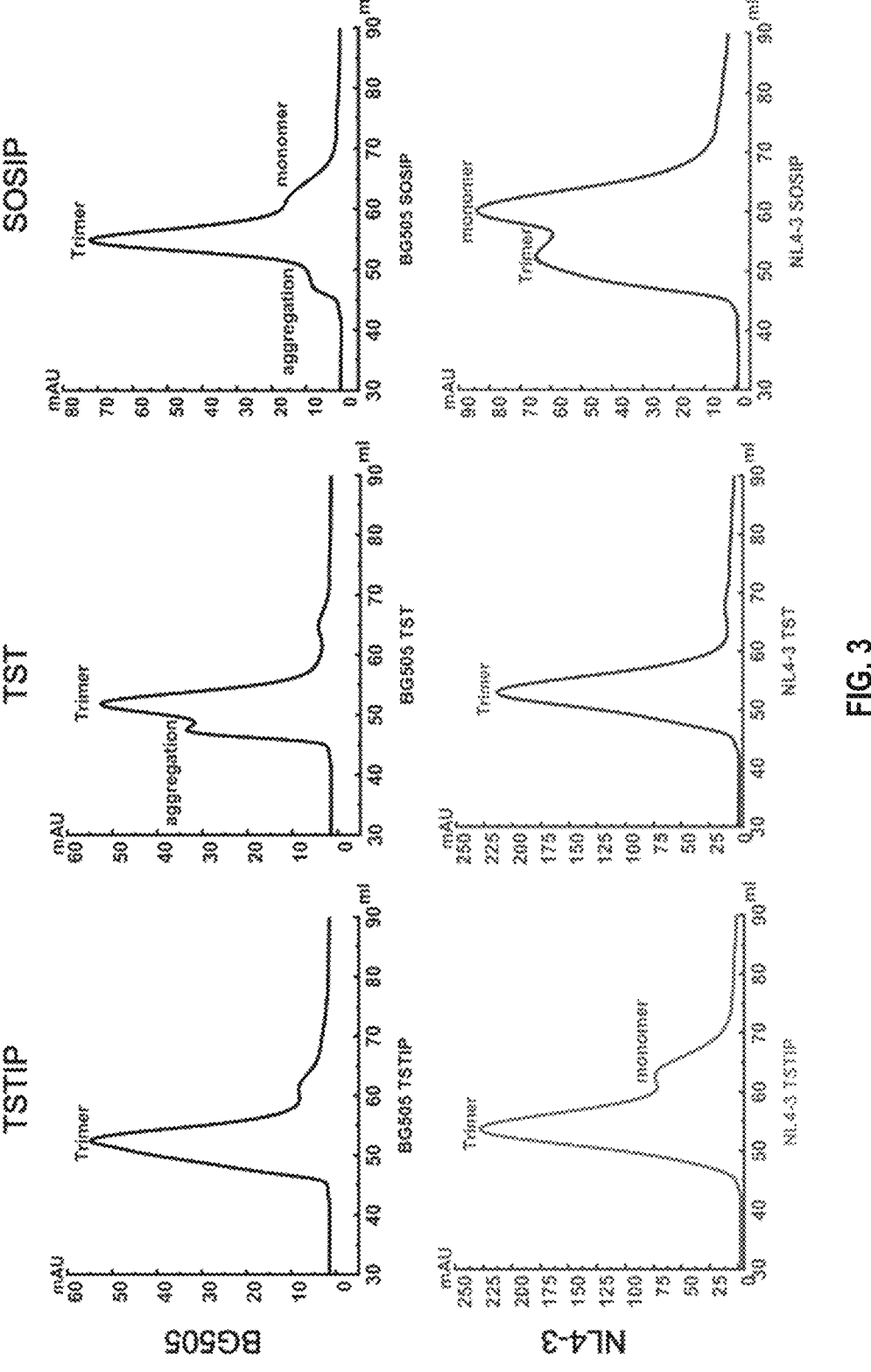
FIG. 3 shows the molecular sieve superdex200-16/600 purification results of the modified gp140 trimer, in which A represents BG505 strain, B represents NL4-3 strain. The molecular sieve chromatography results of TSTIP protein and TST protein showed a single elution peak, while the chromatographic result of SOSIP protein showed three elution peaks, indicating that the components of the proteins TSTIP and TST of the present invention were more uniform than those of SOSIP.

The molecular sieve purification results are shown in FIG. 3. It could be seen that the components of BG505/NL4-3TSTIP designed by the inventors were more simple than those of BG505/NL4-3, while the molecular sieve purification pattern of BG505/NL4-3TSTIP showed obvious peaks for monomers and multimers, indicating that the TSTIP protein and TST protein of the present invention had a higher trimer content.

Figure 4C:
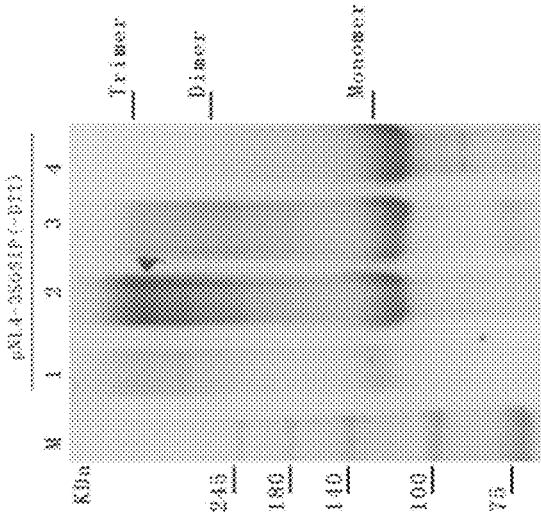
FIGS. 4A to 4C show the results of non-reducing polyacrylamide gel electrophoresis of the modified gp140 trimer after molecular sieve purification. A represents BG505 TSTIP, B represents NL4-3 TSTIP, C represents BG505 SOISP. The results showed that after molecular sieve purification, the main component of the protein TSTIP of the present invention was trimer, and had a trimer content higher than that of SOSIP.
Figure 4B:
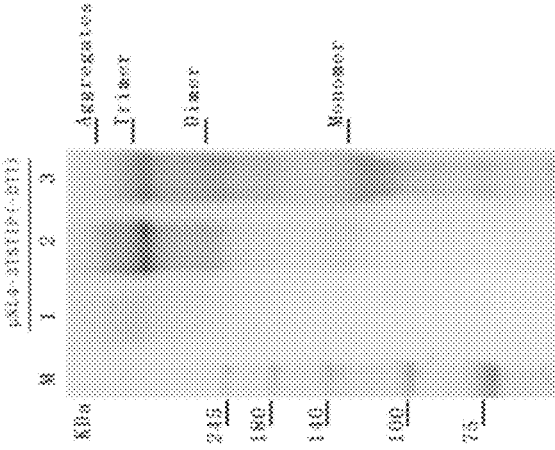
Figure 4A:
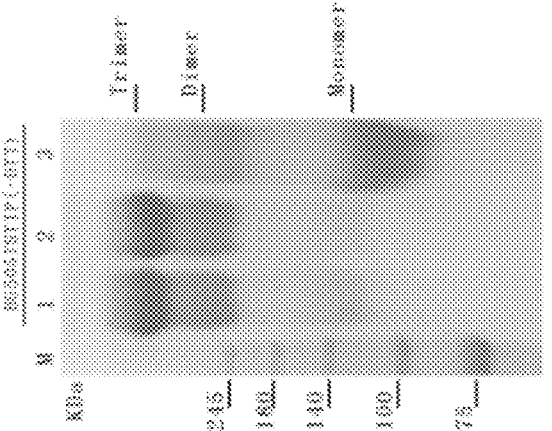

SDS-PAGE of Molecular Sieve Purified Samples:

The samples of different elution volumes collected during the molecular sieve purification were concentrated in Vivaspin 20 ml, 100 KD concentrator tubes to 1 μg/μl, and marked as 1, 2, 3, 4 according to the order of elution. 50 μl of each of the samples was taken and added with 10 μl of non-reducing 6 Loading Buffer, mixed well, 10 μl of non-reduced sample was taken and electrophoresed at 80V voltage for 120 min in 8% SDS-PAGE, and the electrophoresis bands were displayed after staining with Coomassie brilliant blue. The electrophoresis results were shown in FIGS. 4A to 4C. It could be seen that the main component of the BG505/NL4-3TSTIP was gp140 trimer after superdex200-16/600 purification, while the BG505/NL4-3SOSIP contained a large amount of gp140 monomer.

Thermal Stability Analysis by Differential Scanning Calorimetry (DSC)

Instrument system: VP-Capillary produced by GE Healthcare

The sample was the purified concentrated protein of Example 2.

Figure 5:
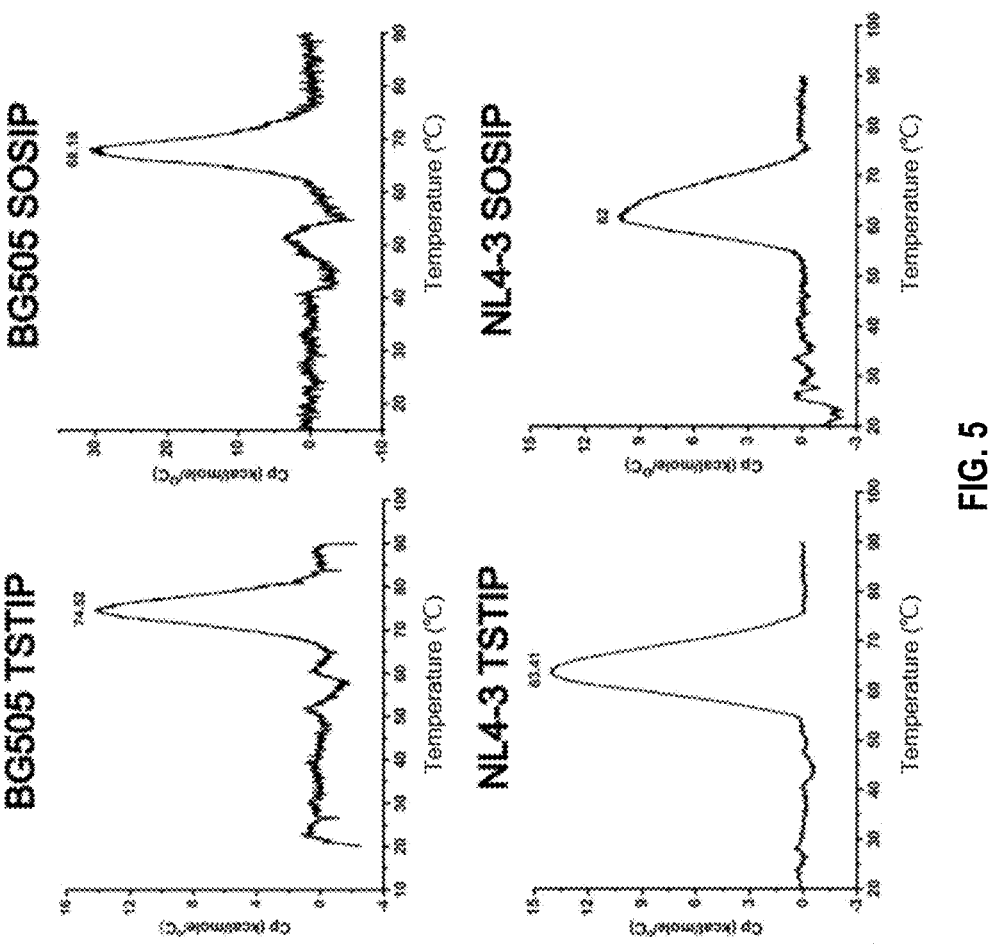
FIG. 5 shows the Tm measurement results of the modified gp140 trimer by differential scanning calorimetry (DSC). The results showed that the Tm of the protein BG505 TSTIP of the present invention was 74.5° C., and the Tm of NL4-3 TSTIP was 63.41° C., which was higher than the Tm of the control protein BG505 SOSIP: 68.2° C. and the Tm of the control protein NL4-3 SOSIP: 62° C. This shows that the thermal stability of the modified protein is higher than that of the corresponding control protein SOSIP.

The sample-loading tank was washed once with an acidic or weakly alkaline washing solution, and washed 3 times with deionized water; 400 μL of the sample and corresponding buffer solution thereof each was pipetted into EP tube, and centrifuged to remove sediment and air bubbles; 300 μL of buffer solution was pipetted into the sample-loading tank and control tank, respectively, and rinsed 3 times, then 300 μL of buffer solution was added to the sample-loading tank and control tank with avoiding air bubbles during the addition process; the DSC software and instrument were turned on, the number of scan cycles was set, and when the DP value in the scan cycle was stabilized between ±0.2, it was allowed to perform circular scanning and the baseline equilibration was carried out for no less than 3 times; when the last circular scanning was completed, and the temperature dropped to between 30° C. and 10° C., the buffer in the sample tank was sucked out, and 300111 of protein sample to be tested was added quickly, and the scanning test was continued; the scan rate was set as: 90° C./h. After scanning, Origin7.0 was used to process the data. The results were shown in FIG. 5. The Tm of the protein BG505-TSTIP of the present invention was 74.51° C., the Tm of the control protein BG505-SOSIP was significantly lower than that of BG505-TSTIP, which was 68.18° C. The Tm of NL4-3-TSTIP was 63.41° C., and the Tm of NL4-3-SOSIP was 62.00° C.; although the Tm of the one based on NL4-3 strain did not increase significantly, it was improved to a certain extent compared with the reported optimal design NL4-3SOSIP. These results indicated that our design could improve the thermal stability of the protein to a certain extent, and its thermal stability could be greatly improved in some strains.

Example 4: Identification of BG505/NL4-3TSTIP Antigenicity and Immunogenicity Enzyme-Linked Immunosorbent Assay (ELISA)

Broad-spectrum neutralizing antibodies such as PGT121, PGT125, VRC01, 2G12, B12 and non-neutralizing antibodies such as 17b, 447-52D, F105, F240 were selected to carry out ELISA antigenicity analysis on BG505/NL4-3TSTIP and BG505/NL4-3SOSIP, and the specific process was as follows:

(1) BG505/NL4-3TSTIP and BG505/NL4-3SOSIP trimer proteins were diluted with 1×CB to 1 μg/Ml, coated at 100 μL/well on a 96-well plate, and allowed to stand in a 37° C. incubator for 2 h;

(2) the plate was washed once and spin-dried, and blocked with ED (180 μL/well) in a 37° C. incubator for 2 h;

(3) the plate was washed once and spin-dried. The 96-well u-bottom plate was taken, the antibody was diluted to 1 μg/ml or 10 μg/ml, and added to the first well of the U-bottom plates, repeats of two wells were performed for each antibody, with 150 μl at first well, and 3-fold dilution with 11 gradients. 100 μl of the diluted antibody was transferred into the 96-well ELISA plates coated with BG505/NL4-3TSTIP and BG505/NL4-3SOSIP, and reacted at 37° C. for 1 hour.

Figure 6:
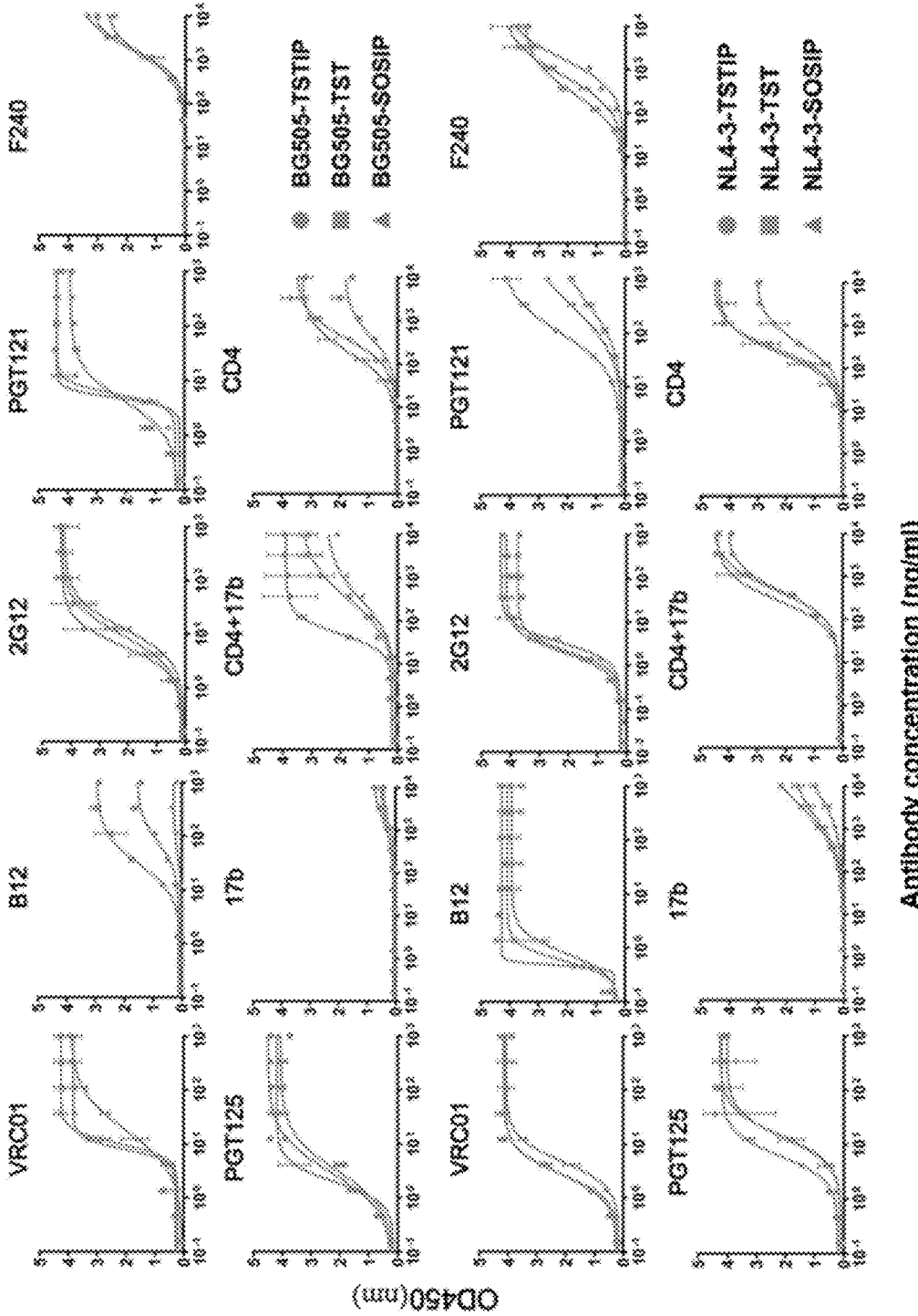
FIG. 6 shows the enzyme-linked immunosorbent assay (ELISA) results of the modified gp140 trimer with various reported human monoclonal antibodies. The antibodies used include broad-spectrum neutralizing antibodies VRC01, B12, PGT121, PGT125, 2G12, non-broad-spectrum neutralizing antibodies F105, F240, 17b, and HIV-1 receptor molecule CD4. The results showed that the proteins BGTSTIP and NL4-3 TSTIP of the present invention had a binding ability to various reported broad-spectrum neutralizing antibodies and non-broad-spectrum neutralizing antibodies that was basically equivalent to that of the control proteins BG505 SOSIP and NL4-3 SOSIP, and could recognize and bind well to CD4 receptor molecule. In addition, like SOSIP, the recognition of the modified protein by CD4 would induce the conformational change of the protein of the present invention, thereby exposing the 17b binding site.

(4) the plate was washed 5 times and spin-dried. The secondary antibody GAH-HRP (1:5000) was added into the 96-well plate, 100 μL/well, and reacted at 37° C. for 45 minutes;

(5) the plate was washed 5 times, color development was performed at room temperature for min, then stopped, and detection was carried out at wavelength of 450 nm on a microplate reader; GraphPad Prism 5 (GraphPad, USA) software was used for data analysis. The results are shown in FIG. 6.

It could be seen that BG505/NL4-3TSTIP had strong reactivity with broad-spectrum neutralizing antibodies such as PGT121, PGT125, VRC01, 2G12, and B12, but weak reactivity with non-neutralizing antibodies such as 17b, F105, and F240. 17b, F105, and F240 were antibodies targeting non-neutralizing epitopes such as CDi, CD4bs, and gp41, respectively, which indicated that BG505/NL4-3TSTIP did not expose such non-neutralizing epitopes, but well presented key epitopes such as CD4bs, out Glycan, V3, etc. Overall, the reactivities of BG505/NL4-3TSTIP with various broad-spectrum neutralizing antibodies and non-neutralizing antibodies remained comparable to those of the control protein BG505/NL4-3SOSIP.

Immunological Evaluation of BG505/NL4-3TSTIP in Animals

White mice: female, 6 weeks old, purchased from Shanghai Slack Experimental Animal Co., Ltd. Four groups of immunized mice were set up, with 6 mice in each group, and BG505/NL4-3TSTIP and BG505/NL4-3SOSIP prepared in Example 2 were used as immune proteins. The proteins were diluted with normal saline, mixed with aluminum hydroxide adjuvant at a ratio of 1:1 by volume, so that the proteins were adsorbed on the adjuvant, and the mice were immunized intraperitoneally. The mouse immunization protocols were shown in Table 1.

TABLE 1

| Mouse immunization protocol | | | |
| --- | --- | --- | --- |
| Group | Immunogen | Dose | Period (weeks) |
| A | NL4-3TSTIP | 10 μg/animal | 2 |
| B | NL4-3SOSIP | 10 μg/animal | 2 |
| C | BG505/NL4-3TSTIP | 10 μg/animal | 2 |
| D | BG505/NL4-3SOSIP | 10 μg/animal | 2 |

The blood was collected from mouse eyeball before immunization, and immunization was carried out according to the immunization protocol in Table 1. The blood was collected from mouse eyeball before each immunization, and after the sixth injection of immunization, the blood was collected from mouse eyeball and the mice were treated with neck dislocation. After the blood sample was placed at 37° C. for 30 minutes, it was centrifuged at 13300 rpm for 10 minutes, and the serum was collected for HIV-1 pseudovirus neutralization and antibody titer determination.

Figure 7:
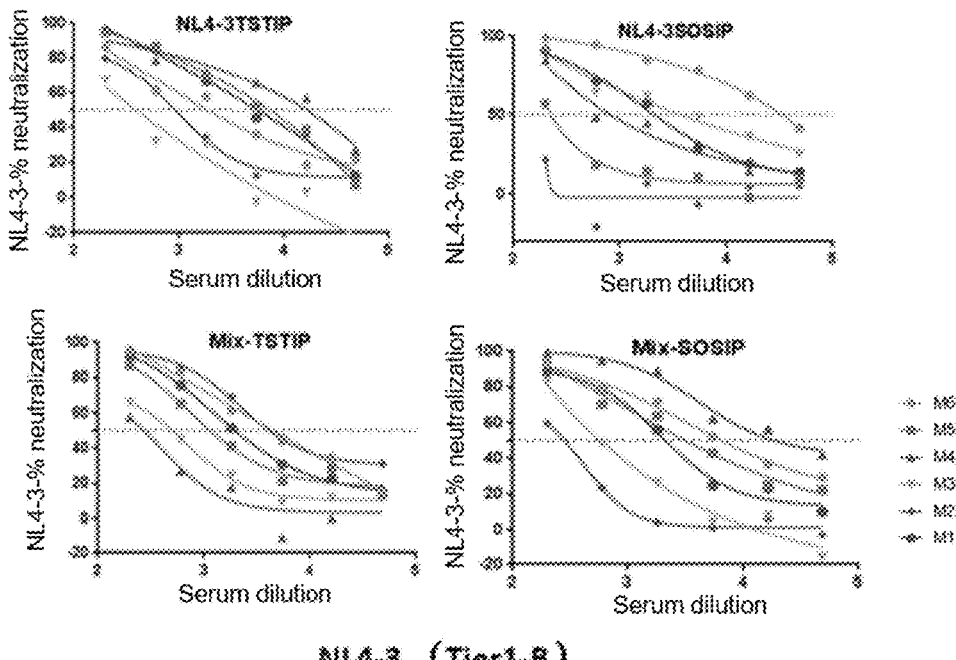
FIG. 7 shows the results of the virus neutralization experiment of the immune serum samples obtained by immunizing BALB/C mice with the modified gp140 trimer on the B subtype NL4-3 and B subtype 2626 strain viruses; wherein, M1 to M6 referred to different mice, respectively. The results showed that the modified protein TSTIP and the control protein could induce a strong neutralizing response against the corresponding strain after immunizing mice, but could not induce neutralizing response against the Tier2 strain of the same subtype. The modified protein TSTIP and the control protein SOSIP showed comparable immunogenicity.
Figure 7:
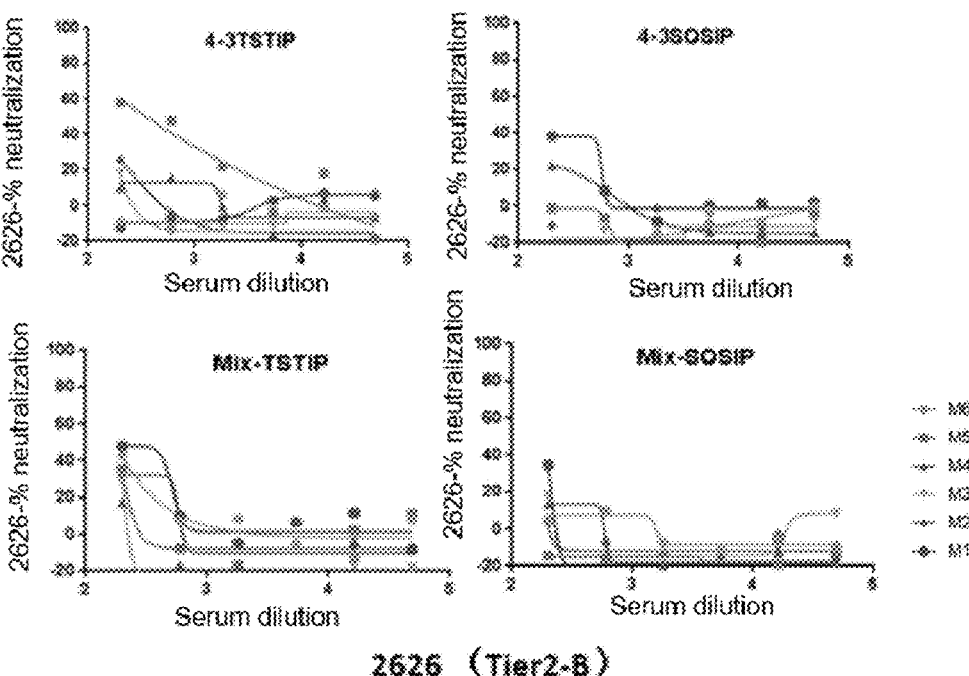

The serum sample collected after the sixth injection was used to perform the virus neutralization experiment, and the results are shown in FIG. 7. For all four groups of mice, a strong neutralization response against NL4-3 was detected, but no neutralization response to the tier2 strain TRO11 of the same subtype was detected. The results showed that the BG505/NL4-3TSTIP of the present invention could induce a strong neutralizing antibody response against the corresponding strain, but it was difficult to generate a neutralizing response against other strains. In general, the protein of the present invention maintained a level of immunogenicity comparable to that of the control protein SOSIP. Those skilled in the art know that it is possible to induce virus cross-neutralizing antibodies by introducing amino acid mutations of cross-reactivity epitopes based on the protein of the present invention.

Example 5: Production and Identification of Bal.26-TSTIP Pseudoviral Particle Construction of Bal.26-TSTIP and NL4-3-TSTIP Pseudoviruses The Bal26 TSTIP pseudovirus produced by the present inventors was obtained by co-transfecting 293FT cells (Invitrogen) with HIV-1 backbone plasmid pfNL43-dGPE-EGFP (Addgene) and envelope plasmid VRC8400-Bal26-TSTIP-gp160.

Acquisition of Envelope Gene and Backbone Gene

The backbone plasmid was pfNL43-dGPE-EGFP, purchased from addgene. The plasmid was obtained by modifying NL4-3 infectious clone, and contained gag, pol, tat, rev and other genes necessary for virus packaging, but its Env gene had been partially replaced by the EGFP gene, resulting in the silencing of the Env gene, so that the production of pseudovirus could be performed by co-trans-fecting only one expression plasmid expressing Env. The expression vector of the envelope gene used in the present invention was VRC8400 which was preserved in our labo-ratory. The inventor carried out the TSTIP design for the full length of the Env gene of Bal.26 based on the design of BG505 TSTIP protein, and cloned the full-length Bal.26 TSTIP gene (which encoded SEQ ID NO: 16) carrying the virus's own signal peptide between the EcoRV and BglII restriction sites of the VRC8400 vector, to construct a VRC8400-Bal.26-TSTIP-gp160 expression plasmid. The obtained pseudovirus was called BaL.26-SD-FS. In addi-tion, a pseudovirus (BaL.26-WT) obtained based on the wild-type gp160 sequence of the Bal.26 strain was used as a control.

Production of Pseudovirus:

The production of pseudovirus adopted the method of PEI transient transfection, the mixture of pfNL43-dGPE-EGFP plasmid and envelope plasmid of VRC8400-Bal.26 TSTIP gp160 plasmid, and PEI were diluted in 90 μl of normal saline respectively, and the two were fully mixed and allowed to stand for 18 minutes to form a plasmid-PEI complex, and co-transfected into 293FT cells at ratios of PEI:plasmid=2:1, pfNL43-dGPE-EGFP:VRC8400 Bal.26 TSTIP gp160=1:1, with the amount of plasmid of 20 m/plate. After 6 hours of transfection, fresh complete DMEM medium was replaced, and culturing was performed at 37° C., 5% $CO_2$ for 48 hours to obtain a supernatant as a virus liquid.

Verification of Pseudovirus Packaging Capability

The above-mentioned transfected 293FT cells and cell transfection supernatant were harvested, lysed with cell lysis buffer for 1 hour, the cell lysate supernatant was collected by centrifugation, and subjected to western blot, and the spe-cific steps were as follows:

(1) 20 μl of cell lysate and virus liquid supernatant were taken and electrophoresed at 80V on 8% SDS poly-acrylamide gel.

(2) after 2 hours, the gel was transferred to a nitrocellulose membrane with two layers of filter paper placed on each of its upside and downside, 1×Trans-Blot® Turbo™ Transfer Buffer (SDS) was used as transfer buffer for semi-dry transfer, with the transferring time of 30 min.

(3) the membrane was washed with deionized water, and the membrane was blocked with blocking solution 1 (purchased from Xiamen Wantai) for 2 h.

(4) the monoclonal antibody 3A7 screened in the labora-tory was used as the primary antibody, the primary antibody was diluted in ED11 (purchased from Xiamen Wantai) at a concentration of 1 μg/ml, and incubated for 1 hour at room temperature on a shaker.

(5) the membrane was washed with 1×PBST washing solution for 3 times, 5 min for each time, and washed with deionized water once, the secondary antibody GAM-HRP was diluted in ED11 (purchased from Bei-jing Wantai) at a ratio of 1:5000, and incubated at room temperature for min on a shaker.

Figure 8B:
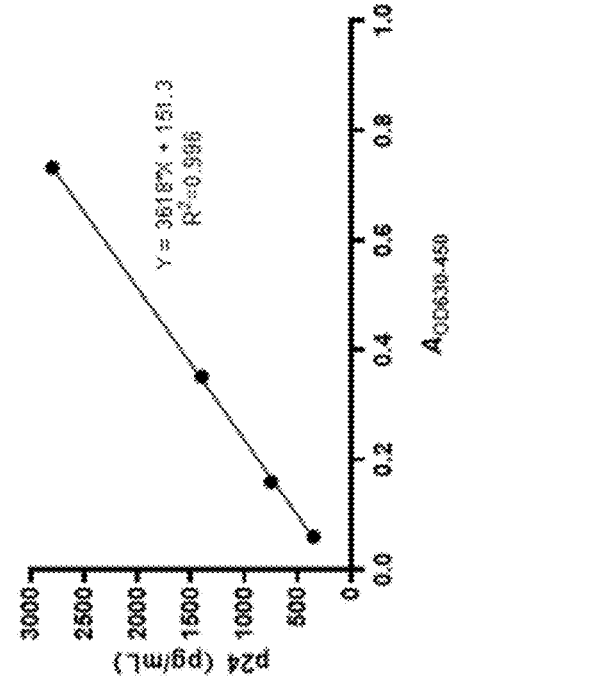
FIG. 8B shows the quantitative results of p24 of the pseudovirus based on the modified gp140 trimer. The results showed that both the transfected cells and the collected virus supernatant had the expression of full-length TSTIP protein, and the content of p24 in the supernatant of the pseudovirus of the present invention was decreased in some extent compared with the wild-type pseudovirus, but certain amounts of p24 and Env could still be detected, indicating that the pseudovirus of the present invention could be normally packaged to form a complete pseudoviral particle, but the yield might be reduced to a certain extent.
Figure 8A:
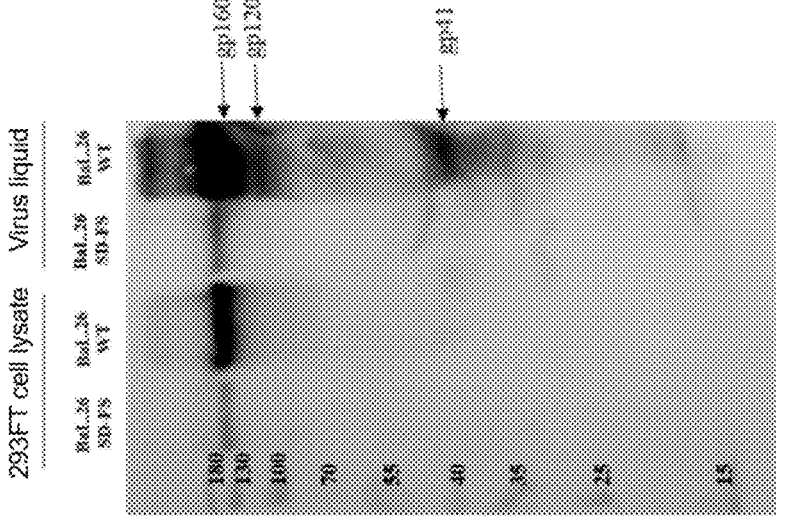
FIG. 8A shows the results of western blot of the pseudovirus based on the modified gp140 trimer.

(6) the membrane was washed with 1×PBST washing solution for 3 times, 5 min for each time, and washed with deionized water once, and then exposed for color development. The results of Western blot are shown in FIG. 8A, in which the Env protein was detected in both cell lysate and virus liquid.

Figure 9:
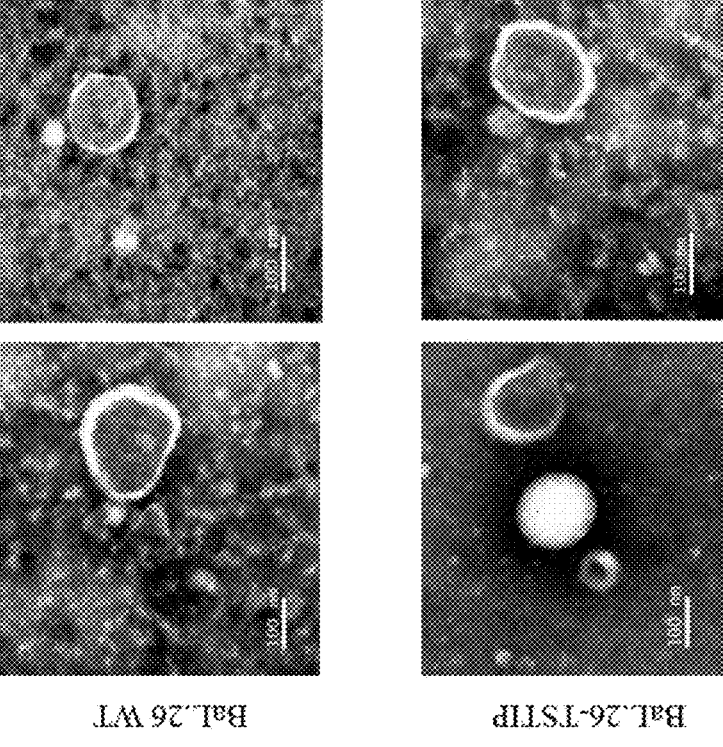
FIG. 9 shows the results of negative staining electron microscopy of the pseudoviral particles based on the modified gp140 trimer. It showed that the pseudoviral particles similar to the wild-type pseudovirus could be seen under the negative staining electron microscope.

At the same time, the virus liquid was diluted by 5-fold dilution for 6 gradients, and the p24 content in the virus liquid supernatant was detected by ELISA method, and the fitting curve was made according to the reaction of the p24 standard substance in the gradient dilution, and the fitting curve was Y=3618*X+151.3 (FIG. 8B), $R^2$ was 0.996, which had a good linear relationship. The quantitative results of p24 were shown in Table 2. At the same time, the samples of the harvested pseudovirus liquid were observed by negative staining electron microscope, and the results were shown in FIG. 9. Based on the above results, the p24 content of the pseudovirus produced by the present inven-tion had decreased to a certain extent, but within an accept-able range, the expression of Env protein could be detected in the supernatant, and obvious pseudoviral particles could be observed under negative staining electron microscope, indicating that the pseudovirus of the present invention could be normally packaged to form pseudoviral particles.

TABLE 2

| Detection of p24 content | | | |
| --- | --- | --- | --- |
| Sample | Dilution fold | AOD630-450 | p24 (ng/mL) |
| BaL.26-SD-FS | 25 | 0.402 | 40.08 |
| BaL.26-WT | 25 | 0.729 | 69.72 |
| Negative control | 1 | 0.008 | 0.18 |

Verification of Pseudovirus Infection Ability

Figure 10:
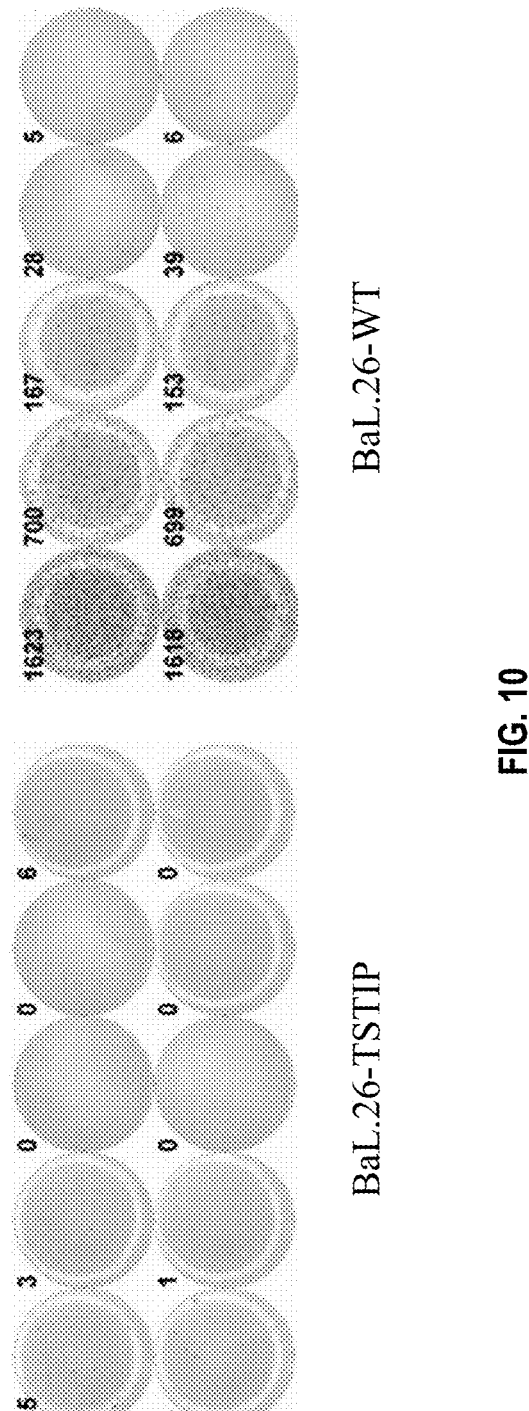
FIG. 10 shows the infectivity detection results of the pseudovirus based on the modified gp140 trimer by using the Elispot method with LacZ as reporter gene. It showed that the wild-type pseudovirus maintained normal infectivity, while the pseudovirus of the present invention had lost the infectivity, which was in line with the inventor's expectation.

The harvested virus liquid was diluted in a U-bottom 96-well plate, 100 μl of virus liquid was added in the first well, 5-fold dilution was performed for 5 times in sequence, and each well contained 15 μg/ml DEAE to promote the infectivity of pseudovirus to cells. TZM-b1 cells were cultured in a 96-well cell culture plate in advance at 37° C., 5% $CO_2$ until the cell density reached 80%, the diluted pseudovirus liquid was transferred to TZM-b 1 cells, and after the cells were infected with the virus for 40-48 h, two methods (i.e., chemiluminescence and ELISPOT) were used to detect the infectivity of the produced pseudovirus to the target cells. The results were shown in FIG. 10, and both detection methods showed that the pseudovirus modified by TSTIP design almost completely lost its ability to infect, while the natural pseudovirus could normally infect TZM-b1 cells.

The verification of the production, packaging and infec-tivity of the NL4-3TSTIP and NL4-3WT pseudoviral par-ticles were carried out according to the verification methods for the production, packaging and infectivity of the above-mentioned Bal26 pseudovirus.

Example 6: Identification of Pseudoviral Particle Immunogenicity

Production and Purification of Pseudoviral Particle

According to the method for producing pseudovirus in Example 5, large scale production of pseudoviral particles (e.g., NL4-3-TSTIP and un-mutated NL4-3-WT pseudoviral particles) was performed by transfection of 293FT cells, and the virus supernatant was harvested and subjected to density gradient centrifugation and purification to obtain pseudovi-ral particles, and the specific process was as follows:

(1) 20% sucrose solution was prepared in advance and filtered with a 0.224 μm syringe filter into a sterile tube;

(2) a set of internal and external tubes and the cap were cleaned and wiped with 75% alcohol, dried by tapping and irradiated with ultraviolet light for 30 minutes in a safety cabinet; the pre-concentrated virus was mixed and centrifuged at 3000 rpm for 7 minutes;

(3) 0.45 μm syringe filter and 10 ml syringe were used to filter the virus supernatant into the ultracentrifuge internal tube (30 ml of virus liquid/tube); a 10 ml syringe was used to draw 5 ml/tube of 20% sucrose solution and connected with a 5 cm needle, and then it was inserted to the bottom of the tube set containing the virus liquid, to add sucrose solution slowly;

(4) the tube set was arranged in pairs 1-4, 2-5, 3-6 correspondingly, and labeled with sample signs. After addition of the samples, balance with electronic analytical balance was performed so that the error between the corresponding two tubes was less than 0.0005 g;

(5) the caps of tube sets were tightened after confirming there was no wrong, the tube sets were hung on the corresponding position on sw28 rotor; vacuuming was performed, and the parameters were set as 25000 rpm, 2.5 h, 4° C., the maximum up speed, and down speed with brakes;

(6) after centrifugation, the vacuum button was pressed to introduce air, the centrifuge tubes were gently taken out, the supernatant was discarded in a safety cabinet, sterile PBS was added to dissolve overnight, and the liquid was collected as a concentrated virus sample.

The obtained HIV-1 virus-like particles were resuspended in PBS, and the p24 and Env of the virus were quantified by the following methods.

Quantification of p254

1. Antibody coating: 16G12 antibody was diluted with PB7.4, and coated at 100 ng/well (100 μL) 16G12 on a 96-well plate, and the coating was carried out overnight at 4° C.

2. Blocking: the 96-well plate was washed once with PB ST, spin-dried, added with 180 μL of ED solution, and blocked for 2 h at 37° C. or overnight at 4° C.

3. Virus incubation: PBS was used as buffer solution to serially dilute the virus in a U bottom plate (p24 standard substance was added to the plate at 350, 700, 1400 and 2800 pg/mL), 100 μL (volume) per well, then added with lysis buffer, 20 μl (volume) per well. It was transferred to a 96-well plate and incubated at 37° C. for 1 h.

4. Secondary antibody reaction: the 96-well plate was washed 5 times with PBST washing solution, spin-dried. 100 μL of 2F2-HRP secondary antibody solution (1:10000 diluted in ED11 solution) was added to each well, and incubated in a 37° C. incubator for 45 min.

5. Color development: the 96-well plate was washed 5 times with PBST washing solution, spin-dried, and 100 μL of the A/B color development solutions mixed at equal volume was added to each well, and incubated at 37° C. for 10 min.

6. Stopping: 50 μL of sulfuric acid stopping solution was added to each well, the 96-well plate was placed in a microplate reader to read OD650-450 nm.

7. The p24 standard substance was used as a reference to make a standard curve to calculate the p24 content in the virus.

Quantification of Env

1. GNL coating: GNL at 500 ng/well (100 μl) was coated on a 96-well plate, the buffer was PBS, and the coating was performed overnight at 4° C.

2. Blocking: the plate was washed once with PBST, spin-dried, added with 180 μL of ED solution, and blocked for 2 hours at 37° C. or overnight at 4° C.

3. Virus coating: the virus liquid was diluted with ED as diluent solution (gp140 at a starting concentration of 1 μg/ml was used as the standard), transferred into the 96-well plate, and incubated at 37° C. for 1 hour after sealing the plate.

4. Primary antibody reaction: the plate was washed 5 times with PB ST washing solution, and spin-dried. 100 Ill of VRC01 (1 μg/ml diluted in ED11 solution) was added to each well, and incubated at 37° C. for 1 hour after sealing the plate.

4. Secondary antibody reaction: the plate was washed 5 times with PBST washing solution, and spin-dried. 100 μL of GAH-HRP secondary antibody solution (1:5000 diluted in ED11 solution) was added to each well, and incubated at 37° C. for 45 min after sealing the plate.

5. Color development: the 96-well plate was washed 5 times with PBST washing solution, and spin-dried. 100 μL of the A/B color development solutions mixed at equal volume was added to each well, and incubated to react in a 37° C. incubator for 10 min.

6. Stopping: 50 μL of sulfuric acid stopping solution was added to each well, the 96-well plate was place in a microplate reader to read OD650-450 nm.

7. The gp140 standard substance was used as a reference to make a standard curve to calculate the Env content in the virus.

Identification of Pseudovirus Immunogenicity

After quantification of p24 and Env of the NL4-3 pseudoviral particles, the mouse immunization experiment of the NL4-3 pseudoviral particles were performed with the immunization protocol shown in Table 3. The 6-week-old female mice, purchased from Shanghai Slack Experimental Animal Co., Ltd., were divided into five experimental groups, A/B/C/D/E, 5 mice in each group. Combined with aluminum adjuvant, a total of five injections of intraperitoneal immunization were performed, and the immunization period was 2 weeks/injection. The blood samples were collected from mouse eyeball before immunization at 0/2/4/6/8 weeks and at the week, and then the mice were treated with neck dislocation. The blood samples were placed at 37° C. for 30 minutes, then centrifuged at 13300 rpm for 10 minutes, and the serum samples were collected for determination of Env and P24 specific binding antibody titers and HIV-1 pseudovirus neutralizing antibody titers. The experimental results showed that the pseudovirus of the present invention could induce neutralizing antibody responses and exhibited good immunogenicity.

TABLE 3

| Immunization protocol of NL4-3 pseudoviral particle | | | | |
|---|---|---|---|---|
| Injection No. | Group A | Group B | Group C | Group D | Group E |
| 1 | NL4-3TSTIP pseudovirus 2 µg(Env) | NL4-3 WT pseudovirus 2 µg(Env) | NL4-3TSTIP gp140(2 µg) | NL4-3SOSIP gp140(2 µg) | NL4-3TSTIP pseudovirus 2 µg(Env) + NL4-3TSTIP gp140(2 µg) |
| 2 | NL4-3TSTIP pseudovirus 2 µg(Env) | NL4-3 WT pseudovirus 2 µg(Env) | NL4-3TSTIP gp140(2 µg) | NL4-3SOSIP gp140(2 µg) | NL4-3TSTIP pseudovirus 2 µg(Env) + NL4-3TSTIP gp140(2 µg) |
| 3 | NL4-3TSTIP pseudovirus 2 µg(Env) | NL4-3 WT pseudovirus 2 µg(Env) | NL4-3TSTIP gp140(2 µg) | NL4-3SOSIP gp140(2 µg) | NL4-3TSTIP pseudovirus 2 µg(Env) + NL4-3TSTIP gp140(2 µg) |
| 4 | NL4-3TSTIP pseudovirus 2 µg(Env) | NL4-3 WT pseudovirus 2 µg(Env) | NL4-3TSTIP gp140(2 µg) | NL4-3SOSIP gp140(2 µg) | NL4-3TSTIP pseudovirus 2 µg(Env) + NL4-3TSTIP gp140(2 µg) |
| 5 | NL4-3TSTIP pseudovirus 2 µg(Env) | NL4-3 WT pseudovirus 2 µg(Env) | NL4-3TSTIP gp140(2 µg) | NL4-3SOSIP gp140(2 µg) | NL4-3TSTIP pseudovirus 2 µg(Env) + NL4-3TSTIP gp140(2 µg) |

Example 7: Production and Characterization of NL4-3 Virus Particles

The full-length Env sequence of NL4-3 strain was designed with reference to the design of TSTIP protein, and the obtained full-length TSTIP gp160 gene (which encoded the amino acid sequence set forth in SEQ ID NO: 17) was codon-optimized to obtain base sequence suitable for expression in mammalian cells, and then sent to Sangon Biotech (Shanghai) Co., Ltd for gene synthesis, and cloned into the genomes of two strains to replace the wild-type Env gene. 1 µl of each of the synthesized plasmids was taken to transform Stb13 competent cell (purchased from Shanghai Weidi Biotechnology Co., Ltd.), then coated on an ampicillin-containing solid medium, and cultured at 30° C. for 12-14 hours; after a single colony was clearly visible, it was picked and placed in a test tube containing 3 ml of ampicillin-containing LB medium, cultured under shaking at 220 rpm at 30° C. for 12 hours; 500 µl of the bacterial liquid was taken and mixed with 500 µl of 50% glycerol, and then cryopreserved at −20° C. The bacterial liquid was inoculated into 500 ml of LB medium and cultured, for plasmid extraction. The extraction process of plasmid referred to the extraction process of pcDNA3.1 NL4-3/BG505 TSTIP plasmid in Example 1. The extracted plasmid was transiently transfected into 293FT adherent cells, with the transfection reagent of PEI, and by using the transfection method referring to the pseudovirus production process as mentioned in the production and identification of Bal.26-TSTIP pseudoviral particle in Example 5. After 48 hours of transfection, the transfection supernatant was collected, the NL4-3 TSTIP virus particles were purified, and the collected virus particles were verified for their packaging ability and infectivity, and the specific methods referred to the methods described in Example 5. The experimental results showed that the virus obtained by the above method could be normally packaged to form virus particles, and the virus modified by TSTIP design almost completely lost its ability to infect.

Example 8: Identification of Immunogenicity of Virus Particles

According to the method of Example 7, a sufficient amount of virus particles was obtained, and detected for the p24 and Env content by using the p24 and Env quantification method in Example 6. NL4-3 TSTIP virus particle immunization experiment was carried out according to the immunization protocol shown in Table 4. Six-week-old female white mice were purchased from Shanghai Slack Experimental Animal Co., Ltd., and two experimental groups A/B were set up, five mice in each group. Taking Env content as a reference, the group A was immunized with virus particles containing 2 µg-Env, and the group B was immunized with 2 µg of purified gp140 protein. Combined with aluminum adjuvant, intraperitoneal immunization was carried out, the immunization period was 2 weeks/injection, and there was a total of 5 injections for the immunization. The blood samples of mice were collected from eyeball before the immunization at weeks and at the $10^{th}$ week, and then the mice were treated with neck dislocation. After the blood samples were placed at 37° C. for 30 minutes, they were centrifuged at 13300 rpm for 10 minutes, and the serum samples were collected for the determination of Env and P24-specific binding antibody titers and HIV-1 pseudovirus neutralizing antibody titers. The experimental results showed that the virus of the present invention could induce neutralizing antibody responses and exhibited good immunogenicity.

TABLE 4

| Immunization protocol of NL4-3 virus particle | | |
|---|---|---|
| Injection No. | Group A | Group B |
| 1 | NL4-3TSTIP pseudovirus 2 µg(Env) | NL4-3TSTIP gp140(2 µg) |

TABLE 4-continued

| | Immunization protocol of NL4-3 virus particle | |
|---|---|---|
| Injection No. | Group A | Group B |
| 2 | NL4-3TSTIP pseudovirus 2 μg(Env) | NL4-3TSTIP gp140(2 μg) |
| 3 | NL4-3TSTIP pseudovirus 2 μg(Env) | NL4-3TSTIP gp140(2 μg) |
| 4 | NL4-3TSTIP pseudovirus 2 μg(Env) | NL4-3TSTIP gp140(2 μg) |
| 5 | NL4-3TSTIP pseudovirus 2 μg(Env) | NL4-3TSTIP gp140(2 μg) |

Example 9: Design and Characterization of Various TSTIP-Based Proteins

Based on the amino acid sequence of BG505 TSTIP (SEQ ID NO: 3), WNSSWSN and AKRRVVGREKR, which needed to be deleted due to the design of TSTIP, were introduced at the linkage region of β27 and gp120 and the linkage region of gp120 and α8 of BG505 TSTIP respectively to obtain SEQ ID NO: 5 (BGTSTIP-Full).

Based on the amino acid sequence of NL4-3TSTIP (SEQ ID NO: 4), WNSSWSN and AKRRVVGREKR, which needed to be deleted due to the design of TSTIP, were introduced at the linkage region of β27 and gp120 and the linkage region of gp120 and α8 of NL4-3TSTIP respectively to obtain SEQ ID NO: 6 (NL4-3TSTIP Full).

GGGGS (SEQ ID NO: 28) was introduced at the linkage region of β27 and gp120 and the linkage region of gp120 and α8 of BG505 TSTIP, respectively, to obtain SEQ ID NO: 7 (BG505-TSTIP G1).

GGGGS was introduced at the linkage region of β27 and gp120 and the linkage region of gp120 and α8 of NL4-3TSTIP, respectively, to obtain SEQ ID NO: 8 (NL4-3-TSTIP G1).

GGGGSGGGGS (SEQ ID NO: 29) was introduced at the linkage region of β27 and gp120 and the linkage region of gp120 and α8 of BG505 TSTIP, respectively, to obtain SEQ ID NO: 9 (BG505-TSTIP G2).

GGGGSGGGGS was introduced at the linkage region of β27 and gp120 and the linkage region of gp120 and α8 of NL4-3TSTIP, respectively, to obtain SEQ ID NO: 10 (NL4-3-TSTIP G2).

Figure 11A:
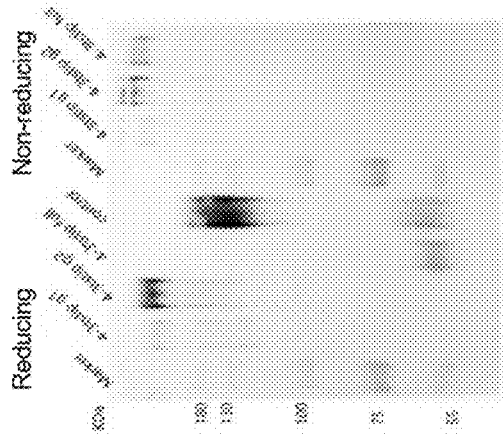
FIG. 11A shows the results of reducing SDS polyacrylamide gel electrophoresis of the modified gp140 trimers BG505/NL4-3 TSTIP G1/G2/Full. It showed that the molecular weights of BG505 TSTIP-G2 and NL4-3 TSTIP-G1 were larger than expected, the two proteins could still be dimers under reducing conditions, while no target proteins with high purity were available for BGTSTIP-Full, NL4-3-G1 and NL4-3-Full after purification. In contrast, the protein TSTIP of the present invention had a broader range of application.
Figure 11A:
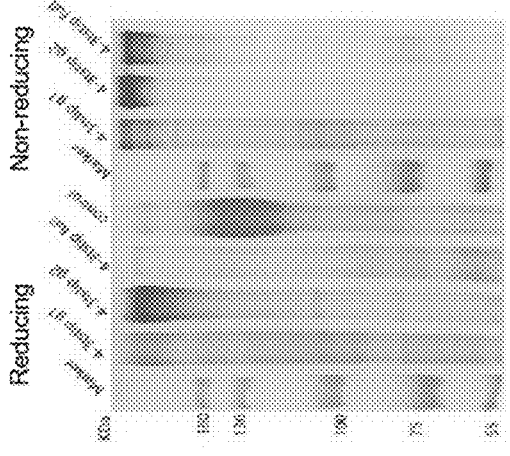
Figure 11A:
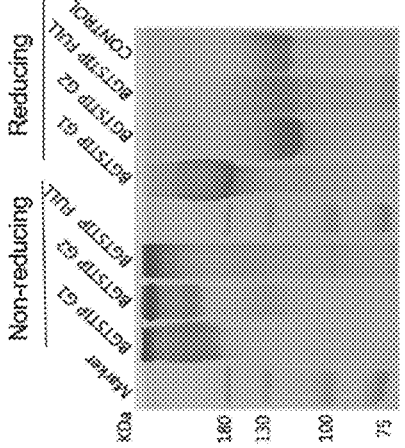

According to the steps of Examples 1, 2, 3, and 4, a series of studies were carried out on the six proteins obtained above. The results of SDS-polyacrylamide gel electrophoresis of the six proteins were shown in FIG. 11A, in which the purity of BGTSTIP-Full, NL4-3TSTIP Full and 8NL4-3-TSTIP G1 proteins decreased in some extent after one-step Ni column purification; the Coomassie brilliant blue staining of BGTSTIP-G1 and NL4-3 TSTIP G2 under reducing conditions showed >180 KD bands, which might be the dimer forms thereof, while BG505-TSTIP G2 showed similar purity and molecular weight to BG505 TSTIP.

Figure 11B:
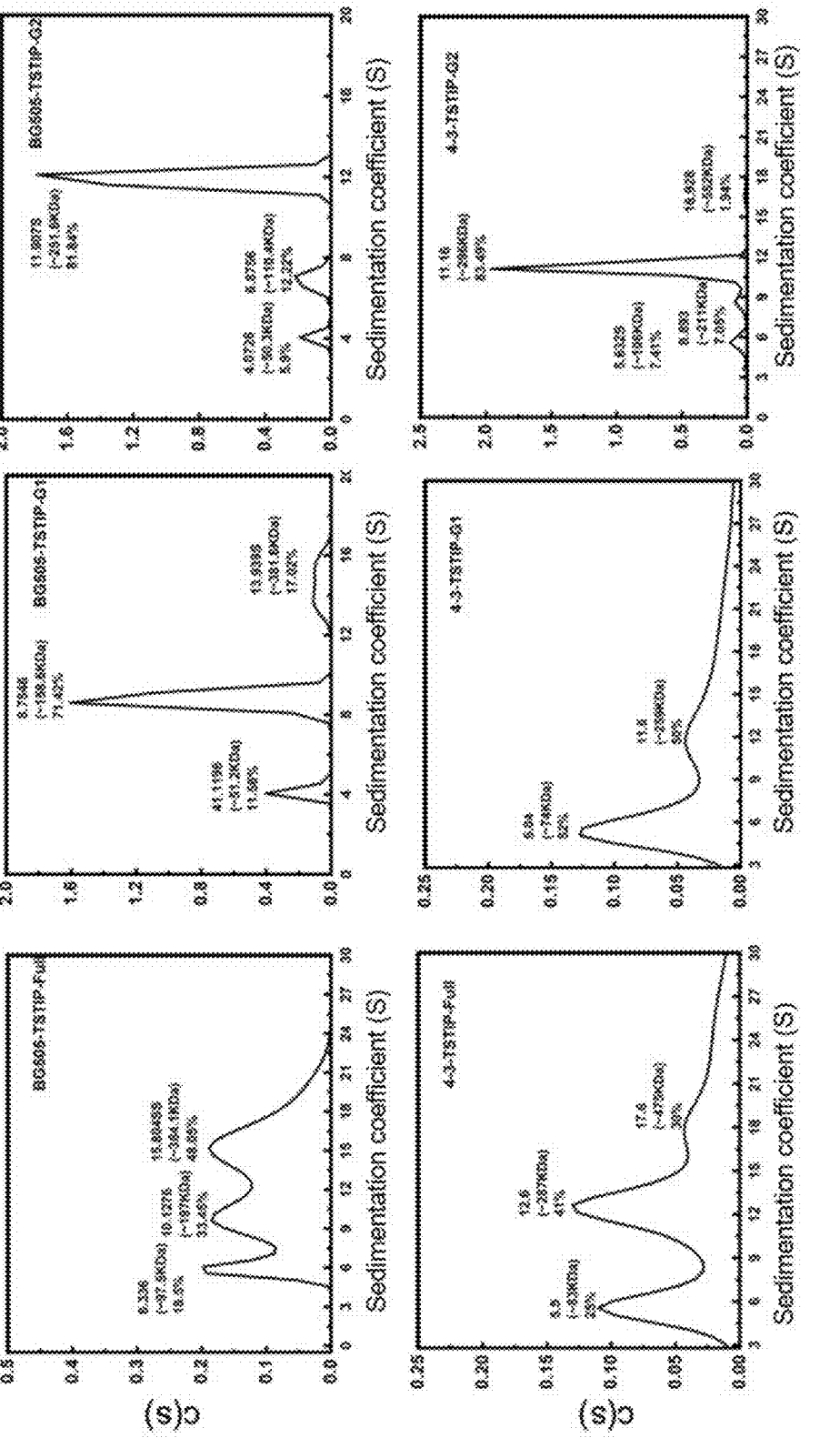
FIG. 11B shows the AUC results of the modified gp140 trimers BG505/NL4-3 TSTIP G1/G2/Full, which were consistent with the results of SDS-PAGE.

The four high-purity proteins were subjected to analytical ultracentrifugation, and the results were shown in FIG. 11B, in which this result was consistent with the results of SDS polyacrylamide gel electrophoresis in the previous step (14A), that was, the molecular weights of BGTSTIP G1 and NL4-3TSTIP G2 were greater than the molecular weight of monomer gp140, while the purity of BG505 TSTIP was significantly lower than that of BGTSTIP. This showed that the linkage region of β27 and gp120, and the linkage region of gp120 and α8 had obvious effects on the forms of Env protein. Moreover, different modifications of the same strain could result in differences of expression level, and the mutation of Ile→Pro at position 559 could effectively increase the protein production. Specifically, the expression levels were summarized in Table 3.

Figure 12:
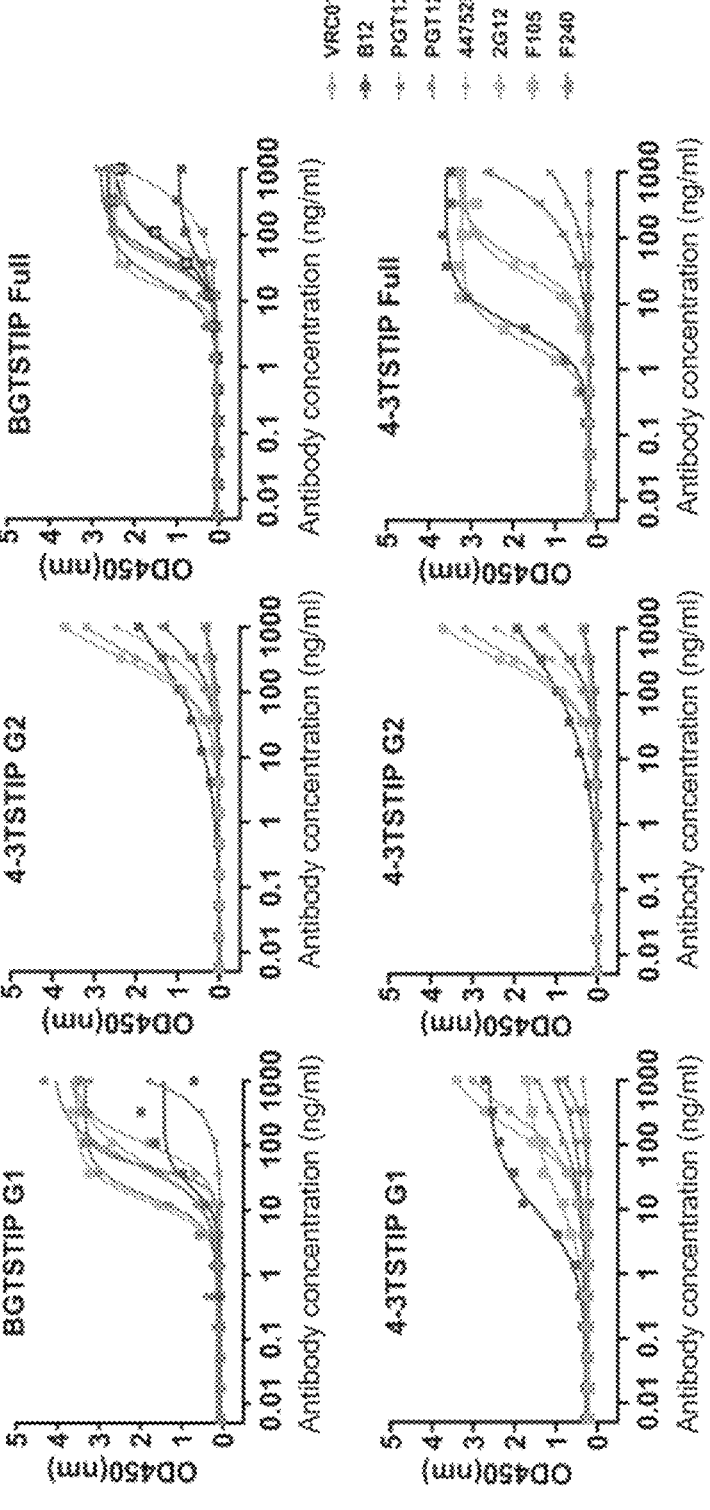
FIG. 12 shows the results of enzyme-linked immunosorbent assay of the modified gp140 trimers BG505/NL4-3 TSTIP G1/G2/Full with various reported antibodies. It showed that the six proteins could all react with various antibodies and had certain activities, but the reactivity of some proteins was weaker than that of the protein TSTIP of the present invention.

The ELISA experiment results of the six proteins with various reported human monoclonal antibodies were shown in FIG. 12. Even some proteins had a relatively lower purity, the purified six proteins could all be well recognized by various antibodies, which proved their activity.

Figure 13:
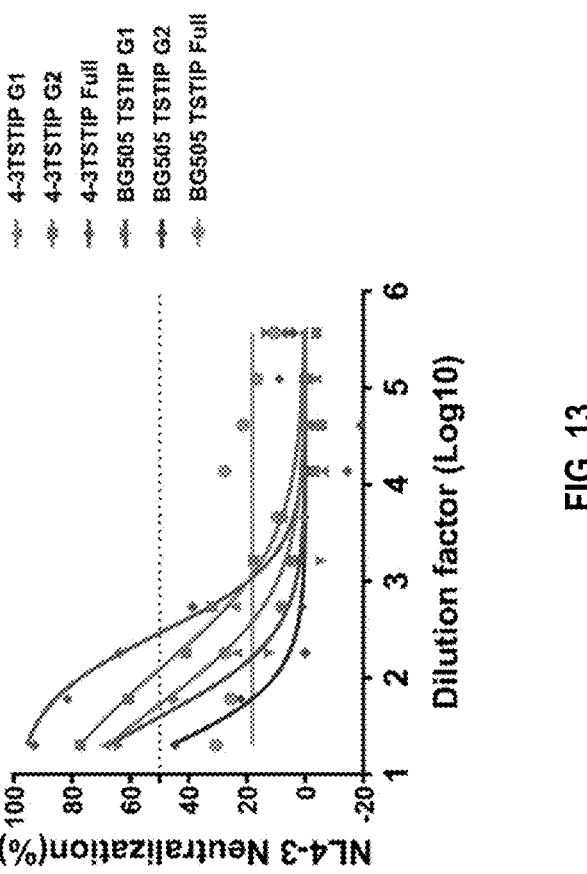
FIG. 13 shows the virus neutralization experiment of the immune serum samples obtained by immunizing BALB/C mice with various modified gp140 trimers on B subtype NL4-3 strain. The results showed that all six proteins could induce neutralizing antibody responses in mice.

According to the above immunization protocol, we immunized BABL/C mice with the six purified proteins. The results of animal immunization experiments showed that all the six proteins could induce neutralizing antibody responses in mice, as shown in FIG. 13. In addition, pseudoviral particles and virus particles were further constructed based on these proteins, and mouse immunization experiments were carried out to detect their immunogenicity.

TABLE 3

| | Summary of protein expression levels | | | | |
|---|---|---|---|---|---|
| | BG505 Env | | | | |
| | BGTSTIP | BGSOSIP | BGTSTIP-G1 | BGTSTIP-G2 | BGTSTIP-full |
| Expression level (mg/L) | 40 | 20 | 9 | 27 | 6 |
| | NL4-3 Env | | | | |
| | 4-3TSTIP | 4-3SOSIP | 4-3TSTIP-G1 | 4-3TSTIP-G2 | 4-3TSTIP-full |
| Expression level (mg/L) | 37 | 19 | 3 | 25 | 5 |

Example 10: Application of TSTIP Modification in Strains of Multiple Subtypes

In order to further confirm the effect of the TSTIP design on different strains, the inventors applied a design method similar to BG505/NL4-3-TSTIP to the Env proteins of various strains. Table 4 showed 12 global-representative strains. Since the expression and identification of proteins of subtype A and subtype B strains had been completed, one strain of each subtype except subtype A and subtype B was selected from the 12 global pseudovirus strains, to carry out the TSTIP modification of Env protein in the gp140 proteins of the selected 5 strains, including 25710 (C), X1632 (G), CH119 (BC), CNE8 (AE), and 246F3 (AC). According to a series of experimental steps and methods such as cloning, expression and purification, and characterization as described above, the TSTIP-gp140 proteins of the five strains were studied, and the series of results were shown in FIGS. 14A to 14D.

Figure 14A:
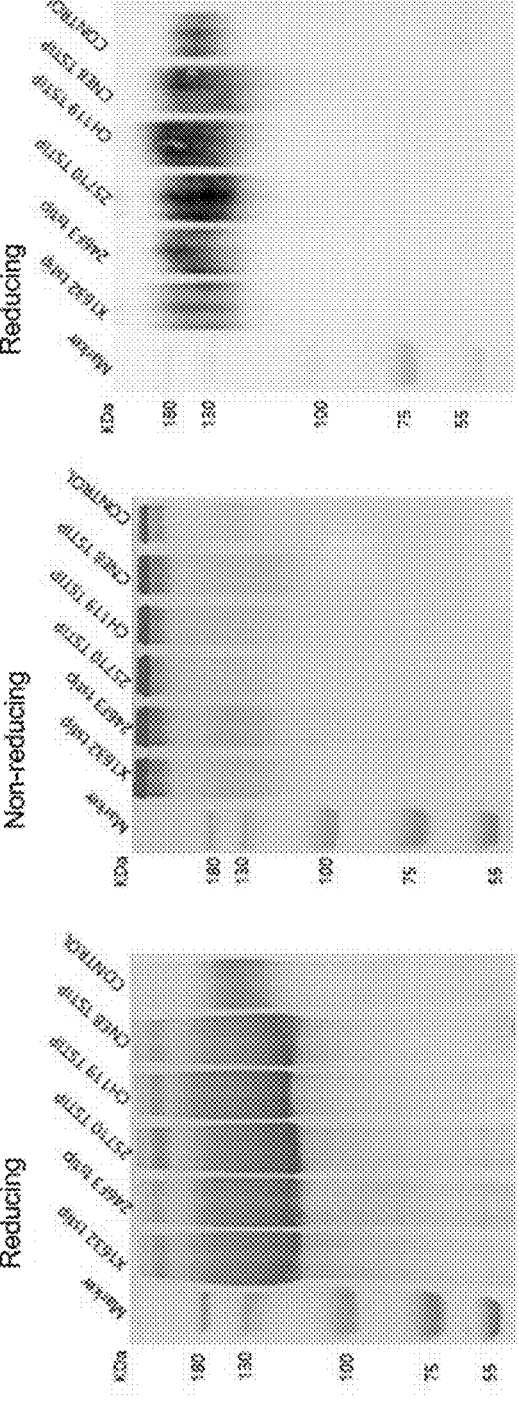
FIG. 14A shows the SDS polyacrylamide gel electrophoresis results of the modified gp140 trimers of various strains. The results showed that the modified proteins of the various strains were well expressed, and could be purified to reach a higher purity. Under the reducing SDS-PAGE, the proteins of the present invention showed a single band, which proved that the subunits thereof were linked by a stable covalent linkage.

The results of SDS polyacrylamide gel electrophoresis in FIG. 14A showed that the TSTIP proteins of the five strains all had a relatively higher purity after one-step Ni column purification, and a molecular weight of about 140 KD under the reducing SDS PAGE, indicating that the subunits in the proteins of the present invention were linked together by stable covalent interaction as expected.

Figure 14B:
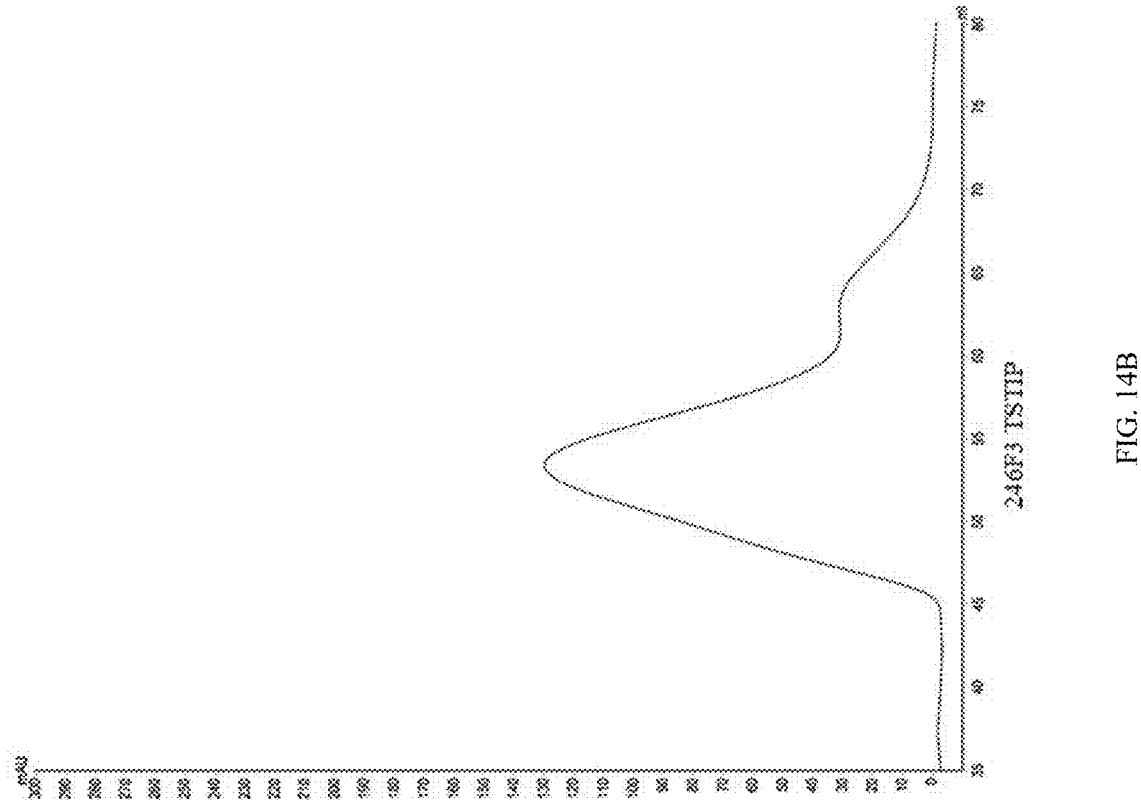
FIG. 14B shows the molecular sieve superdex200 16/600 purification results of TSTIP protein of the five strains, showing that the molecular sieve peaks of the five proteins of the present invention were relatively single, indicating better protein uniformity, and the proteins obtained by applying the strategy of the present invention to different strains formed trimers as main component.
Figure 14B:
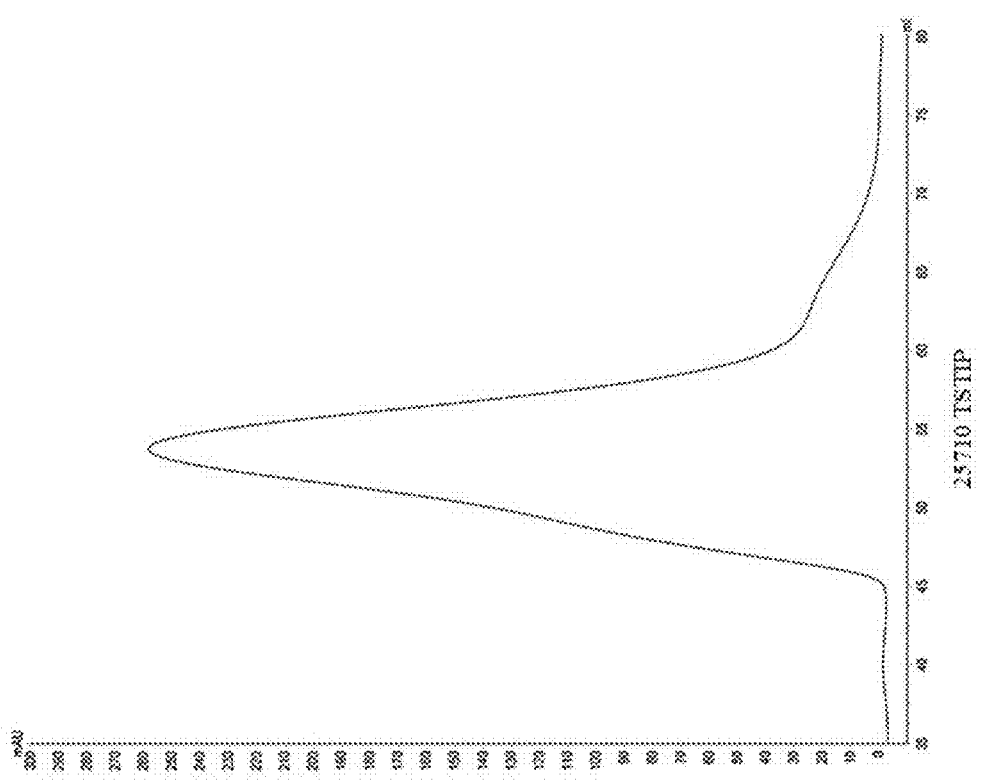
Figure 14B:
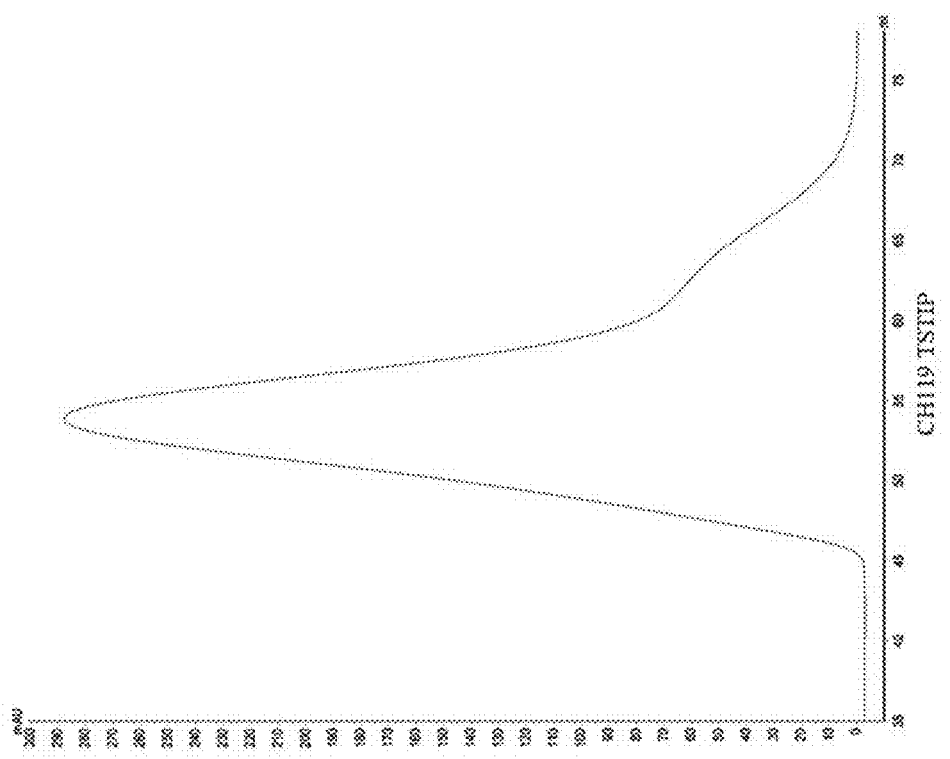
Figure 14B:
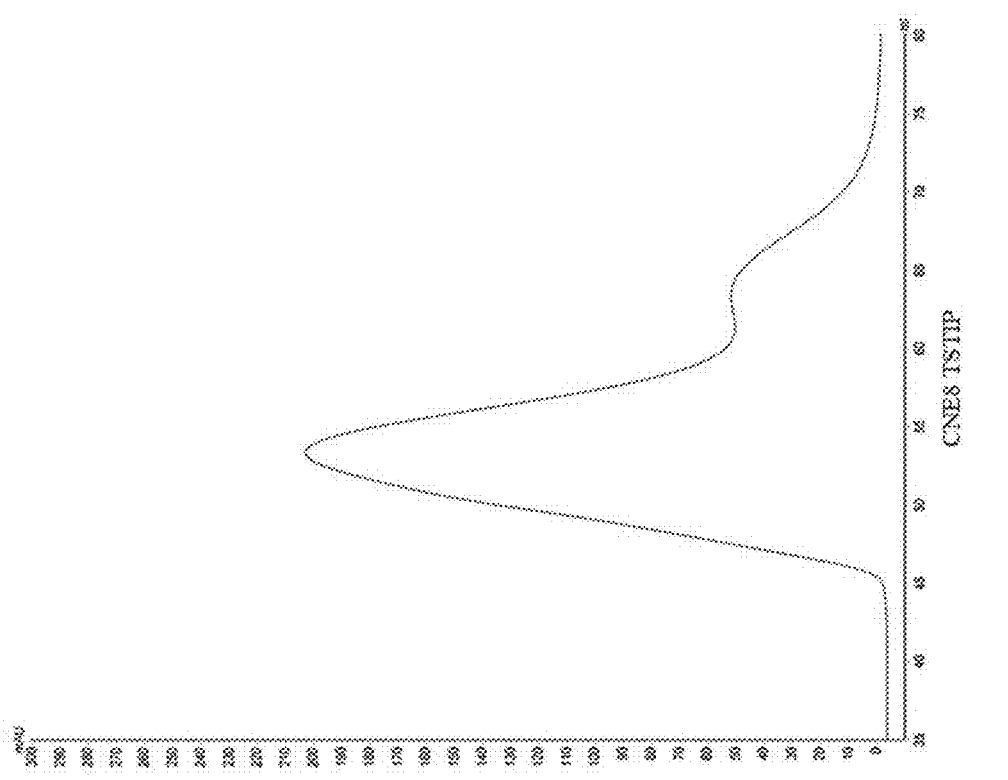
Figure 14B:
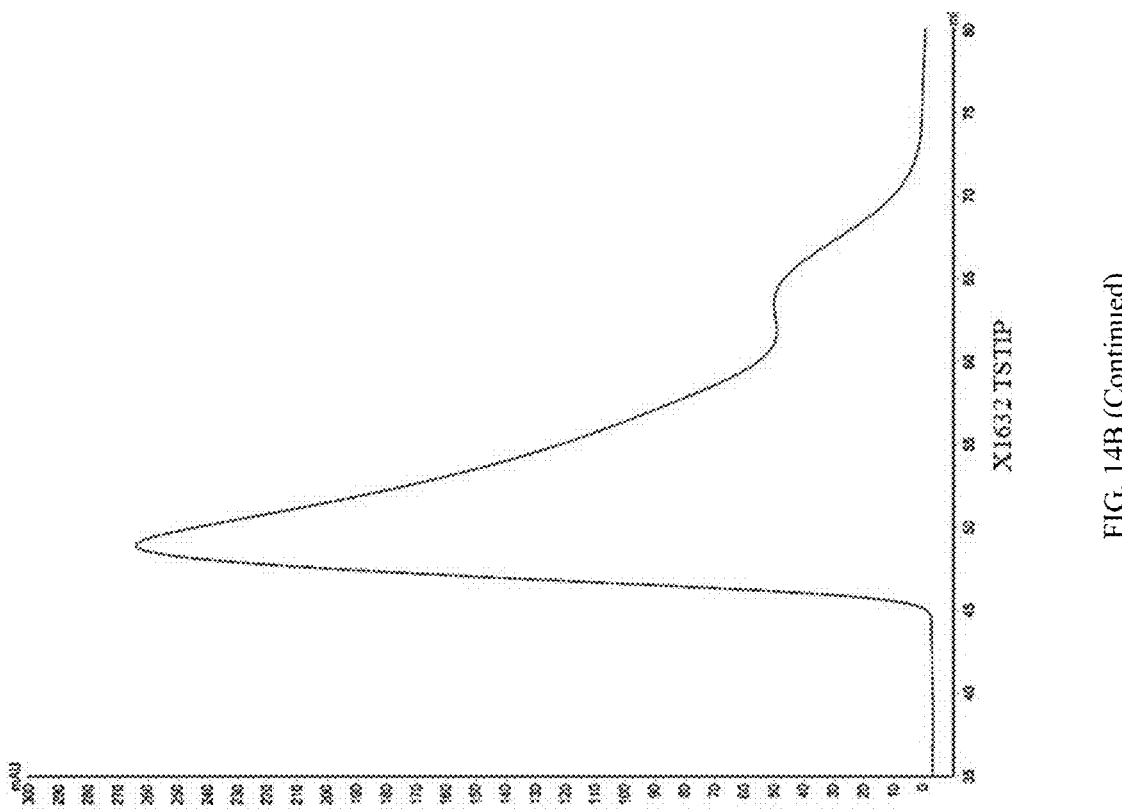

FIG. 14B showed the superdex200 16/600 molecular sieve chromatography results of the five TSTIP proteins, which showed that the elution peaks were relatively single, indicating that the components of the five proteins of the present invention were relatively uniform in natural state, with trimers as majority.

Figure 14C:
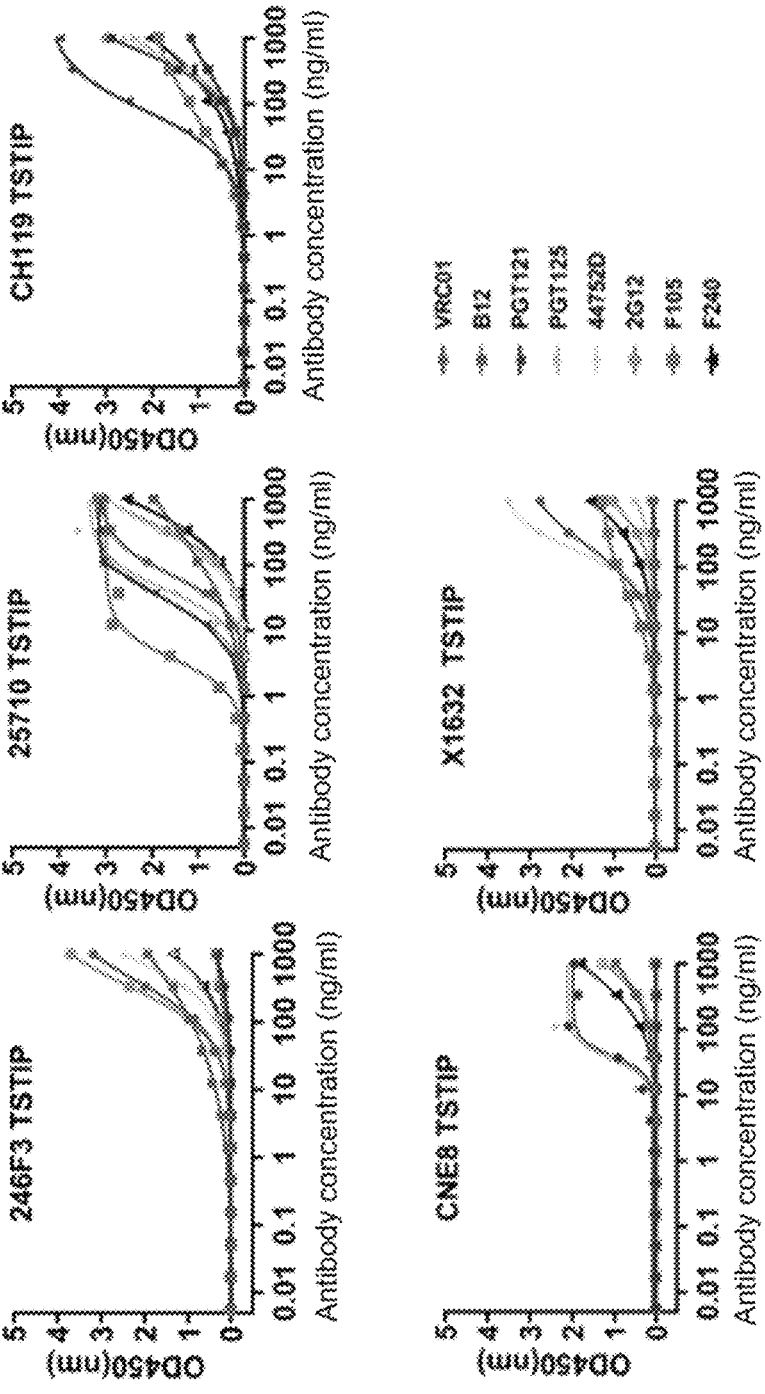
FIG. 14C shows the results of enzyme-linked immunosorbent assay of the proteins of the five strains with various antibodies, showing that the five proteins of the present invention had certain reactivity with various reported antibodies, proving their good activities.

FIG. 14C showed the enzyme-linked immunoassay (ELISA) results of the five proteins with various reported antibodies, which showed that the proteins of different strains had different recognition and binding abilities to the antibody of the same type. The results showed that the TSTIP proteins of the five strains produced by the inventors all had good activity.

Figure 14D:
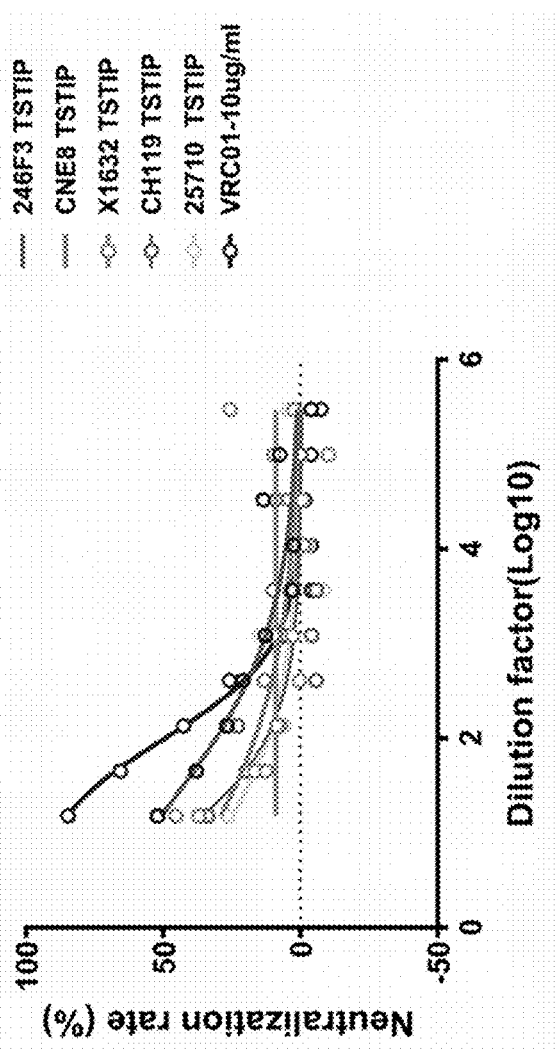
FIG. 14D shows the neutralization test results of pseudovirus by the serum samples obtained by immunization with TSTIP proteins of the five strains, wherein the strains detected by immune serum samples of CH119 TSTIP and X1632 TSTIP were the corresponding CH119 and X1632 strains respectively; the strain detected by immune serum samples of 25710 and 246F3 TSTIP was BJOX200; the strain detected by immune serum sample of CNE8 TSTIP was TR011. The results showed that the immune serum samples of the fourth injection of TSTIP protein of the five strains all detected virus neutralization to some extent, indicating that the immunization of TSTIP protein of different strains could stimulate neutralization responses in mice.
Figure 15A:
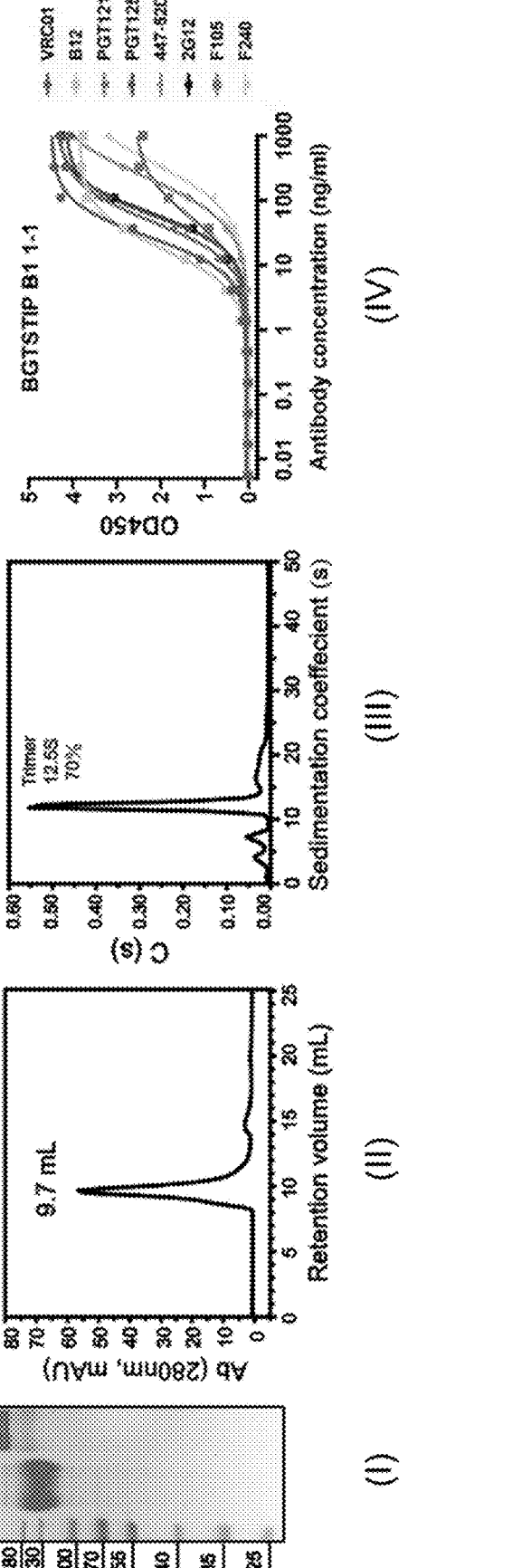
FIGS. 15A to 15K show the experimental results of electrophoresis (I), molecular sieve purification (II), analytical ultracentrifugation (III), and ELISA (IV) of each TSTIP protein construct in Example 11.
Figure 15B:
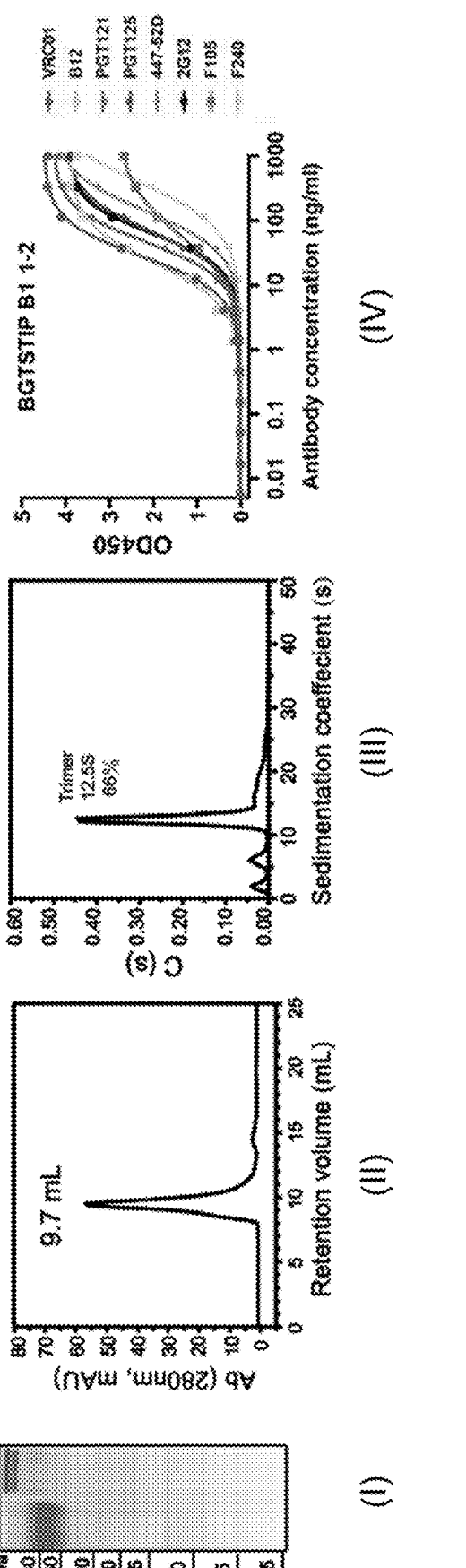
Figure 15C:
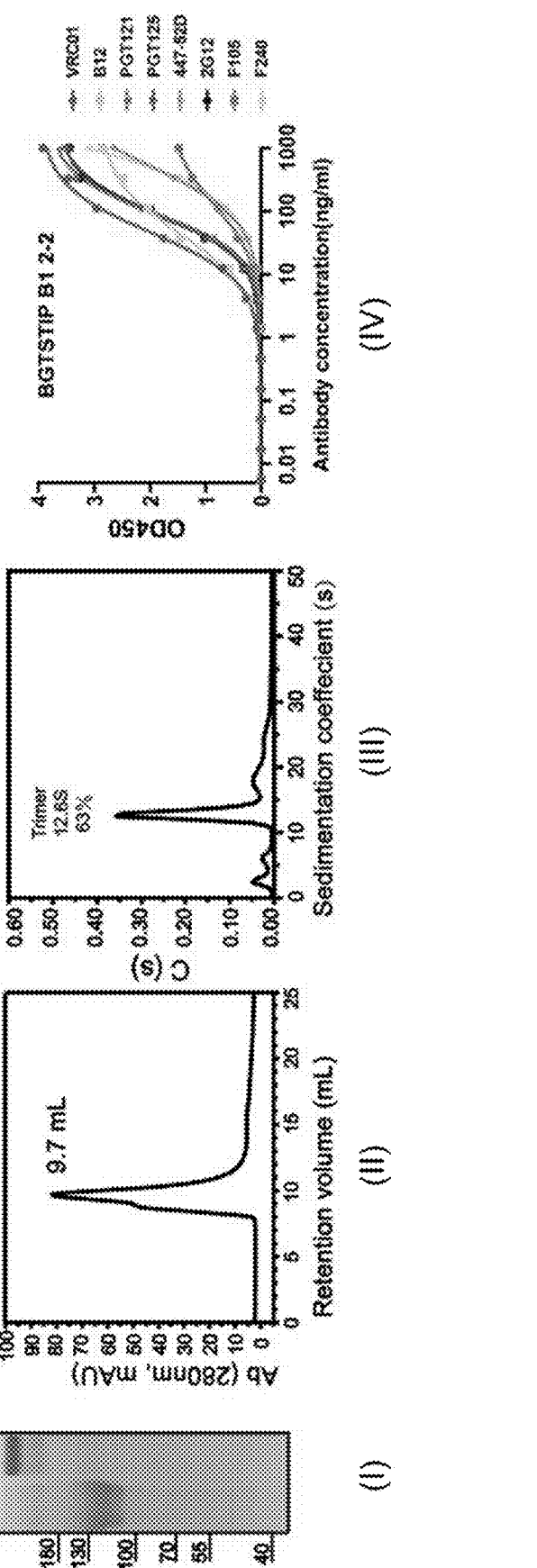
Figure 15D:
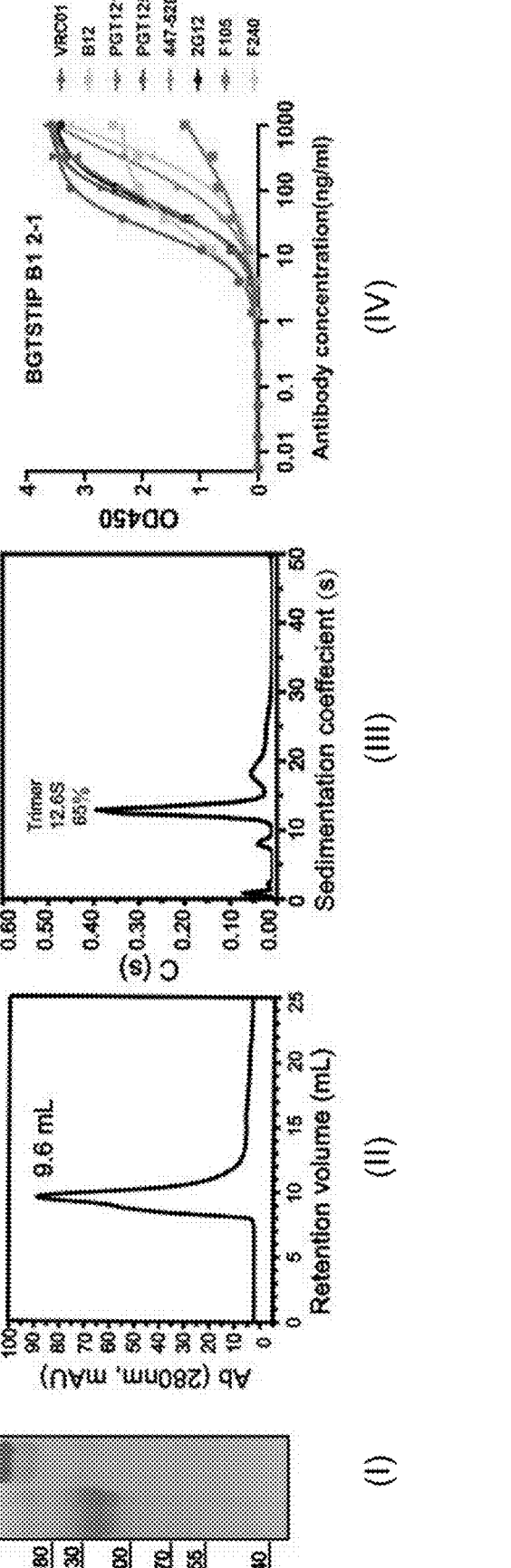
Figure 15E:
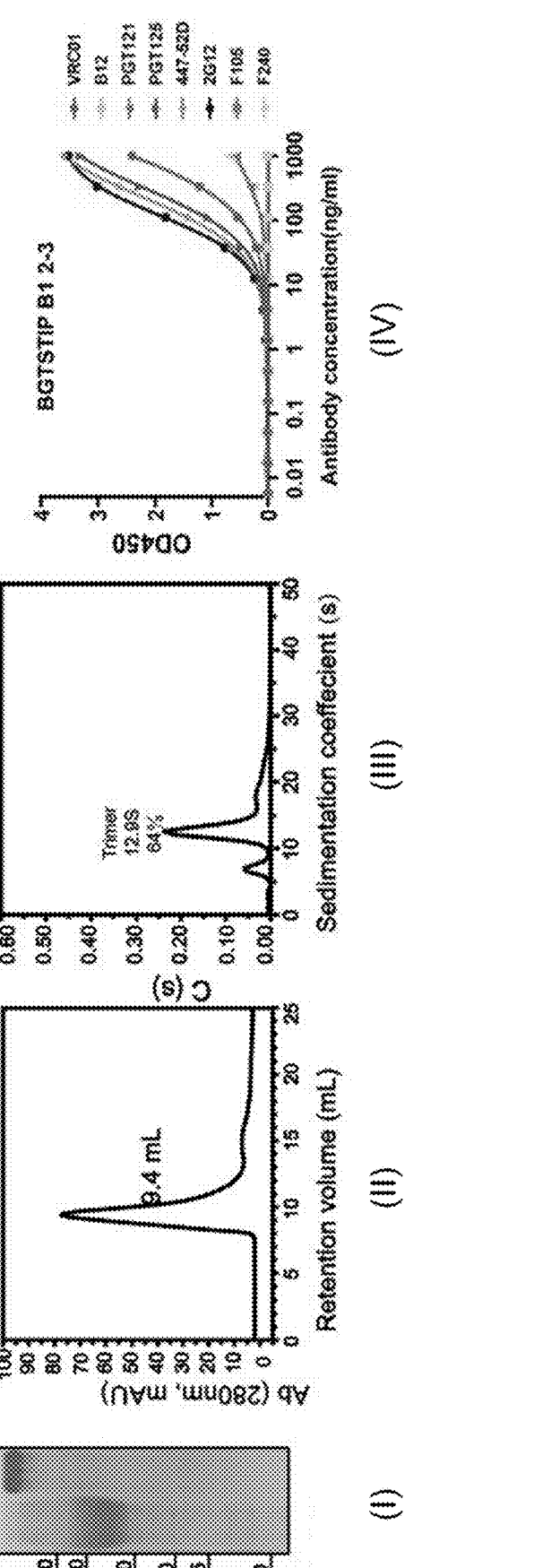
Figure 15F:
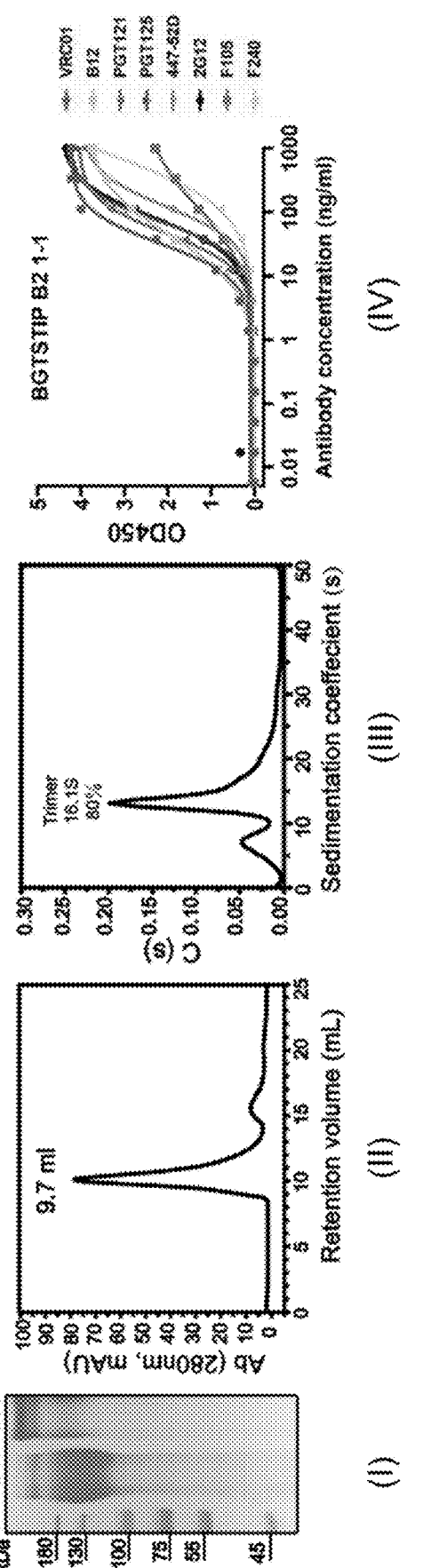
Figure 15G:
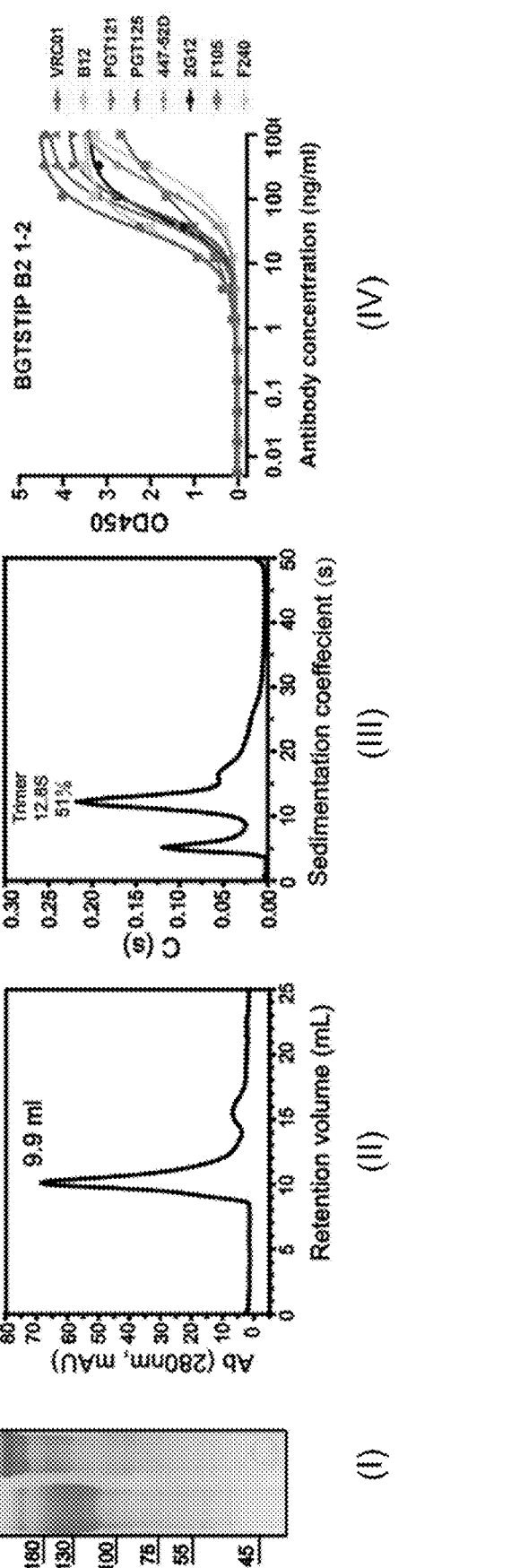
Figure 15H:
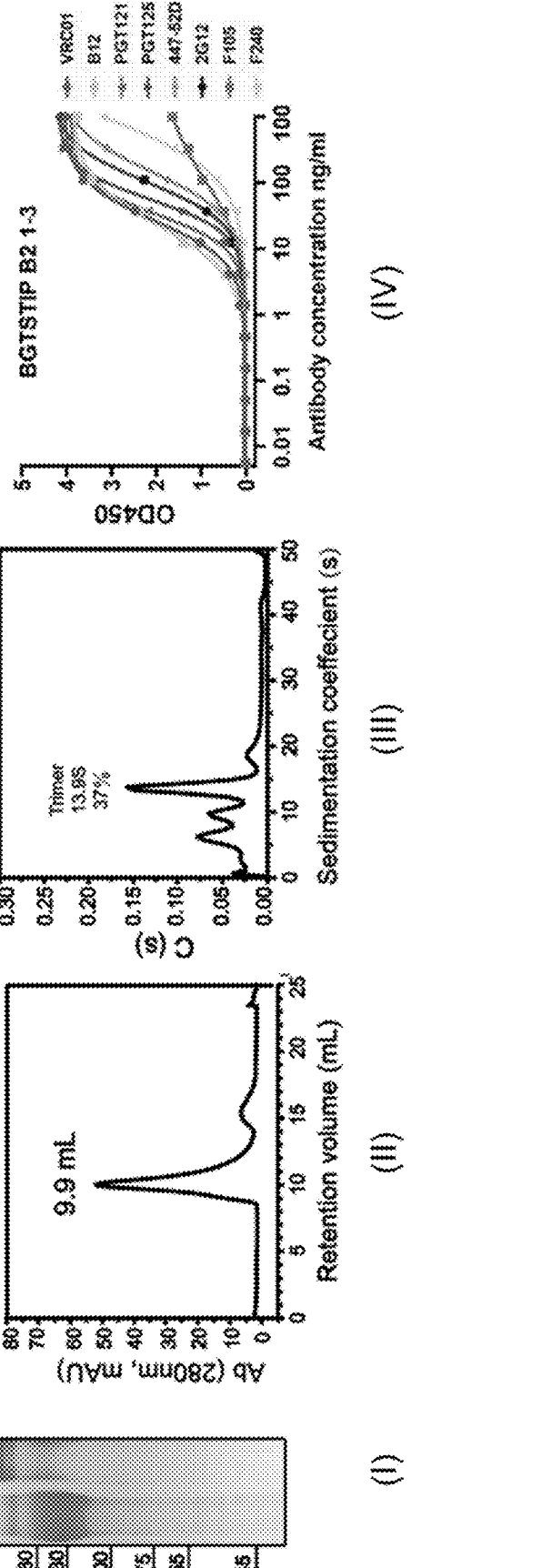
Figure 15I:
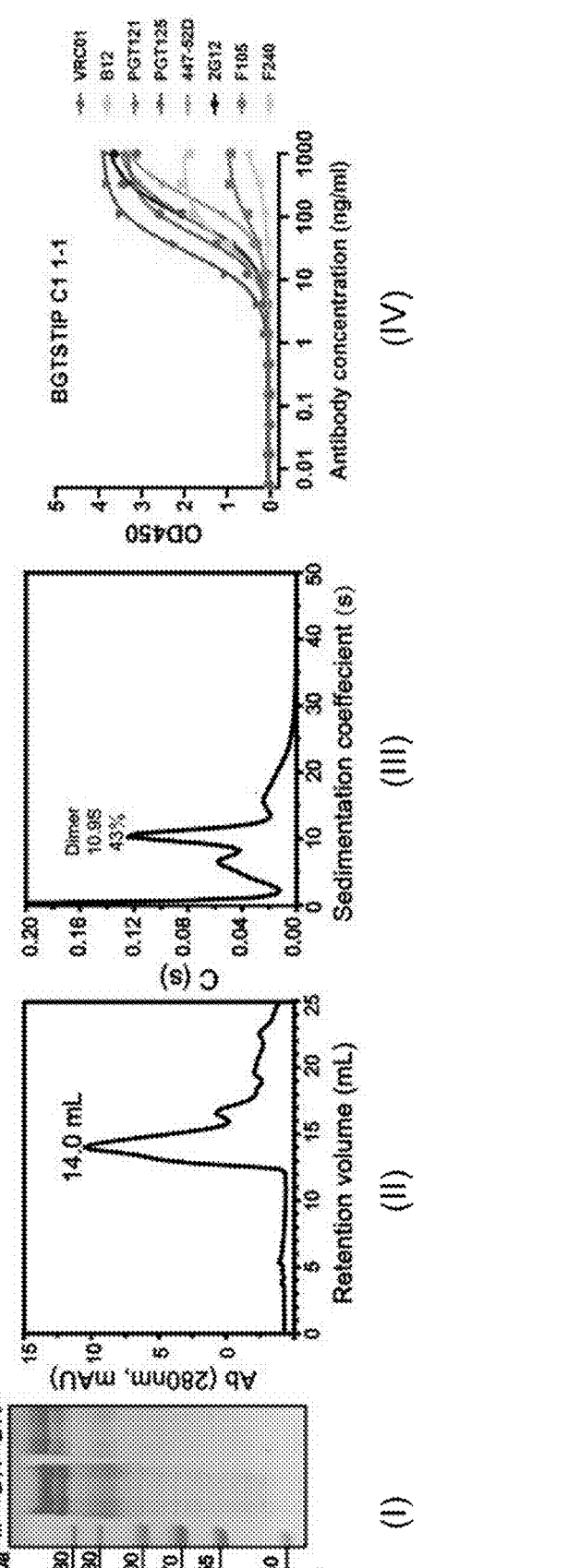
Figure 15J:
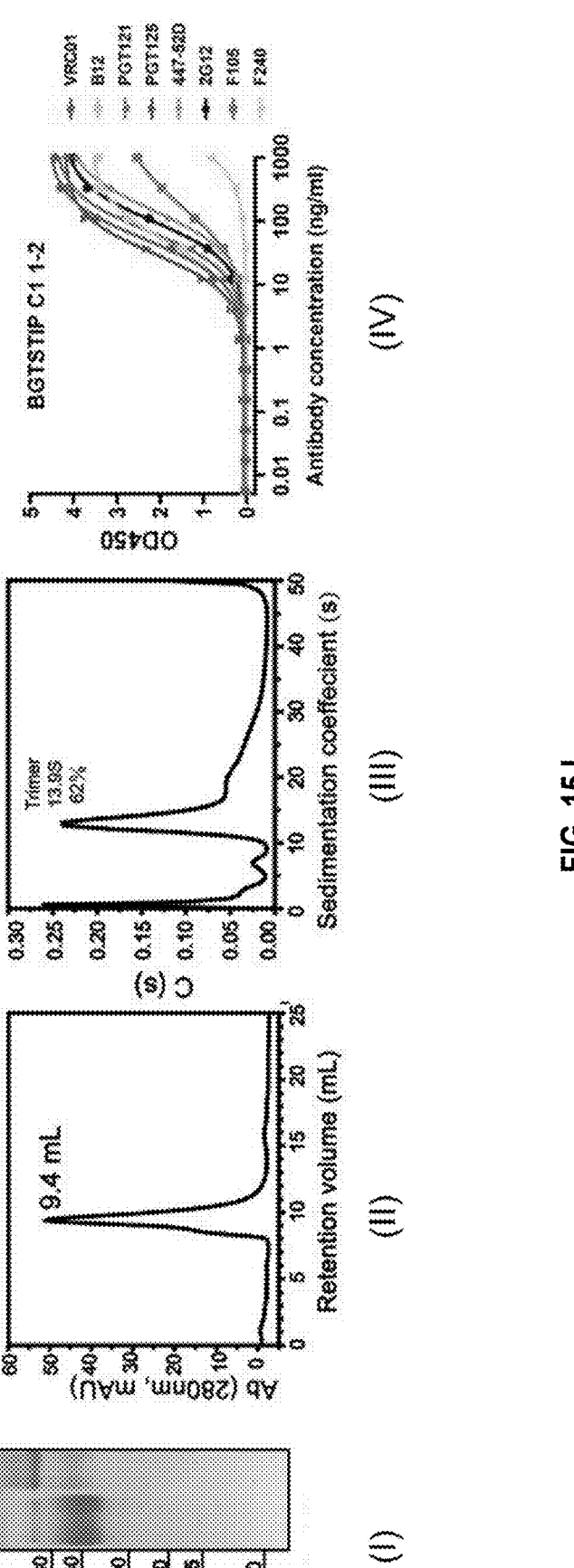
Figure 15K:
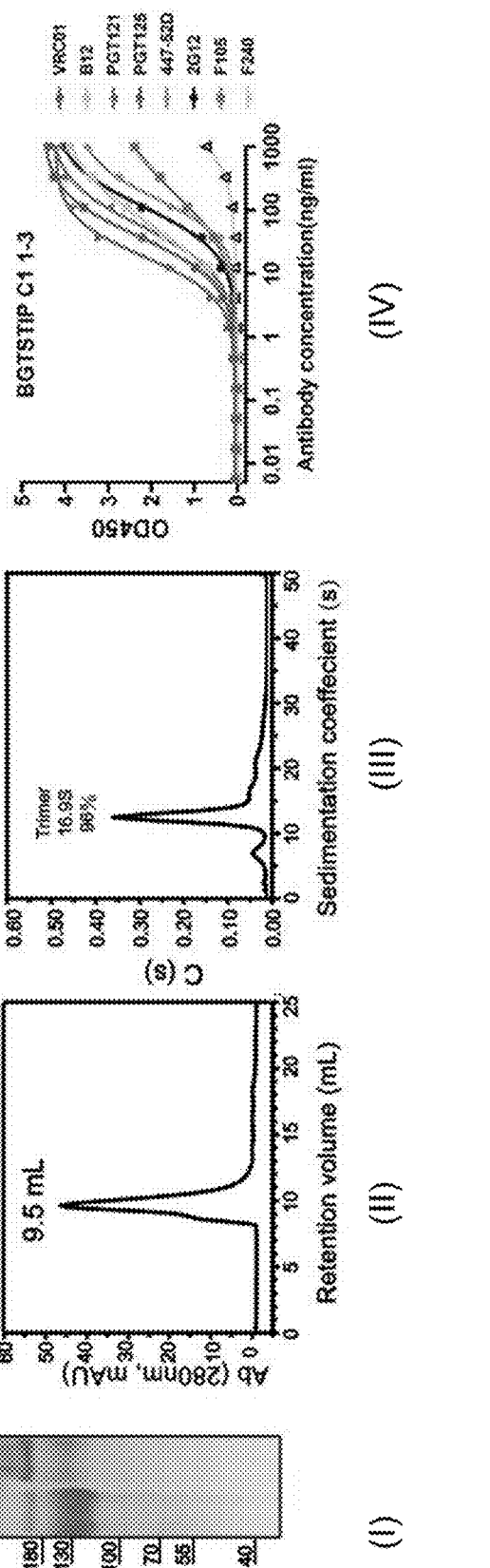

FIG. 14D showed the neutralization experiment of serum samples after immunizing BALB/C mice with the five proteins, and the results indicated that the immunization with TSTIP proteins of different strains could stimulate mice to produce a neutralizing response.

TABLE 4

Twelve global pseudoviruses

| Isolate strain | Subtype | Region |
| --- | --- | --- |
| TRO11 | B | Italy |
| 25710 | C | India |
| 398F1 | A | Tanzania |
| CNE8 | CRF01_AE | China |
| X2278 | B | Spain |
| BJOX002000 | CRF07_BC | China |
| X1632 | G | Spain |
| CE1176 | C | Malawi |
| 246F3 | AC | Tanzania |
| CH119 | CRF07_BC | China |
| CE0217 | C | Malawi |
| CNE55 | CRF01_AE | China |

TABLE 5

Summary of TSTIP protein expression levels of five subtypes

| | TSTIP | | | | |
| --- | --- | --- | --- | --- | --- |
| | 246F3 | 25710 | CH119 | CNE8 | X1632 |
| Expression level (mg/L) | 14.7 | 24 | 60 | 27 | 36 |

Example 11: Design and Activity Identification of Other TSTIP-Based Proteins 11.1 Protein Design
1. BG-B1(1/1)
The amino acid sequence AKRRVVG (not including the furin cleavage site) deleted after β26 and the sequence WNSSWSN (or homologous sequence) deleted after β27 were added back, that was, AKRRVVG was added back after β26 with further insertion of GGGGS after it, and WNSSWSN was added back before α8 with further insertion of GGGGS before it. The modified sequence based on the BG505 strain was set forth in SEQ ID NO:30.

2. BG-B1(1/2)
The amino acid sequence AKRRVVG (not including the furin cleavage site) deleted after β26 and the sequence WNSSWSN (or homologous sequence) deleted after β27 were added back, that was, AKRRVVG was added back after β26 with further insertion of GGGGS after it, and WNSSWSN was added back before α8 with further insertion of (GGGGS) 2 before it. The modified sequence based on the BG505 strain was set forth in SEQ ID NO:31.

3. BG-B1(2/2)
The amino acid sequence AKRRVVG (not including the furin cleavage site) deleted after β26 and the sequence WNSSWSN (or homologous sequence) deleted after β27 were added back, that was, AKRRVVG was added back after β26 with further insertion of (GGGGS) 2 after it, and WNSSWSN was added back before α8 with further insertion of (GGGGS) 2 before it. The modified sequence based on the BG505 strain was set forth in SEQ ID NO:32.

4. BG-B1(2/1)
The amino acid sequence AKRRVVG (not including the furin cleavage site) deleted after β26 and the sequence WNSSWSN (or homologous sequence) deleted after β27 were added back, that was, AKRRVVG was added back after β26 with further insertion of (GGGGS) 2 after it, and WNSSWSN was added back before α8 with further insertion of GGGGS before it. The modified sequence based on the BG505 strain was set forth in SEQ ID NO:33.

5. BG-B1(2/3)
The amino acid sequence AKRRVVG (not including the furin cleavage site) deleted after β26 and the sequence WNSSWSN (or homologous sequence) deleted after β27 were added back, that was, AKRRVVG was added back after β26 with further insertion of (GGGGS) 2 after it, and WNSSWSN was added back before α8 with further insertion of (GGGGS) 3 before it. The modified sequence based on the BG505 strain was set forth in SEQ ID NO:34.

6. BG-B2(1-1)
The amino acid sequence AKRRVVG (not including the furin cleavage site) deleted after β26 and the sequence WNSSWSN (or homologous sequence) deleted after β27 were added back, that was, AKRRVVG was added back after β26 with further insertion of GGGGS after it, and WNSSWSN was added back before α8 with further insertion of GGGGS before it; in addition, a cys mutation was introduced between gp120 and gp41 subunits by referring to the design of SOSIP in order to expect the formation of a disulfide bond, which specifically comprised that Ala at position 501 was mutated to cys, and Thr at position 605 was mutated to cys. The modified sequence based on the BG505 strain was set forth in SEQ ID NO:35.

7. BG-B2(1-2)
The amino acid sequence AKRRVVG (not including the furin cleavage site) deleted after β26 and the sequence WNSSWSN (or homologous sequence) deleted after β27 were added back, that was, AKRRVVG was added back after β26 with further insertion of GGGGS after it, and WNSSWSN was added back before α8 with further insertion of (GGGGS) 2 before it; in addition, a cys mutation was introduced between gp120 and gp41 subunits by referring to the design of SOSIP in order to expect the formation of a disulfide bond, which specifically comprised that Ala at position 501 was mutated to cys, and Thr at position 605 was mutated to cys. The modified sequence based on the BG505 strain was set forth in SEQ ID NO:36.

8. BG-B2(1-3)

The amino acid sequence AKRRVVG (not including the furin cleavage site) deleted after β26 and the sequence WNSSWSN (or homologous sequence) deleted after β27 were added back, that was, AKRRVVG was added back after β26 with further insertion of GGGGS after it, and WNSSWSN was added back before α8 with further insertion of (GGGGS) 3 before it; in addition, a cys mutation was introduced between gp120 and gp41 subunits by referring to the design of SOSIP in order to expect the formation of a disulfide bond, which specifically comprised that Ala at position 501 was mutated to cys, and Thr at position 605 was mutated to cys. The modified sequence based on the BG505 strain was set forth in SEQ ID NO:37.

9. BG-C1(1/1)

The amino acid sequence AKRRVVG (or its homologous sequence, not including the furin cleavage site) deleted after β26 and the sequence WNSSWSN (or homologous sequence) deleted after β27 were added back, that was, WNSSWSN was added back after β27 with further insertion of GGGGS after it, and AKRRVVG was added back before α8 with further insertion of GGGGS after it. The modified sequence based on the BG505 strain was set forth in SEQ ID NO:38.

10. BG-C1(1/2)

The amino acid sequence AKRRVVG (or its homologous sequence, not including the furin cleavage site) deleted after β26 and the sequence WNSSWSN (or homologous sequence) deleted after β27 were added back, that was, WNSSWSN was added back after β27 with further insertion of GGGGS after it, and AKRRVVG was added back before α8 with further insertion of (GGGGS) 2 after it. The modified sequence based on the BG505 strain was set forth in SEQ ID NO:39.

11. BG-C1(1/3)

The amino acid sequence AKRRVVG (or its homologous sequence, not including the furin cleavage site) deleted after β26 and the sequence WNSSWSN (or homologous sequence) deleted after β27 were added back, that was, WNSSWSN was added back after β27 with further insertion of GGGGS after it, and AKRRVVG was added back before α8 with further insertion of (GGGGS) 3 after it. The modified sequence based on the BG505 strain was set forth in SEQ ID NO: 40.

11.2 SDS-PAGE:

These proteins were prepared and purified using the methods described in the above Examples 1-2, the concentrated samples were diluted to 1 μg/μl, then two tubes of 50 μl samples were taken, and 10 μl of reducing loading buffer and 10 μl of non-reducing loading buffer were added, respectively, to prepare reduced samples and non-reduced samples, and the reduced samples were placed in a boiling water bath at 100° C. for 10 minutes. The reduced samples and non-reduced samples in an amount of 10 μl were taken and electrophoresed at 80V for 120 min in 8% SDS PAGE, and the electrophoresis bands were displayed after Coomassie brilliant blue staining.

The results of electrophoresis were shown in the panel (I) of FIGS. 15A to 15K. The SDS-PAGE analysis showed that after one-step Ni-EXCEL purification, the above-mentioned designs could obtain high-purity proteins; under the condition of adding reducing loading buffer, except for BG-C1 (1/1), the main bands showed by other optimized proteins were all 140 KD, while bands of multimer were showed under the condition of non-reducing loading buffer. This indicated that in the optimized designed proteins, similar to the original TSTIP protein, the gp120 and gp41 extracellular regions were still connected via a stable covalent linkage.

11.3 Molecular Sieve Purification:

Instrument system: AKTA Pure type preparative liquid chromatograph;

Chromatographic column: superdex 200 10/300

Column volume: 24 ml

Buffer: PBS (20 mM phosphate buffer, pH7.5, 150 mM NaCl)

Detector wavelength: 280 nm

Flow rate: 0.5 ml/min

The samples were purified and concentrated proteins.

The purification procedure comprised: the superdex200 10/300 was equilibrated with 1 column volume of PBS, a target protein to be purified was loaded with 500 μl sample loop, and molecular sieve purification of the sample to be purified was performed at inject mode. The components of the sample would be eluted according to molecular weights thereof in order, from high to low, and a diagram of peaks after purification was saved. The molecular sieve purification results were shown in the panel (II) of FIGS. 15A to 15K. Each of the proteins showed an obvious single elution peak on the molecular sieve spectrum. Among them, BG-B1 (1/1), BG-B1(1/2), BG-B1(2-1), BG-B1(2-2), BG-B1(2-3), BG-B2(1-1), BG-B2(1-2), BG-B2(1-3), BG-C1(1/2), BG-B1(1/3) all had main elution peaks at an elution volume of about 9.5 ml, which were peaks of trimer, while BG-C1 (1/1) had an elution volume of 14 ml showing a peak of dimer.

11.4 Homogeneity Analysis and Molecular Weight Prediction of Proteins After Analytical Ultracentrifugation (AUC)

The above-mentioned purified proteins were subjected to analytical ultracentrifugation, and the AUC results were shown in the panel (III) of FIGS. 15A to 15K. The results showed that BG-B1(1/1), BG-B1(1/2), BG-B1(2-1), BG-B1 (2-2), BG-B1(2-3), BG-B2(1-1), BG-B2(1-2), BG-B2(1-3), BG-C1(1/2), BG-B1(1/3) were mainly trimers, while BG-C1(1/1) was mainly dimers, and this result was consistent with result of molecular sieve.

11.5 Enzyme-Linked Immunosorbent Assay (ELISA)

Using the enzyme-linked immunosorbent assay described in Example 4, the antigenicity of these above-mentioned purified proteins was identified. The results were shown in the panel (IV) of FIGS. 15A to 15K. The results showed that these proteins had antigenicity, and the modification of linker at the linkage region could adjust their antigenic activity.

Although the specific embodiments of the present invention have been described in detail, those skilled in the art will understand that: according to all the teachings that have been disclosed, various modifications and changes can be made to the details, and these changes are all within the protection scope of the present invention. The full scope of the present invention is given by the claims appended hereto and any equivalents thereof.

What is claimed is:

1. A recombinant protein, which comprises gp120 and gp41 ectodomain (gp41ECTO) derived from human immunodeficiency virus (HIV), wherein the gp120 is located between β27 and α8 of the gp41ECTO;

and the recombinant protein comprises: α6, α7, β27 of gp41ECTO; gp120; α8, α9 of gp41ECTO, from its N-terminal to C-terminal;

and wherein:

(i) the gp41ECTO comprises a substitution of 1-12 consecutive amino acids in a linkage region between β27 and α8 with gp120; and wherein the linkage region corresponds to amino acid positions 607-618 of a gp160 sequence of isolate HXB2; or ii) the gp120 is inserted between adjacent amino acids in a linkage region between β27 and α8 of gp41ECTO; and wherein the linkage region corresponds to amino acid positions 607-618 of a gp160 sequence of isolate HXB2.

2. The recombinant protein according to claim 1, wherein the gp41ECTO comprises a substitution of 7 consecutive amino acids in a region corresponding to amino acid positions 610-616 of the gp160 sequence of isolate HXB2 with gp120.

3. The recombinant protein according to claim 1, wherein the recombinant protein comprises a disulfide bond between amino acid positions corresponding to positions 501 and 605 of a gp160 sequence of isolate HXB2.

4. The recombinant protein according to claim 1, wherein the N-terminal and/or C-terminal of the gp120 is linked to the gp41ECTO via a direct linkage or a peptide linker.

5. The recombinant protein according to claim 1, which further possesses one or more of the following features:

(1) the gp41ECTO comprises the following amino acid substitution: I559P;

(2) the gp120 comprises the following amino acid substitution: T332N;

(3) the gp120 comprises the following amino acid substitutions: E64K and H66R;

(4) the gp120 comprises the following amino acid substitution: A316W;

(5) the N-linked glycosylation site (PNGS) near the CD4bs epitope of the gp120 is replaced to prevent glycosylation; wherein the PNGS is selected from the group consisting of N276, N301, N360, N463;

(6) the gp120 comprises an internal disulfide bond between I201C and A433C;

(7) the recombinant protein comprises a disulfide bond between E49C and L555C;

the numbering of the above positions is according to the numbering in gp160 of HIV-1 isolate HXB2.

6. The recombinant protein according to claim 1, wherein the gp41ECTO and gp120 are derived from the same or different HIV-1 strains.

7. The recombinant protein according to claim 1, comprising an amino acid sequence selected from:

(1) an amino acid sequence consisting of amino acid residues at positions 40 to 651 of the sequence set forth in SEQ ID NO: 1;

(2) an amino acid sequence consisting of amino acid residues at positions 40 to 652 of the sequence set forth in SEQ ID NO:2;

(3) an amino acid sequence consisting of amino acid residues at positions 40 to 651 of the sequence set forth in SEQ ID NO:3;

(4) an amino acid sequence consisting of amino acid residues at positions 40 to 652 of the sequence set forth in SEQ ID NO:4;

(5) an amino acid sequence consisting of amino acid residues at positions 40 to 665 of the sequence set forth in SEQ ID NO:5;

(6) an amino acid sequence consisting of amino acid residues at positions 40 to 678 of the sequence set forth in SEQ ID NO:6;

(7) an amino acid sequence consisting of amino acid residues at positions 40 to 661 of the sequence set forth in SEQ ID NO:7;

(8) an amino acid sequence consisting of amino acid residues at positions 40 to 666 of the sequence set forth in SEQ ID NO:8;

(9) an amino acid sequence consisting of amino acid residues at positions 40 to 671 of the sequence set forth in SEQ ID NO:9;

(10) an amino acid sequence consisting of amino acid residues at positions 40 to 676 of the sequence set forth in SEQ ID NO:10;

(11) an amino acid sequence consisting of amino acid residues at positions 36 to 607 of the sequence set forth in SEQ ID NO:11;

(12) an amino acid sequence consisting of amino acid residues at positions 36 to 646 of the sequence set forth in SEQ ID NO:12;

(13) an amino acid sequence consisting of amino acid residues at positions 36 to 648 of the sequence set forth in SEQ ID NO:13;

(14) an amino acid sequence consisting of amino acid residues at positions 36 to 638 of the sequence set forth in SEQ ID NO:14;

(15) an amino acid sequence consisting of amino acid residues at positions 36 to 639 of the sequence set forth in SEQ ID NO:15;

(16) an amino acid sequence consisting of amino acid residues at positions 36 to 836 of the sequence set forth in SEQ ID NO:16;

(17) an amino acid sequence consisting of amino acid residues at positions 36 to 673 of the sequence set forth in SEQ ID NO:30;

(18) an amino acid sequence consisting of amino acid residues at positions 36 to 678 of the sequence set forth in SEQ ID NO:31;

(19) an amino acid sequence consisting of amino acid residues at positions 36 to 683 of the sequence set forth in SEQ ID NO:32;

(20) an amino acid sequence consisting of amino acid residues at positions 36 to 678 of the sequence set forth in SEQ ID NO:33;

(21) an amino acid sequence consisting of amino acid residues at positions 36 to 688 of the sequence set forth in SEQ ID NO:34;

(22) an amino acid sequence consisting of amino acid residues at positions 36 to 670 of the sequence set forth in SEQ ID NO:35;

(23) an amino acid sequence consisting of amino acid residues at positions 36 to 676 of the sequence set forth in SEQ ID NO:36;

(24) an amino acid sequence consisting of amino acid residues at positions 36 to 680 of the sequence set forth in SEQ ID NO:37;

(25) an amino acid sequence consisting of amino acid residues at positions 36 to 673 of the sequence set forth in SEQ ID NO:38;

(26) an amino acid sequence consisting of amino acid residues at positions 36 to 678 of the sequence set forth in SEQ ID NO:39; or

(27) an amino acid sequence consisting of amino acid residues at positions 36 to 683 of the sequence set forth in SEQ ID NO:40.

8. The recombinant protein according to claim 1, wherein the recombinant protein comprises a signal peptide and/or a Kozak consensus sequence at its N-terminal; and/or the recombinant protein comprises a tag sequence at its C-terminal.

9. A fusion protein, which comprises the recombinant protein according to claim 1, and transmembrane region and intracellular region sequences of gp41 linked to its C-terminal.

10. The fusion protein according to claim 9, comprising an amino acid sequence selected from:

(1) an amino acid sequence consisting of amino acid residues at positions 33 to 836 of the sequence set forth in SEQ ID NO: 16; or (2) an amino acid sequence consisting of amino acid residues at positions 34 to 837 of the sequence set forth in SEQ ID NO:17.

11. A multimer comprising a plurality of monomers, wherein each monomer is independently the recombinant protein according to claim 1 or a fusion protein comprising the recombinant protein and transmembrane region and intracellular region sequences of gp41 linked to its C-terminal.

12. An isolated nucleic acid molecule, which comprises a nucleotide sequence encoding:

(i) the recombinant protein according to claim 1, (ii) a fusion protein comprising the recombinant protein of (i) and transmembrane region and intracellular region sequences of gp41 linked to its C-terminal, or (iii) a multimer comprising a plurality of monomers, wherein each monomer is independently selected from the recombinant protein of (i) or the fusion protein of (ii).

13. A vector, which comprises the isolated nucleic acid molecule according to claim 3.

14. An isolated host cell which comprises the isolated nucleic acid molecule according to claim 12 or a vector comprising the isolated nucleic acid molecule.

15. A particle, displaying on its surface:

(i) the recombinant protein according to claim 1, (ii) a fusion protein comprising the recombinant protein of (i) and transmembrane region and intracellular region sequences of gp41 linked to its C-terminal, or (iii) a multimer comprising a plurality of monomers, wherein each monomer is independently selected from the recombinant protein of (i) or the fusion protein of (ii);

and wherein the particle is a liposome or a nanoparticle.

16. A pseudoviral particle, comprising on its surface:

(i) the recombinant protein according to claim 1, (ii) a fusion protein comprising the recombinant protein of (i) and transmembrane region and intracellular region sequences of gp41 linked to its C-terminal, or (iii) a multimer comprising a plurality of monomers, wherein each monomer is independently selected from the recombinant protein of (i) or the fusion protein of (ii).

17. A packaging system for producing a pseudoviral particle, which comprises: (i) an expression vector comprising the nucleic acid molecule according to claim 12, and (ii) a packaging vector.

18. A modified HIV virus, which expresses a fusion protein as its envelope protein; the fusion protein comprising the recombinant protein of claim 1 and transmembrane region and intracellular region sequences of gp41 linked to its C-terminal.

19. An isolated nucleic acid molecule, which comprises a nucleotide sequence encoding the genome of the modified HIV virus according to claim 18.

20. A vector, which comprises the isolated nucleic acid molecule according to claim 19.

21. A composition, which comprises any one of (i)-(ix):

(i) the recombinant protein according to claim 1;

(ii) a fusion protein comprising the recombinant protein of (i) and transmembrane region and intracellular region sequences of gp41 linked to its C-terminal;

(iii) a multimer comprising a plurality of monomers, wherein each monomer is independently selected from the recombinant protein of (i) or the fusion protein of (ii);

(iv) an isolated nucleic acid molecule or vector or host cell comprising a nucleotide sequence encoding any one of (i)-(iii);

(v) a particle displaying on its surface any one of (i)-(iii);

(vi) a pseudoviral particle displaying on its surface any one of (i)-(iii);

(vii) a packaging system comprising (a) an expression vector comprising the nucleic acid molecule of (iv), and (b) a packaging vector;

(viii) a modified HIV virus expressing the fusion protein of (ii) as its envelope protein;

(ix) an isolated nucleic acid molecule or vector comprising a nucleotide sequence encoding the genome of the modified HIV virus of (viii).

22. The composition according to claim 21, wherein the composition is an immunogenic composition or a vaccine.

23. The composition according to claim 21, which comprises an antiretroviral agent selected from a nucleoside reverse transcriptase inhibitor, a non-nucleoside reverse transcriptase inhibitor, a protease inhibitor, and a fusion protein inhibitor.

24. A method for inducing an immune response against HIV in a subject or for preventing and/or treating an HIV infection in a subject, which comprises administering to a subject in need thereof an immunologically effective amount of any one of (i)-(x):

(i) the recombinant protein according to claim 1;

(ii) a fusion protein comprising the recombinant protein of (i) and transmembrane region and intracellular region sequences of gp41 linked to its C-terminal;

(iii) a multimer comprising a plurality of monomers, wherein each monomer is independently selected from the recombinant protein of (i) or the fusion protein of (ii);

(iv) an isolated nucleic acid molecule or vector or host cell comprising a nucleotide sequence encoding any one of (i)-(iii);

(v) a particle displaying on its surface any one of (i)-(iii);

(vi) a pseudoviral particle displaying on its surface any one of (i)-(iii);

(vii) a packaging system comprising (a) an expression vector comprising the nucleic acid molecule of (iv), and (b) a packaging vector;

(viii) a modified HIV virus expressing the fusion protein of (ii) as its envelope protein;

(ix) an isolated nucleic acid molecule or vector comprising a nucleotide sequence encoding the genome of the modified HIV virus of (viii); or (x) a composition comprising any of the foregoing.

25. The recombinant protein according to claim 1, wherein the gp120 is located between amino acid positions corresponding to positions 609 and 610 of the gp160 sequence of isolate HXB2; or, the gp120 is located between amino acid positions corresponding to positions 616 and 617 of the gp160 sequence of isolate HXB2.

26. The recombinant protein according to claim 1, wherein:

(i) the gp120 is a modified gp120 that has a furin cleavage site containing a mutation to prevent being cleaved compared to a natural gp120, or the furin cleavage site is deleted in the modified gp120 compared to the natural gp120;

(ii) the gp120 is a modified gp120 that has C-terminal truncation of 1-11 amino acids compared with a natural gp120, or that has a deletion of 1-11 consecutive amino acids in a region corresponding to amino acid positions 501-511 of a gp160 sequence of isolate HXB2; or (iii) the gp120 is a natural gp120.

27. The recombinant protein of claim 4, wherein the peptide linker is (GmS)n, wherein m is an integer selected from 1-4, and n is an integer selected from 1-3.

28. The fusion protein of claim 9, wherein the transmembrane region and intracellular region sequences of gp41 and the gp41ECTO in the recombinant protein are derived from the same HIV-1 strain.

29. The method of claim 24, wherein the subject is a human.

* * * * *